United States Patent
Gourguechon

(10) Patent No.: US 10,787,662 B2
(45) Date of Patent: Sep. 29, 2020

(54) METHODS AND COMPOSITIONS FOR THE MAKING AND USING OF GUIDE NUCLEIC ACIDS

(71) Applicant: Arc Bio, LLC, Cambridge, MA (US)

(72) Inventor: Stephane B. Gourguechon, San Mateo, CA (US)

(73) Assignee: ARC BIO, LLC, Cambridge, MA (US)

( * ) Notice: Subject to any disclaimer, the term of this patent is extended or adjusted under 35 U.S.C. 154(b) by 73 days.

(21) Appl. No.: 15/742,862

(22) PCT Filed: Dec. 7, 2016

(86) PCT No.: PCT/US2016/065420
§ 371 (c)(1),
(2) Date: Jan. 8, 2018

(87) PCT Pub. No.: WO2017/100343
PCT Pub. Date: Jun. 15, 2017

(65) Prior Publication Data
US 2019/0270984 A1 Sep. 5, 2019

Related U.S. Application Data

(60) Provisional application No. 62/298,963, filed on Feb. 23, 2016, provisional application No. 62/264,262, filed on Dec. 7, 2015.

(51) Int. Cl.
| | | |
|---|---|---|
| *C12N 15/00* | (2006.01) |
| *C12N 15/10* | (2006.01) |
| *C12N 9/22* | (2006.01) |
| *C12N 15/113* | (2010.01) |
| *C12N 15/115* | (2010.01) |
| *C12N 15/62* | (2006.01) |
| *C12N 15/63* | (2006.01) |
| *C40B 40/06* | (2006.01) |
| *A61K 48/00* | (2006.01) |
| *C12N 15/11* | (2006.01) |

(52) U.S. Cl.
CPC .......... *C12N 15/1068* (2013.01); *A61K 48/00* (2013.01); *C12N 9/22* (2013.01); *C12N 15/111* (2013.01); *C12N 15/113* (2013.01); *C12N 15/115* (2013.01); *C12N 15/62* (2013.01); *C12N 15/63* (2013.01); *C40B 40/06* (2013.01); *C12N 2310/20* (2017.05); *C12N 2320/10* (2013.01); *C12N 2750/14143* (2013.01); *C12N 2800/70* (2013.01)

(58) Field of Classification Search
None
See application file for complete search history.

(56) References Cited

U.S. PATENT DOCUMENTS

| | | | |
|---|---|---|---|
| 5,948,902 A | 9/1999 | Honkanen et al. |
| 9,102,944 B2 | 8/2015 | Ness et al. |
| 2005/0233340 A1 | 10/2005 | Barrett et al. |
| 2006/0088821 A1 | 4/2006 | Short |
| 2011/0256593 A1 | 10/2011 | Hsieh et al. |
| 2013/0298265 A1 | 11/2013 | Cunnac et al. |
| 2014/0030704 A1 | 1/2014 | Mikawa |
| 2014/0068797 A1 | 3/2014 | Doudna et al. |
| 2014/0087378 A1 | 3/2014 | Chatre et al. |
| 2014/0273226 A1* | 9/2014 | Wu ...................... C12N 15/907 435/455 |
| 2014/0357523 A1 | 12/2014 | Zeiner et al. |
| 2015/0059010 A1 | 2/2015 | Cigan et al. |
| 2015/0094212 A1 | 4/2015 | Gottimukkala et al. |
| 2015/0211002 A1 | 7/2015 | Keefe et al. |
| 2015/0284789 A1 | 10/2015 | Hogers |
| 2016/0053304 A1 | 2/2016 | Wurtzel et al. |
| 2016/0115530 A1 | 4/2016 | Kladde et al. |
| 2016/0208241 A1* | 7/2016 | Tsai ...................... C12Q 1/6806 |
| 2016/0237488 A1 | 8/2016 | Ke et al. |
| 2016/0354752 A1 | 12/2016 | Banyai et al. |
| 2016/0362680 A1 | 12/2016 | Armour et al. |
| 2017/0121694 A1 | 5/2017 | May et al. |

FOREIGN PATENT DOCUMENTS

| | | |
|---|---|---|
| WO | WO-2015/050501 A1 | 4/2015 |
| WO | WO-2015/089473 A9 | 6/2015 |
| WO | WO-2015089473 A1 * | 6/2015 |
| WO | WO-2015131101 A1 * | 9/2015 |
| WO | WO-2015/173436 A1 | 11/2015 |
| WO | WO-2016/100955 A2 | 6/2016 |
| WO | WO-2016/100955 A3 | 6/2016 |
| WO | WO-2016/196805 A1 | 12/2016 |
| WO | WO-2017/031360 A1 | 2/2017 |

(Continued)

OTHER PUBLICATIONS

Score result for Brower-Toland SEQ No. 1 WO2015131101-A1 published Sep. 3, 2015 (Year: 2015).*

(Continued)

*Primary Examiner* — Catherine S Hibbert

(74) *Attorney, Agent, or Firm* — Quarles & Brady LLP

(57) ABSTRACT

Provided herein are methods and compositions to make guide nucleic acids (gNAs), nucleic acids encoding gNAs, collections of gNAs, and nucleic acids encoding for a collection of gNAs from any source nucleic acid. Also provided herein are methods and compositions to use the resulting gNAs, nucleic acids encoding gNAs, collections of gNAs, and nucleic acids encoding for a collection of gNAs in a variety of applications.

21 Claims, 7 Drawing Sheets

Specification includes a Sequence Listing.

(56) References Cited

FOREIGN PATENT DOCUMENTS

| WO | WO-2017/062723 A9 | 4/2017 |
|---|---|---|
| WO | WO-2017/081097 A1 | 5/2017 |
| WO | WO-2017/100343 A1 | 6/2017 |
| WO | WO-2017/147345 A1 | 8/2017 |
| WO | WO-2018/227025 A1 | 12/2018 |

OTHER PUBLICATIONS

Score result for Wu SEQ No. 1 US2014/0273226 published Sep. 18, 2014 (Year: 2014).*
International Search Report dated May 4, 2017, for PCT Application No. PCT/US2016/065420, filed on Dec. 7, 2016, 8 pages.
Lane, A.B. et al. (2015). "Enzymatically generated CRISPR libraries for genome labeling and screening," *Dev. Cell* 34:373-378.
Loman, N.J. et al. (2012). "High-throughput bacterial genome sequencing: an embarrassment of choice, a world of opportunity," *Nature Review Microbiol.* 10:599-606.
Ran, F.A. et al. (2015). "In vivo genome editing using *Staphylococcus aureus* Cas9," Nature 520:186-191.
Written Opinion of the International Searching Authority dated May 4, 2017, for PCT Application No. PCT/US2016/065420, filed on Dec. 7, 2016, 20 pages.
Ma, M. et al. (2013). "A guide RNA sequence design platform for the CRISPR/Cas9 system for model organism genomes," *Biomed. Res. Int.* vol. 2013, pp. 1-4.
Briner, A.E. et al. (2014). "Guide RNA functional modules direct Cas9 activity and orthogonality," *Mol. Cell.* 56:333-339.
Extended European Search Report dated Aug. 21, 2019, for EP Application No. 16 873 782.3, filed on Dec. 7, 2016, 6 pages.
Koike-Yusa, H. et al. (2014). "Genome-wide recessive genetic screening in mammalian cells with a lentiviral CRISPR-guide RNA library," Nature Biotechnology 32:267-273.
Schmidt, T. et al. (2015). "Synthesis of an arrayed sgRNA library targeting the human genome," Scientific Reports 5:14987, 10 total pages.
Vidigal, J.A. and Ventura, A. (2015). "Rapid and efficient one-step generation of paired gRNA CRISPR-Cas9 libraries," Nature Communications 6:8083, 7 total pages.
Zhou, Y. et al. (2014). "High-throughput screening of a CRISPR/Cas9 library for functional genomics in human cells," Nature 509:487-491, and 11 pages supplemental information,.
International Search Report dated Sep. 25, 2018, for PCT Application No. PCT/US2018/036563, filed on Jun. 7, 2018, 4 pages.
Written Opinion of the International Searching Authority dated Sep. 25, 2018, for PCT Application No. PCT/US2018/036563, filed on Jun. 7, 2018, 37 pages.
U.S. Appl. No. 16/619,055, filed Jun. 7, 2018, by Gourguechon et al. (Copy not attached).

\* cited by examiner

201 Genomic or other source DNA

202 Nt.CviPII and T7 Endonuclease I treatment

203 Ligate T7/MlyI adapters

204 PCR amplify with T7 and MlyI primers

205 Digest with MlyI, separates HGG from gRNA targeting sequence

206 Ligate gRNA stem-loop sequences

METHODS AND COMPOSITIONS FOR THE MAKING AND USING OF GUIDE NUCLEIC ACIDS

CROSS-REFERENCE

This is a U.S. National Stage Application under 35 U.S.C. § 371 of International Application No. PCT/US2016/065420, filed on Dec. 7, 2016, which claims the benefit of U.S. Provisional Application No. 62/264,262, filed Dec. 7, 2015, and of U.S. Provisional Application No. 62/298,963, filed Feb. 23, 2016, each of which is hereby incorporated by reference in its entirety.

INCORPORATION BY REFERENCE OF SEQUENCE LISTING

The present application is being filed with a Sequence Listing in electronic format. The Sequence Listing is provided as a file entitled ARCB-003/02US_SeqList.txt, created Nov. 19, 2018, which is 816,892 bytes in size. The information in electronic format of the Sequence Listing is incorporated by reference in its entirety.

BACKGROUND

Human clinical DNA samples and sample libraries such as cDNA libraries derived from RNA contain highly abundant sequences that have little informative value and increase the cost of sequencing. While methods have been developed to deplete these unwanted sequences (e.g., via hybridization capture), these methods are often time-consuming and can be inefficient.

Although a guide nucleic acid (gNA) mediated nuclease systems (such as guide RNA (gRNA)-mediated Cas systems) can efficiently deplete any target DNA, targeted depletion of very high numbers of unique DNA molecules is not feasible. For example, a sequencing library derived from human blood may contain >99% human genomic DNA. Using a gRNA-mediated Cas9 system-based method to deplete this genomic DNA to detect an infectious agent circulating in the human blood would require extremely high numbers of gRNAs (about 10-100 million gRNAs), in order to ensure that a gRNA will be present every 30-50 base pairs (bp), and that no target DNA will be missed. Very large numbers of gRNAs can be predicted computationally and then synthesized chemically, but at a prohibitively expensive cost.

Therefore, there is a need in the art to provide a cost-effective method of converting any DNA into a gNA (e.g., gRNA) library to enable, for example, genome-wide depletion of unwanted DNA sequences from those of interest, without prior knowledge about their sequences. Provided herein are methods and compositions that address this need.

SUMMARY

Provided herein are compositions and methods to generate gNAs and collections of gNAs from any source nucleic acid. For example, gRNAs and collections of gRNAs can be generated from source DNA, such as genomic DNA. Such gNAs and collections of the same are useful for a variety of applications, including depletion, partitioning, capture, or enrichment of target sequences of interest, genome-wide labeling, genome-wide editing, genome-wide functional screens, and genome-wide regulation.

In one aspect, the invention described herein provides a collection of nucleic acids, a plurality of the nucleic acids in the collection comprising: a first segment comprising a regulatory region; a second segment encoding a targeting sequence; and a third segment encoding a nucleic acid-guided nuclease system protein-binding sequence, wherein at least 10% of the nucleic acids in the collection vary in size. In another aspect, the invention described herein provides a collection of nucleic acids, a plurality of the nucleic acids in the collection comprising: a first segment comprising a regulatory region; a second segment encoding a targeting sequence, wherein the size of the second segment is greater than 21 bp; and a third segment encoding a nucleic acid-guided nuclease system protein-binding sequence. In some embodiments, the nucleic acid-guided nuclease system protein is a CRISPR/Cas system protein. In some embodiments, the size of the second segment varies from 15-250 bp across the collection of nucleic acids. In some embodiments, at least 10% of the second segments in the collection are greater than 21 bp. In some embodiments, the size of the second segment is not 20 bp. In some embodiments, the size of the second segment is not 21 bp. In some embodiments, the collection of nucleic acids is a collection of DNA. In some embodiments, the second segment is single stranded DNA. In some embodiments, the third segment is single stranded DNA. In some embodiments, the second segment is double stranded DNA. In some embodiments, the third segment is double stranded DNA. In some embodiments, the regulatory region is a region capable of binding a transcription factor. In some embodiments, the regulatory region comprises a promoter. In some embodiments, the promoter is selected from the group consisting of T7, SP6, and T3. In some embodiments, the targeting sequence is directed at a mammalian genome, eukaryotic genome, prokaryotic genome, or a viral genome. In some embodiments, the targeting sequence is directed at repetitive or abundant DNA. In some embodiments, the targeting sequence is directed at mitochondrial DNA, ribosomal DNA, Alu DNA, centromeric DNA, SINE DNA, LINE DNA, or STR DNA. In some embodiments, the sequence of the second segments is selected from Table 3 and/or Table 4. In some embodiments, the collection comprises at least $10^2$ unique nucleic acid molecules. In some embodiments, the targeting sequence is at least 80% complementary to the strand opposite to a sequence of nucleotides 5' to a PAM sequence. In some embodiments, the collection comprises targeting sequences directed to sequences of interest spaced about every 10,000 bp or less across the genome of an organism. In some embodiments, the PAM sequence is AGG, CGG, or TGG. In some embodiments, the PAM sequence is specific for a CRISPR/Cas system protein selected from the group consisting of Cas9, Cpf1, Cas3, Cas8a-c, Cas10, Cse1, Csy1, Csn2, Cas4, Csm2, and Cm5. In some embodiments, the third segment comprises DNA encoding a gRNA stem-loop sequence. In some embodiments, the third segment encodes for a RNA comprising the sequence GUUUUAGAGCUAGAAAUAGCAAGUUAAAAUAAGGCUAGUCCGUUAUCAACUUGAAAAAGUGGCACCGAGUCGGUGCUUUUUUU (SEQ ID NO: 1) or encodes for a RNA comprising the sequence GUUUUAGAGCUAUGCUGAAACAGCAUAGCAAGUUAAAAUAAGGCUAGUCCGUUAUCAACUUGA AAAAGUGGCACCGAGUCGGUGCUUUUUUC (SEQ ID NO: 2). In some embodiments, the sequence of the third segment encodes for a crRNA and a tracrRNA. In some embodiments, the nucleic acid-guided nuclease system protein is from a bacterial species. In some embodiments, the nucleic acid-guided nuclease system protein is from an archaea species. In some embodiments, the CRISPR/Cas system protein is a Type I, Type II, or Type III protein. In some embodiments, the CRISPR/Cas system protein is selected from the group consisting of Cas9, Cpf1, Cas3, Cas8a-c, Cas10, Cse1, Csy1, Csn2, Cas4, Csm2, Cm5, dCas9 and cas9 nickase. In some embodiments, the third segment comprises DNA encoding a Cas9-binding sequence. In some embodiments, a plurality of third segments of the collection encode for a first nucleic acid-guided nuclease system protein binding sequence, and a plurality of the third segments of the collection encode for a second nucleic acid-guided nuclease system protein binding sequence. In some embodiments, the third segments of the collection encode for a plurality of different binding sequences of a plurality of different binding sequences of a plurality of different nucleic acid-guided nuclease system proteins.

In another aspect, the invention described herein provides for a collection of guide RNAs (gRNAs), comprising: a first RNA segment a targeting sequence; and a second RNA segment comprising a nucleic acid-guided nuclease system protein-binding sequence, wherein at least 10% of the gRNAs in the collection vary in size. In some embodiments, the nucleic acid-guided nuclease system protein is a CRISPR/Cas system protein. In some embodiments, the size of the first segment varies from 15-250 bp across the collection of gRNAs. In some embodiments, the at least 10% of the first segments in the collection are greater than 21 bp. In some embodiments, the size of the first segment is not 20 bp. In some embodiments, the size of the first segment is not 21 bp. In some embodiments, the targeting sequence is directed at a mammalian genome, eukaryotic genome, prokaryotic genome, or viral genome. In some embodiments, the targeting sequence is directed at repetitive or abundant DNA. In some embodiments, the targeting sequence is directed at mitochondrial DNA, ribosomal DNA, Alu DNA, centromeric DNA, SINE DNA, LINE DNA, or STR DNA. In some embodiments, the sequence of the first segments is RNA encoded by sequences selected from Table 3 and/or Table 4. In some embodiments, the collection comprises at least $10^2$ unique gRNAs. In some embodiments, the gRNAs comprise cytosine, guanine, and adenine. In some embodiments, a subset of the gRNAs further comprises thymine. In some embodiments, a subset of the gRNAs further comprises uracil. In some embodiments, the first segment is at least 80% complementary to a target genomic sequence of interest. In some embodiments, the targeting sequence is at least 80% complementary to the strand opposite to a sequence of nucleotides 5' to a PAM sequence. In some embodiments the PAM sequence is AGG, CGG, or TGG. In some embodiments, the PAM sequence is specific for a CRISPR/Cas system protein selected from the group consisting of Cas9, Cpf1, Cas3, Cas8a-c, Cas10, Cse1, Csy1, Csn2, Cas4, Csm2, and Cm5. In some embodiments, the second segment comprises a gRNA stem-loop sequence. In some embodiments, the third segment comprises DNA encoding a gRNA stem-loop sequence. In some embodiments, the third segment comprises the sequence GUUUUAGAGCUAGAAAUAG-CAAGUUAAAAUAAGGCUAGUCCGUUAUCAAC-UUGAAAAAGUGGCA CCGAGUCGGUGCUUUUUUU (SEQ ID NO: 1) or comprises the sequence GUUUUA-GAGCUAUGCUGGAAACAGCAUAG-CAAGUUAAAAUAAGGCUAGUCCGUUAUCAAC-UUGA AAAAGUGGCACCGAGUCGGUGCUUUUUUC (SEQ ID NO: 2). In some embodiments, the second segment comprises a crRNA and a tracrRNA. In some embodiments, the nucleic acid-guided nuclease system protein is from a bacterial species. In some embodiments, the nucleic acid-guided nuclease system protein is from an archaea species. In some embodiments, the CRISPR/Cas system protein is a Type I, Type II, or Type III protein. In some embodiments, the CRISPR/Cas system protein is selected from the group consisting of Cas9, Cpf1, Cas3, Cas8a-c, Cas10, Cse1, Csy1, Csn2, Cas4, Csm2, Cm5, dCas9 and cas9 nickase. In some embodiments, the second segment comprises a Cas9-binding sequence. In some embodiments, at least 10% of the gRNAs in the collection vary in their 5' terminal-end sequence. In some embodiments, the collection comprises targeting sequences directed to sequences of interest spaced every 10,000 bp or less across the genome of an organism. In some embodiments, a plurality of second segments of the collection comprise a first nucleic acid-guided nuclease system protein binding sequence, and a plurality of the second segments of the collection comprise a second nucleic acid-guided nuclease system protein binding sequence. In some embodiments, the second segments of the collection comprise a plurality of different binding sequences of a plurality of different nucleic acid-guided nuclease system proteins. In some embodiments, a plurality of the gRNAs of the collection are attached to a substrate. In some embodiments, a plurality of the gRNAs of the collection comprise a label. In some particular embodiments, a plurality of the gRNAs of the collection comprise different labels.

In another aspect, the invention described herein provides nucleic acid comprising: a first segment comprising a regulatory region; a second segment encoding a targeting sequence, wherein the targeting sequence is greater than 30 bp; and a third segment encoding a nucleic acid encoding a nucleic acid-guided nuclease system protein-binding sequence. In some embodiments, the nucleic acid-guided nuclease is a CRISPR/Cas system protein. In some embodiments, the nucleic acid is DNA. In some embodiments, the second segment is single stranded DNA. In some embodiments, the third segment is single stranded DNA. In some embodiments, the second segment is double stranded DNA. In some embodiments, the third segment is double stranded DNA. In some embodiments, the regulatory region is a region capable of binding a transcription factor. In some embodiments, the regulatory region comprises a promoter. In some embodiments, the promoter is selected from the group consisting of T7, SP6, and T3. In some embodiments, the targeting sequence is directed at a mammalian genome, eukaryotic genome, prokaryotic genome, or a viral genome. In some embodiments, the targeting sequence is directed at abundant or repetitive DNA. In some embodiments, the targeting sequence is directed at mitochondrial DNA, ribosomal DNA, Alu DNA, centromeric DNA, SINE DNA, LINE DNA, or STR DNA. In some embodiments, the sequence of the second segments is selected from Table 3 and/or Table 4. In some embodiments, the targeting sequence is at least 80% complementary to the strand opposite to a sequence of nucleotides 5' to a PAM sequence. In some embodiments, the target genomic sequence of interest is 5' upstream of a PAM sequence. In some embodiments, the PAM sequence is specific for a CRISPR/Cas system protein selected from the group consisting of Cas9, Cpf1, Cas3, Cas8a-c, Cas10, Cse1, Csy1, Csn2, Cas4, Csm2, and Cm5. In some embodiments, the third segment comprises DNA encoding a gRNA stem-loop sequence. In some embodiments, the third segment comprises DNA encoding a gRNA stem-loop sequence. In some embodiments, the third segment encodes for a RNA comprising the sequence GUUUAGAGCUAGAAAUAGCAAGUUAAAAUAAGGCUAGUCCGUUAUCAACUUGAAAAAGUGGCA CCGAGUCGGUGCUUUUUU (SEQ ID NO: 1) or encodes for a RNA comprising the sequence GUUUAGAGCUAUGCUGGAAACAGCAUAGCAAGUUAAAAUAAGGCUAGUCCGUUAUCAACUUGA AAAAGUGGCACCGAGUCGGUGCUUUUUUC (SEQ ID NO: 2). In some embodiments, the nucleic acid-guided nuclease system protein is from a bacterial species. In some embodiments, the nucleic acid-guided nuclease system protein is from an archaea species. In some embodiments, the CRISPR/Cas system protein is a Type I, Type II, or Type III protein. In some embodiments, the CRISPR/Cas system protein is selected from the group consisting of Cas9, Cpf1, Cas3, Cas8a-c, Cas10, Cse1, Csy1, Csn2, Cas4, Csm2, Cm5, dCas9 and cas9 nickase. In some embodiments, the third segment comprises DNA encoding a Cas9-binding sequence.

In another aspect, the invention described herein provides a guide RNA comprising a first segment comprising a targeting sequence, wherein the size of the first segment is greater than 30 bp; and a second segment comprising a nucleic acid-guided nuclease system protein-binding sequence. In some embodiments, the nucleic acid-guided nuclease is a CRISPR/Cas system protein. In some embodiments, the gRNA comprises an adenine, a guanine, and a cytosine. In some embodiments, the gRNA further comprises a thymine. In some embodiments, the gRNA further comprises a uracil. In some embodiments, the size of the first RNA segment is between 30 and 250 bp. In some embodiments, the targeting sequence is directed at a mammalian genome, eukaryotic genome, prokaryotic genome, or viral genome. In some embodiments, the targeting sequence is directed at repetitive or abundant DNA. In some embodiments, the targeting sequence is directed at mitochondrial DNA, ribosomal DNA, Alu DNA, centromeric DNA, SINE DNA, LINE DNA, or STR DNA. In some embodiments, the first segment is at least 80% complementary to the target genomic sequence of interest. In some embodiments, the targeting sequence is at least 80% complementary to the strand opposite to a sequence of nucleotides 5' to a PAM sequence. In some embodiments, the second segment comprises a gRNA stem-loop sequence. In some embodiments, the sequence of the second segment comprises GUUUAGAGCUAGAAAUAGCAAGUUAAAAUAAGGCUAGUCCGUUAUCAACUUGAAAAAGUGGCA CCGAGUCGGUGCUUUUUUU (SEQ ID NO: 1) or comprises the sequence GUUUAGAGCUAUGCUGGAAACAGCAUAGCAAGUUAAAAUAAGGCUAGUCCGUUAUCAACUUGA AAAAGUGGCACCGAGUCGGUGCUUUUUUC (SEQ ID NO: 2). In some embodiments, the sequence of the third segment comprises a crRNA and a tracrRNA. In some embodiments, the nucleic acid-guided nuclease system protein is from a bacterial species. In some embodiments, the nucleic acid-guided nuclease system protein is from an archaea species. In some embodiments, the CRISPR/Cas system protein is a Type I, Type II, or Type III protein. In some embodiments, the CRISPR/Cas system protein is selected from the group consisting of Cas9, Cpf1, Cas3, Cas8a-c, Cas10, Cse1, Csy1, Csn2, Cas4, Csm2, Cm5, dCas9 and cas9 nickase. In some embodiments, the second segment is a Cas9-binding sequence.

In another aspect, the invention provides a complex comprising a nucleic acid-guided nuclease system protein and a comprising a first segment comprising a targeting sequence, wherein the size of the first segment is greater than 30 bp; and a second segment comprising a nucleic acid-guided nuclease system protein-binding sequence.

In another aspect, the invention described herein provides a method for depleting and partitioning of targeted sequences in a sample, enriching a sample for non-host nucleic acids, or serially depleting targeted nucleic acids in a sample comprising: providing nucleic acids extracted from a sample; and contacting the sample with a plurality of complexes comprising (i) any one of the collection of gRNAs provided herein; and (ii) nucleic acid-guided nuclease system proteins. In some embodiments, the nucleic acid-guided nuclease system proteins are CRISPR/Cas system proteins. In some embodiments, the CRISPR/Cas system proteins are Cas9 proteins.

In another aspect, the invention provides a method of making a collection of nucleic acids, each comprising a DNA encoding a targeting sequence ligated to a DNA encoding a nucleic acid-guided nuclease system protein-binding sequence, comprising: (a) providing double-stranded DNA molecules, each comprising a sequence of interest 5' to a PAM sequence, and its reverse complementary sequence on the opposite strand; (b) performing an enzymatic digestion reaction on the double stranded DNA molecules, wherein cleavages are generated at the PAM sequence and/or its reverse complementary sequence on the opposite strand, but never completely remove the PAM sequence and/or its reverse complementary sequence on the opposite strand from the double stranded DNA; (c) ligating adapters comprising a recognition sequence to the resulting DNA molecules of step b; (d) contacting the DNA molecules of step c with an restriction enzyme that recognizes the recognition sequence of step c, whereby generating DNA fragments comprising blunt-ended double strand breaks immediately 5' to the PAM sequence, whereby removing the PAM sequence and the adapter containing the enzyme recognition site; and (e) ligating the resulting double stranded DNA fragments of step d with a DNA encoding a nucleic acid-guided nuclease system protein-binding sequence, whereby generating a plurality of DNA fragments, each comprising a DNA encoding a targeting sequence ligated to a DNA encoding a nucleic acid-guided nuclease system protein-binding sequence. In some embodiments, the nucleic acid-guided nuclease is a CRISPR/Cas nucleic acid-guided nuclease system protein. In some embodiments, the starting DNA molecules of the collection further comprise a regulatory sequence upstream of the sequence of interest 5' to the PAM sequence. In some embodiments, the regulatory sequence comprises a promoter. In some embodiments, the promoter comprises a T7, Sp6, or T3 sequence. In some embodiments, the double stranded DNA molecules are genomic DNA, intact DNA, or sheared DNA. In some embodiments, the genomic DNA is human, mouse, avian, fish, plant, insect, bacterial, or viral. In some embodiments, the DNA segments encoding a targeting sequence are at least 22 bp. In some embodiments, the DNA segments encoding a targeting sequence are 15-250 bp in size range. In some embodiments, the PAM sequence is AGG, CGG, or TGG. In some embodiments, the PAM sequence is specific for a CRISPR/Cas system protein selected from the group consisting of Cas9, Cpf1, Cas3, Cas8a-c, Cas10, Cse1, Csy1, Csn2, Cas4, Csm2, and Cm5. In some embodiments, step (b) further comprises (1) contacting the DNA molecules with an enzyme capable of creating a nick in a single strand at a CCD site, whereby generating a plurality of nicked double stranded DNA molecules, each comprising a sequence of interest followed by an HGG sequence, wherein the DNA molecules are nicked at the CCD sites; and (2) contacting the nicked double stranded DNA molecules with an endonuclease, whereby generating a plurality of double stranded DNA fragments, each comprising a sequence of interest followed by an NGG sequence wherein residual nucleotides from HGG and/or CCD sequences is (are) left behind. In some embodiments, step (d) further comprises PCR amplification of the adaptor-ligated DNA fragments from step (c) before cutting with the restriction enzyme recognizing the recognition sequence of step (c), wherein after PCR, the recognition sequence is positioned 3' of the PAM sequence, and a regulatory sequence is positioned at the 5' distal end of the PAM sequence. In some embodiments, the enzymatic reaction of step (b) comprises the use of a Nt.CviPII enzyme, and a T7 Endonuclease I enzyme. In some embodiments, step (c) further comprises a blunt-end reaction with a T4 DNA Polymerase, if the adapter to be ligated does not comprise an overhang. In some embodiments, the adapter of step (c) is either (1) double stranded, comprising a restriction enzyme recognition sequence in one strand, and a regulatory sequence in the other strand, if the adapter is Y-shaped and comprises an overhang; or (2) has a palindromic enzyme recognition sequence in both strands, if the adapter is not Y-shaped. In some embodiments, the restriction enzyme of step (d) is MlyI. In some embodiments, the restriction enzyme of step (d) is BaeI. In some embodiments, step (d) further comprises contacting the DNA molecules with an XhoI enzyme. In some embodiments, in step (e) the DNA encoding a nucleic acid-guided nuclease system-protein binding sequence encodes for a RNA comprising the sequence GUUUUAGAGCUAGAAAUAG-CAAGUUAAAAUAAGGCUAGUCCGUUAUCAAC-UUGAAAAAGUGGCA CCGAGUCGGUGCUUUUUUU (SEQ ID NO: 1) or encodes for a RNA comprising the sequence GUUUUAGAGCUAUGCUGGAAACAG-CAUAGCAAGUUAAAAUAAGGCUAGUCCGUUAU-CAACUUGA AAAAGUGGCACCGAGUCGGUGC-UUUUUUUC (SEQ ID NO: 2). In some embodiments, the targeted sequences of interest are spaced every 10,000 bp or less across the genome of an organism.

In another aspect, the invention provides a method of making a collection of nucleic acids, each comprising a DNA encoding a targeting sequence ligated to a DNA encoding a nucleic acid-guided nuclease system protein-binding sequence, comprising: (a) providing a plurality of double stranded DNA molecules, each comprising a sequence of interest, an NGG site, and its complement CCN site; (b) contacting the molecules with an enzyme capable of creating a nick in a single strand at a CCN site, whereby generating a plurality of nicked double stranded DNA molecules, each comprising a sequence of interest 5' to the NGG site, wherein the DNA molecules are nicked at the CCD sites; (c) contacting the nicked double stranded DNA molecules with an endonuclease, whereby generating a plurality of double stranded DNA fragments, each comprising a sequence of interest, wherein the fragments comprise an terminal overhang; (d) contacting the double stranded DNA fragments with an enzyme without 5' to 3' exonuclease activity to blunt end the double stranded DNA fragments, whereby generating a plurality of blunt ended double stranded fragments, each comprising a sequence of interest; (e) contacting the blunt ended double stranded fragments of step d with an enzyme that cleaves the terminal NGG site; and (f) ligating the resulting double stranded DNA fragments of step e with a DNA encoding a nucleic acid-guided nuclease system-protein binding sequence, whereby generating a plurality of DNA fragments, each comprising a targeting sequence ligated to a DNA encoding a nucleic acid-guided nuclease system protein-binding sequence. In some embodiments, the nucleic acid-guided nuclease is a CRISPR/Cas system protein. In some embodiments, the plurality of double stranded DNA molecules have a regulatory sequence 5' upstream of the NGG sites. In some embodiments, the regulatory sequence comprises a T7, SP6, or T3 sequence. In some embodiments, the NGG site comprises AGG, CGG, or TGG, and the CCN site comprises CCT, CCG, or CCA. In some embodiments, the plurality of double stranded DNA molecules, each comprising a sequence of interest comprise sheared fragments of genomic DNA. In some embodiments, the genomic DNA is mammalian, prokaryotic, eukaryotic, avian, bacterial or viral. In some embodiments, the plurality of double stranded DNA molecules in step (a) are at least 500 bp. In some embodiments, the enzyme in step b is a Nt.CviPII enzyme. In some embodiments, the enzyme in step c is a T7 Endonuclease I. In some embodiments, the enzyme in step d is a T4 DNA Polymerase. In some embodiments, in step f the DNA encoding a nucleic acid-guided nuclease system-protein binding sequence encodes for a RNA comprising the sequence GUUUUAGAGCUAGAAAUAG-CAAGUUAAAAUAAGGCUAGUCCGUUAUCAAC-UUGAAAAAGUGGCA CCGAGUCGGUGCUUUUUUU (SEQ ID NO: 1) or encodes for a RNA comprising the sequence GUUUUAGAGCUAUGCUGGAAACAG-CAUAGCAAGUUAAAAUAAGGCUAGUCCGUUAU-CAACUUGA AAAAGUGGCACCGAGUCGGUGC-UUUUUUUC (SEQ ID NO: 2). In some embodiments, the step e additionally comprises ligating adaptors carrying a MlyI recognition site and digesting with MlyI enzyme. In some embodiments, the sequence of interest is spaced every 10,000 bp or less across the genome.

In another aspect, the invention provides a method of making a collection of nucleic acids, each comprising a DNA encoding a targeting sequence and a DNA encoding a nucleic acid-guided nuclease system protein-binding sequence, comprising: (a) providing genomic DNA comprising a plurality of sequences of interest, comprising NGG and CCN sites; (b) contacting the genomic DNA with an enzyme capable of creating nicks in the genomic DNA, whereby generating nicked genomic DNA, nicked at CCN sites; (c) contacting the nicked genomic DNA with an endonuclease, whereby generating double stranded DNA fragments, with an overhang; (d) ligating the DNA with overhangs from step c to a Y-shaped adapter, thereby introducing a restriction enzyme recognition sequence only at 3' of the NGG site and a regulatory sequence 5' of the sequence of interest; (e) contacting the product from step d with an enzyme that cleaves away the NGG site together with the adaptor carrying the enzyme recognition sequence; and (f) ligating the resulting double stranded DNA fragments of step e with a DNA encoding a nucleic acid-guided nuclease system protein-binding sequence, whereby generating a plurality of DNA fragments, each comprising a sequence of interest ligated to a DNA encoding a nucleic acid-guided nuclease system protein-binding sequence. In some embodiments, the nucleic acid-guided nuclease is a CRISPR/Cas system protein. In some embodiments, the NGG site comprises AGG, CGG, or TGG, and CCN site comprises CCT, CCG, or CCA. In some embodiments, the regulatory sequence comprises a promoter sequence. In some embodiments, the promoter sequence comprises a T7, SP6, or T3 sequence. In some embodiments, the DNA fragments are sheared fragments of genomic DNA.

In some embodiments, the genomic DNA is mammalian, prokaryotic, eukaryotic, or viral. In some embodiments, the fragments are at least 200 bp. In some embodiments, the enzyme in step b is a Nt.CviPII enzyme. In some embodiments, the enzyme in step c is a T7 Endonuclease I. In some embodiments, step d further comprises PCR amplification of the adaptor-ligated DNA. In some embodiments, in step f, the DNA encoding nucleic acid-guided nuclease system protein-binding sequence encodes for a RNA comprising the sequence GUUUUAGAGCUAGAAAUAGCAAGUUAAAAUAAGGCUAGUCCGUUAUCAACUUGAAAAAGUGGCA CCGAGUCGGUGCUUUUUUU (SEQ ID NO: 1) or encodes for a RNA comprising the sequence GUUUUAGAGCUAUGCUGGAAACAGCAUAGCAAGUUAAAAUAAGGCUAGUCCGUUAUCAACUUGA AAAAGUGGCACCGAGUCGGUGCUUUUUUC (SEQ ID NO: 2). In some embodiments, the enzyme removing NGG site in step e is MlyI. In some embodiments, the target of interest of the collection is spaced every 10,000 bp or less across the genome.

In another aspect, the invention provides kits and/or reagents useful for performing a method of making a collection of nucleic acids, each comprising a DNA encoding a targeting sequence ligated to a DNA encoding a nucleic acid-guided nuclease system protein-binding sequence, as described in the embodiments herein.

In another aspect, the invention described herein provides kit comprising a collection of nucleic acids, a plurality of the nucleic acids in the collection comprising: a first segment comprising a regulatory region; a second segment encoding a targeting sequence; and a third segment encoding a CRISPR/Cas system protein-binding sequence, wherein at least 10% of the nucleic acids in the collection vary in size.

In another aspect, the invention described herein provides a kit comprising a collection of nucleic acids, a plurality of the nucleic acids in the collection comprising: a first segment comprising a regulatory region; a second segment encoding a targeting sequence, wherein the size of the second segment is greater than 21 bp; and a third segment encoding a CRISPR/Cas system protein-binding sequence.

In another aspect, the invention described herein provides a kit comprising a collection of guide RNAs comprising a first RNA segment a targeting sequence; and a second RNA segment comprising a CRISPR/Cas system protein-binding sequence, wherein at least 10% of the gRNAs in the collection vary in size.

In another aspect, the invention described herein provides a method of making a collection of guide nucleic acids, comprising: a. obtaining abundant cells in a source sample; b. collecting nucleic acids from said abundant cells; and c. preparing a collection of guide nucleic acids (gNAs) from said nucleic acids. In some embodiments, said abundant cells comprise cells from one or more most abundant bacterial species in said source sample. In some embodiments, said abundant cells comprise cells from more than one species. In some embodiments, said abundant cells comprise human cells. In some embodiments, said abundant cells comprise animal cells. In some embodiments, said abundant cells comprise plant cells. In some embodiments, said abundant cells comprise bacterial cells. In some embodiments, the method further comprises contacting nucleic acid-guided nucleases with said library of gNAs to form nucleic acid-guided nuclease-gNA complexes. In some embodiments, the method further comprises using said nucleic acid-guided nuclease-gNA complexes to cleave target nucleic acids at target sites, wherein said gNAs are complementary to said target sites. In some embodiments, said target nucleic acids are from said source sample. In some embodiments, a species of said target nucleic acids is the same as a species of said source sample. In some embodiments, said species of said target nucleic acids and said species of said source sample is human. In some embodiments, said species of said target nucleic acids and said species of said source sample is animal. In some embodiments, said species of said target nucleic acids and said species of said source sample is plant.

In another aspect, the invention described herein provides a method of making a collection of nucleic acids, each comprising a targeting sequence, comprising: a. obtaining source DNA; b. nicking said source DNA with a nicking enzyme at nicking enzyme recognition sites, thereby producing double-stranded breaks at proximal nicks; and c. repairing overhangs of said double-stranded breaks, thereby producing a double-stranded fragment comprising (i) a targeting sequence and (ii) said nicking enzyme recognition site. In another aspect, the invention described herein provides a method of making a collection of nucleic acids, each comprising a targeting sequence, comprising: a. obtaining source DNA; b. nicking said source DNA with a nicking enzyme at nicking enzyme recognition sites, thereby producing a nick; and c. synthesizing a new strand from said nick, thereby producing a single-stranded fragment of said source DNA comprising a targeting sequence. In some embodiments, the method further comprises producing a double-stranded fragment comprising said targeting sequence from said single-stranded fragment. In some embodiments, said producing said double-stranded fragment comprises random priming and extension. In some embodiments, said random priming is conducted with a primer comprising a random n-mer region and a promoter region. In some embodiments, said random n-mer region is a random hexamer region. In some embodiments, said random n-mer region is a random octamer region. In some embodiments, said promoter region is a T7 promoter region. In some embodiments, the method further comprises ligating a nuclease recognition site nucleic acid comprising a nuclease recognition site to said double-stranded fragment. In some embodiments, said nuclease recognition site corresponds to a nuclease that cuts at a distance from said nuclease recognition site equal to the length of said nicking enzyme recognition sites. In some embodiments, said nuclease recognition site is a MlyI recognition site. In some embodiments, said nuclease recognition site is a BaeI recognition site. In some embodiments, the method further comprises digesting said double-stranded fragment with said nuclease, thereby removing said nicking enzyme recognition site from said double-stranded fragment. In some embodiments, the method further comprises ligating said double-stranded fragment to a nucleic acid-guided nuclease system protein recognition site nucleic acid comprising a nucleic acid-guided nuclease system protein recognition site. In some embodiments, said nucleic acid-guided nuclease system protein recognition site comprises a guide RNA stem-loop sequence. In some embodiments, said nuclease recognition site corresponds to a nuclease that cuts at a distance from said nuclease recognition site equal to a length of said targeting sequence. In some embodiments, said length of said targeting sequence is 20 base pairs. In some embodiments, said nuclease recognition site is a MmeI recognition site. In some embodiments, the method further comprises digesting said double-stranded fragment with said nuclease. In some embodiments, said nuclease recognition site corresponds to a nuclease that cuts at a distance from said nuclease recognition site equal to a length of said targeting sequence plus a length of said nicking enzyme recognition sites. In some embodiments, said length of said targeting sequence plus a length of said nicking enzyme recognition sites is 23 base pairs. In some embodiments, said nuclease recognition site is a EcoP15I recognition site. In some embodiments, the method further comprises digesting said double-stranded fragment with said nuclease. In some embodiments, the method further comprises ligating said double-stranded fragment to a nucleic acid-guided nuclease system protein recognition site nucleic acid comprising a nucleic acid-guided nuclease system protein recognition site. In some embodiments, said nucleic acid-guided nuclease system protein recognition site comprises a guide RNA stem-loop sequence.

In another aspect, the invention described herein provides a kit comprising all essential reagents and instructions for carrying out the methods of aspects of the invention described herein.

DETAILED DESCRIPTION OF THE INVENTION

Figure 1:
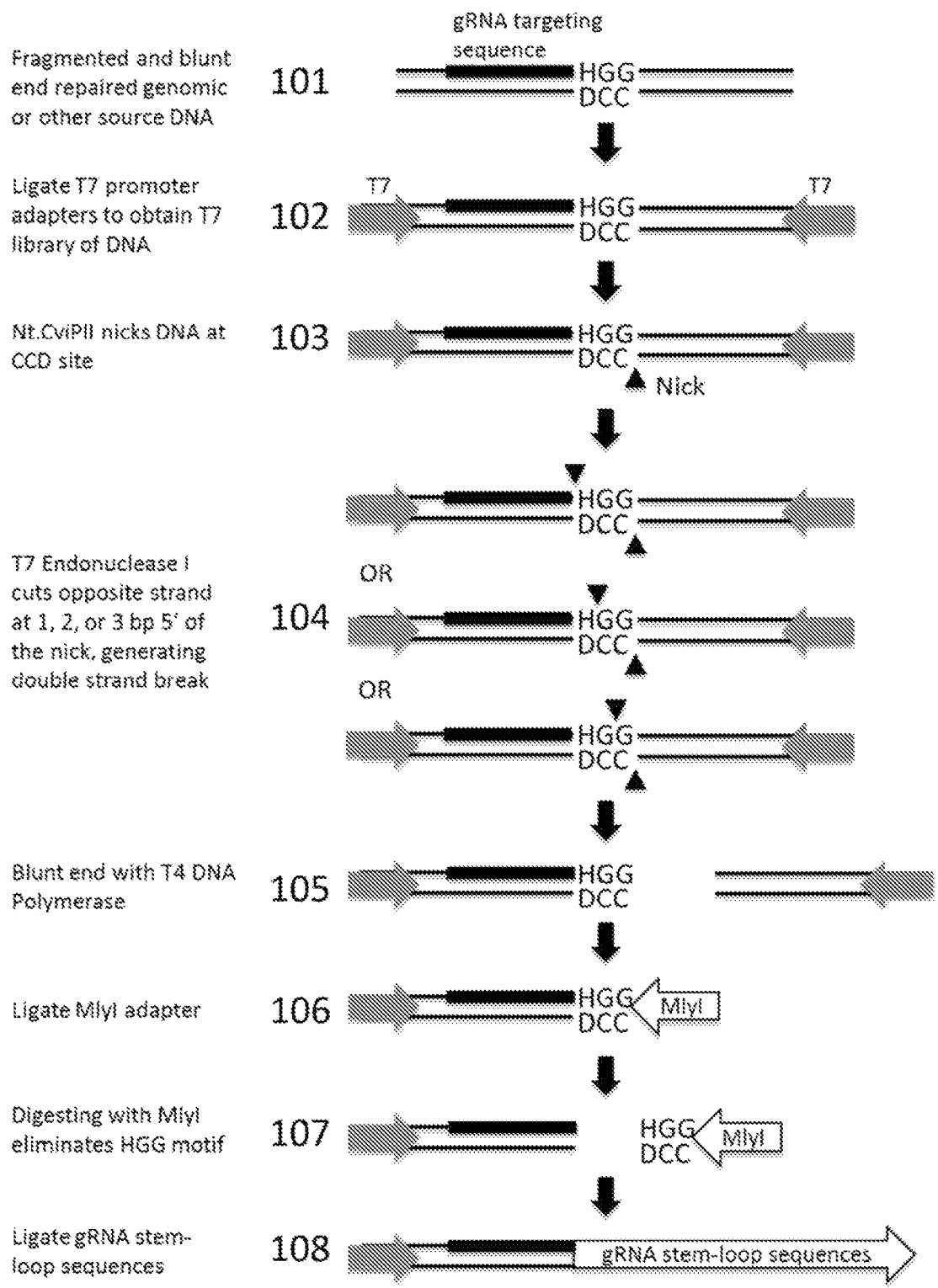
FIG. 1 illustrates an exemplary scheme for producing a collection of gRNAs (a gRNA library) from genomic DNA.

There is a need in the art for a scalable, low-cost approach to generate large numbers of diverse guide nucleic acids (gNAs) (e.g., gRNAs, gDNAs) for a variety of downstream applications.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Numeric ranges are inclusive of the numbers defining the range.

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

The term "nucleic acid," as used herein, refers to a molecule comprising one or more nucleic acid subunits. A nucleic acid can include one or more subunits selected from adenosine (A), cytosine (C), guanine (G), thymine (T) and uracil (U), and modified versions of the same. A nucleic acid comprises deoxyribonucleic acid (DNA), ribonucleic acid (RNA), combinations, or derivatives thereof. A nucleic acid may be single-stranded and/or double-stranded.

The nucleic acids comprise "nucleotides", which, as used herein, is intended to include those moieties that contain purine and pyrimidine bases, and modified versions of the same. Such modifications include methylated purines or pyrimidines, acylated purines or pyrimidines, alkylated riboses or other heterocycles. In addition, the term "nucleotide" or "polynucleotide" includes those moieties that contain hapten or fluorescent labels and may contain not only conventional ribose and deoxyribose sugars, but other sugars as well. Modified nucleosides, nucleotides or polynucleotides also include modifications on the sugar moiety, e.g., wherein one or more of the hydroxyl groups are replaced with halogen atoms or aliphatic groups, or are functionalized as ethers, amines, or the like.

The term "nucleic acids" and "polynucleotides" are used interchangeably herein. Polynucleotide is used to describe a nucleic acid polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbones, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides.

Unless otherwise indicated, nucleic acids are written left to right in 5' to 3' orientation; amino acid sequences are written left to right in amino to carboxy orientation, respectively.

The term "cleaving," as used herein, refers to a reaction that breaks the phosphodiester bonds between two adjacent nucleotides in both strands of a double-stranded DNA molecule, thereby resulting in a double-stranded break in the DNA molecule.

The term "nicking" as used herein, refers to a reaction that breaks the phosphodiester bond between two adjacent nucleotides in only one strand of a double-stranded DNA molecule, thereby resulting in a break in one strand of the DNA molecule.

The term "cleavage site, as used herein, refers to the site at which a double-stranded DNA molecule has been cleaved.

The "nucleic acid-guided nuclease-gNA complex" refers to a complex comprising a nucleic acid-guided nuclease protein and a guide nucleic acid (gNA, for example a gRNA or a gDNA). For example the "Cas9-gRNA complex" refers to a complex comprising a Cas9 protein and a guide RNA (gRNA). The nucleic acid-guided nuclease may be any type of nucleic acid-guided nuclease, including but not limited to wild type nucleic acid-guided nuclease, a catalytically dead nucleic acid-guided nuclease, or a nucleic acid-guided nuclease-nickase.

The term "nucleic acid-guided nuclease-associated guide NA" refers to a guide nucleic acid (guide NA). The nucleic acid-guided nuclease-associated guide NA may exist as an isolated nucleic acid, or as part of a nucleic acid-guided nuclease-gNA complex, for example a Cas9-gRNA complex.

The terms "capture" and "enrichment" are used interchangeably herein, and refer to the process of selectively isolating a nucleic acid region containing: sequences of interest, targeted sites of interest, sequences not of interest, or targeted sites not of interest.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The term "genomic region," as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example.

The term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment," as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adapter ligated (in which case it has an adapter ligated to one or both ends of the fragment, or to at least the 5' end of a molecule), or may not be adapter ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example Such an oligonucleotide may be employed in an assay that uses a sample containing a test genome, where the test genome contains a binding site for the oligonucleotide.

The term "ligating," as used herein, refers to the enzymatically catalyzed joining of the terminal nucleotide at the 5' end of a first DNA molecule to the terminal nucleotide at the 3' end of a second DNA molecule.

If two nucleic acids are "complementary," each base of one of the nucleic acids base pairs with corresponding nucleotides in the other nucleic acid. The term "complementary" and "perfectly complementary" are used synonymously herein.

The term "separating," as used herein, refers to physical separation of two elements (e.g., by size or affinity, etc.) as well as degradation of one element, leaving the other intact. For example, size exclusion can be employed to separate nucleic acids, including cleaved targeted sequences.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. Until they become covalently linked, the first and second strands are distinct molecules. For ease of description, the "top" and "bottom" strands of a double-stranded nucleic acid in which the top and bottom strands have been covalently linked will still be described as the "top" and "bottom" strands. In other words, for the purposes of this disclosure, the top and bottom strands of a double-stranded DNA do not need to be separated molecules. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand. If an oligonucleotide binds or anneals to both strands of a double-stranded DNA, the oligonucleotide may have two regions, a first region that hybridizes with the top strand of the double-stranded DNA, and a second region that hybridizes with the bottom strand of the double-stranded DNA.

The term "double-stranded DNA molecule" refers to both double-stranded DNA molecules in which the top and bottom strands are not covalently linked, as well as double-stranded DNA molecules in which the top and bottom stands are covalently linked. The top and bottom strands of a double-stranded DNA are base paired with one other by Watson-Crick interactions.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the $T_m$ of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired). Nucleic acid may also be denatured chemically (e.g., using urea or NaOH).

The term "genotyping," as used herein, refers to any type of analysis of a nucleic acid sequence, and includes sequencing, polymorphism (SNP) analysis, and analysis to identify rearrangements.

The term "sequencing," as used herein, refers to a method by which the identity of consecutive nucleotides of a polynucleotide are obtained.

The term "next-generation sequencing" refers to the so-called parallelized sequencing-by-synthesis or sequencing-by-ligation platforms, for example, those currently employed by Illumina, Life Technologies, and Roche, etc. Next-generation sequencing methods may also include nanopore sequencing methods or electronic-detection based methods such as Ion Torrent technology commercialized by Life Technologies.

The term "complementary DNA" or cDNA refers to a double-stranded DNA sample that was produced from an RNA sample by reverse transcription of RNA (using primers such as random hexamers or oligo-dT primers) followed by second-strand synthesis by digestion of the RNA with RNaseH and synthesis by DNA polymerase.

The term "RNA promoter adapter" is an adapter that contains a promoter for a bacteriophage RNA polymerase, e.g., the RNA polymerase from bacteriophage T3, T7, SP6 or the like.

Other definitions of terms may appear throughout the specification.

For any of the structural and functional characteristics described herein, methods of determining these characteristics are known in the art.

Guide Nucleic Acids (gNAs)

Provided herein are guide nucleic acids (gNAs) derivable from any nucleic acid source. The gNAs can be guide RNAs (gRNAs) or guide DNAs (gDNAs). The nucleic acid source can be DNA or RNA. Provided herein are methods to generate gNAs from any source nucleic acid, including DNA from a single organism, or mixtures of DNA from multiple organisms, or mixtures of DNA from multiple species, or DNA from clinical samples, or DNA from forensic samples, or DNA from environmental samples, or DNA from metagenomic DNA samples (for example a sample that contains more than one species of organism). Examples of any source DNA include, but are not limited to any genome, any genome fragment, cDNA, synthetic DNA, or a DNA collection (e.g. a SNP collection, DNA libraries). The gNAs provided herein can be used for genome-wide applications.

In some embodiments, the gNAs are derived from genomic sequences (e.g., genomic DNA). In some embodiments, the gNAs are derived from mammalian genomic sequences. In some embodiments, the gNAs are derived from eukaryotic genomic sequences. In some embodiments, the gNAs are derived from prokaryotic genomic sequences. In some embodiments, the gNAs are derived from viral genomic sequences. In some embodiments, the gNAs are derived from bacterial genomic sequences. In some embodiments, the gNAs are derived from plant genomic sequences. In some embodiments, the gNAs are derived from microbial genomic sequences. In some embodiments, the gNAs are derived from genomic sequences from a parasite, for example a eukaryotic parasite.

In some embodiments, the gNAs are derived from repetitive DNA. In some embodiments, the gNAs are derived from abundant DNA. In some embodiments, the gNAs are derived from mitochondrial DNA. In some embodiments, the gNAs are derived from ribosomal DNA. In some embodiments, the gNAs are derived from centromeric DNA. In some embodiments, the gNAs are derived from DNA comprising Alu elements (Alu DNA). In some embodiments, the gNAs are derived from DNA comprising long interspersed nuclear elements (LINE DNA). In some embodiments, the gNAs are derived from DNA comprising short interspersed nuclear elements (SINE DNA). In some embodiments the abundant DNA comprises ribosomal DNA. In some embodiments, the abundant DNA comprises host DNA (e.g., host genomic DNA or all host DNA). In an example, the gNAs can be derived from host DNA (e.g., human, animal, plant) for the depletion of host DNA to allow for easier analysis of other DNA that is present (e.g., bacterial, viral, or other metagenomic DNA). In another example, the gNAs can be derived from the one or more most abundant types (e.g., species) in a mixed sample, such as the one or more most abundant bacteria species in a metagenomic sample. The one or more most abundant types (e.g., species) can comprise the two, three, four, five, six, seven, eight, nine, ten, or more than ten most abundant types (e.g., species). The most abundant types can be the most abundant kingdoms, phyla or divisions, classes, orders, families, genuses, species, or other classifications. The most abundant types can be the most abundant cell types, such as epithelial cells, bone cells, muscle cells, blood cells, adipose cells, or other cell types. The most abundant types can be non-cancerous cells. The most abundant types can be cancerous cells. The most abundant types can be animal, human, plant, fungal, bacterial, or viral. gNAs can be derived from both a host and the one or more most abundant non-host types (e.g., species) in a sample, such as from both human DNA and the DNA of the one or more most abundant bacterial species. In some embodiments, the abundant DNA comprises DNA from the more abundant or most abundant cells in a sample. For example, for a specific sample, the highly abundant cells can be extracted and their DNA can be used to produce gNAs; these gNAs can be used to produce depletion library and applied to original sample to enable or enhance sequencing or detection of low abundance targets.

In some embodiments, the gNAs are derived from DNA comprising short terminal repeats (STRs).

In some embodiments, the gNAs are derived from a genomic fragment, comprising a region of the genome, or the whole genome itself. In one embodiment, the genome is a DNA genome. In another embodiment, the genome is a RNA genome.

In some embodiments, the gNAs are derived from a eukaryotic or prokaryotic organism; from a mammalian organism or a non-mammalian organism; from an animal or a plant; from a bacteria or virus; from an animal parasite; from a pathogen.

In some embodiments, the gNAs are derived from any mammalian organism. In one embodiment the mammal is a human. In another embodiment the mammal is a livestock animal, for example a horse, a sheep, a cow, a pig, or a donkey. In another embodiment, a mammalian organism is a domestic pet, for example a cat, a dog, a gerbil, a mouse, a rat. In another embodiment the mammal is a type of a monkey.

In some embodiments, the gNAs are derived from any bird or avian organism. An avian organism includes but is not limited to chicken, turkey, duck and goose.

In some embodiments, the gNAs are derived from a plant. In one embodiment, the plant is rice, maize, wheat, rose, grape, coffee, fruit, tomato, potato, or cotton.

In some embodiments, the gNAs are derived from a species of bacteria. In one embodiment, the bacteria are tuberculosis-causing bacteria.

In some embodiments, the gNAs are derived from a virus.

In some embodiments, the gNAs are derived from a species of fungi.

In some embodiments, the gNAs are derived from a species of algae.

In some embodiments, the gNAs are derived from any mammalian parasite.

In some embodiments, the gNAs are derived from any mammalian parasite. In one embodiment, the parasite is a worm. In another embodiment, the parasite is a malaria-causing parasite. In another embodiment, the parasite is a Leishmaniasis-causing parasite. In another embodiment, the parasite is an amoeba.

In some embodiments, the gNAs are derived from a nucleic acid target. Contemplated targets include, but are not limited to, pathogens; single nucleotide polymorphisms (SNPs), insertions, deletions, tandem repeats, or translocations; human SNPs or STRs; potential toxins; or animals, fungi, and plants. In some embodiments, the gRNAs are derived from pathogens, and are pathogen-specific gNAs.

In some embodiments, a guide NA of the invention comprises a first NA segment comprising a targeting sequence, wherein the targeting sequence is 15-250 bp; and a second NA segment comprising a nucleic acid guided nuclease system (e.g., CRISPR/Cas system) protein-binding sequence. In some embodiments, the targeting sequence is greater than 21 bp, greater than 22 bp, greater than 23 bp, greater than 24 bp, greater than 25 bp, greater than 26 bp, greater than 27 bp, greater than 28 bp, greater than 29 bp, greater than 30 bp, greater than 40 bp, greater than 50 bp, greater than 60 bp, greater than 70 bp, greater than 80 bp, greater than 90 bp, greater than 100 bp, greater than 110 bp, greater than 120 bp, greater than 130 bp, greater than 140 bp, or even greater than 150 bp. In an exemplary embodiment, the targeting sequence is greater than 30 bp. In some embodiments, the targeting sequences of the present invention range in size from 30-50 bp. In some embodiments, targeting sequences of the present invention range in size from 30-75 bp. In some embodiments, targeting sequences of the present invention range in size from 30-100 bp. For example, a targeting sequence can be at least 15 bp, 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, 110 bp, 120 bp, 130 bp, 140 bp, 150 bp, 160 bp, 170 bp, 180 bp, 190 bp, 200 bp, 210 bp, 220 bp, 230 bp, 240 bp, or 250 bp. In specific embodiments, the targeting sequence is at least 22 bp. In specific embodiments, the targeting sequence is at least 30 bp.

In some embodiments, target-specific gNAs can comprise a nucleic acid sequence that is complementary to a region on the opposite strand of the targeted nucleic acid sequence 5' to a PAM sequence, which can be recognized by a nucleic acid-guided nuclease system (e.g., CRISPR/Cas system) protein. In some embodiments the targeted nucleic acid sequence is immediately 5' to a PAM sequence. In specific embodiments, the nucleic acid sequence of the gNA that is complementary to a region in a target nucleic acid is 15-250 bp. In specific embodiments, the nucleic acid sequence of the gNA that is complementary to a region in a target nucleic acid is 22, 23, 24, 25, 30, 35, 40, 45, 50, 60, 70, 75, 80, 90, or 100 bp.

In some particular embodiments, the targeting sequence is not 20 bp. In some particular embodiments, the targeting sequence is not 21 bp.

In some embodiments, the gNAs comprise any purines or pyrimidines (and/or modified versions of the same). In some embodiments, the gNAs comprise adenine, uracil, guanine, and cytosine (and/or modified versions of the same). In some embodiments, the gNAs comprise adenine, thymine, guanine, and cytosine (and/or modified versions of the same). In some embodiments, the gNAs comprise adenine, thymine, guanine, cytosine and uracil (and/or modified versions of the same).

In some embodiments, the gNAs comprise a label, are attached to a label, or are capable of being labeled. In some embodiments, the gNA comprises is a moiety that is further capable of being attached to a label. A label includes, but is not limited to, enzyme, an enzyme substrate, an antibody, an antigen binding fragment, a peptide, a chromophore, a lumiphore, a fluorophore, a chromogen, a hapten, an antigen, a radioactive isotope, a magnetic particle, a metal nanoparticle, a redox active marker group (capable of undergoing a redox reaction), an aptamer, one member of a binding pair, a member of a FRET pair (either a donor or acceptor fluorophore), and combinations thereof.

In some embodiments, the gNAs are attached to a substrate. The substrate can be made of glass, plastic, silicon, silica-based materials, functionalized polystyrene, functionalized polyethyleneglycol, functionalized organic polymers, nitrocellulose or nylon membranes, paper, cotton, and materials suitable for synthesis. Substrates need not be flat. In some embodiments, the substrate is a 2-dimensional array. In some embodiments, the 2-dimensional array is flat. In some embodiments, the 2-dimensional array is not flat, for example, the array is a wave-like array. Substrates include any type of shape including spherical shapes (e.g., beads). Materials attached to substrates may be attached to any portion of the substrates (e.g., may be attached to an interior portion of a porous substrates material). In some embodiments, the substrate is a 3-dimensional array, for example, a microsphere. In some embodiments, the microsphere is magnetic. In some embodiments, the microsphere is glass. In some embodiments, the microsphere is made of polystyrene. In some embodiments, the microsphere is silica-based. In some embodiments, the substrate is an array with interior surface, for example, is a straw, tube, capillary, cylindrical, or microfluidic chamber array. In some embodiments, the substrate comprises multiple straws, capillaries, tubes, cylinders, or chambers.

Nucleic Acids Encoding gNAs

Also provided herein are nucleic acids encoding for gNAs (e.g., gRNAs or gDNAs). In some embodiments, by encoding it is meant that a gNA results from the transcription of a nucleic acid encoding for a gNA (e.g., gRNA). In some embodiments, by encoding, it is meant that the nucleic acid is a template for the transcription of a gNA (e.g., gRNA). In some embodiments, by encoding, it is meant that a gNA results from the reverse transcription of a nucleic acid encoding for a gNA. In some embodiments, by encoding, it is meant that the nucleic acid is a template for the reverse transcription of a gNA. In some embodiments, by encoding, it is meant that a gNA results from the amplification of a nucleic acid encoding for a gNA. In some embodiments, by encoding, it is meant that the nucleic acid is a template for the amplification of a gNA.

In some embodiments the nucleic acid encoding for a gNA comprises a first segment comprising a regulatory region; a second segment comprising targeting sequence, wherein the second segment can range from 15 bp-250 bp; and a third segment comprising a nucleic acid encoding a nucleic acid-guided nuclease system (e.g., CRISPR/Cas system) protein-binding sequence.

In some embodiments, the nucleic acids encoding for gNAs comprise DNA. In some embodiments, the first segment is double stranded DNA. In some embodiments, the first segment is single stranded DNA. In some embodiments, the second segment is single stranded DNA. In some embodiments, the third segment is single stranded DNA. In some embodiments, the second segment is double stranded DNA. In some embodiments, the third segment is double stranded DNA.

In some embodiments, the nucleic acids encoding for gNAs comprise RNA.

In some embodiments the nucleic acids encoding for gNAs comprise DNA and RNA.

In some embodiments, the regulatory region is a region capable of binding a transcription factor. In some embodiments, the regulatory region comprises a promoter. In some embodiments, the promoter is selected from the group consisting of T7, SP6, and T3.

Collections of gNAs

Provided herein are collections (interchangeably referred to as libraries) of gNAs.

As used herein, a collection of gNAs denotes a mixture of gNAs containing at least $10^2$ unique gNAs. In some embodiments a collection of gNAs contains at least $10^2$, at least $10^3$, at least $10^4$, at least $10^5$, at least $10^6$, at least $10^7$, at least $10^8$, at least $10^9$, at least $10^{10}$ unique gNAs. In some embodiments a collection of gNAs contains a total of at least $10^2$, at least $10^3$, at least $10^4$, at least $10^5$, at least $10^6$, at least $10^7$, at least $10^8$, at least $10^9$, at least $10^{10}$ gNAs.

In some embodiments, a collection of gNAs comprises a first NA segment comprising a targeting sequence; and a second NA segment comprising a nucleic acid-guided nuclease system (e.g., CRISPR/Cas system) protein-binding sequence, wherein at least 10% of the gNAs in the collection vary in size. In some embodiments, the first and second segments are in 5'- to 3'-order'.

In some embodiments, the size of the first segment varies from 15-250 bp, or 30-100 bp, or 22-30 bp, or 15-50 bp, or 15-75 bp, or 15-100 bp, or 15-125 bp, or 15-150 bp, or 15-175 bp, or 15-200 bp, or 15-225 bp, or 15-250 bp, or 22-50 bp, or 22-75 bp, or 22-100 bp, or 22-125 bp, or 22-150 bp, or 22-175 bp, or 22-200 bp, or 22-225 bp, or 22-250 bp across the collection of gNAs.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the first segments in the collection are greater than 21 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the first segments in the collection are greater than 25 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the first segments in the collection are greater than 30 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the first segments in the collection are 15-50 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the first segments in the collection are 30-100 bp.

In some particular embodiments, the size of the first segment is not 20 bp.

In some particular embodiments, the size of the first segment is not 21 bp.

In some embodiments, the gNAs and/or the targeting sequence of the gNAs in the collection of gRNAs comprise unique 5' ends. In some embodiments, the collection of gNAs exhibit variability in sequence of the 5' end of the targeting sequence, across the members of the collection. In some embodiments, the collection of gNAs exhibit variability at least 5%, or at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75% variability in the sequence of the 5' end of the targeting sequence, across the members of the collection.

In some embodiments, the 3' end of the gNA targeting sequence can be any purine or pyrimidine (and/or modified versions of the same). In some embodiments, the 3' end of the gNA targeting sequence is an adenine. In some embodiments, the 3' end of the gNA targeting sequence is a guanine. In some embodiments, the 3' end of the gNA targeting sequence is a cytosine. In some embodiments, the 3' end of the gNA targeting sequence is a uracil. In some embodiments, the 3' end of the gNA targeting sequence is a thymine. In some embodiments, the 3' end of the gNA targeting sequence is not cytosine.

In some embodiments, the collection of gNAs comprises targeting sequences which can base-pair with the targeted DNA, wherein the target of interest is spaced at least every 1 bp, at least every 2 bp, at least every 3 bp, at least every 4 bp, at least every 5 bp, at least every 6 bp, at least every 7 bp, at least every 8 bp, at least every 9 bp, at least every 10 bp, at least every 11 bp, at least every 12 bp, at least every 13 bp, at least every 14 bp, at least every 15 bp, at least every 16 bp, at least every 17 bp, at least every 18 bp, at least every 19 bp, 20 bp, at least every 25 bp, at least every 30 bp, at least every 40 bp, at least every 50 bp, at least every 100 bp, at least every 200 bp, at least every 300 bp, at least every 400 bp, at least every 500 bp, at least every 600 bp, at least every 700 bp, at least every 800 bp, at least every 900 bp, at least every 1000 bp, at least every 2500 bp, at least every 5000 bp, at least every 10,000 bp, at least every 15,000 bp, at least every 20,000 bp, at least every 25,000 bp, at least every 50,000 bp, at least every 100,000 bp, at least every 250,000 bp, at least every 500,000 bp, at least every 750,000 bp, or even at least every 1,000,000 bp across a genome of interest.

In some embodiments, the collection of gNAs comprises a first NA segment comprising a targeting sequence; and a second NA segment comprising a nucleic acid-guided nuclease system (e.g., CRISPR/Cas system) protein-binding sequence, wherein the gNAs in the collection can have a variety of second NA segments with various specificities for protein members of the nucleic acid-guided nuclease system (e.g., CRISPR/Cas system). For example a collection of gNAs as provided herein, can comprise members whose second segment comprises a nucleic acid-guided nuclease system (e.g., CRISPR/Cas system) protein-binding sequence specific for a first nucleic acid-guided nuclease system (e.g., CRISPR/Cas system) protein; and also comprises members whose second segment comprises a nucleic acid-guided nuclease system (e.g., CRISPR/Cas system) protein-binding sequence specific for a second nucleic acid-guided nuclease system (e.g., CRISPR/Cas system) protein, wherein the first and second nucleic acid-guided nuclease system (e.g., CRISPR/Cas system) proteins are not the same. In some embodiments a collection of gNAs as provided herein comprises members that exhibit specificity to at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or even at least 20 nucleic acid-guided nuclease system (e.g., CRISPR/Cas system) proteins. In one specific embodiment, a collection of gNAs as provided herein comprises members that exhibit specificity for a Cas9 protein and another protein selected from the group consisting of Cpf1, Cas3, Cas8a-c, Cas10, Cse1, Csy1, Csn2, Cas4, Csm2, and Cm5.

In some embodiments, a plurality of the gNA members of the collection are attached to a label, comprise a label or are capable of being labeled. In some embodiments, the gNA comprises is a moiety that is further capable of being attached to a label. A label includes, but is not limited to, enzyme, an enzyme substrate, an antibody, an antigen binding fragment, a peptide, a chromophore, a lumiphore, a fluorophore, a chromogen, a hapten, an antigen, a radioactive isotope, a magnetic particle, a metal nanoparticle, a redox active marker group (capable of undergoing a redox reaction), an aptamer, one member of a binding pair, a member of a FRET pair (either a donor or acceptor fluorophore), and combinations thereof.

In some embodiments, a plurality of the gNA members of the collection are attached to a substrate. The substrate can be made of glass, plastic, silicon, silica-based materials, functionalized polystyrene, functionalized polyethyleneglycol, functionalized organic polymers, nitrocellulose or nylon membranes, paper, cotton, and materials suitable for synthesis. Substrates need not be flat. In some embodiments, the substrate is a 2-dimensional array. In some embodiments, the 2-dimensional array is flat. In some embodiments, the 2-dimensional array is not flat, for example, the array is a wave-like array. Substrates include any type of shape including spherical shapes (e.g., beads). Materials attached to substrates may be attached to any portion of the substrates (e.g., may be attached to an interior portion of a porous substrates material). In some embodiments, the substrate is a 3-dimensional array, for example, a microsphere. In some embodiments, the microsphere is magnetic. In some embodiments, the microsphere is glass. In some embodiments, the microsphere is made of polystyrene. In some embodiments, the microsphere is silica-based. In some embodiments, the substrate is an array with interior surface, for example, is a straw, tube, capillary, cylindrical, or microfluidic chamber array. In some embodiments, the substrate comprises multiple straws, capillaries, tubes, cylinders, or chambers.

Collections of Nucleic Acids Encoding gNAs

Provided herein are collections (interchangeably referred to as libraries) of nucleic acids encoding for gNAs (e.g., gRNAs or gDNAs). In some embodiments, by encoding it is meant that a gNA results from the transcription of a nucleic acid encoding for a gNA. In some embodiments, by encoding, it is meant that the nucleic acid is a template for the transcription of a gNA.

As used herein, a collection of nucleic acids encoding for gNAs denotes a mixture of nucleic acids containing at least $10^2$ unique nucleic acids. In some embodiments a collection of nucleic acids encoding for gNAs contains at least $10^2$, at least $10^3$, at least $10^4$, at least $10^5$, at least $10^6$, at least $10^7$, at least $10^8$, at least $10^9$, at least $10^{10}$ unique nucleic acids encoding for gNAs. In some embodiments a collection of nucleic acids encoding for gNAs contains a total of at least $10^2$, at least $10^3$, at least $10^4$, at least $10^5$, at least $10^6$, at least $10^7$, at least $10^8$, at least $10^9$, at least $10^{10}$ nucleic acids encoding for gNAs.

In some embodiments, a collection of nucleic acids encoding for gNAs comprises a first segment comprising a regulatory region; a second segment comprising a targeting sequence; and a third segment comprising a nucleic acid encoding a nucleic acid-guided nuclease system (e.g., CRISPR/Cas system) protein-binding sequence, wherein at least 10% of the nucleic acids in the collection vary in size.

In some embodiments, the first, second, and third segments are in 5'- to 3'-order'.

In some embodiments, the nucleic acids encoding for gNAs comprise DNA. In some embodiments, the first segment is single stranded DNA. In some embodiments, the first segment is double stranded DNA. In some embodiments, the second segment is single stranded DNA. In some embodiments, the third segment is single stranded DNA. In some embodiments, the second segment is double stranded DNA. In some embodiments, the third segment is double stranded DNA.

In some embodiments, the nucleic acids encoding for gNAs comprise RNA.

In some embodiments the nucleic acids encoding for gNAs comprise DNA and RNA.

In some embodiments, the regulatory region is a region capable of binding a transcription factor. In some embodiments, the regulatory region comprises a promoter. In some embodiments, the promoter is selected from the group consisting of T7, SP6, and T3.

In some embodiments, the size of the second segments (targeting sequence) in the collection varies from 15-250 bp, or 30-100 bp, or 22-30 bp, or 15-50 bp, or 15-75 bp, or 15-100 bp, or 15-125 bp, or 15-150 bp, or 15-175 bp, or 15-200 bp, or 15-225 bp, or 15-250 bp, or 22-50 bp, or 22-75 bp, or 22-100 bp, or 22-125 bp, or 22-150 bp, or 22-175 bp, or 22-200 bp, or 22-225 bp, or 22-250 bp across the collection of gNAs.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the second segments in the collection are greater than 21 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the second segments in the collection are greater than 25 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the second segments in the collection are greater than 30 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the second segments in the collection are 15-50 bp.

In some embodiments, at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% of the second segments in the collection are 30-100 bp.

In some particular embodiments, the size of the second segment is not 20 bp.

In some particular embodiments, the size of the second segment is not 21 bp.

In some embodiments, the gNAs and/or the targeting sequence of the gNAs in the collection of gNAs comprise unique 5' ends. In some embodiments, the collection of gNAs exhibit variability in sequence of the 5' end of the targeting sequence, across the members of the collection. In some embodiments, the collection of gNAs exhibit variability at least 5%, or at least 10%, or at least 15%, or at last 20%, or at least 25%, or at least 30%, or at least 35%, or at least 40%, or at least 45%, or at least 50%, or at least 55%, or at least 60%, or at least 65%, or at least 70%, or at least 75% variability in the sequence of the 5' end of the targeting sequence, across the members of the collection.

In some embodiments, the collection of nucleic acids comprises targeting sequences, wherein the target of interest is spaced at least every 1 bp, at least every 2 bp, at least every 3 bp, at least every 4 bp, at least every 5 bp, at least every 6 bp, at least every 7 bp, at least every 8 bp, at least every 9 bp, at least every 10 bp, at least every 11 bp, at least every 12 bp, at least every 13 bp, at least every 14 bp, at least every 15 bp, at least every 16 bp, at least every 17 bp, at least every 18 bp, at least every 19 bp, 20 bp, at least every 25 bp, at least every 30 bp, at least every 40 bp, at least every 50 bp, at least every 100 bp, at least every 200 bp, at least every 300 bp, at least every 400 bp, at least every 500 bp, at least every 600 bp, at least every 700 bp, at least every 800 bp, at least every 900 bp, at least every 1000 bp, at least every 2500 bp, at least every 5000 bp, at least every 10,000 bp, at least every 15,000 bp, at least every 20,000 bp, at least every 25,000 bp, at least every 50,000 bp, at least every 100,000 bp, at least every 250,000 bp, at least every 500,000 bp, at least every 750,000 bp, or even at least every 1,000,000 bp across a genome of interest.

In some embodiments, the collection of nucleic acids encoding for gNAs comprise a third segment encoding for a nucleic acid-guided nuclease system (e.g., CRISPR/Cas system) protein-binding sequence, wherein the segments in the collection vary in their specificity for protein members of the nucleic acid-guided nuclease system (e.g., CRISPR/Cas system). For example, a collection of nucleic acids encoding for gNAs as provided herein, can comprise members whose third segment encode for a nucleic acid-guided nuclease system (e.g., CRISPR/Cas system) protein-binding sequence specific for a first nucleic acid-guided nuclease system (e.g., CRISPR/Cas system) protein; and also comprises members whose third segment encodes for a nucleic acid-guided nuclease system (e.g., CRISPR/Cas system) protein-binding sequence specific for a second nucleic acid-guided nuclease system (e.g., CRISPR/Cas system) protein, wherein the first and second nucleic acid-guided nuclease system (e.g., CRISPR/Cas system) proteins are not the same. In some embodiments, a collection of nucleic acids encoding for gNAs as provided herein comprises members that exhibit specificity to at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or even at least 20 nucleic acid-guided nuclease system (e.g., CRISPR/Cas system) proteins. In one specific embodiment, a collection of nucleic acids encoding for gNAs as provided herein comprises members that exhibit specificity for a Cas9 protein and another protein selected from the group consisting of Cpf1, Cas3, Cas8a-c, Cas10, Cse1, Csy1, Csn2, Cas4, Csm2, and Cm5.

Sequences of Interest

Provided herein are gNAs and collections of gNAs, derived from any source DNA (for example from genomic DNA, cDNA, artificial DNA, DNA libraries), that can be used to target sequences of interest in a sample for a variety of applications including, but not limited to, enrichment, depletion, capture, partitioning, labeling, regulation, and editing. The gNAs comprise a targeting sequence, directed at sequences of interest.

In some embodiments, the sequences of interest are genomic sequences (genomic DNA). In some embodiments, the sequences of interest are mammalian genomic sequences. In some embodiments, the sequences of interest are eukaryotic genomic sequences. In some embodiments, the sequences of interest are prokaryotic genomic sequences. In some embodiments, the sequences of interest are viral genomic sequences. In some embodiments, the sequences of interest are bacterial genomic sequences. In some embodiments, the sequences of interest are plant genomic sequences. In some embodiments, the sequences of interest are microbial genomic sequences. In some embodiments, the sequences of interest are genomic sequences from a parasite, for example a eukaryotic parasite. In some embodiments, the sequences of interest are host genomic sequences (e.g., the host organism of a microbiome, a parasite, or a pathogen). In some embodiments, the sequences of interest are abundant genomic sequences, such as sequences from the genome or genomes of the most abundant species in a sample.

In some embodiments, the sequences of interest comprise repetitive DNA. In some embodiments, the sequences of interest comprise abundant DNA. In some embodiments, the sequences of interest comprise mitochondrial DNA. In some embodiments, the sequences of interest comprise ribosomal DNA. In some embodiments, the sequences of interest comprise centromeric DNA. In some embodiments, the sequences of interest comprise DNA comprising Alu elements (Alu DNA). In some embodiments, the sequences of interest comprise long interspersed nuclear elements (LINE DNA). In some embodiments, the sequences of interest comprise short interspersed nuclear elements (SINE DNA). In some embodiments, the abundant DNA comprises ribosomal DNA.

In some embodiments, the sequences of interest comprise single nucleotide polymorphisms (SNPs), short tandem repeats (STRs), cancer genes, inserts, deletions, structural variations, exons, genetic mutations, or regulatory regions.

In some embodiments, the sequences of interest can be a genomic fragment, comprising a region of the genome, or the whole genome itself. In one embodiment, the genome is a DNA genome. In another embodiment, the genome is a RNA genome.

In some embodiments, the sequences of interest are from a eukaryotic or prokaryotic organism; from a mammalian organism or a non-mammalian organism; from an animal or a plant; from a bacteria or virus; from an animal parasite; from a pathogen.

In some embodiments, the sequences of interest are from any mammalian organism. In one embodiment the mammal is a human. In another embodiment the mammal is a livestock animal, for example a horse, a sheep, a cow, a pig, or a donkey. In another embodiment, a mammalian organism is a domestic pet, for example a cat, a dog, a gerbil, a mouse, a rat. In another embodiment the mammal is a type of a monkey.

In some embodiments, the sequences of interest are from any bird or avian organism. An avian organism includes but is not limited to chicken, turkey, duck and goose.

In some embodiments, the sequences of interest are from a plant. In one embodiment, the plant is rice, maize, wheat, rose, grape, coffee, fruit, tomato, potato, or cotton.

In some embodiments, the sequences of interest are from a species of bacteria. In one embodiment, the bacteria are tuberculosis-causing bacteria.

In some embodiments, the sequences of interest are from a virus.

In some embodiments, the sequences of interest are from a species of fungi.

In some embodiments, the sequences of interest are from a species of algae.

In some embodiments, the sequences of interest are from any mammalian parasite.

In some embodiments, the sequences of interest are obtained from any mammalian parasite. In one embodiment, the parasite is a worm. In another embodiment, the parasite is a malaria-causing parasite. In another embodiment, the parasite is a Leishmaniasis-causing parasite. In another embodiment, the parasite is an amoeba.

In some embodiments, the sequences of interest are from a pathogen.

Targeting Sequences

As used herein, a targeting sequence is one that directs the gNA to the sequences of interest in a sample. For example, a targeting sequence targets a particular sequence of interest, for example the targeting sequence targets a genomic sequence of interest.

Provided herein are gNAs and collections of gNAs that comprise a segment that comprises a targeting sequence. Also provided herein, are nucleic acids encoding for gNAs, and collections of nucleic acids encoding for gNAs that comprise a segment encoding for a targeting sequence.

In some embodiments, the targeting sequence comprises DNA.

In some embodiments, the targeting sequence comprises RNA.

In some embodiments, the targeting sequence comprises RNA, and shares at least 70% sequence identity, at least 75% sequence identity, at least 80% sequence identity, at least 85% sequence identity, at least 90% sequence identity, at least 95% sequence identity, or shares 100% sequence identity to a sequence 5' to a PAM sequence on a sequence of interest, except that the RNA comprises uracils instead of thymines. In some embodiments, the PAM sequence is AGG, CGG, or TGG.

In some embodiments, the targeting sequence comprises DNA, and shares at least 70% sequence identity, at least 75% sequence identity, at least 80% sequence identity, at least 85% sequence identity, at least 90% sequence identity, at least 95% sequence identity, or shares 100% sequence identity to a sequence 5' to a PAM sequence on a sequence of interest.

In some embodiments, the targeting sequence comprises RNA and is complementary to the strand opposite to a sequence of nucleotides 5' to a PAM sequence. In some embodiments, the targeting sequence is at least 70% complementary, at least 75% complementary, at least 80% complementary, at least 85% complementary, at least 90% complementary, at least 95% complementary, or is 100% complementary to the strand opposite to a sequence of nucleotides 5' to a PAM sequence. In some embodiments, the PAM sequence is AGG, CGG, or TGG.

In some embodiments, the targeting sequence comprises DNA and is complementary to the strand opposite to a sequence of nucleotides 5' to a PAM sequence. In some embodiments, the targeting sequence is at least 70% complementary, at least 75% complementary, at least 80% complementary, at least 85% complementary, at least 90% complementary, at least 95% complementary, or is 100% complementary to the strand opposite to a sequence of nucleotides 5' to a PAM sequence. In some embodiments, the PAM sequence is AGG, CGG, or TGG.

In some embodiments, a DNA encoding for a targeting sequence of a gRNA shares at least 70% sequence identity, at least 75% sequence identity, at least 80% sequence identity, at least 85% sequence identity, at least 90% sequence identity, at least 95% sequence identity, or shares 100% sequence identity to the strand opposite to a sequence of nucleotides 5' to a PAM sequence. In some embodiments, the PAM sequence is AGG, CGG, or TGG.

In some embodiments, a DNA encoding for a targeting sequence of a gRNA is complementary to the strand opposite to a sequence of nucleotides 5' to a PAM sequence and is at least 70% complementary, at least 75% complementary, at least 80% complementary, at least 85% complementary, at least 90% complementary, at least 95% complementary, or is 100% complementary to a sequence 5' to a PAM sequence on a sequence of interest. In some embodiments, the PAM sequence is AGG, CGG, or TGG.

Nucleic Acid-Guided Nuclease System Proteins

Provided herein are gNAs and collections of gNAs comprising a segment that comprises a nucleic acid-guided nuclease system (e.g., CRISPR/Cas system) protein-binding sequence. Also provided herein, are nucleic acids encoding for gNAs, and collections of nucleic acids encoding for gNAs that comprise a segment encoding a nucleic acid-guided nuclease system (e.g., CRISPR/Cas system) protein-binding sequence. A nucleic acid-guided nuclease system can be an RNA-guided nuclease system. A nucleic acid-guided nuclease system can be a DNA-guided nuclease system.

Methods of the present disclosure can utilize nucleic acid-guided nucleases. As used herein, a "nucleic acid-guided nuclease" is any nuclease that cleaves DNA, RNA or DNA/RNA hybrids, and which uses one or more nucleic acid guide nucleic acids (gNAs) to confer specificity. Nucleic acid-guided nucleases include CRISPR/Cas system proteins as well as non-CRISPR/Cas system proteins.

The nucleic acid-guided nucleases provided herein can be DNA guided DNA nucleases; DNA guided RNA nucleases; RNA guided DNA nucleases; or RNA guided RNA nucleases. The nucleases can be endonucleases. The nucleases can be exonucleases. In one embodiment, the nucleic acid-guided nuclease is a nucleic acid-guided-DNA endonuclease. In one embodiment, the nucleic acid-guided nuclease is a nucleic acid-guided-RNA endonuclease.

A nucleic acid-guided nuclease system protein-binding sequence is a nucleic acid sequence that binds any protein member of a nucleic acid-guided nuclease system. For example, a CRISPR/Cas system protein-binding sequence is a nucleic acid sequence that binds any protein member of a CRISPR/Cas system.

In some embodiments, the nucleic acid-guided nuclease is selected from the group consisting of CAS Class I Type I, CAS Class I Type III, CAS Class I Type IV, CAS Class II Type II, and CAS Class II Type V. In some embodiments, CRISPR/Cas system proteins include proteins from CRISPR Type I systems, CRISPR Type II systems, and CRISPR Type III systems. In some embodiments, the nucleic acid-guided nuclease is selected from the group consisting of Cas9, Cpf1, Cas3, Cas8a-c, Cas10, Cse1, Csy1, Csn2, Cas4, Csm2, Cm5, Csf1, C2c2, and NgAgo.

In some embodiments, nucleic acid-guided nuclease system proteins (e.g., CRISPR/Cas system proteins) can be from any bacterial or archaeal species.

In some embodiments, the nucleic acid-guided nuclease system proteins (e.g., CRISPR/Cas system proteins) are from, or are derived from nucleic acid-guided nuclease system proteins (e.g., CRISPR/Cas system proteins) from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius,* *Filifactor alocis, Legionella pneumophila, Suterella wadsworthensis,* or *Corynebacter diphtheria.*

In some embodiments, examples of nucleic acid-guided nuclease system (e.g., CRISPR/Cas system) proteins can be naturally occurring or engineered versions.

In some embodiments, naturally occurring nucleic acid-guided nuclease system (e.g., CRISPR/Cas system) proteins include Cas9, Cpf1, Cas3, Cas8a-c, Cas10, Cse1, Csy1, Csn2, Cas4, Csm2, and Cm5. Engineered versions of such proteins can also be employed.

In some embodiments, engineered examples of nucleic acid-guided nuclease system (e.g., CRISPR/Cas system) proteins include catalytically dead nucleic acid-guided nuclease system proteins. The term "catalytically dead" generally refers to a nucleic acid-guided nuclease system protein that has inactivated nucleases (e.g., HNH and RuvC nucleases). Such a protein can bind to a target site in any nucleic acid (where the target site is determined by the guide NA), but the protein is unable to cleave or nick the target nucleic acid (e.g., double-stranded DNA). In some embodiments, the nucleic acid-guided nuclease system catalytically dead protein is a catalytically dead CRISPR/Cas system protein, such as catalytically dead Cas9 (dCas9). Accordingly, the dCas9 allows separation of the mixture into unbound nucleic acids and dCas9-bound fragments. In one embodiment, a dCas9/gRNA complex binds to targets determined by the gRNA sequence. The dCas9 bound can prevent cutting by Cas9 while other manipulations proceed. In another embodiment, the dCas9 can be fused to another enzyme, such as a transposase, to target that enzyme's activity to a specific site. Naturally occurring catalytically dead nucleic acid-guided nuclease system proteins can also be employed.

In some embodiments, engineered examples of nucleic acid-guided nuclease (e.g., CRISPR/Cas) system proteins also include nucleic acid-guided nickases (e.g., Cas nickases). A nucleic acid-guided nickase refers to a modified version of a nucleic acid-guided nuclease system protein, containing a single inactive catalytic domain. In one embodiment, the nucleic acid-guided nickase is a Cas nickase, such as Cas9 nickase. A Cas9 nickase may contain a single inactive catalytic domain, for example, either the RuvC- or the HNH-domain. With only one active nuclease domain, the Cas9 nickase cuts only one strand of the target DNA, creating a single-strand break or "nick". Depending on which mutant is used, the guide NA-hybridized strand or the non-hybridized strand may be cleaved. Nucleic acid-guided nickases bound to 2 gNAs that target opposite strands will create a double-strand break in a target double-stranded DNA. This "dual nickase" strategy can increase the specificity of cutting because it requires that both nucleic acid-guided nuclease/gNA (e.g., Cas9/gRNA) complexes be specifically bound at a site before a double-strand break is formed. Naturally occurring nickase nucleic acid-guided nuclease system proteins can also be employed.

In some embodiments, engineered examples of nucleic acid-guided nuclease system proteins also include nucleic acid-guided nuclease system fusion proteins. For example, a nucleic acid-guided nuclease (e.g., CRISPR/Cas) system protein may be fused to another protein, for example an activator, a repressor, a nuclease, a fluorescent molecule, a radioactive tag, or a transposase.

In some embodiments, the nucleic acid-guided nuclease system protein-binding sequence comprises a gNA (e.g., gRNA) stem-loop sequence.

In some embodiments, a double-stranded DNA sequence encoding the gNA (e.g., gRNA) stem-loop sequence comprises the following DNA sequence on one strand (5'>3', GTTTTAGAGCTAGAAATAGCAAGT-TAAAATAAGGCTAGTCCGTTATCAACTT-GAAAAAGTGGCACCG AGTCGGTGCTTTTTTT) (SEQ ID NO: 3), and its reverse-complementary DNA on the other strand (5'>3', AAAAAAAGCACCGACTCGGTGC-CACTTTTTCAAGTTGATAACGGACTAGCCTTATTT-TAACTTGCTAT TTCTAGCTCTAAAAC) (SEQ ID NO: 4).

In some embodiments, a single-stranded DNA sequence encoding the gNA (e.g., gRNA) stem-loop sequence comprises the following DNA sequence: (5'>3', AAAAAAAGCACCGACTCGGTGC-CACTTTTTCAAGTTGATAACGGACTAGCCTTATTT-TAACTTGCTAT TTCTAGCTCTAAAAC) (SEQ ID NO: 4), wherein the single-stranded DNA serves as a transcription template.

In some embodiments, the gNA (e.g., gRNA) stem-loop sequence comprises the following RNA sequence: (5'>3', GUUUUAGAGCUAGAAAUAG-CAAGUUAAAAUAAGGCUAGUCCGUUAUCAAC-UUGAAAAAGUGGCA CCGAGUCGGUGC-UUUUUUU) (SEQ ID NO: 1).

In some embodiments, a double-stranded DNA sequence encoding the gNA (e.g., gRNA) stem-loop sequence comprises the following DNA sequence on one strand (5'>3', GTTTTAGAGCTATGCTGGAAACAGCATAGCAAGT-TAAAATAAGGCTAGTCCGTTATCAACTTGAAAA AGTGGCACCGAGTCGGTGCTTTTTTTC) (SEQ ID NO: 5), and its reverse-complementary DNA on the other strand (5'>3', GAAAAAAAGCACCGACTCGGTGC-CACTTTTTCAAGTTGATAACGGACTAGCCTTATTT-TAACTTGCT ATGCTGTTTCCAG-CATAGCTCTAAAAC) (SEQ ID NO: 6).

In some embodiments, a single-stranded DNA sequence encoding the gNA (e.g., gRNA) stem-loop sequence comprises the following DNA sequence: (5'>3', GAAAAAAAGCACCGACTCGGTGC-CACTTTTTCAAGTTGATAACGGACTAGCCTTATTT-TAACTTGCT ATGCTGTTTCCAG-CATAGCTCTAAAAC) (SEQ ID NO: 6), wherein the single-stranded DNA serves as a transcription template.

In some embodiments, the gNA (e.g., gRNA) stem-loop sequence comprises the following RNA sequence: (5'>3', GUUUUAGAGCUAUGCUGGAAACAGCAUAG-CAAGUUAAAAUAAGGCUAGUCCGUUAUCAAC-UUGA AAAAGUGGCACCGAGUCGGUGC-UUUUUUUC) (SEQ ID NO: 2).

In some embodiments, provided herein is a nucleic acid encoding for a gNA (e.g., gRNA) comprising a first segment comprising a regulatory region; a second segment encoding a targeting sequence; and a third segment comprising a nucleic acid encoding a nucleic acid-guided nuclease (e.g., CRISPR/Cas) system protein-binding sequence. In some embodiments, the third segment comprises a single transcribed component, which upon transcription yields a NA (e.g., RNA) stem-loop sequence. In some embodiments, the third segment comprising a single transcribed component that encodes for the gNA (e.g., gRNA) stem-loop sequence is double-stranded, comprises the following DNA sequence on one strand (5'>3', GTTTTAGAGCTAGAAATAG-CAAGTTAAAATAAGGCTAGTCCGTTATCAACTT-GAAAAAGTGGCACCG AGTCGGTGCTTTTTTT) (SEQ ID NO: 3), and its reverse-complementary DNA on the other strand (5'>3', AAAAAAAGCACCGACTCGGTGC-CACTTTTTCAAGTTGATAACGGACTAGCCTTATTT-TAACTTGCTAT TTCTAGCTCTAAAAC) (SEQ ID NO: 4). In some embodiments, the third segment comprising a single transcribed component that encodes for the gNA (e.g., gRNA) stem-loop sequence is single-stranded, and comprises the following DNA sequence: (5'>3', AAAAAAAGCACCGACTCGGTGC-CACTTTTTCAAGTTGATAACGGACTAGCCTTATTT-TAACTTGCTAT TTCTAGCTCTAAAAC) (SEQ ID NO: 4), wherein the single-stranded DNA serves as a transcription template. In some embodiments, upon transcription from the single transcribed component, the resulting gNA (e.g., gRNA) stem-loop sequence comprises the following RNA sequence: (5'>3', GUUUUAGAGCUAGAAAUAG-CAAGUUAAAAUAAGGCUAGUCCGUUAUCAAC-UUGAAAAAGUGGCA CCGAGUCGGUGC-UUUUUUU) (SEQ ID NO: 1). In some embodiments, the third segment comprising a single transcribed component that encodes for the gNA (e.g., gRNA) stem-loop sequence is double-stranded, comprises the following DNA sequence on one strand (5'>3', GTTTTAGAGCTATGCTGGAAACA-GCATAGCAAGTTAAAATAAGGCTAGTCCGTTAT-CAACTTGAAAA AGTGGCACCGAGTCGGT-GCTTTTTTTC) (SEQ ID NO: 5), and its reverse-complementary DNA on the other strand (5'>3', GAAAAAAAGCACCGACTCGGTGC-CACTTTTTCAAGTTGATAACGGACTAGCCTTATTT-TAACTTGCT ATGCTGTTTCCAG-CATAGCTCTAAAAC) (SEQ ID NO: 6). In some embodiments, the third segment comprising a single transcribed component that encodes for the gNA (e.g., gRNA) stem-loop sequence is single-stranded, and comprises the following DNA sequence: (5'>3', GAAAAAAAGCAC-CGACTCGGTGCCACTTTTTCAAGTTGATAACG-GACTAGCCTTATTTTAACTTGCT ATGCTGTTTCCAG-CATAGCTCTAAAAC) (SEQ ID NO: 6), wherein the single-stranded DNA serves as a transcription template. In some embodiments, upon transcription from the single transcribed component, the yielded gRNA stem-loop sequence comprises the following RNA sequence: (5'>3', GUUUUA-GAGCUAUGCUGGAAACAGCAUAG-CAAGUUAAAAUAAGGCUAGUCCGUUAUCAAC-UUGA AAAAGUGGCACCGAGUCGGUGCUUUUUUUC) (SEQ ID NO: 2). In some embodiments, the third segment comprises two sub-segments, which encode for a crRNA and a tracrRNA upon transcription. In some embodiment, the crRNA does not comprise the N20 plus the extra sequence which can hybridize with tracrRNA. In some embodiments, the crRNA comprises the extra sequence which can hybridize with tracrRNA. In some embodiments, the two sub-segments are independently transcribed. In some embodiments, the two sub-segments are transcribed as a single unit. In some embodiments, the DNA encoding the crRNA comprises $N_{target}$GTTTTAGAGCTATGCT-GTTTTG (SEQ ID NO: 7), where $N_{target}$ represents the targeting sequence. In some embodiments, the DNA encoding the tracrRNA comprises the sequence GGAACCAT-TCAAAACAGCATAGCAAGTTAAAATAAGGCTAGTC-CGTTATCAACTTGAAAAAGTGGC ACCGAGTCGGTGCTTTTTTT (SEQ ID NO: 8).

In some embodiments, provided herein is a nucleic acid encoding for a gNA (e.g., gRNA) comprising a first segment comprising a regulatory region; a second segment encoding a targeting sequence; and a third segment comprising a nucleic acid encoding a nucleic acid-guided nuclease (e.g., CRISPR/Cas) system protein-binding sequence. In some embodiments, the third segment comprises a DNA sequence, which upon transcription yields a gRNA stem-loop sequence capable of binding a nucleic acid-guided nuclease (e.g., CRISPR/Cas) system protein. In one embodiment, the DNA sequence can be double-stranded. In some embodiments, the third segment double stranded DNA comprises the following DNA sequence on one strand (5'>3', GTTTTAGAGCTA-GAAATAGCAAGTTAAAATAAGGCTAGTCCGTTAT-CAACTTGAAAAAGTGGCACCG AGTCGGT-GCTTTTTTT) (SEQ ID NO: 3), and its reverse-complementary DNA on the other strand (5'>3', AAAAAAAGCACCGACTCGGTGC-CACTTTTTCAAGTTGATAACGGACTAGCCTTATTT-TAACTTGCTAT TTCTAGCTCTAAAAC) (SEQ ID NO: 4). In some embodiments, the third segment double stranded DNA comprises the following DNA sequence on one strand (5'>3', GTTTTAGAGCTATGCTGGAAACAGCATAG-CAAGTTAAAATAAGGCTAGTCCGTTATCAACTT-GAAAA AGTGGCACCGAGTCGGTGCTTTTTTC) (SEQ ID NO: 5), and its reverse-complementary DNA on the other strand (5'>3', GAAAAAAAGCACCGACTCGGT-GCCACTTTTTCAAGTTGATAACGGACTAGCCTT-ATTTTAACTTGCT ATGCTGTTTCCAG-CATAGCTCTAAAAC) (SEQ ID NO: 6). In one embodiment, the DNA sequence can be single-stranded. In some embodiments, the third segment single stranded DNA comprises the following DNA sequence (5'>3', AAAAAAAGCACCGACTCGGTGC-CACTTTTTCAAGTTGATAACGGACTAGCCTTATTT-TAACTTGCTAT TTCTAGCTCTAAAAC) (SEQ ID NO: 4), wherein the single-stranded DNA serves as a transcription template. In some embodiments, the third segment single stranded DNA comprises the following DNA sequence (5'>3', GAAAAAAAGCACCGACTCGGTGC-CACTTTTTCAAGTTGATAACGGACTAGCCTTATTT-TAACTTGCT ATGCTGTTTCCAG-CATAGCTCTAAAAC) (SEQ ID NO: 6), wherein the single-stranded DNA serves as a transcription template. In some embodiments, the third segment comprises a DNA sequence which, upon transcription, yields a first RNA sequence that is capable of forming a hybrid with a second RNA sequence, and which hybrid is capable of CRISPR/Cas system protein binding. In some embodiments, the third segment is double-stranded DNA comprising the DNA sequence on one strand: (5'>3', GTTTTAGAGCTATGCT-GTTTTG) (SEQ ID NO: 9) and its reverse complementary DNA sequence on the other strand: (5'>3', CAAAACAG-CATAGCTCTAAAAC) (SEQ ID NO: 10). In some embodiments, the third segment is single-stranded DNA comprising the DNA sequence of (5'>3', CAAAACAG-CATAGCTCTAAAAC) (SEQ ID NO: 10). In some embodiments, the second segment and the third segment together encode for a crRNA sequence. In some embodiments, the second RNA sequence that is capable of forming a hybrid with the first RNA sequence encoded by the third segment of the nucleic acid encoding a gRNA is a tracrRNA. In some embodiments, the tracrRNA comprises the sequence (5'>3', GGAACCAUUCAAAACAGCAUAG-CAAGUUAAAAUAAGGCUAGUCCGUUAUCAAC-UUGAAAAAGUG GCACCGAGUCGGUGC-UUUUUUU) (SEQ ID NO: 11). In some embodiments, the tracrRNA is encoded by a double-stranded DNA comprising sequence of (5'>3', GGAACCATTCAAAACAGCATAG-CAAGTTAAAATAAGGCTAGTCCGTTATCAACTT-GAAAAGTGGC ACCGAGTCGGTGCTTTTTTT) (SEQ ID NO: 8), and optionally fused with a regulatory sequence at its 5' end. In some embodiments, the regulatory sequence can be bound by a transcription factor. In some embodiments, the regulatory sequence is a promoter. In some embodiments, the regulatory sequence is a T7 promoter, comprising the sequence of (5'>3', GCCTC-GAGCTAATACGACTCACTATAGAG) (SEQ ID NO: 12).

In some embodiments, provided herein is a nucleic acid encoding for a gNA comprising a first segment comprising a regulatory region; a second segment encoding a targeting sequence; and a third segment comprising a nucleic acid encoding a nucleic acid-guided nuclease (e.g., CRISPR/Cas) system protein-binding sequence. In some embodiments, the third segment encodes for a RNA sequence that, upon post-transcriptional cleavage, yields a first RNA segment and a second RNA segment. In some embodiments, the first RNA segment comprises a crRNA and the second RNA segment comprises a tracrRNA, which can form a hybrid and together, provide for nucleic acid-guided nuclease (e.g., CRISPR/Cas) system protein binding. In some embodiments, the third segment further comprises a spacer in between the transcriptional unit for the first RNA segment and the second RNA segment, which spacer comprises an enzyme cleavage site.

In some embodiments, provided herein is a gNA (e.g., gRNA) comprising a first NA segment comprising a targeting sequence and a second NA segment comprising a nucleic acid-guided nuclease (e.g., CRISPR/Cas) system protein-binding sequence. In some embodiments, the size of the first segment is greater than 30 bp. In some embodiments, the second segment comprises a single segment, which comprises the gRNA stem-loop sequence. In some embodiments, the gRNA stem-loop sequence comprises the following RNA sequence: (5'>3', GUUUUAGAGCUAGAAAUAG-CAAGUUAAAAUAAGGCUAGUCCGUUAUCAAC-UUGAAAAAGUGGCA CCGAGUCGGUGC-UUUUUUU) (SEQ ID NO: 1). In some embodiments, the gRNA stem-loop sequence comprises the following RNA sequence: (5'>3', GUUUUAGAGCUAUGCUGGAAACA-GCAUAGCAAGUUAAAAUAAGGCUAGUCCGUUAU-CAACUUGA AAAAGUGGCACCGAGUCGGUGC-UUUUUUUC) (SEQ ID NO: 2). In some embodiments, the second segment comprises two sub-segments: a first RNA sub-segment (crRNA) that forms a hybrid with a second RNA sub-segment (tracrRNA), which together act to direct nucleic acid-guided nuclease (e.g., CRISPR/Cas) system protein binding. In some embodiments, the sequence of the second sub-segment comprises GUUUUAGAGC-UAUGCUGUUUUG. In some embodiments, the first RNA segment and the second RNA segment together forms a crRNA sequence. In some embodiments, the other RNA that will form a hybrid with the second RNA segment is a tracrRNA. In some embodiments the tracrRNA comprises the sequence of 5'>3', GGAACCAUUCAAAACAG-CAUAGCAAGUUAAAAUAAGGCUAGUCCGUUAU-CAACUUGAAAAAGUG GCACCGAGUCGGUGC-UUUUUUU (SEQ ID NO: 11).

CRISPR/Cas System Nucleic Acid-Guided Nucleases

In some embodiments, CRISPR/Cas system proteins are used in the embodiments provided herein. In some embodiments, CRISPR/Cas system proteins include proteins from CRISPR Type I systems, CRISPR Type II systems, and CRISPR Type III systems.

In some embodiments, CRISPR/Cas system proteins can be from any bacterial or archaeal species.

In some embodiments, the CRISPR/Cas system protein is isolated, recombinantly produced, or synthetic.

In some embodiments, the CRISPR/Cas system proteins are from, or are derived from CRISPR/Cas system proteins from *Streptococcus pyogenes, Staphylococcus aureus, Neisseria meningitidis, Streptococcus thermophiles, Treponema* denticola, *Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis*, or *Corynebacter diphtheria.*

In some embodiments, examples of CRISPR/Cas system proteins can be naturally occurring or engineered versions.

In some embodiments, naturally occurring CRISPR/Cas system proteins can belong to CAS Class I Type I, III, or IV, or CAS Class II Type II or V, and can include Cas9, Cas3, Cas8a-c, Cas10, Cse1, Csy1, Csn2, Cas4, Csm2, Cmr5, Csf1, C2c2, and Cpf1.

In an exemplary embodiment, the CRISPR/Cas system protein comprises Cas9.

A "CRISPR/Cas system protein-gNA complex" refers to a complex comprising a CRISPR/Cas system protein and a guide NA (e.g. a gRNA or a gDNA). Where the gNA is a gRNA, the gRNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a gRNA) that contains crRNA and tracrRNA sequences.

A CRISPR/Cas system protein may be at least 60% identical (e.g., at least 70%, at least 80%, or 90% identical, at least 95% identical or at least 98% identical or at least 99% identical) to a wild type CRISPR/Cas system protein. The CRISPR/Cas system protein may have all the functions of a wild type CRISPR/Cas system protein, or only one or some of the functions, including binding activity, nuclease activity, and nuclease activity.

The term "CRISPR/Cas system protein-associated guide NA" refers to a guide NA. The CRISPR/Cas system protein-associated guide NA may exist as isolated NA, or as part of a CRISPR/Cas system protein-gNA complex.

Cas9

In some embodiments, the CRISPR/Cas System protein nucleic acid-guided nuclease is or comprises Cas9. The Cas9 of the present invention can be isolated, recombinantly produced, or synthetic.

Examples of Cas9 proteins that can be used in the embodiments herein can be found in F. A. Ran, L. Cong, W. X. Yan, D. A. Scott, J. S. Gootenberg, A. J. Kriz, B. Zetsche, O. Shalem, X. Wu, K S. Makarova, E. V. Koonin, P. A. Sharp, and F. Zhang; "In vivo genome editing using *Staphylococcus aureus* Cas9," Nature 520, 186-191 (9 Apr. 2015) doi:10.1038/nature14299, which is incorporated herein by reference.

In some embodiments, the Cas9 is a Type II CRISPR system derived from *Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis*, or *Corynebacter diphtheria.*

In some embodiments, the Cas9 is a Type II CRISPR system derived from *S. pyogenes* and the PAM sequence is NGG located on the immediate 3' end of the target specific guide sequence. The PAM sequences of Type II CRISPR systems from exemplary bacterial species can also include: *Streptococcus pyogenes* (NGG), *Staph aureus* (NNGRRT), *Neisseria meningitidis* (NNNNGA TT), *Streptococcus thermophilus* (NNAGAA) and *Treponema denticola* (NAAAAC) which are all usable without deviating from the present invention.

In one exemplary embodiment, Cas9 sequence can be obtained, for example, from the pX330 plasmid (available from Addgene), re-amplified by PCR then cloned into pET30 (from EMD biosciences) to express in bacteria and purify the recombinant 6His tagged protein.

A "Cas9-gNA complex" refers to a complex comprising a Cas9 protein and a guide NA. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas9 protein, or only one or some of the functions, including binding activity, nuclease activity, and nuclease activity.

The term "Cas9-associated guide NA" refers to a guide NA as described above. The Cas9-associated guide NA may exist isolated, or as part of a Cas9-gNA complex.

Non-CRISPR/Cas System Nucleic Acid-Guided Nucleases

In some embodiments, non-CRISPR/Cas system proteins are used in the embodiments provided herein.

In some embodiments, the non-CRISPR/Cas system proteins can be from any bacterial or archaeal species.

In some embodiments, the non-CRISPR/Cas system protein is isolated, recombinantly produced, or synthetic.

In some embodiments, the non-CRISPR/Cas system proteins are from, or are derived from *Aquifex aeolicus, Thermus thermophilus, Streptococcus pyogenes, Staphylococcus aureus, Neisseria meningitidis, Streptococcus thermophiles, Treponema denticola, Francisella tularensis, Pasteurella multocida, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globus, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Legionella pneumophila, Suterella wadsworthensis, Natronobacterium gregoryi*, or *Corynebacter diphtheria.*

In some embodiments, the non-CRISPR/Cas system proteins can be naturally occurring or engineered versions.

In some embodiments, a naturally occurring non-CRISPR/Cas system protein is NgAgo (Argonaute from *Natronobacterium gregoryi*).

A "non-CRISPR/Cas system protein-gNA complex" refers to a complex comprising a non-CRISPR/Cas system protein and a guide NA (e.g. a gRNA or a gDNA). Where the gNA is a gRNA, the gRNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a gRNA) that contains crRNA and tracrRNA sequences.

A non-CRISPR/Cas system protein may be at least 60% identical (e.g., at least 70%, at least 80%, or 90% identical, at least 95% identical or at least 98% identical or at least 99% identical) to a wild type non-CRISPR/Cas system protein. The non-CRISPR/Cas system protein may have all the functions of a wild type non-CRISPR/Cas system protein, or only one or some of the functions, including binding activity, nuclease activity, and nuclease activity.

The term "non-CRISPR/Cas system protein-associated guide NA" refers to a guide NA. The non-CRISPR/Cas system protein-associated guide NA may exist as isolated NA, or as part of a non-CRISPR/Cas system protein-gNA complex.

Catalytically Dead Nucleic Acid-Guided Nucleases

In some embodiments, engineered examples of nucleic acid-guided nucleases include catalytically dead nucleic acid-guided nucleases (CRISPR/Cas system nucleic acid-guided nucleases or non-CRISPR/Cas system nucleic acid-guided nucleases). The term "catalytically dead" generally refers to a nucleic acid-guided nuclease that has inactivated nucleases, for example inactivated HNH and RuvC nucleases. Such a protein can bind to a target site in any nucleic acid (where the target site is determined by the guide NA), but the protein is unable to cleave or nick the nucleic acid.

Accordingly, the catalytically dead nucleic acid-guided nuclease allows separation of the mixture into unbound nucleic acids and catalytically dead nucleic acid-guided nuclease-bound fragments. In one exemplary embodiment, a dCas9/gRNA complex binds to the targets determined by the gRNA sequence. The dCas9 bound can prevent cutting by Cas9 while other manipulations proceed.

In another embodiment, the catalytically dead nucleic acid-guided nuclease can be fused to another enzyme, such as a transposase, to target that enzyme's activity to a specific site.

In some embodiments, the catalytically dead nucleic acid-guided nuclease is dCas9, dCpf1, dCas3, dCas8a-c, dCas10, dCse1, dCsy1, dCsn2, dCas4, dCsm2, dCm5, dCsf1, dC2C2, or dNgAgo.

In one exemplary embodiment the catalytically dead nucleic acid-guided nuclease protein is a dCas9.

Nucleic Acid-Guided Nuclease Nickases

In some embodiments, engineered examples of nucleic acid-guided nucleases include nucleic acid-guided nuclease nickases (referred to interchangeably as nickase nucleic acid-guided nucleases).

In some embodiments, engineered examples of nucleic acid-guided nucleases include CRISPR/Cas system nickases or non-CRISPR/Cas system nickases, containing a single inactive catalytic domain.

In some embodiments, the nucleic acid-guided nuclease nickase is a Cas9 nickase, Cpf1 nickase, Cas3 nickase, Cas8a-c nickase, Cas10 nickase, Cse1 nickase, Csy1 nickase, Csn2 nickase, Cas4 nickase, Csm2 nickase, Cm5 nickase, Csf1 nickase, C2C2 nickase, or a NgAgo nickase.

In one embodiment, the nucleic acid-guided nuclease nickase is a Cas9 nickase.

In some embodiments, a nucleic acid-guided nuclease nickase can be used to bind to target sequence. With only one active nuclease domain, the nucleic acid-guided nuclease nickase cuts only one strand of a target DNA, creating a single-strand break or "nick". Depending on which mutant is used, the guide NA-hybridized strand or the non-hybridized strand may be cleaved. nucleic acid-guided nuclease nickases bound to 2 gNAs that target opposite strands can create a double-strand break in the nucleic acid. This "dual nickase" strategy increases the specificity of cutting because it requires that both nucleic acid-guided nuclease/gNA complexes be specifically bound at a site before a double-strand break is formed.

In exemplary embodiments, a Cas9 nickase can be used to bind to target sequence. The term "Cas9 nickase" refers to a modified version of the Cas9 protein, containing a single inactive catalytic domain, i.e., either the RuvC- or the HNH-domain. With only one active nuclease domain, the Cas9 nickase cuts only one strand of the target DNA, creating a single-strand break or "nick". Depending on which mutant is used, the guide RNA-hybridized strand or the non-hybridized strand may be cleaved. Cas9 nickases bound to 2 gRNAs that target opposite strands will create a double-strand break in the DNA. This "dual nickase" strategy can increase the specificity of cutting because it requires that both Cas9/gRNA complexes be specifically bound at a site before a double-strand break is formed.

Capture of DNA can be carried out using a nucleic acid-guided nuclease nickase. In one exemplary embodiment, a nucleic acid-guided nuclease nickase cuts a single strand of double stranded nucleic acid, wherein the double stranded region comprises methylated nucleotides.

Dissociable and Thermostable Nucleic Acid-Guided Nucleases

In some embodiments, thermostable nucleic acid-guided nucleases are used in the methods provided herein (thermostable CRISPR/Cas system nucleic acid-guided nucleases or thermostable non-CRISPR/Cas system nucleic acid-guided nucleases). In such embodiments, the reaction temperature is elevated, inducing dissociation of the protein; the reaction temperature is lowered, allowing for the generation of additional cleaved target sequences. In some embodiments, thermostable nucleic acid-guided nucleases maintain at least 50% activity, at least 55% activity, at least 60% activity, at least 65% activity, at least 70% activity, at least 75% activity, at least 80% activity, at least 85% activity, at least 90% activity, at least 95% activity, at least 96% activity, at least 97% activity, at least 98% activity, at least 99% activity, or 100% activity, when maintained for at least 75° C. for at least 1 minute. In some embodiments, thermostable nucleic acid-guided nucleases maintain at least 50% activity, when maintained for at least 1 minute at least at 75° C., at least at 80° C., at least at 85° C., at least at 90° C., at least at 91° C., at least at 92° C., at least at 93° C., at least at 94° C., at least at 95° C., 96° C., at least at 97° C., at least at 98° C., at least at 99° C., or at least at 100° C. In some embodiments, thermostable nucleic acid-guided nucleases maintain at least 50% activity, when maintained at least at 75° C. for at least 1 minute, 2 minutes, 3 minutes, 4 minutes, or 5 minutes. In some embodiments, a thermostable nucleic acid-guided nuclease maintains at least 50% activity when the temperature is elevated, lowered to 25° C.–50° C. In some embodiments, the temperature is lowered to 25° C., to 30° C., to 35° C., to 40° C., to 45° C., or to 50° C. In one exemplary embodiment, a thermostable enzyme retains at least 90% activity after 1 min at 95° C.

In some embodiments, the thermostable nucleic acid-guided nuclease is thermostable Cas9, thermostable Cpf1, thermostable Cas3, thermostable Cas8a-c, thermostable Cas10, thermostable Cse1, thermostable Csy1, thermostable Csn2, thermostable Cas4, thermostable Csm2, thermostable Cm5, thermostable Csf1, thermostable C2C2, or thermostable NgAgo.

In some embodiments, the thermostable CRISPR/Cas system protein is thermostable Cas9.

Thermostable nucleic acid-guided nucleases can be isolated, for example, identified by sequence homology in the genome of thermophilic bacteria *Streptococcus thermophilus* and *Pyrococcus furiosus*. Nucleic acid-guided nuclease genes can then be cloned into an expression vector. In one exemplary embodiment, a thermostable Cas9 protein is isolated.

In another embodiment, a thermostable nucleic acid-guided nuclease can be obtained by in vitro evolution of a non-thermostable nucleic acid-guided nuclease. The sequence of a nucleic acid-guided nuclease can be mutagenized to improve its thermostability.

Methods of Making Collections of gNAs

Provided herein are methods that enable the generation of a large number of diverse gRNAs, collections of gNAs, from any source nucleic acid (e.g., DNA). Methods provided herein can employ enzymatic methods including but not limited to digestion, ligation, extension, overhang filling, transcription, reverse transcription, amplification.

Generally, the method can comprise providing a nucleic acid (e.g., DNA); employing a first enzyme (or combinations of first enzymes) that cuts at a part of the PAM sequence in the nucleic acid, in a way that a residual nucleotide sequence from the PAM sequence is left; ligating an adapter that positions a restriction enzyme typeIIS site (an enzyme that cuts outside yet near its recognition motif) at a distance to eliminate the PAM sequence; employing a second typeIIS enzyme (or combination of second enzymes) to eliminate the PAM sequence together with the adapter; and fusing a sequence that can be recognized by protein members of the nucleic acid-guided nuclease (e.g., CRISPR/Cas) system, for example, a gRNA stem-loop sequence. In some embodiments, the first enzymatic reactions cuts part of the PAM sequence in a way that residual nucleotide sequence from the PAM sequence is left, and that the nucleotide sequence immediately 5' to the PAM sequence can be any purine or pyrimidine, not just those with a cytosine 5' to the PAM sequence, for example, not just those that are C/NGG or C/TAG, etc.

Table 1 shows exemplary strategies/protocols to convert any source nucleic acid (e.g., DNA) into a collection of gNAs (e.g., gRNAs) using different restriction enzymes.

TABLE 1

Exemplary strategies for preparing a collection of guide nucleic acids.

| CRISPR/Cas System Species | PAM Sequence | First Enzyme/ Components | Strategy | 3' Adapter sequence with typeIIS enzyme site (provided with only one strand sequence 5' > 3') |
|---|---|---|---|---|
| *Streptococcus pyogenes* (SP); SpCas9 | NGG | CviPII | Nicks immediately 5' of CCD sequence, nicks the other strand with T7 endonuclease I, blunt with T4 DNA polymerase; ligate to adapter; cut with MlyI to remove PAM and adapter; ligate gRNA stem-loop sequence at 3' end | ggGACTCggatccctatagtc (SEQ ID NO: 4421) |
| *Staphylococcus aureus* (SA); SaCas9 | NNGRRT or NNGRR (N) | AlwI | Cut, blunt with T4 DNA polymerase; ligate to adapter SA; cut with EcoP15I to remove PAM and adapter; blunt end; ligate gRNA stem-loop sequence at 3' end | ttttagcggccgcctgctgCTCtacaa agacgatgacgacaagcgt (SEQ ID NO: 4422) |
| *Neisseria meningitidis* (NM) | NNNNGA TT | TfiI | Cut, blunt with T4 DNA polymerase; ligate to adapter NM; cut with EcoRI to eliminate un-wanted DNA and EcoP15I to remove PAM and adapter; blunt end; ligate gRNA stem-loop sequence at 3' end | TCgcggccgcttttattctgctgCTCt acaaagacgatgacgacaagcgt (SEQ ID NO: 4428) |
| *Streptococcus thermophilus* (ST) | NNAGAA W | BsmI | Cut, blunt with T4 DNA polymerase; ligate to adapter ST; cut with EcoP15I to remove PAM and adapter; blunt end; ligate gRNA stem-loop sequence at 3' end | ttgcggccgcttttattctgctgCTCt acaaagacgatgacgacaagcgt (SEQ ID NO: 4429) |
| *Treponema denticola* (TD) | NAAAAC | Cly7489I | Cut, blunt with T4 DNA polymerase; ligate to adapter TD; cut with EcoP15I to remove PAM and adapter | tttagcggccgcctgctgCTCtacaaa gacgatgacgacaagcgt (SEQ ID NO: 4430) |

Table 2 shows additional exemplary strategies/protocols to convert any source nucleic acid (e.g., DNA) into a collection of gNAs (e.g., gRNAs) using different restriction enzymes.

TABLE 2

Additional exemplary strategies for preparing a collection of guide nucleic acids.

| CRISPR/ Cas System Species | PAM Sequence | First Enzyme/ Component | Exemplary Strategy | Adapter oligo sequence (with Inosine overhangs, all in 5' > 3' direction) |
|---|---|---|---|---|
| Streptococcus pyogenes (SP); SpCas9 | NGG | CviPII | Nicks immediately 5' of CCD sequence, nicks the other strand with T7 endonuclease I; ligate to adapter; cut with MlyI to remove PAM and 3' adapter; ligate gRNA stem-loop sequence at 3' end | Adapter oligo 1: ggggGACTCggatccctatagtgatac aaagacgatgacgacaagcg (SEQ ID NO: 4404) Adapter oligo 2: gcctcgagc*t*a*atacgactcactatag ggatccaagtccc (* denotes a phosphorothioate backbone linkage) (SEQ ID NO: 4405) |
| Staphylococcus aureus (SA); SaCas9 | NNGRRT or NNGRR (N) | AlwI | Cut; ligate to adapter SA; cut with EcoP15I to remove PAM and 3' adapter; blunt end; ligate gRNA stem-loop sequence at 3' end | Adapter oligo 1: IttttagcggccgcctgctgCTCtacaaa gacgatgacgacaagcgt (SEQ ID NO: 4422) Adapter oligo 2: gagatcagcttctgcattgatgcGAGcag caggcggccgctaaaa (SEQ ID NO: 4423) |
| Neisseria meningitidis (NM) | NNNNGATT | TfiI | Cut; ligate to adapter NM; cut with EcoP15I to remove PAM and 3' adapter; blunt end; ligate gRNA stem-loop sequence at 3' end | Adapter oligo 1: attTCgcggccgcttttattctgctgCTCt acaaagacgatgacgacaagcgt (SEQ ID NO: 4424) Adapter oligo 2: gagatcagcttctgcattgatgcGAGcag cagaataaaagcggccgcGA (SEQ ID NO: 4425) |
| Streptococcus thermophilus (ST) | NNAGAAW | BsmI | Cut; ligate to adapter ST; cut with EcoP15I to remove PAM and 3' adapter; blunt end; ligate gRNA stem-loop sequence at 3' end | Adapter oligo 1: gcggccgcttttattctgctgCTCtacaaa gacgatgacgacaagcgt (SEQ ID NO: 4426) Adapter oligo 2: gagatcagcttctgcattgatgcGAGcag cagaataaaagcggccgcIG (SEQ ID NO: 4427) |

Exemplary applications of the compositions and methods described herein are provided in FIG. 1, FIG. 2, FIG. 3, FIG. 4, FIG. 5, FIG. 6, and FIG. 7. The figures depict non-limiting exemplary embodiments of the present invention that includes a method of constructing a gNA library (e.g., gRNA library) from input nucleic acids (e.g., DNA), such as genomic DNA (e.g., human genomic DNA).

In FIG. 1, the starting material can be fragmented genomic DNA (e.g., human) or other source DNA. These fragments are blunt-ended before constructing the library 101. T7 promoter adapters are ligated to the blunt-ended DNA fragments 102, which is then PCR amplified. Nt.CviPII is then used to generate a nick on one strand of the PCR product immediately 5' to the CCD sequence 103. T7 Endonuclease I cleaves on the opposite strand 1, 2, or 3 bp 5' of the nick 104. The resulting DNA fragments are blunt-ended with T4 DNA Polymerase, leaving HGG sequence at the end of the DNA fragment 105. The resulting DNA is cleaned and recovered on beads. An adapter carrying MlyI recognition site is ligated to the blunt-ended DNA fragment immediately 3' of HGG sequence 106. MlyI generates a blunt-end cleavage immediately 5' to the HGG sequence, removing HGG together with the adapter sequence 107. The resulting DNA fragments are cleaned and recovered again on beads. A gRNA stem-loop sequence is then ligated to the blunt-end cleaved by MlyI, forming a gRNA library covering the human genome 108. This library of DNA is then PCR amplified and cleaned on beads, ready for in vitro transcription.

Figure 2:
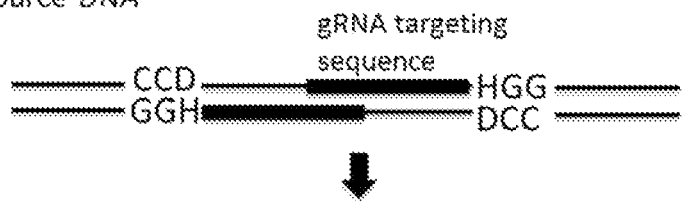
FIG. 2 illustrates another exemplary scheme for producing a collection of gRNAs (a gRNA library) from genomic DNA.
Figure 2:
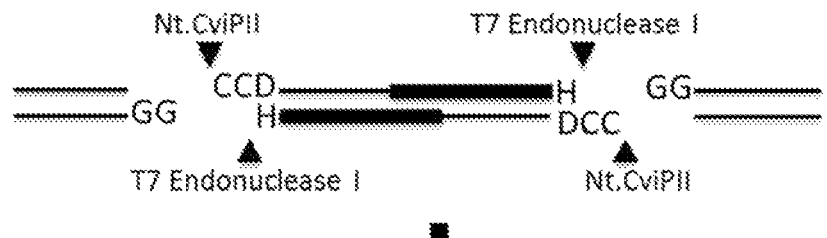
Figure 2:
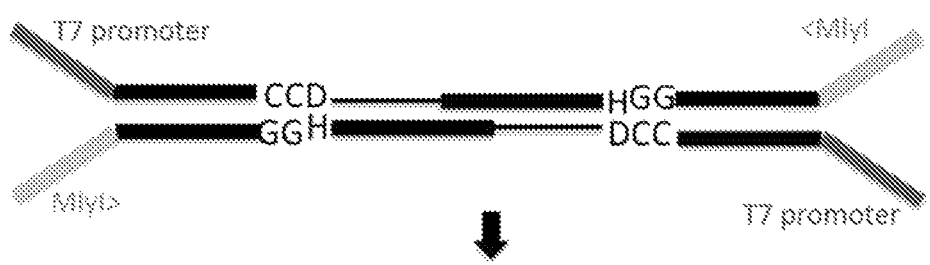
Figure 2:
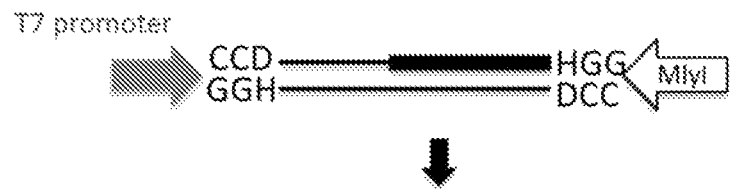
Figure 2:
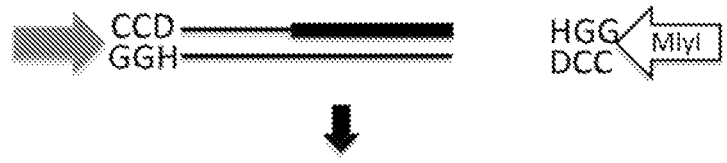
Figure 2:

In FIG. 2, the starting material can intact genomic DNA (e.g., human) or other source DNA 201. Nt.CviPII and T7 Endonuclease I are used to generate nicks on each strand of the human genomic DNA, resulting in smaller DNA fragments 202. DNA fragments of 200-600 bp are size selected on beads, then ligated with Y-shaped adapters carrying a GG overhang on the 5'. One strand of the Y-shaped adapter contains a MlyI recognition site, wherein the other strand contains a mutated MlyI site and a T7 promoter sequence 203. Because of these features, after PCR amplification, the T7 promoter sequence is at the distal end of the HGG sequence, and the MlyI sequence is at the rear end of HGG 204. Digestion with MlyI generates a cleavage immediately 5' of HGG sequence 205. MlyI generates a blunt-end cleavage immediately 5' to the HGG sequence, removing HGG together with the adapter sequence 206. A gRNA stem-loop sequence is then ligated to the blunt-end cleaved by MlyI, forming a gRNA library covering the human genome. This library of DNA is then PCR amplified and cleaned on beads, ready for in vitro transcription.

Figure 3:
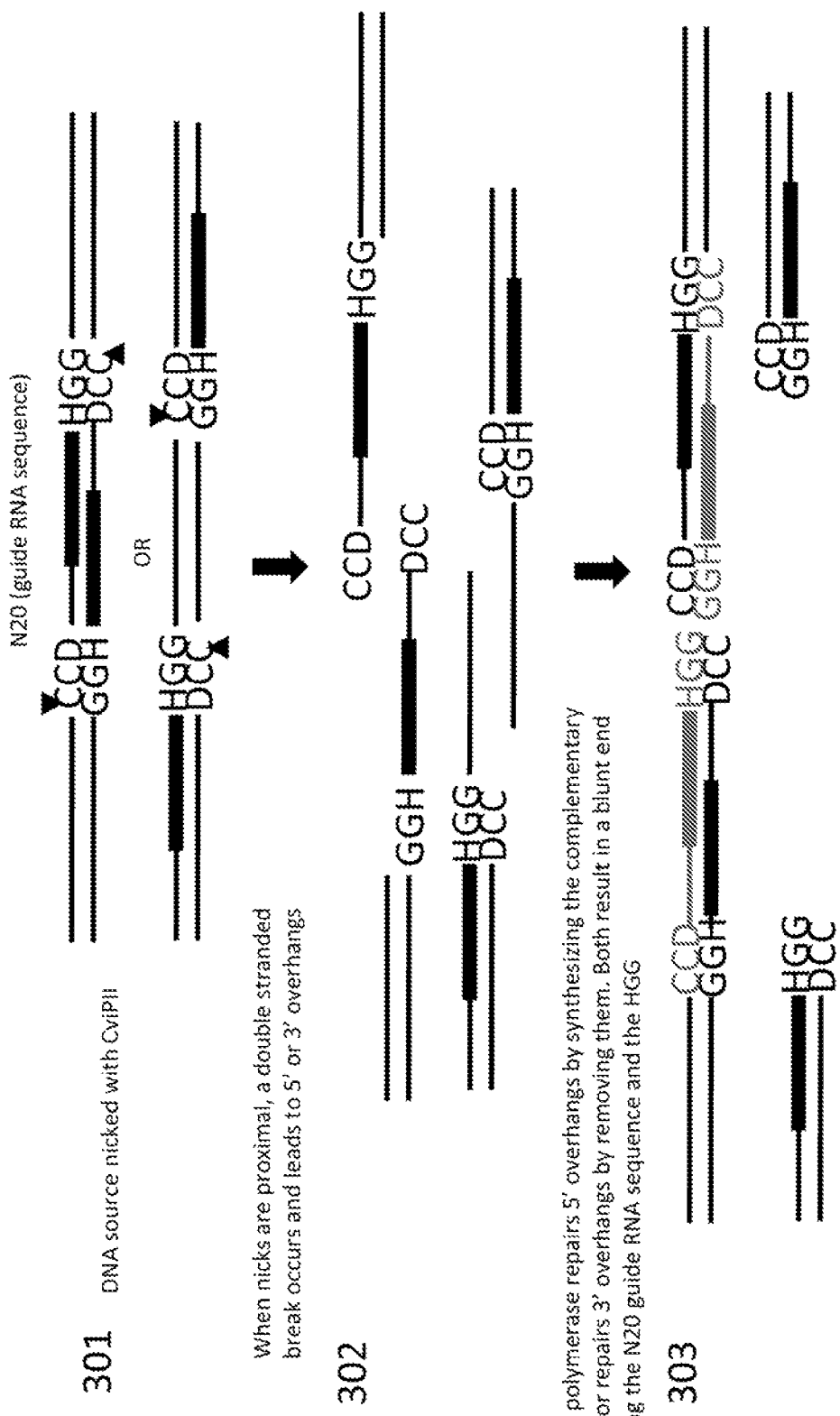
FIG. 3 illustrates an exemplary scheme for nicking of DNA and subsequent treatment with polymerase to generate blunt ends.

In FIG. 3, the source DNA (e.g., genomic DNA) can be nicked 301, for example with a nicking enzyme. In some cases, the nicking enzyme can have a recognition site that is three or fewer bases in length. In some cases, CviPII is used, which can recognize and nick at a sequence of CCD (where D represents a base other than C). Nicks can be proximal, surrounding a region containing the sequence (represented by the thicker line) which will be used to yield the guide RNA N20 sequence. When nicks are proximal, a double stranded break can occur and lead to 5' or 3' overhangs 302. These overhangs can be repaired, for example with a polymerase (e.g., T4 polymerase). In some cases, such as with 5' strands, repair can comprise synthesizing a complementary strand. In some case, such as with 3' strands, repair can comprise removing overhangs. Repair can result in a blunt end including the N20 guide sequence and a sequence complementary to the nick recognition sequence (e.g., HGG, where H represents a base other than G).

Figure 4:
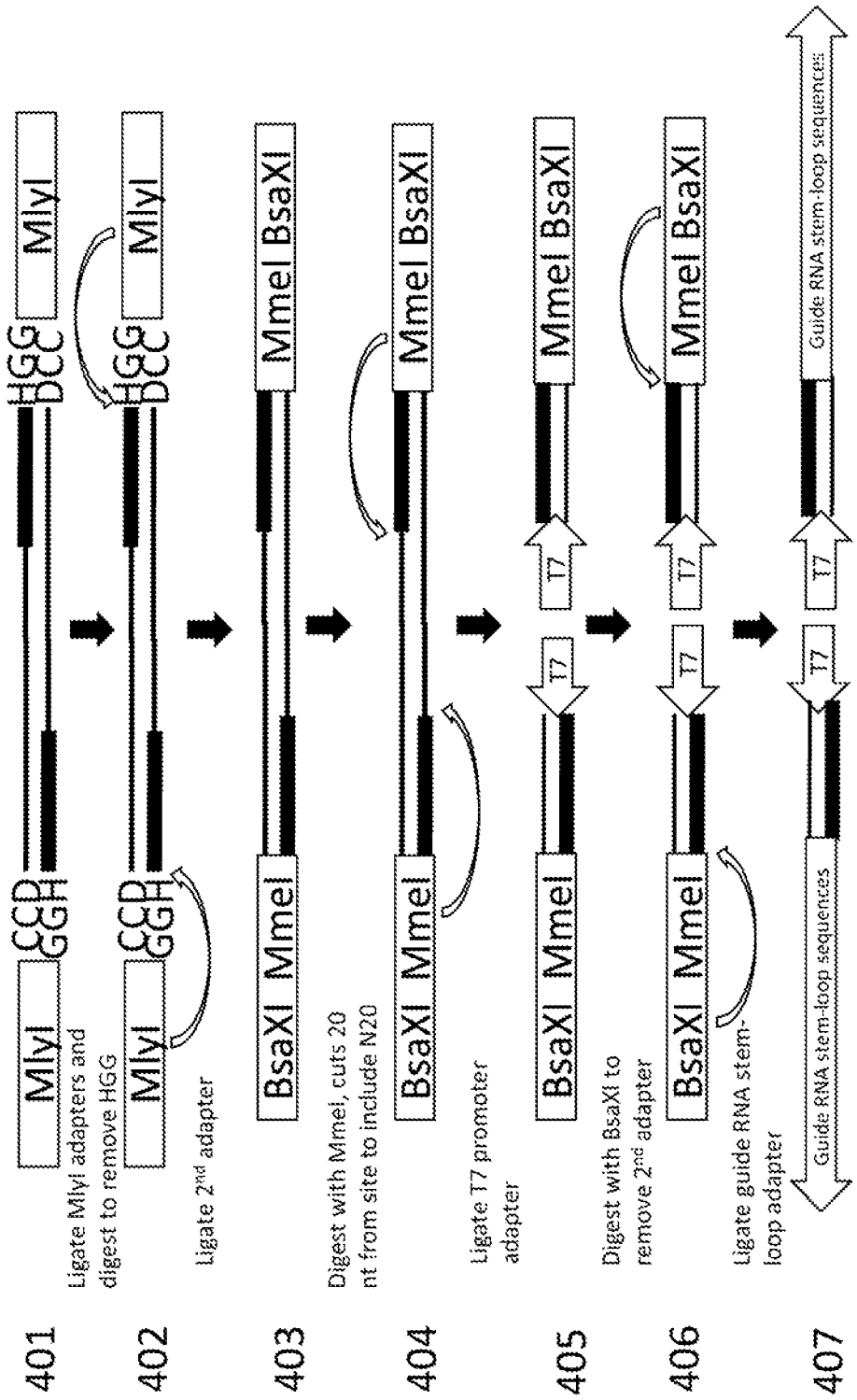
FIG. 4 illustrates an exemplary scheme for sequential production of a library of gNAs using three adapters.

In FIG. 4, continuing for example from the end of FIG. 3, different combinations of adapters can be ligated to the DNA to allow for the desired cleaving. Adapters with a recognition site for a nuclease enzyme that cuts 3 base pairs from the site (e.g., MlyI) can be ligated 401, and digestion at that site can be used to remove a left over sequence, such as an HGG sequence 402. Adapters with a recognition site for a nuclease that cuts 20 base pairs from the site (e.g., MmeI) 403. These adapters can also include a second recognition site for a nuclease that cuts the proper number of nucleotides from the site to later remove the first recognition site (e.g., BsaXI). The first enzyme can be used to cut 20 nucleotides down, thereby keeping the N20 sequence 404. Then, a promoter adapter (e.g., T7) can be ligated next to the N20 sequence 405. Then, the nuclease corresponding to the second recognition site (e.g., BsaXI) can be used to remove the adapter for the site that cuts 20 nucleotides away (e.g., MmeI) 406. Finally, the guide RNA stem-loop sequence adapter can be ligated to the N20 sequence 407 to prepare for guide RNA production.

Figure 5:
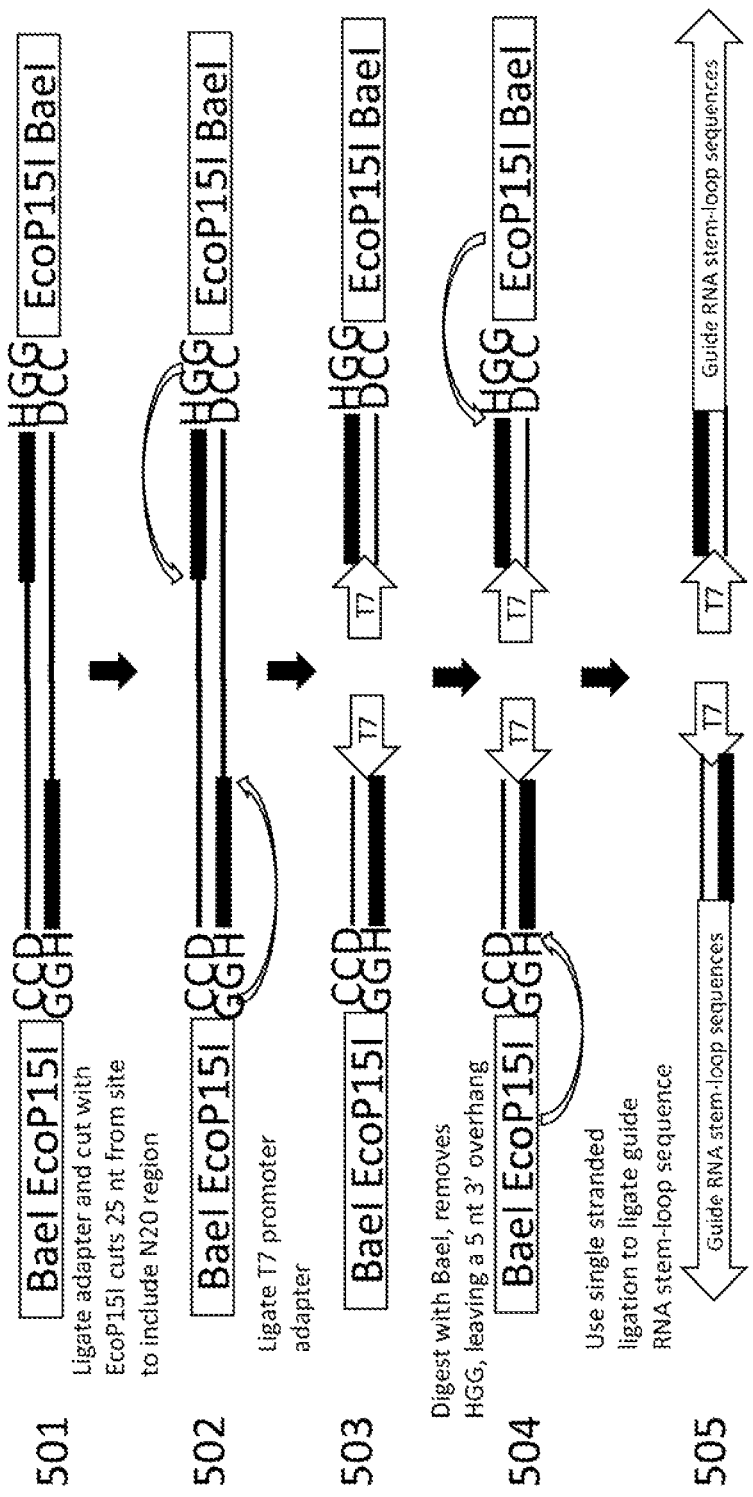
FIG. 5 illustrates an exemplary scheme for sequential production of a library of gNAs using one adapter and one oligo.

Alternatively, the protocol shown in FIG. 5 can follow the end of a protocol such as that shown in FIG. 3. Adapters with a recognition site for a nuclease enzyme that cleaves 25 nucleotides from the site (e.g., EcoP15I) can be ligated to the DNA 501. These adapters can also include a second recognition site for a nuclease that cuts the proper number of nucleotides from the site to later remove the first recognition site (e.g., BaeI) and any other left-over sequence, such as HGG. The enzyme corresponding to the first recognition site (e.g., EcoP15I) can then be used to cleave after the N20 sequence 502. Then, a promoter adapter (e.g., T7) can be ligated next to the N20 sequence 503. The enzyme corresponding to the second recognition site (e.g., BaeI) can then be used to remove the recognition sites and any residual sequence (e.g., HGG) 504. Finally, the guide RNA stem-loop sequence adapter can be ligated (e.g., by single strand ligation) to the N20 sequence 505.

Figure 6:
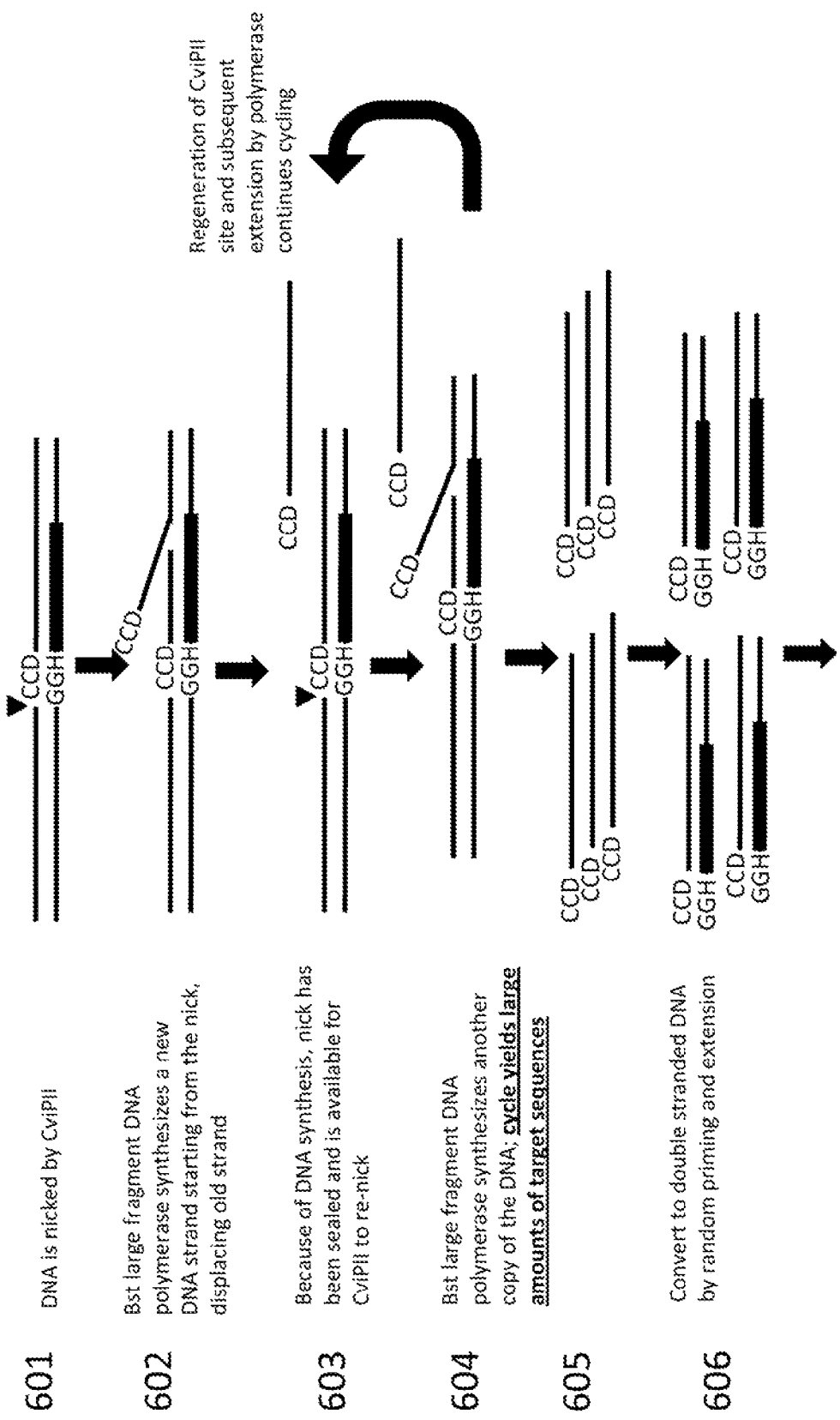
FIG. 6 illustrates an exemplary scheme for generation of a large pool of DNA fragments with blunt ends using Nicking Enzyme Mediated DNA Amplification (NEMDA).

As an alternative to protocols such as that shown in FIG. 3, the protocol shown in FIG. 6 can be used in preparation for protocols such as those shown in FIG. 4 or FIG. 5. A nick can be introduced by a nicking enzyme (e.g., CviPII) 601. In some cases, the nick recognition site is three or fewer bases in length. In some cases, CviPII is used, which can recognize and nick at a sequence of CCD. A polymerase (e.g., Bst large fragment DNA polymerase) can then be used to synthesize a new DNA strand starting from the nick while displacing the old strand 602. Because of the DNA synthesis, the nick can be sealed and made available to be nicked again 603. Subsequent cycles of nicking and synthesis can be used to yield large amounts of target sequences 604. These single stranded copies of target sequences can be made double stranded, for example by random priming and extension. These double stranded nucleic acids comprising N20 sequences can then be further processed by methods disclosed herein, such as those shown in FIG. 4 or FIG. 5.

Figure 7:
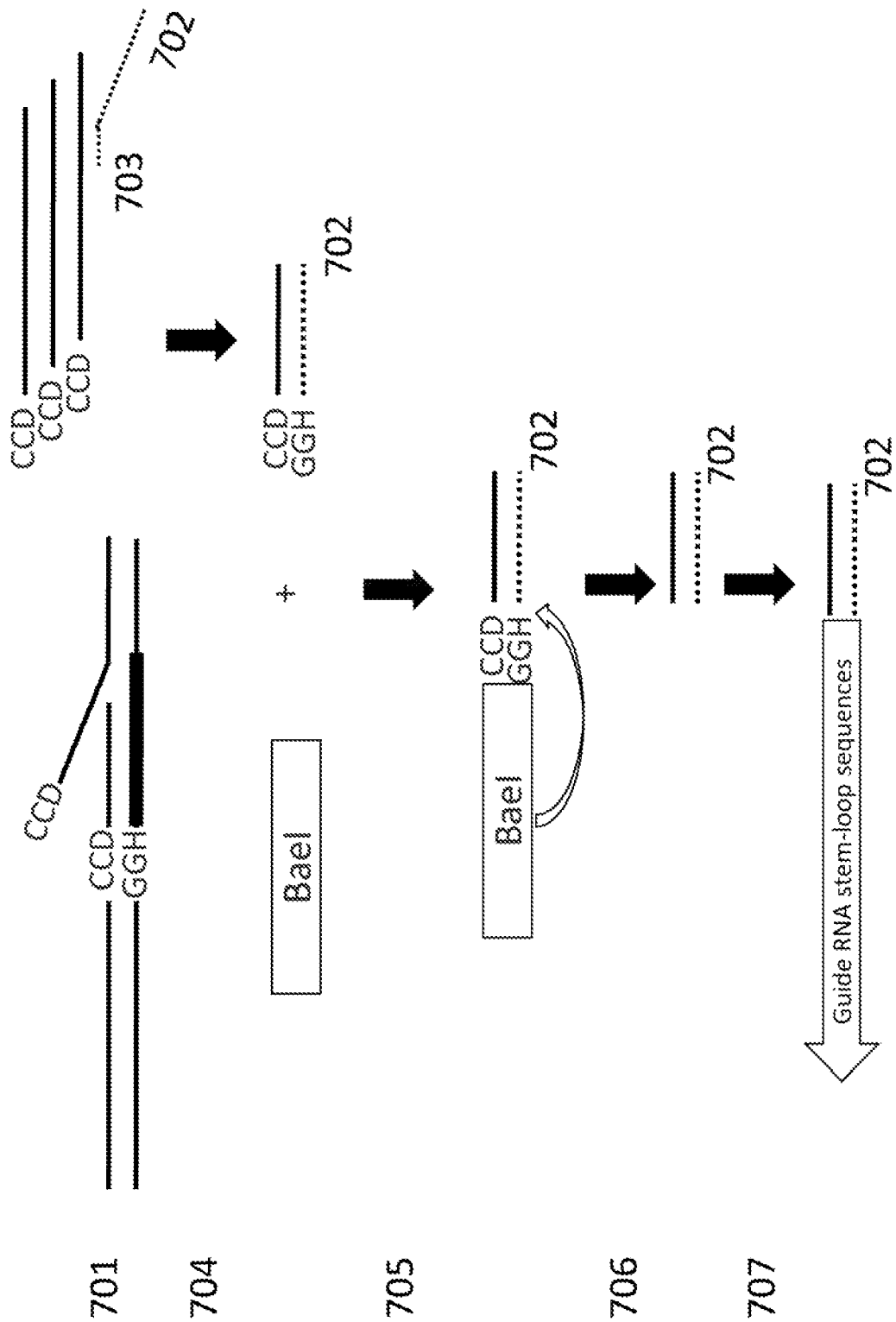
FIG. 7 illustrates an exemplary scheme for generation of a large pool of gNAs using Nicking Enzyme Mediated DNA Amplification (NEMDA).

As another alternative to protocols such as that shown in FIG. 3 or FIG. 6, the protocol shown in FIG. 7 can be used in preparation for protocols such as those shown in FIG. 4 or FIG. 5. A nick can be introduced by a nicking enzyme (e.g., CviPII) 701. In some cases, the nicking enzyme recognition site is three or fewer bases in length. In some cases, CviPII is used, which can recognize and nick at a sequence of CCD. A polymerase (e.g., Bst large fragment DNA polymerase) can then be used to synthesize a new DNA strand starting from the nick while displacing the old strand (e.g., nicking endonuclease-mediated strand-displacement DNA amplification (NEMDA)). The reaction parameters can be adjusted to control the size of the single stranded DNA produced. For example, the nickase:polymerase ratio (e.g., CviPII:Bts large fragment polymerase ratio) can be adjusted. Reaction temperature can also be adjusted. Next, an oligonucleotide can be added 704 which has (in the 5'>3' direction) a promoter (e.g., T7 promoter) 702 followed by a random n-mer (e.g., random 6-mer, random 8-mer) 703. The random n-mer region can bind to a region of the single stranded DNA generated previously. For example, binding can be conducted by denaturing at high temperature followed by rapid cool down, which can allow the random n-mer region to bind to the single stranded DNA generated by NEMDA. In some cases, the DNA is denatured at 98° C. for 7 minutes then cooled down rapidly to 10° C. Extension and/or amplification can be used to produce double-stranded DNA. Blunt ends can be produced, for example enzymatically (e.g., by treatment with DNA polymerase I at 20° C.). This can result in one end ending at the promoter (e.g., T7 promoter) and the other end ending at any nicking enzyme recognition sites (e.g., any CCD sites). These fragments can then be purified, for example by size selection (e.g., by gel purification, capillary electrophoresis, or other fragment separation techniques). In some cases, the target fragments are about 50 base pairs in length (adapter sequence (e.g., T7 adapter)+target N20 sequence+nicking enzyme recognition site or complement (e.g., HGG)). Fragments can then be ligated to an adapter comprising a nuclease recognition site for a nuclease that cuts an appropriate distance away to remove the nicking enzyme recognition site 705. For example, for a three-nucleotide long nicking enzyme recognition site (e.g., CCD for CviPII), BaeI can be used. The appropriate nuclease (e.g., BaeI) can then be used to remove the nuclease recognition site and the nicking enzyme recognition site 706. The remaining nucleic acid sequence (e.g., the N20 site) can then be ligated to the final stem-loop sequence for the guide RNA 707. Amplification (e.g., PCR) can be conducted. Guide RNAs can be produced.

In some embodiments, a collection of gNAs (e.g., gRNAs) targeting human mitochondrial DNA (mtDNA) is created, that can be used for directing nucleic acid-guided nuclease (e.g., Cas9) proteins, comprising the nucleic acid-guided nuclease (e.g., Cas9) target sequence. In some embodiments, the targeting sequence of this collection of gNAs (e.g., gRNAs) are encoded by DNA sequences comprising at least the 20 nt sequence provided in the second column from the right of Table 3 (if the NGG sequence is on positive strand) and Table 4 (if the NGG sequence is on negative strand). In some embodiments, a collection of gRNA nucleic acids, as provided herein, with specificity for human mitochondrial DNA, comprise a plurality of members, wherein the members comprise a plurality of targeting sequences provided in the second column from the right column of Table 3 and/or the second column from the right of Table 4.

TABLE 3 gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 13 | 35 | ATCACCCTATTAACCACTCACGG | 13 | ATCACCCTATTAACCACTCA | 436 |
| 14 | 36 | TCACCCTATTAACCACTCACGGG | 14 | TCACCCTATTAACCACTCAC | 437 |
| 32 | 54 | ACGGGAGCTCTCCATGCATTTGG | 15 | ACGGGAGCTCTCCATGCATT | 438 |
| 45 | 67 | ATGCATTTGGTATTTTCGTCTGG | 16 | ATGCATTTGGTATTTTCGTC | 439 |
| 46 | 68 | TGCATTTGGTATTTTCGTCTGGG | 17 | TGCATTTGGTATTTTCGTCT | 440 |
| 47 | 69 | GCATTTGGTATTTTCGTCTGGGG | 18 | GCATTTGGTATTTTCGTCTG | 441 |
| 48 | 70 | CATTTGGTATTTTCGTCTGGGGG | 19 | CATTTGGTATTTTCGTCTGG | 442 |
| 49 | 71 | ATTTGGTATTTTCGTCTGGGGG | 20 | ATTTGGTATTTTCGTCTGGG | 443 |
| 79 | 101 | GCGATAGCATTGCGAGACGCTGG | 21 | GCGATAGCATTGCGAGACGC | 444 |
| 85 | 107 | GCATTGCGAGACGCTGGAGCCGG | 22 | GCATTGCGAGACGCTGGAGC | 445 |
| 163 | 185 | GCACCTACGTTCAATATTACAGG | 23 | GCACCTACGTTCAATATTAC | 446 |
| 207 | 229 | GTTAATTAATTAATGCTTGTAGG | 24 | GTTAATTAATTAATGCTTGT | 447 |
| 301 | 323 | AACCCCCCCTCCCCCGCTTCTGG | 25 | AACCCCCCCTCCCCCGCTTC | 448 |
| 388 | 410 | AGATTTCAAATTTTATCTTTTGG | 26 | AGATTTCAAATTTTATCTTT | 449 |
| 391 | 413 | TTTCAAATTTTATCTTTTGGCGG | 27 | TTTCAAATTTTATCTTTTGG | 450 |
| 604 | 626 | ATACACTGAAAATGTTTAGACGG | 28 | ATACACTGAAAATGTTTAGA | 451 |
| 605 | 627 | TACACTGAAAATGTTTAGACGGG | 29 | TACACTGAAAATGTTTAGAC | 452 |
| 631 | 653 | ACATCACCCCATAAACAAATAGG | 30 | ACATCACCCCATAAACAAAT | 453 |
| 636 | 658 | ACCCCATAAACAAATAGGTTTGG | 31 | ACCCCATAAACAAATAGGTT | 454 |
| 727 | 749 | TCTAAATCACCACGATCAAAAGG | 32 | TCTAAATCACCACGATCAAA | 455 |
| 788 | 810 | TTAGCCTAGCCACACCCCACGG | 33 | TTAGCCTAGCCACACCCCA | 456 |
| 789 | 811 | TAGCCTAGCCACACCCCACGGG | 34 | TAGCCTAGCCACACCCCCAC | 457 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 851 | 873 | AACTAAGCTATACTAACCCCAGG | 35 | AACTAAGCTATACTAACCCC | 458 |
| 852 | 874 | ACTAAGCTATACTAACCCAGGG | 36 | ACTAAGCTATACTAACCCCA | 459 |
| 856 | 878 | AGCTATACTAACCCCAGGGTTGG | 37 | AGCTATACTAACCCCAGGGT | 460 |
| 880 | 902 | CAATTTCGTGCCAGCCACCGCGG | 38 | CAATTTCGTGCCAGCCACCG | 461 |
| 912 | 934 | TAACCCAAGTCAATAGAAGCCGG | 39 | TAACCCAAGTCAATAGAAGC | 462 |
| 1009 | 1031 | CACAAAATAGACTACGAAAGTGG | 40 | CACAAAATAGACTACGAAAG | 463 |
| 1051 | 1073 | ACAATAGCTAAGACCCAAACTGG | 41 | ACAATAGCTAAGACCCAAAC | 464 |
| 1052 | 1074 | CAATAGCTAAGACCCAAACTGGG | 42 | CAATAGCTAAGACCCAAACT | 465 |
| 1148 | 1170 | AGCCACAGCTTAAAACTCAAAGG | 43 | AGCCACAGCTTAAAACTCAA | 466 |
| 1154 | 1176 | AGCTTAAAACTCAAAGGACCTGG | 44 | AGCTTAAAACTCAAAGGACC | 467 |
| 1157 | 1179 | TTAAAACTCAAAGGACCTGGCGG | 45 | TTAAAACTCAAAGGACCTGG | 468 |
| 1178 | 1200 | GGTGCTTCATATCCCTCTAGAGG | 46 | GGTGCTTCATATCCCTCTAG | 469 |
| 1267 | 1289 | TCTTCAGCAAACCCTGATGAAGG | 47 | TCTTCAGCAAACCCTGATGA | 470 |
| 1306 | 1328 | AGTACCCACGTAAAGACGTTAGG | 48 | AGTACCCACGTAAAGACGTT | 471 |
| 1312 | 1334 | CACGTAAAGACGTTAGGTCAAGG | 49 | CACGTAAAGACGTTAGGTCA | 472 |
| 1326 | 1348 | AGGTCAAGGTGTAGCCCATGAGG | 50 | AGGTCAAGGTGTAGCCCATG | 473 |
| 1329 | 1351 | TCAAGGTGTAGCCCATGAGGTGG | 51 | TCAAGGTGTAGCCCATGAGG | 474 |
| 1339 | 1361 | GCCCATGAGGTGGCAAGAAATGG | 52 | GCCCATGAGGTGGCAAGAAA | 475 |
| 1340 | 1362 | CCCATGAGGTGGCAAGAAATGGG | 53 | CCCATGAGGTGGCAAGAAAT | 476 |
| 1389 | 1411 | GATAGCCCTTATGAAACTTAAGG | 54 | GATAGCCCTTATGAAACTTA | 477 |
| 1390 | 1412 | ATAGCCCTTATGAAACTTAAGGG | 55 | ATAGCCCTTATGAAACTTAA | 478 |
| 1397 | 1419 | TTATGAAACTTAAGGGTCGAAGG | 56 | TTATGAAACTTAAGGGTCGA | 479 |
| 1400 | 1422 | TGAAACTTAAGGGTCGAAGGTGG | 57 | TGAAACTTAAGGGTCGAAGG | 480 |
| 1441 | 1463 | AGTAGAGTGCTTAGTTGAACAGG | 58 | AGTAGAGTGCTTAGTTGAAC | 481 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 1442 | 1464 | GTAGAGTGCTTAGTTGAACAGGG | 59 | GTAGAGTGCTTAGTTGAACA | 482 |
| 1494 | 1516 | CCTCCTCAAGTATACTTCAAAGG | 60 | CCTCCTCAAGTATACTTCAA | 483 |
| 1530 | 1552 | ACCCCTACGCATTTATATAGAGG | 61 | ACCCCTACGCATTTATATAG | 484 |
| 1548 | 1570 | AGAGGAGACAAGTCGTAACATGG | 62 | AGAGGAGACAAGTCGTAACA | 485 |
| 1560 | 1582 | TCGTAACATGGTAAGTGTACTGG | 63 | TCGTAACATGGTAAGTGTAC | 486 |
| 1573 | 1595 | AGTGTACTGGAAAGTGCACTTGG | 64 | AGTGTACTGGAAAGTGCACT | 487 |
| 1620 | 1642 | AAAGCACCCAACTTACACTTAGG | 65 | AAAGCACCCAACTTACACTT | 488 |
| 1726 | 1748 | CATTTACCCAAATAAAGTATAGG | 66 | CATTTACCCAAATAAAGTAT | 489 |
| 1746 | 1768 | AGGCGATAGAAATTGAAACCTGG | 67 | AGGCGATAGAAATTGAAACC | 490 |
| 1770 | 1792 | GCAATAGATATAGTACCGCAAGG | 68 | GCAATAGATATAGTACCGCA | 491 |
| 1771 | 1793 | CAATAGATATAGTACCGCAAGGG | 69 | CAATAGATATAGTACCGCAA | 492 |
| 1809 | 1831 | TAACCAAGCATAATATAGCAAGG | 70 | TAACCAAGCATAATATAGCA | 493 |
| 1862 | 1884 | TAACTAGAAATAACTTTGCAAGG | 71 | TAACTAGAAATAACTTTGCA | 494 |
| 1947 | 1969 | CCGTCTATGTAGCAAAATAGTGG | 72 | CCGTCTATGTAGCAAAATAG | 495 |
| 1948 | 1970 | CGTCTATGTAGCAAAATAGTGGG | 73 | CGTCTATGTAGCAAAATAGT | 496 |
| 1960 | 1982 | AAAATAGTGGGAAGATTTATAGG | 74 | AAAATAGTGGGAAGATTTAT | 497 |
| 1966 | 1988 | GTGGGAAGATTTATAGGTAGAGG | 75 | GTGGGAAGATTTATAGGTAG | 498 |
| 1987 | 2009 | GGCGACAAACCTACCGAGCCTGG | 76 | GGCGACAAACCTACCGAGCC | 499 |
| 1997 | 2019 | CTACCGAGCCTGGTGATAGCTGG | 77 | CTACCGAGCCTGGTGATAGC | 500 |
| 2086 | 2108 | ATTTAACTGTTAGTCCAAAGAGG | 78 | ATTTAACTGTTAGTCCAAAG | 501 |
| 2099 | 2121 | TCCAAAGAGGAACAGCTCTTTGG | 79 | TCCAAAGAGGAACAGCTCTT | 502 |
| 2107 | 2129 | GGAACAGCTCTTTGGACACTAGG | 80 | GGAACAGCTCTTTGGACACT | 503 |
| 2152 | 2174 | AAAAATTTAACACCCATAGTAGG | 81 | AAAAATTTAACACCCATAGT | 504 |
| 2247 | 2269 | CTGAACTCCTCACACCCAATTGG | 82 | CTGAACTCCTCACACCCAAT | 505 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 2414 | 2436 | CCTCACTGTCAACCCAACACAGG | 83 | CCTCACTGTCAACCCAACAC | 506 |
| 2427 | 2449 | CCAACACAGGCATGCTCATAAGG | 84 | CCAACACAGGCATGCTCATA | 507 |
| 2432 | 2454 | ACAGGCATGCTCATAAGAAAGG | 85 | ACAGGCATGCTCATAAGGAA | 508 |
| 2449 | 2471 | GAAAGGTTAAAAAAGTAAAAGG | 86 | GAAAGGTTAAAAAAAGTAAA | 509 |
| 2456 | 2478 | TAAAAAAGTAAAAGGAACTCGG | 87 | TAAAAAAGTAAAAGGAACT | 510 |
| 2515 | 2537 | TCTAGCATCACCAGTATTAGAGG | 88 | TCTAGCATCACCAGTATTAG | 511 |
| 2546 | 2568 | GCCCAGTGACACATGTTTAACGG | 89 | GCCCAGTGACACATGTTTAA | 512 |
| 2552 | 2574 | TGACACATGTTTAACGGCCGCGG | 90 | TGACACATGTTTAACGGCCG | 513 |
| 2571 | 2593 | GCGGTACCCTAACCGTGCAAAGG | 91 | GCGGTACCCTAACCGTGCAA | 514 |
| 2599 | 2621 | TAATCACTTGTTCCTTAAATAGG | 92 | TAATCACTTGTTCCTTAAAT | 515 |
| 2600 | 2622 | AATCACTTGTTCCTTAAATAGGG | 93 | AATCACTTGTTCCTTAAATA | 516 |
| 2614 | 2636 | TAAATAGGGACCTGTATGAATGG | 94 | TAAATAGGGACCTGTATGAA | 517 |
| 2624 | 2646 | CCTGTATGAATGGCTCCACGAGG | 95 | CCTGTATGAATGGCTCCACG | 518 |
| 2625 | 2647 | CTGTATGAATGGCTCCACGAGGG | 96 | CTGTATGAATGGCTCCACGA | 519 |
| 2676 | 2698 | AAATTGACCTGCCCGTGAAGAGG | 97 | AAATTGACCTGCCCGTGAAG | 520 |
| 2679 | 2701 | TTGACCTGCCCGTGAAGAGGCGG | 98 | TTGACCTGCCCGTGAAGAGG | 521 |
| 2680 | 2702 | TGACCTGCCCGTGAAGAGGCGGG | 99 | TGACCTGCCCGTGAAGAGGC | 522 |
| 2711 | 2733 | AGCAAGACGAGAAGACCCTATGG | 100 | AGCAAGACGAGAAGACCCTA | 523 |
| 2755 | 2777 | ACAGTACCTAACAAACCCACAGG | 101 | ACAGTACCTAACAAACCCAC | 524 |
| 2789 | 2811 | CAAACCTGCATTAAAAATTTCGG | 102 | CAAACCTGCATTAAAAATTT | 525 |
| 2793 | 2815 | CCTGCATTAAAAATTTCGGTTGG | 103 | CCTGCATTAAAAATTTCGGT | 526 |
| 2794 | 2816 | CTGCATTAAAAATTTCGGTTGGG | 104 | CTGCATTAAAAATTTCGGTT | 527 |
| 2795 | 2817 | TGCATTAAAAATTTCGGTTGGGG | 105 | TGCATTAAAAATTTCGGTTG | 528 |
| 2804 | 2826 | AATTTCGGTTGGGGCGACCTCGG | 106 | AATTTCGGTTGGGGCGACCT | 529 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 2895 | 2917 | TGATCCAATAACTTGACCAACGG | 107 | TGATCCAATAACTTGACCAA | 530 |
| 2911 | 2933 | CCAACGGAACAAGTTACCCTAGG | 108 | CCAACGGAACAAGTTACCCT | 531 |
| 2912 | 2934 | CAACGGAACAAGTTACCCTAGGG | 109 | CAACGGAACAAGTTACCCTA | 532 |
| 2954 | 2976 | CTAGAGTCCATATCAACAATAGG | 110 | CTAGAGTCCATATCAACAAT | 533 |
| 2955 | 2977 | TAGAGTCCATATCAACAATAGGG | 111 | TAGAGTCCATATCAACAATA | 534 |
| 2974 | 2996 | AGGGTTTACGACCTCGATGTTGG | 112 | AGGGTTTACGACCTCGATGT | 535 |
| 2980 | 3002 | TACGACCTCGATGTTGGATCAGG | 113 | TACGACCTCGATGTTGGATC | 536 |
| 2992 | 3014 | GTTGGATCAGGACATCCCGATGG | 114 | GTTGGATCAGGACATCCCGA | 537 |
| 3010 | 3032 | GATGGTGCAGCCGCTATTAAAGG | 115 | GATGGTGCAGCCGCTATTAA | 538 |
| 3058 | 3080 | TACGTGATCTGAGTTCAGACCGG | 116 | TACGTGATCTGAGTTCAGAC | 539 |
| 3069 | 3091 | AGTTCAGACCGGAGTAATCCAGG | 117 | AGTTCAGACCGGAGTAATCC | 540 |
| 3073 | 3095 | CAGACCGGAGTAATCCAGGTCGG | 118 | CAGACCGGAGTAATCCAGGT | 541 |
| 3110 | 3132 | CAAATTCCTCCCTGTACGAAAGG | 119 | CAAATTCCTCCCTGTACGAA | 542 |
| 3125 | 3147 | ACGAAAGGACAAGAGAAATAAGG | 120 | ACGAAAGGACAAGAGAAATA | 543 |
| 3203 | 3225 | ACCCACACCCACCCAAGAACAGG | 121 | ACCCACACCCACCCAAGAAC | 544 |
| 3204 | 3226 | CCCACACCCACCCAAGAACAGGG | 122 | CCCACACCCACCCAAGAACA | 545 |
| 3217 | 3239 | AAGAACAGGGTTTGTTAAGATGG | 123 | AAGAACAGGGTTTGTTAAGA | 546 |
| 3227 | 3249 | TTTGTTAAGATGGCAGAGCCCGG | 124 | TTTGTTAAGATGGCAGAGCC | 547 |
| 3262 | 3284 | ACTTAAAACTTTACAGTCAGAGG | 125 | ACTTAAAACTTTACAGTCAG | 548 |
| 3294 | 3316 | TCTTCTTAACAACATACCCATGG | 126 | TCTTCTTAACAACATACCCA | 549 |
| 3336 | 3358 | TGTACCCATTCTAATCGCAATGG | 127 | TGTACCCATTCTAATCGCAA | 550 |
| 3370 | 3392 | CTTACCGAACGAAAAATTCTAGG | 128 | CTTACCGAACGAAAAATTCT | 551 |
| 3391 | 3413 | GGCTATATACAACTACGCAAAGG | 129 | GGCTATATACAACTACGCAA | 552 |
| 3406 | 3428 | CGCAAAGGCCCCAACGTTGTAGG | 130 | CGCAAAGGCCCCAACGTTGT | 553 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 3415 | 3437 | CCCAACGTTGTAGGCCCCTACGG | 131 | CCCAACGTTGTAGGCCCCTA | 554 |
| 3416 | 3438 | CCAACGTTGTAGGCCCCTACGGG | 132 | CCAACGTTGTAGGCCCCTAC | 555 |
| 3570 | 3592 | CCTCCCCATACCCAACCCCTGG | 133 | CCTCCCCATACCCAACCCCC | 556 |
| 3586 | 3608 | CCCCTGGTCAACCTCAACCTAGG | 134 | CCCCTGGTCAACCTCAACCT | 557 |
| 3643 | 3665 | GTTTACTCAATCCTCTGATCAGG | 135 | GTTTACTCAATCCTCTGATC | 558 |
| 3644 | 3666 | TTTACTCAATCCTCTGATCAGGG | 136 | TTTACTCAATCCTCTGATCA | 559 |
| 3676 | 3698 | AACTCAAACTACGCCCTGATCGG | 137 | AACTCAAACTACGCCCTGAT | 560 |
| 3757 | 3779 | CTATCAACATTACTAATAAGTGG | 138 | CTATCAACATTACTAATAAG | 561 |
| 3828 | 3850 | ACTCCTGCCATCATGACCCTTGG | 139 | ACTCCTGCCATCATGACCCT | 562 |
| 3892 | 3914 | ACCCCCTTCGACCTTGCCGAAGG | 140 | ACCCCCTTCGACCTTGCCGA | 563 |
| 3893 | 3915 | CCCCCTTCGACCTTGCCGAAGGG | 141 | CCCCCTTCGACCTTGCCGAA | 564 |
| 3894 | 3916 | CCCCTTCGACCTTGCCGAAGGGG | 142 | CCCCTTCGACCTTGCCGAAG | 565 |
| 3913 | 3935 | GGGGAGTCCGAACTAGTCTCAGG | 143 | GGGGAGTCCGAACTAGTCTC | 566 |
| 3937 | 3959 | TTCAACATCGAATACGCCGCAGG | 144 | TTCAACATCGAATACGCCGC | 567 |
| 4015 | 4037 | CTCACCACTACAATCTTCCTAGG | 145 | CTCACCACTACAATCTTCCT | 568 |
| 4287 | 4309 | ACTTTGATAGAGTAAATAATAGG | 146 | ACTTTGATAGAGTAAATAAT | 569 |
| 4311 | 4333 | GCTTAAACCCCCTTATTCTAGG | 147 | GCTTAAACCCCCTTATTTCT | 570 |
| 4386 | 4408 | TCACACCCCATCCTAAAGTAAGG | 148 | TCACACCCCATCCTAAAGTA | 571 |
| 4406 | 4428 | AGGTCAGCTAAATAAGCTATCGG | 149 | AGGTCAGCTAAATAAGCTAT | 572 |
| 4407 | 4429 | GGTCAGCTAAATAAGCTATCGGG | 150 | GGTCAGCTAAATAAGCTATC | 573 |
| 4428 | 4450 | GGCCCATACCCCGAAAATGTTGG | 151 | GGCCCATACCCCGAAAATGT | 574 |
| 4460 | 4482 | TCCCGTACTAATTAATCCCTGG | 152 | TCCCGTACTAATTAATCCCC | 575 |
| 4494 | 4516 | ATCTACTCTACCATCTTTGCAGG | 153 | ATCTACTCTACCATCTTTGC | 576 |
| 4542 | 4564 | CACTGATTTTTTACCTGAGTAGG | 154 | CACTGATTTTTTACCTGAGT | 577 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 4692 | 4714 | CTCTTCAACAATATACTCTCCGG | 155 | CTCTTCAACAATATACTCTC | 578 |
| 4767 | 4789 | ATAGCTATAGCAATAAAACTAGG | 156 | ATAGCTATAGCAATAAAACT | 579 |
| 4799 | 4821 | CTTTCACTTCTGAGTCCCAGAGG | 157 | CTTTCACTTCTGAGTCCCAG | 580 |
| 4809 | 4831 | TGAGTCCCAGAGGTTACCCAAGG | 158 | TGAGTCCCAGAGGTTACCCA | 581 |
| 4827 | 4849 | CAAGGCACCCCTCTGACATCCGG | 159 | CAAGGCACCCCTCTGACATC | 582 |
| 4941 | 4963 | TCAATCTTATCCATCATAGCAGG | 160 | TCAATCTTATCCATCATAGC | 583 |
| 4950 | 4972 | TCCATCATAGCAGGCAGTTGAGG | 161 | TCCATCATAGCAGGCAGTTG | 584 |
| 4953 | 4975 | ATCATAGCAGGCAGTTGAGGTGG | 162 | ATCATAGCAGGCAGTTGAGG | 585 |
| 5010 | 5032 | TACTCCTCAATTACCCACATAGG | 163 | TACTCCTCAATTACCCACAT | 586 |
| 5202 | 5224 | CCATCCACCCTCCTCTCCCTAGG | 164 | CCATCCACCCTCCTCTCCCT | 587 |
| 5205 | 5227 | TCCACCCTCCTCTCCCTAGGAGG | 165 | TCCACCCTCCTCTCCCTAGG | 588 |
| 5223 | 5245 | GGAGGCCTGCCCCCGCTAACCGG | 166 | GGAGGCCTGCCCCCGCTAAC | 589 |
| 5239 | 5261 | TAACCGGCTTTTTGCCCAAATGG | 167 | TAACCGGCTTTTTGCCCAAA | 590 |
| 5240 | 5262 | AACCGGCTTTTTGCCCAATGGG | 168 | AACCGGCTTTTTGCCCAAAT | 591 |
| 5500 | 5522 | TAATAATCTTATAGAAATTTAGG | 169 | TAATAATCTTATAGAAATTT | 592 |
| 5569 | 5591 | CTTAATTTCTGTAACAGCTAAGG | 170 | CTTAATTTCTGTAACAGCTA | 593 |
| 5646 | 5668 | CTAAGCCCTTACTAGACCAATGG | 171 | CTAAGCCCTTACTAGACCAA | 594 |
| 5647 | 5669 | TAAGCCCTTACTAGACCAATGGG | 172 | TAAGCCCTTACTAGACCAAT | 595 |
| 5697 | 5719 | AGCTAAGCACCCTAATCAACTGG | 173 | AGCTAAGCACCCTAATCAAC | 596 |
| 5723 | 5745 | CAATCTACTTCTCCCGCCGCCGG | 174 | CAATCTACTTCTCCCGCCGC | 597 |
| 5724 | 5746 | AATCTACTTCTCCCGCCGCCGGG | 175 | AATCTACTTCTCCCGCCGCC | 598 |
| 5732 | 5754 | TCTCCCGCCGCCGGGAAAAAAGG | 176 | TCTCCCGCCGCCGGGAAAA | 599 |
| 5735 | 5757 | CCCGCCGCCGGGAAAAAAGGCGG | 177 | CCCGCCGCCGGGAAAAAAGG | 600 |
| 5736 | 5758 | CCGCCGCCGGGAAAAAAGGCGGG | 178 | CCGCCGCCGGGAAAAAAGGC | 601 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 5747 | 5769 | AAAAAAGGCGGGAGAAGCCCCGG | 179 | AAAAAAGGCGGGAGAAGCCC | 602 |
| 5751 | 5773 | AAGGCGGGAGAAGCCCCGGCAGG | 180 | AAGGCGGGAGAAGCCCCGGC | 603 |
| 5800 | 5822 | ATTCAATATGAAAATCACCTCGG | 181 | ATTCAATATGAAAATCACCT | 604 |
| 5806 | 5828 | TATGAAAATCACCTCGGAGCTGG | 182 | TATGAAAATCACCTCGGAGC | 605 |
| 5816 | 5838 | ACCTCGGAGCTGGTAAAAGAGG | 183 | ACCTCGGAGCTGGTAAAAAG | 606 |
| 5928 | 5950 | TCTACAAACCACAAAGACATTGG | 184 | TCTACAAACCACAAAGACAT | 607 |
| 5949 | 5971 | GGAACACTATACCTATTATTCGG | 185 | GGAACACTATACCTATTATT | 608 |
| 5961 | 5983 | CTATTATTCGGCGCATGAGCTGG | 186 | CTATTATTCGGCGCATGAGC | 609 |
| 5970 | 5992 | GGCGCATGAGCTGGAGTCCTAGG | 187 | GGCGCATGAGCTGGAGTCCT | 610 |
| 6005 | 6027 | CCTCCTTATTCGAGCCGAGCTGG | 188 | CCTCCTTATTCGAGCCGAGC | 611 |
| 6006 | 6028 | CTCCTTATTCGAGCCGAGCTGGG | 189 | CTCCTTATTCGAGCCGAGCT | 612 |
| 6027 | 6049 | GGCCAGCCAGGCAACCTTCTAGG | 190 | GGCCAGCCAGGCAACCTTCT | 613 |
| 6108 | 6130 | ATAGTAATACCCATCATAATCGG | 191 | ATAGTAATACCCATCATAAT | 614 |
| 6111 | 6133 | GTAATACCCATCATAATCGGAGG | 192 | GTAATACCCATCATAATCGG | 615 |
| 6117 | 6139 | CCCATCATAATCGGAGGCTTTGG | 193 | CCCATCATAATCGGAGGCTT | 616 |
| 6144 | 6166 | TGACTAGTTCCCCTAATAATCGG | 194 | TGACTAGTTCCCCTAATAAT | 617 |
| 6158 | 6180 | AATAATCGGTGCCCCGATATGG | 195 | AATAATCGGTGCCCCCGATA | 618 |
| 6236 | 6258 | CCTGCTCGCATCTGCTATAGTGG | 196 | CCTGCTCGCATCTGCTATAG | 619 |
| 6239 | 6261 | GCTCGCATCTGCTATAGTGGAGG | 197 | GCTCGCATCTGCTATAGTGG | 620 |
| 6243 | 6265 | GCATCTGCTATAGTGGAGGCCGG | 198 | GCATCTGCTATAGTGGAGGC | 621 |
| 6249 | 6271 | GCTATAGTGGAGGCCGGAGCAGG | 199 | GCTATAGTGGAGGCCGGAGC | 622 |
| 6255 | 6277 | GTGGAGGCCGGAGCAGGAACAGG | 200 | GTGGAGGCCGGAGCAGGAAC | 623 |
| 6282 | 6304 | ACAGTCTACCCTCCCTTAGCAGG | 201 | ACAGTCTACCCTCCCTTAGC | 624 |
| 6283 | 6305 | CAGTCTACCCTCCCTTAGCAGGG | 202 | CAGTCTACCCTCCCTTAGCA | 625 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 6300 | 6322 | GCAGGGAACTACTCCCACCCTGG | 203 | GCAGGGAACTACTCCCACCC | 626 |
| 6342 | 6364 | ATCTTCTCCTTACACCTAGCAGG | 204 | ATCTTCTCCTTACACCTAGC | 627 |
| 6360 | 6382 | GCAGGTGTCTCCTCTATCTTAGG | 205 | GCAGGTGTCTCCTCTATCTT | 628 |
| 6361 | 6383 | CAGGTGTCTCCTCTATCTTAGGG | 206 | CAGGTGTCTCCTCTATCTTA | 629 |
| 6362 | 6384 | AGGTGTCTCCTCTATCTTAGGGG | 207 | AGGTGTCTCCTCTATCTTAG | 630 |
| 6495 | 6517 | TCTCTCCCAGTCCTAGCTGCTGG | 208 | TCTCTCCCAGTCCTAGCTGC | 631 |
| 6552 | 6574 | ACCACCTTCTTCGACCCCGCCGG | 209 | ACCACCTTCTTCGACCCCGC | 632 |
| 6555 | 6577 | ACCTTCTTCGACCCCGCCGGAGG | 210 | ACCTTCTTCGACCCCGCCGG | 633 |
| 6558 | 6580 | TTCTTCGACCCCGCCGGAGGAGG | 211 | TTCTTCGACCCCGCCGGAGG | 634 |
| 6597 | 6619 | CAACACCTATTCTGATTTTTCGG | 212 | CAACACCTATTCTGATTTTT | 635 |
| 6630 | 6652 | GTTTATATTCTTATCCTACCAGG | 213 | GTTTATATTCTTATCCTACC | 636 |
| 6636 | 6658 | ATTCTTATCCTACCAGGCTTCGG | 214 | ATTCTTATCCTACCAGGCTT | 637 |
| 6669 | 6691 | CATATTGTAACTTACTACTCCGG | 215 | CATATTGTAACTTACTACTC | 638 |
| 6687 | 6709 | TCCGGAAAAAAGAACCATTTGG | 216 | TCCGGAAAAAAGAACCATT | 639 |
| 6696 | 6718 | AAAGAACCATTTGGATACATAGG | 217 | AAAGAACCATTTGGATACAT | 640 |
| 6701 | 6723 | ACCATTTGGATACATAGGTATGG | 218 | ACCATTTGGATACATAGGTA | 641 |
| 6723 | 6745 | GTCTGAGCTATGATATCAATTGG | 219 | GTCTGAGCTATGATATCAAT | 642 |
| 6732 | 6754 | ATGATATCAATTGGCTTCCTAGG | 220 | ATGATATCAATTGGCTTCCT | 643 |
| 6733 | 6755 | TGATATCAATTGGCTTCCTAGGG | 221 | TGATATCAATTGGCTTCCTA | 644 |
| 6768 | 6790 | GCACACCATATATTTACAGTAGG | 222 | GCACACCATATATTTACAGT | 645 |
| 6831 | 6853 | ATAATCATCGCTATCCCCACCGG | 223 | ATAATCATCGCTATCCCCAC | 646 |
| 6867 | 6889 | AGCTGACTCGCCACACTCCACGG | 224 | AGCTGACTCGCCACACTCCA | 647 |
| 6909 | 6931 | GCTGCAGTGCTCTGAGCCCTAGG | 225 | GCTGCAGTGCTCTGAGCCCT | 648 |
| 6933 | 6955 | TTCATCTTTCTTTTCACCGTAGG | 226 | TTCATCTTTCTTTTCACCGT | 649 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 6936 | 6958 | ATCTTTCTTTTCACCGTAGGTGG | 227 | ATCTTTCTTTTCACCGTAGG | 650 |
| 6945 | 6967 | TTCACCGTAGGTGGCCTGACTGG | 228 | TTCACCGTAGGTGGCCTGAC | 651 |
| 7032 | 7054 | TTCCACTATGTCCTATCAATAGG | 229 | TTCCACTATGTCCTATCAAT | 652 |
| 7053 | 7075 | GGAGCTGTATTTGCCATCATAGG | 230 | GGAGCTGTATTTGCCATCAT | 653 |
| 7056 | 7078 | GCTGTATTTGCCATCATAGGAGG | 231 | GCTGTATTTGCCATCATAGG | 654 |
| 7086 | 7108 | CACTGATTTCCCCTATTCTCAGG | 232 | CACTGATTTCCCCTATTCTC | 655 |
| 7140 | 7162 | CATTTCACTATCATATTCATCGG | 233 | CATTTCACTATCATATTCAT | 656 |
| 7176 | 7198 | TTCTTCCCACAACACTTTCTCGG | 234 | TTCTTCCCACAACACTTTCT | 657 |
| 7185 | 7207 | CAACACTTTCTCGGCCTATCCGG | 235 | CAACACTTTCTCGGCCTATC | 658 |
| 7205 | 7227 | CGGAATGCCCCGACGTTACTCGG | 236 | CGGAATGCCCCGACGTTACT | 659 |
| 7251 | 7273 | TGAAACATCCTATCATCTGTAGG | 237 | TGAAACATCCTATCATCTGT | 660 |
| 7358 | 7380 | AGAAGAACCCTCCATAAACCTGG | 238 | AGAAGAACCCTCCATAAACC | 661 |
| 7371 | 7393 | ATAAACCTGGAGTGACTATATGG | 239 | ATAAACCTGGAGTGACTATA | 662 |
| 7432 | 7454 | ACATAAAATCTAGACAAAAAGG | 240 | ACATAAAATCTAGACAAAAA | 663 |
| 7436 | 7458 | AAAATCTAGACAAAAAGGAAGG | 241 | AAAATCTAGACAAAAAGGA | 664 |
| 7457 | 7479 | GGAATCGAACCCCCCAAAGCTGG | 242 | GGAATCGAACCCCCCAAAGC | 665 |
| 7476 | 7498 | CTGGTTTCAAGCCAACCCATGG | 243 | CTGGTTTCAAGCCAACCCCA | 666 |
| 7499 | 7521 | CCTCCATGACTTTTTCAAAAGG | 244 | CCTCCATGACTTTTTCAAAA | 667 |
| 7544 | 7566 | CTTTGTCAAAGTTAAATTATAGG | 245 | CTTTGTCAAAGTTAAATTAT | 668 |
| 7567 | 7589 | CTAAATCCTATATATCTTAATGG | 246 | CTAAATCCTATATATCTTAA | 669 |
| 7586 | 7608 | ATGGCACATGCAGCGCAAGTAGG | 247 | ATGGCACATGCAGCGCAAGT | 670 |
| 7741 | 7763 | TACTAACATCTCAGACGCTCAGG | 248 | TACTAACATCTCAGACGCTC | 671 |
| 7831 | 7853 | CATCCTTTACATAACAGACGAGG | 249 | CATCCTTTACATAACAGACG | 672 |
| 7865 | 7887 | TCCCTTACCATCAAATCAATTGG | 250 | TCCCTTACCATCAAATCAAT | 673 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 7875 | 7897 | TCAAATCAATTGGCCACCAATGG | 251 | TCAAATCAATTGGCCACCAA | 674 |
| 7904 | 7926 | ACCTACGAGTACACCGACTACGG | 252 | ACCTACGAGTACACCGACTA | 675 |
| 7907 | 7929 | TACGAGTACACCGACTACGGCGG | 253 | TACGAGTACACCGACTACGG | 676 |
| 7955 | 7977 | CCCCCATTATTCCTAGAACCAGG | 254 | CCCCCATTATTCCTAGAACC | 677 |
| 8069 | 8091 | TCATGAGCTGTCCCCACATTAGG | 255 | TCATGAGCTGTCCCCACATT | 678 |
| 8093 | 8115 | TTAAAAACAGATGCAATTCCCGG | 256 | TTAAAAACAGATGCAATTCC | 679 |
| 8131 | 8153 | CACTTTCACCGCTACACGACCGG | 257 | CACTTTCACCGCTACACGAC | 680 |
| 8132 | 8154 | ACTTTCACCGCTACACGACCGGG | 258 | ACTTTCACCGCTACACGACC | 681 |
| 8133 | 8155 | CTTTCACCGCTACACGACCGGGG | 259 | CTTTCACCGCTACACGACCG | 682 |
| 8134 | 8156 | TTTCACCGCTACACGACCGGGGG | 260 | TTTCACCGCTACACGACCGG | 683 |
| 8144 | 8166 | ACACGACCGGGGGTATACTACGG | 261 | ACACGACCGGGGGTATACTA | 684 |
| 8165 | 8187 | GGTCAATGCTCTGAAATCTGTGG | 262 | GGTCAATGCTCTGAAATCTG | 685 |
| 8228 | 8250 | CCCCTAAAAATCTTTGAAATAGG | 263 | CCCCTAAAAATCTTTGAAAT | 686 |
| 8229 | 8251 | CCCTAAAAATCTTTGAAATAGGG | 264 | CCCTAAAAATCTTTGAAATA | 687 |
| 8370 | 8392 | CCCAACTAAATACTACCGTATGG | 265 | CCCAACTAAATACTACCGTA | 688 |
| 8551 | 8573 | TTCATTGCCCCCACAATCCTAGG | 266 | TTCATTGCCCCCACAATCCT | 689 |
| 8698 | 8720 | ATAACCATACACAACACTAAAGG | 267 | ATAACCATACACAACACTAA | 690 |
| 8761 | 8783 | ATTGCCACAACTAACCTCCTCGG | 268 | ATTGCCACAACTAACCTCCT | 691 |
| 8817 | 8839 | ACTATCTATAAACCTAGCCATGG | 269 | ACTATCTATAAACCTAGCCA | 692 |
| 8835 | 8857 | CATGGCCATCCCCTTATGAGCGG | 270 | CATGGCCATCCCCTTATGAG | 693 |
| 8836 | 8858 | ATGGCCATCCCCTTATGAGCGGG | 271 | ATGGCCATCCCCTTATGAGC | 694 |
| 8851 | 8873 | TGAGCGGGCACAGTGATTATAGG | 272 | TGAGCGGGCACAGTGATTAT | 695 |
| 8899 | 8921 | CTAGCCCACTTCTTACCACAAGG | 273 | CTAGCCCACTTCTTACCACA | 696 |
| 8973 | 8995 | ACTCATTCAACCAATAGCCCTGG | 274 | ACTCATTCAACCAATAGCCC | 697 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 9004 | 9026 | CTAACCGCTAACATTACTGCAGG | 275 | CTAACCGCTAACATTACTGC | 698 |
| 9028 | 9050 | CACCTACTCATGCACCTAATTGG | 276 | CACCTACTCATGCACCTAAT | 699 |
| 9243 | 9265 | CCCAGCCCATGACCCCTAACAGG | 277 | CCCAGCCCATGACCCCTAAC | 700 |
| 9244 | 9266 | CCAGCCCATGACCCCTACAGGG | 278 | CCAGCCCATGACCCCTAACA | 701 |
| 9245 | 9267 | CAGCCCATGACCCCTAACAGGGG | 279 | CAGCCCATGACCCCTAACAG | 702 |
| 9273 | 9295 | TCAGCCCTCCTAATGACCTCCGG | 280 | TCAGCCCTCCTAATGACCTC | 703 |
| 9321 | 9343 | TCCATAACGCTCCTCATACTAGG | 281 | TCCATAACGCTCCTCATACT | 704 |
| 9358 | 9380 | CACTAACCATATACCAATGATGG | 282 | CACTAACCATATACCAATGA | 705 |
| 9390 | 9412 | ACACGAGAAAGCACATACCAAGG | 283 | ACACGAGAAAGCACATACCA | 706 |
| 9417 | 9439 | CACACACCACCTGTCCAAAAAGG | 284 | CACACACCACCTGTCCAAAA | 707 |
| 9429 | 9451 | GTCCAAAAAGGCCTTCGATACGG | 285 | GTCCAAAAAGGCCTTCGATA | 708 |
| 9430 | 9452 | TCCAAAAAGGCCTTCGATACGGG | 286 | TCCAAAAAGGCCTTCGATAC | 709 |
| 9471 | 9493 | TCAGAAGTTTTTTTCTTCGCAGG | 287 | TCAGAAGTTTTTTTCTTCGC | 710 |
| 9522 | 9544 | CTAGCCCCTACCCCCCAATTAGG | 288 | CTAGCCCCTACCCCCCAATT | 711 |
| 9525 | 9547 | GCCCCTACCCCCCAATTAGGAGG | 289 | GCCCCTACCCCCCAATTAGG | 712 |
| 9526 | 9548 | CCCCTACCCCCCAATTAGGAGGG | 290 | CCCCTACCCCCCAATTAGGA | 713 |
| 9532 | 9554 | CCCCCCAATTAGGAGGGCACTGG | 291 | CCCCCCAATTAGGAGGGCAC | 714 |
| 9543 | 9565 | GGAGGGCACTGGCCCCCAACAGG | 292 | GGAGGGCACTGGCCCCCAAC | 715 |
| 9606 | 9628 | ACATCCGTATTACTCGCATCAGG | 293 | ACATCCGTATTACTCGCATC | 716 |
| 9692 | 9714 | ACTGCTTATTACAATTTTACTGG | 294 | ACTGCTTATTACAATTTTAC | 717 |
| 9693 | 9715 | CTGCTTATTACAATTTTACTGGG | 295 | CTGCTTATTACAATTTTACT | 718 |
| 9756 | 9778 | TCTCCCTTCACCATTTCCGACGG | 296 | TCTCCCTTCACCATTTCCGA | 719 |
| 9765 | 9787 | ACCATTTCCGACGGCATCTACGG | 297 | ACCATTTCCGACGGCATCTA | 720 |
| 9789 | 9811 | TCAACATTTTTTGTAGCCACAGG | 298 | TCAACATTTTTTGTAGCCAC | 721 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 9798 | 9820 | TTTGTAGCCACAGGCTTCCACGG | 299 | TTTGTAGCCACAGGCTTCCA | 722 |
| 9816 | 9838 | CACGGACTTCACGTCATTATTGG | 300 | CACGGACTTCACGTCATTAT | 723 |
| 9885 | 9907 | TTTACATCCAAACATCACTTTGG | 301 | TTTACATCCAAACATCACTT | 724 |
| 9910 | 9932 | TCGAAGCCGCCGCCTGATACTGG | 302 | TCGAAGCCGCCGCCTGATAC | 725 |
| 9926 | 9948 | ATACTGGCATTTTGTAGATGTGG | 303 | ATACTGGCATTTTGTAGATG | 726 |
| 9963 | 9985 | TATGTCTCCATCTATTGATGAGG | 304 | TATGTCTCCATCTATTGATG | 727 |
| 9964 | 9986 | ATGTCTCCATCTATTGATGAGGG | 305 | ATGTCTCCATCTATTGATGA | 728 |
| 10122 | 10144 | TTTTGACTACCACAACTCAACGG | 306 | TTTTGACTACCACAACTCAA | 729 |
| 10155 | 10177 | AAATCCACCCCTTACGAGTGCGG | 307 | AAATCCACCCCTTACGAGTG | 730 |
| 10343 | 10365 | CATCATCCTAGCCCTAAGTCTGG | 308 | CATCATCCTAGCCCTAAGTC | 731 |
| 10365 | 10387 | GCCTATGAGTGACTACAAAAAGG | 309 | GCCTATGAGTGACTACAAAA | 732 |
| 10385 | 10407 | AGGATTAGACTGAACCGAATTGG | 310 | AGGATTAGACTGAACCGAAT | 733 |
| 10500 | 10522 | GCATTTACCATCTCACTTCTAGG | 311 | GCATTTACCATCTCACTTCT | 734 |
| 10551 | 10573 | TCCTCCCTACTATGCCTAGAAGG | 312 | TCCTCCCTACTATGCCTAGA | 735 |
| 10664 | 10686 | CTTTGCCGCCTGCGAAGCAGCGG | 313 | CTTTGCCGCCTGCGAAGCAG | 736 |
| 10667 | 10689 | TGCCGCCTGCGAAGCAGCGGTGG | 314 | TGCCGCCTGCGAAGCAGCGG | 737 |
| 10668 | 10690 | GCCGCCTGCGAAGCAGCGGTGGG | 315 | GCCGCCTGCGAAGCAGCGGT | 738 |
| 10704 | 10726 | GTCTCAATCTCCAACACATATGG | 316 | GTCTCAATCTCCAACACATA | 739 |
| 10972 | 10994 | ACTCCTACCCCTCACAATCATGG | 317 | ACTCCTACCCCTCACAATCA | 740 |
| 11128 | 11150 | AACCACACTTATCCCACCTTGG | 318 | AACCACACTTATCCCCACCT | 741 |
| 11147 | 11169 | TTGGCTATCATCACCCGATGAGG | 319 | TTGGCTATCATCACCCGATG | 742 |
| 11174 | 11196 | CAGCCAGAACGCCTGAACGCAGG | 320 | CAGCCAGAACGCCTGAACGC | 743 |
| 11204 | 11226 | TTCCTATTCTACACCCTAGTAGG | 321 | TTCCTATTCTACACCCTAGT | 744 |
| 11252 | 11274 | ATTTACACTCACAACACCCTAGG | 322 | ATTTACACTCACAACACCCT | 745 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 11369 | 11391 | ATAGTAAAGATACCTCTTTACGG | 323 | ATAGTAAAGATACCTCTTTA | 746 |
| 11417 | 11439 | CATGTCGAAGCCCCCATCGCTGG | 324 | CATGTCGAAGCCCCCATCGC | 747 |
| 11418 | 11440 | ATGTCGAAGCCCCCATCGCTGGG | 325 | ATGTCGAAGCCCCCATCGCT | 748 |
| 11453 | 11475 | GCCGCAGTACTCTTAAAACTAGG | 326 | GCCGCAGTACTCTTAAAACT | 749 |
| 11456 | 11478 | GCAGTACTCTTAAAACTAGGCGG | 327 | GCAGTACTCTTAAAACTAGG | 750 |
| 11462 | 11484 | CTCTTAAAACTAGGCGGCTATGG | 328 | CTCTTAAAACTAGGCGGCTA | 751 |
| 11540 | 11562 | TTCCTTGTACTATCCCTATGAGG | 329 | TTCCTTGTACTATCCCTATG | 752 |
| 11669 | 11691 | CAAACCCCTGAAGCTTCACCGG | 330 | CAAACCCCTGAAGCTTCAC | 753 |
| 11696 | 11718 | GTCATTCTCATAATCGCCACGG | 331 | GTCATTCTCATAATCGCCCA | 754 |
| 11697 | 11719 | TCATTCTCATAATCGCCCACGGG | 332 | TCATTCTCATAATCGCCCAC | 755 |
| 11777 | 11799 | CGCATCATAATCCTCTCTCAAGG | 333 | CGCATCATAATCCTCTCTCA | 756 |
| 11866 | 11888 | ACCCCCCACTATTAACCTACTGG | 334 | ACCCCCCACTATTAACCTAC | 757 |
| 11867 | 11889 | CCCCCCACTATTAACCTACTGGG | 335 | CCCCCCACTATTAACCTACT | 758 |
| 11927 | 11949 | AATATCACTCTCCTACTTACAGG | 336 | AATATCACTCTCCTACTTAC | 759 |
| 11985 | 12007 | ACATATTTACCACAACACAATGG | 337 | ACATATTTACCACAACACAA | 760 |
| 11986 | 12008 | CATATTTACCACAACACAATGGG | 338 | CATATTTACCACAACACAAT | 761 |
| 11987 | 12009 | ATATTTACCACAACACAATGGGG | 339 | ATATTTACCACAACACAATG | 762 |
| 12104 | 12126 | CTCAACCCCGACATCATTACCGG | 340 | CTCAACCCCGACATCATTAC | 763 |
| 12105 | 12127 | TCAACCCCGACATCATTACCGGG | 341 | TCAACCCCGACATCATTACC | 764 |
| 12164 | 12186 | GATTGTGAATCTGACAACAGAGG | 342 | GATTGTGAATCTGACAACAG | 765 |
| 12235 | 12257 | TGCCCCCATGTCTAACAACATGG | 343 | TGCCCCCATGTCTAACAACA | 766 |
| 12254 | 12276 | ATGGCTTTCTCAACTTTTAAAGG | 344 | ATGGCTTTCTCAACTTTTAA | 767 |
| 12272 | 12294 | AAAGGATAACAGCTATCCATTGG | 345 | AAAGGATAACAGCTATCCAT | 768 |
| 12279 | 12301 | AACAGCTATCCATTGGTCTTAGG | 346 | AACAGCTATCCATTGGTCTT | 769 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 12294 | 12316 | GTCTTAGGCCCCAAAAATTTTGG | 347 | GTCTTAGGCCCCAAAAATTT | 770 |
| 12608 | 12630 | CTGTAGCATTGTTCGTTACATGG | 348 | CTGTAGCATTGTTCGTTACA | 771 |
| 12742 | 12764 | AACCTATTCCAACTGTTCATCGG | 349 | AACCTATTCCAACTGTTCAT | 772 |
| 12750 | 12772 | CCAACTGTTCATCGGCTGAGAGG | 350 | CCAACTGTTCATCGGCTGAG | 773 |
| 12751 | 12773 | CAACTGTTCATCGGCTGAGAGGG | 351 | CAACTGTTCATCGGCTGAGA | 774 |
| 12757 | 12779 | TTCATCGGCTGAGAGGGCGTAGG | 352 | TTCATCGGCTGAGAGGGCGT | 775 |
| 12847 | 12869 | GCAATCCTATACAACCGTATCGG | 353 | GCAATCCTATACAACCGTAT | 776 |
| 12856 | 12878 | TACAACCGTATCGGCGATATCGG | 354 | TACAACCGTATCGGCGATAT | 777 |
| 12958 | 12980 | CCAAGCCTCACCCCACTACTAGG | 355 | CCAAGCCTCACCCCACTACT | 778 |
| 12979 | 13001 | GGCCTCCTCCTAGCAGCAGCAGG | 356 | GGCCTCCTCCTAGCAGCAGC | 779 |
| 12997 | 13019 | GCAGGCAAATCAGCCCAATTAGG | 357 | GCAGGCAAATCAGCCCAATT | 780 |
| 13030 | 13052 | TGACTCCCCTCAGCCATAGAAGG | 358 | TGACTCCCCTCAGCCATAGA | 781 |
| 13081 | 13103 | TCAAGCACTATAGTTGTAGCAGG | 359 | TCAAGCACTATAGTTGTAGC | 782 |
| 13156 | 13178 | CAAACTCTAACACTATGCTTAGG | 360 | CAAACTCTAACACTATGCTT | 783 |
| 13246 | 13268 | TTCTCCACTTCAAGTCAACTAGG | 361 | TTCTCCACTTCAAGTCAACT | 784 |
| 13267 | 13289 | GGACTCATAATAGTTACAATCGG | 362 | GGACTCATAATAGTTACAAT | 785 |
| 13345 | 13367 | GCCATACTATTTATGTGCTCCGG | 363 | GCCATACTATTTATGTGCTC | 786 |
| 13346 | 13368 | CCATACTATTTATGTGCTCCGGG | 364 | CCATACTATTTATGTGCTCC | 787 |
| 13393 | 13415 | GAACAAGATATTCGAAAAATAGG | 365 | GAACAAGATATTCGAAAAAT | 788 |
| 13396 | 13418 | CAAGATATTCGAAAAATAGGAGG | 366 | CAAGATATTCGAAAAATAGG | 789 |
| 13441 | 13463 | ACTTCAACCTCCCTCACCATTGG | 367 | ACTTCAACCTCCCTCACCAT | 790 |
| 13459 | 13481 | ATTGGCAGCCTAGCATTAGCAGG | 368 | ATTGGCAGCCTAGCATTAGC | 791 |
| 13477 | 13499 | GCAGGAATACCTTTCCTCACAGG | 369 | GCAGGAATACCTTTCCTCAC | 792 |
| 13612 | 13634 | ATAATTCTTCTCACCCTAACAGG | 370 | ATAATTCTTCTCACCCTAAC | 793 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 13686 | 13708 | ACTAAACCCCATTAAACGCCTGG | 371 | ACTAAACCCCATTAAACGCC | 794 |
| 13693 | 13715 | CCCATTAAACGCCTGGCAGCCGG | 372 | CCCATTAAACGCCTGGCAGC | 795 |
| 13708 | 13730 | GCAGCCGGAAGCCTATTCGCAGG | 373 | GCAGCCGGAAGCCTATTCGC | 796 |
| 13804 | 13826 | GCCCTCGCTGTCACTTTCCTAGG | 374 | GCCCTCGCTGTCACTTTCCT | 797 |
| 13894 | 13916 | TTTTATTTCTCCAACATACTCGG | 375 | TTTTATTTCTCCAACATACT | 798 |
| 13936 | 13958 | CACCGCACAATCCCCTATCTAGG | 376 | CACCGCACAATCCCCTATCT | 799 |
| 14059 | 14081 | ATCATCACCTCAACCCAAAAAGG | 377 | ATCATCACCTCAACCCAAAA | 800 |
| 14237 | 14259 | TACAAAGCCCCCGCACCAATAGG | 378 | TACAAAGCCCCCGCACCAAT | 801 |
| 14417 | 14439 | ACCCCTGACCCCCATGCCTCAGG | 379 | ACCCCTGACCCCCATGCCTC | 802 |
| 14579 | 14601 | AATACTAAACCCCCATAAATAGG | 380 | AATACTAAACCCCCATAAAT | 803 |
| 14585 | 14607 | AAACCCCCATAAATAGGAGAAGG | 381 | AAACCCCCATAAATAGGAGA | 804 |
| 14664 | 14686 | CATACATCATTATTCTCGCACGG | 382 | CATACATCATTATTCTCGCA | 805 |
| 14825 | 14847 | ATCTCCGCATGATGAAACTTCGG | 383 | ATCTCCGCATGATGAAACTT | 806 |
| 14837 | 14859 | TGAAACTTCGGCTCACTCCTTGG | 384 | TGAAACTTCGGCTCACTCCT | 807 |
| 14867 | 14889 | CTGATCCTCCAAATCACCACAGG | 385 | CTGATCCTCCAAATCACCAC | 808 |
| 14951 | 14973 | ATCACTCGAGACGTAAATTATGG | 386 | ATCACTCGAGACGTAAATTA | 809 |
| 14981 | 15003 | ATCCGCTACCTTCACGCCAATGG | 387 | ATCCGCTACCTTCACGCCAA | 810 |
| 15020 | 15042 | ATCTGCCTCTTCCTACACATCGG | 388 | ATCTGCCTCTTCCTACACAT | 811 |
| 15021 | 15043 | TCTGCCTCTTCCTACACATCGGG | 389 | TCTGCCTCTTCCTACACATC | 812 |
| 15026 | 15048 | CTCTTCCTACACATCGGGCGAGG | 390 | CTCTTCCTACACATCGGGCG | 813 |
| 15038 | 15060 | ATCGGGCGAGGCCTATATTACGG | 391 | ATCGGGCGAGGCCTATATTA | 814 |
| 15071 | 15093 | TACTCAGAAACCTGAAACATCGG | 392 | TACTCAGAAACCTGAAACAT | 815 |
| 15113 | 15135 | ACTATAGCAACAGCCTTCATAGG | 393 | ACTATAGCAACAGCCTTCAT | 816 |
| 15131 | 15153 | ATAGGCTATGTCCTCCCGTGAGG | 394 | ATAGGCTATGTCCTCCCGTG | 817 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 15149 | 15171 | TGAGGCCAAATATCATTCTGAGG | 395 | TGAGGCCAAATATCATTCTG | 818 |
| 15150 | 15172 | GAGGCCAAATATCATTCTGAGGG | 396 | GAGGCCAAATATCATTCTGA | 819 |
| 15151 | 15173 | AGGCCAAATATCATTCTGAGGGG | 397 | AGGCCAAATATCATTCTGAG | 820 |
| 15194 | 15216 | CTATCCGCCATCCCATACATTGG | 398 | CTATCCGCCATCCCATACAT | 821 |
| 15195 | 15217 | TATCCGCCATCCCATACATTGGG | 399 | TATCCGCCATCCCATACATT | 822 |
| 15221 | 15243 | GACCTAGTTCAATGAATCTGAGG | 400 | GACCTAGTTCAATGAATCTG | 823 |
| 15224 | 15246 | CTAGTTCAATGAATCTGAGGAGG | 401 | CTAGTTCAATGAATCTGAGG | 824 |
| 15334 | 15356 | CCTCCTATTCTTGCACGAAACGG | 402 | CCTCCTATTCTTGCACGAAA | 825 |
| 15335 | 15357 | CTCCTATTCTTGCACGAAACGGG | 403 | CTCCTATTCTTGCACGAAAC | 826 |
| 15353 | 15375 | ACGGGATCAAACAACCCCTAGG | 404 | ACGGGATCAAACAACCCCT | 827 |
| 15416 | 15438 | TACACAATCAAAGACGCCCTCGG | 405 | TACACAATCAAAGACGCCCT | 828 |
| 15476 | 15498 | CTATTCTCACCAGACCTCCTAGG | 406 | CTATTCTCACCAGACCTCCT | 829 |
| 15590 | 15612 | CGATCCGTCCCTAACAAACTAGG | 407 | CGATCCGTCCCTAACAAACT | 830 |
| 15593 | 15615 | TCCGTCCCTAACAAACTAGGAGG | 408 | TCCGTCCCTAACAAACTAGG | 831 |
| 15740 | 15762 | CTCCTCATTCTAACCTGAATCGG | 409 | CTCCTCATTCTAACCTGAAT | 832 |
| 15743 | 15765 | CTCATTCTAACCTGAATCGGAGG | 410 | CTCATTCTAACCTGAATCGG | 833 |
| 15776 | 15798 | AGCTACCCTTTTACCATCATTGG | 411 | AGCTACCCTTTTACCATCAT | 834 |
| 15861 | 15883 | TTGAAAACAAAATACTCAAATGG | 412 | TTGAAAACAAAATACTCAAA | 835 |
| 15862 | 15884 | TGAAAACAAAATACTCAAATGGG | 413 | TGAAAACAAAATACTCAAAT | 836 |
| 15906 | 15928 | AATACACCAGTCTTGTAAACCGG | 414 | AATACACCAGTCTTGTAAAC | 837 |
| 15928 | 15950 | GAGATGAAAACCTTTTTCCAAGG | 415 | GAGATGAAAACCTTTTTCCA | 838 |
| 16012 | 16034 | AACTATTCTCTGTTCTTTCATGG | 416 | AACTATTCTCTGTTCTTTCA | 839 |
| 16013 | 16035 | ACTATTCTCTGTTCTTTCATGGG | 417 | ACTATTCTCTGTTCTTTCAT | 840 |
| 16014 | 16036 | CTATTCTCTGTTCTTTCATGGGG | 418 | CTATTCTCTGTTCTTTCATG | 841 |

TABLE 3-continued gRNA target sequence for human mtDNA carrying NGG sequence on the (+) strand.

| Chr start position (+ strand) | Chr end position (+ strand) | nt sequence on the (+) strand containing gRNA target sequence followed by NGG | SEQ ID NO | 20 nt gRNA target sequence (will encode the gRNA targeting sequence) | SEQ ID NO |
|---|---|---|---|---|---|
| 16026 | 16048 | CTTTCATGGGGAAGCAGATTTGG | 419 | CTTTCATGGGGAAGCAGATT | 842 |
| 16027 | 16049 | TTTCATGGGGAAGCAGATTTGGG | 420 | TTTCATGGGGAAGCAGATTT | 843 |
| 16108 | 16130 | CAGCCACCATGAATATTGTACGG | 421 | CAGCCACCATGAATATTGTA | 844 |
| 16252 | 16274 | AAAGCCACCCCTCACCCACTAGG | 422 | AAAGCCACCCCTCACCCACT | 845 |
| 16348 | 16370 | CAAATCCCTTCTCGTCCCCATGG | 423 | CAAATCCCTTCTCGTCCCCA | 846 |
| 16367 | 16389 | ATGGATGACCCCCCTCAGATAGG | 424 | ATGGATGACCCCCCTCAGAT | 847 |
| 16368 | 16390 | TGGATGACCCCCCTCAGATAGGG | 425 | TGGATGACCCCCCTCAGATA | 848 |
| 16369 | 16391 | GGATGACCCCCCTCAGATAGGGG | 426 | GGATGACCCCCCTCAGATAG | 849 |
| 16434 | 16456 | GAGTGCTACTCTCCTCGCTCCGG | 427 | GAGTGCTACTCTCCTCGCTC | 850 |
| 16435 | 16457 | AGTGCTACTCTCCTCGCTCCGGG | 428 | AGTGCTACTCTCCTCGCTCC | 851 |
| 16449 | 16471 | CGCTCCGGGCCCATAACACTTGG | 429 | CGCTCCGGGCCCATAACACT | 852 |
| 16450 | 16472 | GCTCCGGGCCCATAACACTTGGG | 430 | GCTCCGGGCCCATAACACTT | 853 |
| 16451 | 16473 | CTCCGGGCCCATAACACTTGGGG | 431 | CTCCGGGCCCATAACACTTG | 854 |
| 16452 | 16474 | TCCGGGCCCATAACACTTGGGGG | 432 | TCCGGGCCCATAACACTTGG | 855 |
| 16482 | 16504 | AGTGAACTGTATCCGACATCTGG | 433 | AGTGAACTGTATCCGACATC | 856 |
| 16495 | 16517 | CGACATCTGGTTCCTACTTCAGG | 434 | CGACATCTGGTTCCTACTTC | 857 |
| 16496 | 16518 | GACATCTGGTTCCTACTTCAGGG | 435 | GACATCTGGTTCCTACTTCA | 858 |

TABLE 4 gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 17 | 39 | CCCTATTAACCACTCACGGGAGC | 859 | GCTCCCGTGAGTGGTTAATA | 2628 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 18 | 40 | CCTATTAACCACTCACGGGAGCT | 860 | AGCTCCCGTGAGTGGTTAAT | 2629 |
| 26 | 48 | CCACTCACGGGAGCTCTCCATGC | 861 | GCATGGAGAGCTCCCGTGAG | 2630 |
| 43 | 65 | CCATGCATTTGGTATTTTCGTCT | 862 | AGACGAAAATACCAAATGCA | 2631 |
| 104 | 126 | CCGGAGCACCCTATGTCGCAGTA | 863 | TACTGCGACATAGGGTGCTC | 2632 |
| 112 | 134 | CCCTATGTCGCAGTATCTGTCTT | 864 | AAGACAGATACTGCGACATA | 2633 |
| 113 | 135 | CCTATGTCGCAGTATCTGTCTTT | 865 | AAAGACAGATACTGCGACAT | 2634 |
| 140 | 162 | CCTGCCTCATCCTATTATTTATC | 866 | GATAAATAATAGGATGAGGC | 2635 |
| 144 | 166 | CCTCATCCTATTATTTATCGCAC | 867 | GTGCGATAAATAATAGGATG | 2636 |
| 150 | 172 | CCTATTATTTATCGCACCTACGT | 868 | ACGTAGGTGCGATAAATAAT | 2637 |
| 166 | 188 | CCTACGTTCAATATTACAGGCGA | 869 | TCGCCTGTAATATTGAACGT | 2638 |
| 261 | 283 | CCACTTTCCACACAGACATCATA | 870 | TATGATGTCTGTGTGGAAAG | 2639 |
| 268 | 290 | CCACACAGACATCATAACAAAAA | 871 | TTTTTGTTATGATGTCTGTG | 2640 |
| 298 | 320 | CCAAACCCCCCCTCCCCCGCTTC | 872 | GAAGCGGGGGAGGGGGGGTT | 2641 |
| 304 | 326 | CCCCCCTCCCCCGCTTCTGGCCA | 873 | TGGCCAGAAGCGGGGGAGGG | 2642 |
| 305 | 327 | CCCCCTCCCCCGCTTCTGGCCAC | 874 | GTGGCCAGAAGCGGGGGAGG | 2643 |
| 306 | 328 | CCCCTCCCCCGCTTCTGGCCACA | 875 | TGTGGCCAGAAGCGGGGGAG | 2644 |
| 307 | 329 | CCCTCCCCCGCTTCTGGCCACAG | 876 | CTGTGGCCAGAAGCGGGGGA | 2645 |
| 308 | 330 | CCTCCCCCGCTTCTGGCCACAGC | 877 | GCTGTGGCCAGAAGCGGGGG | 2646 |
| 311 | 333 | CCCCCGCTTCTGGCCACAGCACT | 878 | AGTGCTGTGGCCAGAAGCGG | 2647 |
| 312 | 334 | CCCCGCTTCTGGCCACAGCACTT | 879 | AAGTGCTGTGGCCAGAAGCG | 2648 |
| 313 | 335 | CCCGCTTCTGGCCACAGCACTTA | 880 | TAAGTGCTGTGGCCAGAAGC | 2649 |
| 314 | 336 | CCGCTTCTGGCCACAGCACTTAA | 881 | TTAAGTGCTGTGGCCAGAAG | 2650 |
| 324 | 346 | CCACAGCACTTAAACACATCTCT | 882 | AGAGATGTGTTTAAGTGCTG | 2651 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 348 | 370 | CCAAACCCCAAAAACAAAGAACC | 883 | GGTTCTTTGTTTTTGGGGTT | 2652 |
| 353 | 375 | CCCCAAAAACAAAGAACCCTAAC | 884 | GTTAGGGTTCTTTGTTTTTG | 2653 |
| 354 | 376 | CCCAAAAACAAAGAACCCTAACA | 885 | TGTTAGGGTTCTTTGTTTTT | 2654 |
| 355 | 377 | CCAAAAACAAAGAACCCTAACAC | 886 | GTGTTAGGGTTCTTTGTTTT | 2655 |
| 369 | 391 | CCCTAACACCAGCCTAACCAGAT | 887 | ATCTGGTTAGGCTGGTGTTA | 2656 |
| 370 | 392 | CCTAACACCAGCCTAACCAGATT | 888 | AATCTGGTTAGGCTGGTGTT | 2657 |
| 377 | 399 | CCAGCCTAACCAGATTTCAAATT | 889 | AATTTGAAATCTGGTTAGGC | 2658 |
| 381 | 403 | CCTAACCAGATTTCAAATTTTAT | 890 | ATAAAATTTGAAATCTGGTT | 2659 |
| 386 | 408 | CCAGATTTCAAATTTTATCTTTT | 891 | AAAAGATAAAATTTGAAATC | 2660 |
| 433 | 455 | CCCCCCAACTAACACATTATTTT | 892 | AAAATAATGTGTTAGTTGGG | 2661 |
| 434 | 456 | CCCCCAACTAACACATTATTTTC | 893 | GAAAATAATGTGTTAGTTGG | 2662 |
| 435 | 457 | CCCCAACTAACACATTATTTTCC | 894 | GGAAAATAATGTGTTAGTTG | 2663 |
| 436 | 458 | CCCAACTAACACATTATTTTCCC | 895 | GGGAAAATAATGTGTTAGTT | 2664 |
| 437 | 459 | CCAACTAACACATTATTTTCCCC | 896 | GGGGAAAATAATGTGTTAGT | 2665 |
| 456 | 478 | CCCCTCCCACTCCCATACTACTA | 897 | TAGTAGTATGGGAGTGGGAG | 2666 |
| 457 | 479 | CCCTCCCACTCCCATACTACTAA | 898 | TTAGTAGTATGGGAGTGGGA | 2667 |
| 458 | 480 | CCTCCCACTCCCATACTACTAAT | 899 | ATTAGTAGTATGGGAGTGGG | 2668 |
| 461 | 483 | CCCACTCCCATACTACTAATCTC | 900 | GAGATTAGTAGTATGGGAGT | 2669 |
| 462 | 484 | CCACTCCCATACTACTAATCTCA | 901 | TGAGATTAGTAGTATGGGAG | 2670 |
| 467 | 489 | CCCATACTACTAATCTCATCAAT | 902 | ATTGATGAGATTAGTAGTAT | 2671 |
| 468 | 490 | CCATACTACTAATCTCATCAATA | 903 | TATTGATGAGATTAGTAGTA | 2672 |
| 494 | 516 | CCCCCGCCCATCCTACCCAGCAC | 904 | GTGCTGGGTAGGATGGGCGG | 2673 |
| 495 | 517 | CCCCGCCCATCCTACCCAGCACA | 905 | TGTGCTGGGTAGGATGGGCG | 2674 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 496 | 518 | CCCGCCCATCCTACCCAGCACAC | 906 | GTGTGCTGGGTAGGATGGGC | 2675 |
| 497 | 519 | CCGCCCATCCTACCCAGCACACA | 907 | TGTGTGCTGGGTAGGATGGG | 2676 |
| 500 | 522 | CCCATCCTACCCAGCACACACAC | 908 | GTGTGTGTGCTGGGTAGGAT | 2677 |
| 501 | 523 | CCATCCTACCCAGCACACACACA | 909 | TGTGTGTGTGCTGGGTAGGA | 2678 |
| 505 | 527 | CCTACCCAGCACACACACACCGC | 910 | GCGGTGTGTGTGCTGGGT | 2679 |
| 509 | 531 | CCCAGCACACACACACCGCTGCT | 911 | AGCAGCGGTGTGTGTGTGCT | 2680 |
| 510 | 532 | CCAGCACACACACACCGCTGCTA | 912 | TAGCAGCGGTGTGTGTGTGC | 2681 |
| 524 | 546 | CCGCTGCTAACCCCATACCCCGA | 913 | TCGGGGTATGGGGTTAGCAG | 2682 |
| 534 | 556 | CCCCATACCCCGAACCAACCAAA | 914 | TTTGGTTGGTTCGGGGTATG | 2683 |
| 535 | 557 | CCCATACCCCGAACCAACCAAAC | 915 | GTTTGGTTGGTTCGGGGTAT | 2684 |
| 536 | 558 | CCATACCCCGAACCAACCAAACC | 916 | GGTTTGGTTGGTTCGGGGTA | 2685 |
| 541 | 563 | CCCCGAACCAACCAAACCCCAAA | 917 | TTTGGGGTTTGGTTGGTTCG | 2686 |
| 542 | 564 | CCCGAACCAACCAAACCCCAAAG | 918 | CTTTGGGGTTTGGTTGGTTC | 2687 |
| 543 | 565 | CCGAACCAACCAAACCCCAAAGA | 919 | TCTTTGGGGTTTGGTTGGTT | 2688 |
| 548 | 570 | CCAACCAAACCCCAAAGACACCC | 920 | GGGTGTCTTTGGGGTTTGGT | 2689 |
| 552 | 574 | CCAAACCCCAAAGACACCCCCCA | 921 | TGGGGGGTGTCTTTGGGGTT | 2690 |
| 557 | 579 | CCCCAAAGACACCCCCCACAGTT | 922 | AACTGTGGGGGGTGTCTTTG | 2691 |
| 558 | 580 | CCCAAAGACACCCCCCACAGTTT | 923 | AAACTGTGGGGGGTGTCTTT | 2692 |
| 559 | 581 | CCAAAGACACCCCCCACAGTTTA | 924 | TAAACTGTGGGGGGTGTCTT | 2693 |
| 568 | 590 | CCCCCCACAGTTTATGTAGCTTA | 925 | TAAGCTACATAAACTGTGGG | 2694 |
| 569 | 591 | CCCCCACAGTTTATGTAGCTTAC | 926 | GTAAGCTACATAAACTGTGG | 2695 |
| 570 | 592 | CCCCACAGTTTATGTAGCTTACC | 927 | GGTAAGCTACATAAACTGTG | 2696 |
| 571 | 593 | CCCACAGTTTATGTAGCTTACCT | 928 | AGGTAAGCTACATAAACTGT | 2697 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 572 | 594 | CCACAGTTTATGTAGCTTACCTC | 929 | GAGGTAAGCTACATAAACTG | 2698 |
| 591 | 613 | CCTCCTCAAAGCAATACACTGAA | 930 | TTCAGTGTATTGCTTTGAGG | 2699 |
| 594 | 616 | CCTCAAAGCAATACACTGAAAAT | 931 | ATTTTCAGTGTATTGCTTTG | 2700 |
| 637 | 659 | CCCCATAAACAAATAGGTTTGGT | 932 | ACCAAACCTATTTGTTTATG | 2701 |
| 638 | 660 | CCCATAAACAAATAGGTTTGGTC | 933 | GACCAAACCTATTTGTTTAT | 2702 |
| 639 | 661 | CCATAAACAAATAGGTTTGGTCC | 934 | GGACCAAACCTATTTGTTTA | 2703 |
| 660 | 682 | CCTAGCCTTTCTATTAGCTCTTA | 935 | TAAGAGCTAATAGAAAGGCT | 2704 |
| 665 | 687 | CCTTTCTATTAGCTCTTAGTAAG | 936 | CTTACTAAGAGCTAATAGAA | 2705 |
| 705 | 727 | CCCCGTTCCAGTGAGTTCACCCT | 937 | AGGGTGAACTCACTGGAACG | 2706 |
| 706 | 728 | CCCGTTCCAGTGAGTTCACCCTC | 938 | GAGGGTGAACTCACTGGAAC | 2707 |
| 707 | 729 | CCGTTCCAGTGAGTTCACCCTCT | 939 | AGAGGGTGAACTCACTGGAA | 2708 |
| 712 | 734 | CCAGTGAGTTCACCCTCTAAATC | 940 | GATTTAGAGGGTGAACTCAC | 2709 |
| 724 | 746 | CCCTCTAAATCACCACGATCAAA | 941 | TTTGATCGTGGTGATTTAGA | 2710 |
| 725 | 747 | CCTCTAAATCACCACGATCAAAA | 942 | TTTTGATCGTGGTGATTTAG | 2711 |
| 736 | 758 | CCACGATCAAAAGGAACAAGCAT | 943 | ATGCTTGTTCCTTTTGATCG | 2712 |
| 792 | 814 | CCTAGCCACACCCCCACGGGAAA | 944 | TTTCCCGTGGGGGTGTGGCT | 2713 |
| 797 | 819 | CCACACCCCCACGGGAAACAGCA | 945 | TGCTGTTTCCCGTGGGGGTG | 2714 |
| 802 | 824 | CCCCCACGGGAAACAGCAGTGAT | 946 | ATCACTGCTGTTTCCCGTGG | 2715 |
| 803 | 825 | CCCCACGGGAAACAGCAGTGATT | 947 | AATCACTGCTGTTTCCCGTG | 2716 |
| 804 | 826 | CCCACGGGAAACAGCAGTGATTA | 948 | TAATCACTGCTGTTTCCCGT | 2717 |
| 805 | 827 | CCACGGGAAACAGCAGTGATTAA | 949 | TTAATCACTGCTGTTTCCCG | 2718 |
| 828 | 850 | CCTTTAGCAATAAACGAAAGTTT | 950 | AAACTTTCGTTTATTGCTAA | 2719 |
| 867 | 889 | CCCCAGGGTTGGTCAATTTCGTG | 951 | CACGAAATTGACCAACCCTG | 2720 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 868 | 890 | CCCAGGGTTGGTCAATTTCGTGC | 952 | GCACGAAATTGACCAACCCT | 2721 |
| 869 | 891 | CCAGGGTTGGTCAATTTCGTGCC | 953 | GGCACGAAATTGACCAACCC | 2722 |
| 890 | 912 | CCAGCCACCGCGGTCACACGATT | 954 | AATCGTGTGACCGCGGTGGC | 2723 |
| 894 | 916 | CCACCGCGGTCACACGATTAACC | 955 | GGTTAATCGTGTGACCGCGG | 2724 |
| 897 | 919 | CCGCGGTCACACGATTAACCCAA | 956 | TTGGGTTAATCGTGTGACCG | 2725 |
| 915 | 937 | CCCAAGTCAATAGAAGCCGGCGT | 957 | ACGCCGGCTTCTATTGACTT | 2726 |
| 916 | 938 | CCAAGTCAATAGAAGCCGGCGTA | 958 | TACGCCGGCTTCTATTGACT | 2727 |
| 931 | 953 | CCGGCGTAAAGAGTGTTTTAGAT | 959 | ATCTAAAACACTCTTTACGC | 2728 |
| 956 | 978 | CCCCCTCCCCAATAAAGCTAAAA | 960 | TTTTAGCTTTATTGGGAGG | 2729 |
| 957 | 979 | CCCCTCCCCAATAAAGCTAAAAC | 961 | GTTTTAGCTTTATTGGGGAG | 2730 |
| 958 | 980 | CCCTCCCCAATAAAGCTAAAACT | 962 | AGTTTTAGCTTTATTGGGA | 2731 |
| 959 | 981 | CCTCCCCAATAAAGCTAAAACTC | 963 | GAGTTTTAGCTTTATTGGGG | 2732 |
| 962 | 984 | CCCCAATAAAGCTAAAACTCACC | 964 | GGTGAGTTTTAGCTTTATTG | 2733 |
| 963 | 985 | CCCAATAAAGCTAAAACTCACCT | 965 | AGGTGAGTTTTAGCTTTATT | 2734 |
| 964 | 986 | CCAATAAAGCTAAAACTCACCTG | 966 | CAGGTGAGTTTTAGCTTTAT | 2735 |
| 983 | 1005 | CCTGAGTTGTAAAAAACTCCAGT | 967 | ACTGGAGTTTTTTACAACTC | 2736 |
| 1001 | 1023 | CCAGTTGACACAAAATAGACTAC | 968 | GTAGTCTATTTTGTGTCAAC | 2737 |
| 1064 | 1086 | CCCAAACTGGGATTAGATACCCC | 969 | GGGGTATCTAATCCCAGTTT | 2738 |
| 1065 | 1087 | CCAAACTGGGATTAGATACCCCA | 970 | TGGGGTATCTAATCCCAGTT | 2739 |
| 1083 | 1105 | CCCCACTATGCTTAGCCCTAAAC | 971 | GTTTAGGGCTAAGCATAGTG | 2740 |
| 1084 | 1106 | CCCACTATGCTTAGCCCTAAACC | 972 | GGTTTAGGGCTAAGCATAGT | 2741 |
| 1085 | 1107 | CCACTATGCTTAGCCCTAAACCT | 973 | AGGTTTAGGGCTAAGCATAG | 2742 |
| 1098 | 1120 | CCCTAAACCTCAACAGTTAAATC | 974 | GATTTAACTGTTGAGGTTTA | 2743 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 1099 | 1121 | CCTAAACCTCAACAGTTAAATCA | 975 | TGATTTAACTGTTGAGGTTT | 2744 |
| 1105 | 1127 | CCTCAACAGTTAAATCAACAAAA | 976 | TTTTGTTGATTTAACTGTTG | 2745 |
| 1135 | 1157 | CCAGAACACTACGAGCCACAGCT | 977 | AGCTGTGGCTCGTAGTGTTC | 2746 |
| 1150 | 1172 | CCACAGCTTAAAACTCAAAGGAC | 978 | GTCCTTTGAGTTTTAAGCTG | 2747 |
| 1172 | 1194 | CCTGGCGGTGCTTCATATCCCTC | 979 | GAGGGATATGAAGCACCGCC | 2748 |
| 1190 | 1212 | CCCTCTAGAGGAGCCTGTTCTGT | 980 | ACAGAACAGGCTCCTCTAGA | 2749 |
| 1191 | 1213 | CCTCTAGAGGAGCCTGTTCTGTA | 981 | TACAGAACAGGCTCCTCTAG | 2750 |
| 1203 | 1225 | CCTGTTCTGTAATCGATAAACCC | 982 | GGGTTTATCGATTACAGAAC | 2751 |
| 1223 | 1245 | CCCCGATCAACCTCACCACCTCT | 983 | AGAGGTGGTGAGGTTGATCG | 2752 |
| 1224 | 1246 | CCCGATCAACCTCACCACCTCTT | 984 | AAGAGGTGGTGAGGTTGATC | 2753 |
| 1225 | 1247 | CCGATCAACCTCACCACCTCTTG | 985 | CAAGAGGTGGTGAGGTTGAT | 2754 |
| 1233 | 1255 | CCTCACCACCTCTTGCTCAGCCT | 986 | AGGCTGAGCAAGAGGTGGTG | 2755 |
| 1238 | 1260 | CCACCTCTTGCTCAGCCTATATA | 987 | TATATAGGCTGAGCAAGAGG | 2756 |
| 1241 | 1263 | CCTCTTGCTCAGCCTATATACCG | 988 | CGGTATATAGGCTGAGCAAG | 2757 |
| 1253 | 1275 | CCTATATACCGCCATCTTCAGCA | 989 | TGCTGAAGATGGCGGTATAT | 2758 |
| 1261 | 1283 | CCGCCATCTTCAGCAAACCCTGA | 990 | TCAGGGTTTGCTGAAGATGG | 2759 |
| 1264 | 1286 | CCATCTTCAGCAAACCCTGATGA | 991 | TCATCAGGGTTTGCTGAAGA | 2760 |
| 1278 | 1300 | CCCTGATGAAGGCTACAAAGTAA | 992 | TTACTTTGTAGCCTTCATCA | 2761 |
| 1279 | 1301 | CCTGATGAAGGCTACAAAGTAAG | 993 | CTTACTTTGTAGCCTTCATC | 2762 |
| 1310 | 1332 | CCCACGTAAAGACGTTAGGTCAA | 994 | TTGACCTAACGTCTTTACGT | 2763 |
| 1311 | 1333 | CCACGTAAAGACGTTAGGTCAAG | 995 | CTTGACCTAACGTCTTTACG | 2764 |
| 1340 | 1362 | CCCATGAGGTGGCAAGAAATGGG | 996 | CCCATTTCTTGCCACCTCAT | 2765 |
| 1341 | 1363 | CCATGAGGTGGCAAGAAATGGGC | 997 | GCCCATTTCTTGCCACCTCA | 2766 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 1375 | 1397 | CCCCAGAAAACTACGATAGCCCT | 998 | AGGGCTATCGTAGTTTTCTG | 2767 |
| 1376 | 1398 | CCCAGAAAACTACGATAGCCCTT | 999 | AAGGGCTATCGTAGTTTTCT | 2768 |
| 1377 | 1399 | CCAGAAAACTACGATAGCCCTTA | 1000 | TAAGGGCTATCGTAGTTTTC | 2769 |
| 1394 | 1416 | CCCTTATGAAACTTAAGGGTCGA | 1001 | TCGACCCTTAAGTTTCATAA | 2770 |
| 1395 | 1417 | CCTTATGAAACTTAAGGGTCGAA | 1002 | TTCGACCCTTAAGTTTCATA | 2771 |
| 1465 | 1487 | CCCTGAAGCGCGTACACACCGCC | 1003 | GGCGGTGTGTACGCGCTTCA | 2772 |
| 1466 | 1488 | CCTGAAGCGCGTACACACCGCCC | 1004 | GGGCGGTGTGTACGCGCTTC | 2773 |
| 1483 | 1505 | CCGCCCGTCACCCTCCTCAAGTA | 1005 | TACTTGAGGAGGGTGACGGG | 2774 |
| 1486 | 1508 | CCCGTCACCCTCCTCAAGTATAC | 1006 | GTATACTTGAGGAGGGTGAC | 2775 |
| 1487 | 1509 | CCGTCACCCTCCTCAAGTATACT | 1007 | AGTATACTTGAGGAGGGTGA | 2776 |
| 1493 | 1515 | CCCTCCTCAAGTATACTTCAAAG | 1008 | CTTTGAAGTATACTTGAGGA | 2777 |
| 1494 | 1516 | CCTCCTCAAGTATACTTCAAAGG | 1009 | CCTTTGAAGTATACTTGAGG | 2778 |
| 1497 | 1519 | CCTCAAGTATACTTCAAAGGACA | 1010 | TGTCCTTTGAAGTATACTTG | 2779 |
| 1531 | 1553 | CCCCTACGCATTTATATAGAGGA | 1011 | TCCTCTATATAAATGCGTAG | 2780 |
| 1532 | 1554 | CCCTACGCATTTATATAGAGGAG | 1012 | CTCCTCTATATAAATGCGTA | 2781 |
| 1533 | 1555 | CCTACGCATTTATATAGAGGAGA | 1013 | TCTCCTCTATATAAATGCGT | 2782 |
| 1601 | 1623 | CCAGAGTGTAGCTTAACACAAAG | 1014 | CTTTGTGTTAAGCTACACTC | 2783 |
| 1626 | 1648 | CCCAACTTACACTTAGGAGATTT | 1015 | AAATCTCCTAAGTGTAAGTT | 2784 |
| 1627 | 1649 | CCAACTTACACTTAGGAGATTTC | 1016 | GAAATCTCCTAAGTGTAAGT | 2785 |
| 1662 | 1684 | CCGCTCTGAGCTAAACCTAGCCC | 1017 | GGGCTAGGTTTAGCTCAGAG | 2786 |
| 1677 | 1699 | CCTAGCCCCAAACCCACTCCACC | 1018 | GGTGGAGTGGGTTTGGGGCT | 2787 |
| 1682 | 1704 | CCCCAAACCCACTCCACCTTACT | 1019 | AGTAAGGTGGAGTGGGTTTG | 2788 |
| 1683 | 1705 | CCCAAACCCACTCCACCTTACTA | 1020 | TAGTAAGGTGGAGTGGGTTT | 2789 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 1684 | 1706 | CCAAACCCACTCCACCTTACTAC | 1021 | GTAGTAAGGTGGAGTGGGTT | 2790 |
| 1689 | 1711 | CCCACTCCACCTTACTACCAGAC | 1022 | GTCTGGTAGTAAGGTGGAGT | 2791 |
| 1690 | 1712 | CCACTCCACCTTACTACCAGACA | 1023 | TGTCTGGTAGTAAGGTGGAG | 2792 |
| 1695 | 1717 | CCACCTTACTACCAGACAACCTT | 1024 | AAGGTTGTCTGGTAGTAAGG | 2793 |
| 1698 | 1720 | CCTTACTACCAGACAACCTTAGC | 1025 | GCTAAGGTTGTCTGGTAGTA | 2794 |
| 1706 | 1728 | CCAGACAACCTTAGCCAAACCAT | 1026 | ATGGTTTGGCTAAGGTTGTC | 2795 |
| 1714 | 1736 | CCTTAGCCAAACCATTTACCCAA | 1027 | TTGGGTAAATGGTTTGGCTA | 2796 |
| 1720 | 1742 | CCAAACCATTTACCCAAATAAAG | 1028 | CTTTATTTGGGTAAATGGTT | 2797 |
| 1725 | 1747 | CCATTTACCCAAATAAAGTATAG | 1029 | CTATACTTTATTTGGGTAAA | 2798 |
| 1732 | 1754 | CCCAAATAAAGTATAGGCGATAG | 1030 | CTATCGCCTATACTTTATTT | 2799 |
| 1733 | 1755 | CCAAATAAAGTATAGGCGATAGA | 1031 | TCTATCGCCTATACTTTATT | 2800 |
| 1764 | 1786 | CCTGGCGCAATAGATATAGTACC | 1032 | GGTACTATATCTATTGCGCC | 2801 |
| 1785 | 1807 | CCGCAAGGGAAAGATGAAAAATT | 1033 | AATTTTTCATCTTTCCCTTG | 2802 |
| 1812 | 1834 | CCAAGCATAATATAGCAAGGACT | 1034 | AGTCCTTGCTATATTATGCT | 2803 |
| 1837 | 1859 | CCCCTATACCTTCTGCATAATGA | 1035 | TCATTATGCAGAAGGTATAG | 2804 |
| 1838 | 1860 | CCCTATACCTTCTGCATAATGAA | 1036 | TTCATTATGCAGAAGGTATA | 2805 |
| 1839 | 1861 | CCTATACCTTCTGCATAATGAAT | 1037 | ATTCATTATGCAGAAGGTAT | 2806 |
| 1845 | 1867 | CCTTCTGCATAATGAATTAACTA | 1038 | TAGTTAATTCATTATGCAGA | 2807 |
| 1889 | 1911 | CCAAAGCTAAGACCCCCGAAACC | 1039 | GGTTTCGGGGGTCTTAGCTT | 2808 |
| 1901 | 1923 | CCCCCGAAACCAGACGAGCTACC | 1040 | GGTAGCTCGTCTGGTTTCGG | 2809 |
| 1902 | 1924 | CCCCGAAACCAGACGAGCTACCT | 1041 | AGGTAGCTCGTCTGGTTTCG | 2810 |
| 1903 | 1925 | CCCGAAACCAGACGAGCTACCTA | 1042 | TAGGTAGCTCGTCTGGTTTC | 2811 |
| 1904 | 1926 | CCGAAACCAGACGAGCTACCTAA | 1043 | TTAGGTAGCTCGTCTGGTTT | 2812 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 1910 | 1932 | CCAGACGAGCTACCTAAGAACAG | 1044 | CTGTTCTTAGGTAGCTCGTC | 2813 |
| 1922 | 1944 | CCTAAGAACAGCTAAAAGAGCAC | 1045 | GTGCTCTTTTAGCTGTTCTT | 2814 |
| 1946 | 1968 | CCCGTCTATGTAGCAAAATAGTG | 1046 | CACTATTTTGCTACATAGAC | 2815 |
| 1947 | 1969 | CCGTCTATGTAGCAAAATAGTGG | 1047 | CCACTATTTTGCTACATAGA | 2816 |
| 1996 | 2018 | CCTACCGAGCCTGGTGATAGCTG | 1048 | CAGCTATCACCAGGCTCGGT | 2817 |
| 2000 | 2022 | CCGAGCCTGGTGATAGCTGGTTG | 1049 | CAACCAGCTATCACCAGGCT | 2818 |
| 2005 | 2027 | CCTGGTGATAGCTGGTTGTCCAA | 1050 | TTGGACAACCAGCTATCACC | 2819 |
| 2024 | 2046 | CCAAGATAGAATCTTAGTTCAAC | 1051 | GTTGAACTAAGATTCTATCT | 2820 |
| 2057 | 2079 | CCCACAGAACCCTCTAAATCCCC | 1052 | GGGGATTTAGAGGGTTCTGT | 2821 |
| 2058 | 2080 | CCACAGAACCCTCTAAATCCCCT | 1053 | AGGGGATTTAGAGGGTTCTG | 2822 |
| 2066 | 2088 | CCCTCTAAATCCCCTTGTAAATT | 1054 | AATTTACAAGGGGATTTAGA | 2823 |
| 2067 | 2089 | CCTCTAAATCCCCTTGTAAATTT | 1055 | AAATTTACAAGGGGATTTAG | 2824 |
| 2076 | 2098 | CCCCTTGTAAATTTAACTGTTAG | 1056 | CTAACAGTTAAATTTACAAG | 2825 |
| 2077 | 2099 | CCCTTGTAAATTTAACTGTTAGT | 1057 | ACTAACAGTTAAATTTACAA | 2826 |
| 2078 | 2100 | CCTTGTAAATTTAACTGTTAGTC | 1058 | GACTAACAGTTAAATTTACA | 2827 |
| 2100 | 2122 | CCAAAGAGGAACAGCTCTTTGGA | 1059 | TCCAAAGAGCTGTTCCTCTT | 2828 |
| 2136 | 2158 | CCTTGTAGAGAGAGTAAAAAATT | 1060 | AATTTTTTACTCTCTCTACA | 2829 |
| 2164 | 2186 | CCCATAGTAGGCCTAAAAGCAGC | 1061 | GCTGCTTTTAGGCCTACTAT | 2830 |
| 2165 | 2187 | CCATAGTAGGCCTAAAAGCAGCC | 1062 | GGCTGCTTTTAGGCCTACTA | 2831 |
| 2175 | 2197 | CCTAAAAGCAGCCACCAATTAAG | 1063 | CTTAATTGGTGGCTGCTTTT | 2832 |
| 2186 | 2208 | CCACCAATTAAGAAAGCGTTCAA | 1064 | TTGAACGCTTTCTTAATTGG | 2833 |
| 2189 | 2211 | CCAATTAAGAAAGCGTTCAAGCT | 1065 | AGCTTGAACGCTTTCTTAAT | 2834 |
| 2217 | 2239 | CCCACTACCTAAAAAATCCCAAA | 1066 | TTTGGGATTTTTTAGGTAGT | 2835 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 2218 | 2240 | CCACTACCTAAAAAATCCCAAAC | 1067 | GTTTGGGATTTTTTAGGTAG | 2836 |
| 2224 | 2246 | CCTAAAAAATCCCAAACATATAA | 1068 | TTATATGTTTGGGATTTTTT | 2837 |
| 2234 | 2256 | CCCAAACATATAACTGAACTCCT | 1069 | AGGAGTTCAGTTATATGTTT | 2838 |
| 2235 | 2257 | CCAAACATATAACTGAACTCCTC | 1070 | GAGGAGTTCAGTTATATGTT | 2839 |
| 2254 | 2276 | CCTCACACCCAATTGGACCAATC | 1071 | GATTGGTCCAATTGGGTGTG | 2840 |
| 2261 | 2283 | CCCAATTGGACCAATCTATCACC | 1072 | GGTGATAGATTGGTCCAATT | 2841 |
| 2262 | 2284 | CCAATTGGACCAATCTATCACCC | 1073 | GGGTGATAGATTGGTCCAAT | 2842 |
| 2271 | 2293 | CCAATCTATCACCCTATAGAAGA | 1074 | TCTTCTATAGGGTGATAGAT | 2843 |
| 2282 | 2304 | CCCTATAGAAGAACTAATGTTAG | 1075 | CTAACATTAGTTCTTCTATA | 2844 |
| 2283 | 2305 | CCTATAGAAGAACTAATGTTAGT | 1076 | ACTAACATTAGTTCTTCTAT | 2845 |
| 2328 | 2350 | CCTCCGCATAAGCCTGCGTCAGA | 1077 | TCTGACGCAGGCTTATGCGG | 2846 |
| 2331 | 2353 | CCGCATAAGCCTGCGTCAGATTA | 1078 | TAATCTGACGCAGGCTTATG | 2847 |
| 2340 | 2362 | CCTGCGTCAGATTAAAACACTGA | 1079 | TCAGTGTTTTAATCTGACGC | 2848 |
| 2378 | 2400 | CCCAATATCTACAATCAACCAAC | 1080 | GTTGGTTGATTGTAGATATT | 2849 |
| 2379 | 2401 | CCAATATCTACAATCAACCAACA | 1081 | TGTTGGTTGATTGTAGATAT | 2850 |
| 2396 | 2418 | CCAACAAGTCATTATTACCCTCA | 1082 | TGAGGGTAATAATGACTTGT | 2851 |
| 2413 | 2435 | CCCTCACTGTCAACCCAACACAG | 1083 | CTGTGTTGGGTTGACAGTGA | 2852 |
| 2414 | 2436 | CCTCACTGTCAACCCAACACAGG | 1084 | CCTGTGTTGGGTTGACAGTG | 2853 |
| 2426 | 2448 | CCCAACACAGGCATGCTCATAAG | 1085 | CTTATGAGCATGCCTGTGTT | 2854 |
| 2427 | 2449 | CCAACACAGGCATGCTCATAAGG | 1086 | CCTTATGAGCATGCCTGTGT | 2855 |
| 2488 | 2510 | CCCCGCCTGTTTACCAAAAACAT | 1087 | ATGTTTTTGGTAAACAGGCG | 2856 |
| 2489 | 2511 | CCCGCCTGTTTACCAAAAACATC | 1088 | GATGTTTTTGGTAAACAGGC | 2857 |
| 2490 | 2512 | CCGCCTGTTTACCAAAAACATCA | 1089 | TGATGTTTTTGGTAAACAGG | 2858 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 2493 | 2515 | CCTGTTTACCAAAAACATCACCT | 1090 | AGGTGATGTTTTTGGTAAAC | 2859 |
| 2501 | 2523 | CCAAAAACATCACCTCTAGCATC | 1091 | GATGCTAGAGGTGATGTTTT | 2860 |
| 2513 | 2535 | CCTCTAGCATCACCAGTATTAGA | 1092 | TCTAATACTGGTGATGCTAG | 2861 |
| 2525 | 2547 | CCAGTATTAGAGGCACCGCCTGC | 1093 | GCAGGCGGTGCCTCTAATAC | 2862 |
| 2540 | 2562 | CCGCCTGCCCAGTGACACATGTT | 1094 | AACATGTGTCACTGGGCAGG | 2863 |
| 2543 | 2565 | CCTGCCCAGTGACACATGTTTAA | 1095 | TTAAACATGTGTCACTGGGC | 2864 |
| 2547 | 2569 | CCCAGTGACACATGTTTAACGGC | 1096 | GCCGTTAAACATGTGTCACT | 2865 |
| 2548 | 2570 | CCAGTGACACATGTTTAACGGCC | 1097 | GGCCGTTAAACATGTGTCAC | 2866 |
| 2569 | 2591 | CCGCGGTACCCTAACCGTGCAAA | 1098 | TTTGCACGGTTAGGGTACCG | 2867 |
| 2577 | 2599 | CCCTAACCGTGCAAAGGTAGCAT | 1099 | ATGCTACCTTTGCACGGTTA | 2868 |
| 2578 | 2600 | CCTAACCGTGCAAAGGTAGCATA | 1100 | TATGCTACCTTTGCACGGTT | 2869 |
| 2583 | 2605 | CCGTGCAAAGGTAGCATAATCAC | 1101 | GTGATTATGCTACCTTTGCA | 2870 |
| 2611 | 2633 | CCTTAAATAGGGACCTGTATGAA | 1102 | TTCATACAGGTCCCTATTTA | 2871 |
| 2624 | 2646 | CCTGTATGAATGGCTCCACGAGG | 1103 | CCTCGTGGAGCCATTCATAC | 2872 |
| 2639 | 2661 | CCACGAGGGTTCAGCTGTCTCTT | 1104 | AAGAGACAGCTGAACCCTCG | 2873 |
| 2670 | 2692 | CCAGTGAAATTGACCTGCCCGTG | 1105 | CACGGGCAGGTCAATTTCAC | 2874 |
| 2683 | 2705 | CCTGCCCGTGAAGAGGCGGGCAT | 1106 | ATGCCCGCCTCTTCACGGGC | 2875 |
| 2687 | 2709 | CCCGTGAAGAGGCGGGCATAACA | 1107 | TGTTATGCCCGCCTCTTCAC | 2876 |
| 2688 | 2710 | CCGTGAAGAGGCGGGCATAACAC | 1108 | GTGTTATGCCCGCCTCTTCA | 2877 |
| 2726 | 2748 | CCCTATGGAGCTTTAATTTATTA | 1109 | TAATAAATTAAAGCTCCATA | 2878 |
| 2727 | 2749 | CCTATGGAGCTTTAATTTATTAA | 1110 | TTAATAAATTAAAGCTCCAT | 2879 |
| 2761 | 2783 | CCTAACAAACCCACAGGTCCTAA | 1111 | TTAGGACCTGTGGGTTTGTT | 2880 |
| 2770 | 2792 | CCCACAGGTCCTAAACTACCAAA | 1112 | TTTGGTAGTTTAGGACCTGT | 2881 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 2771 | 2793 | CCACAGGTCCTAAACTACCAAAC | 1113 | GTTTGGTAGTTTAGGACCTG | 2882 |
| 2779 | 2801 | CCTAAACTACCAAACCTGCATTA | 1114 | TAATGCAGGTTTGGTAGTTT | 2883 |
| 2788 | 2810 | CCAAACCTGCATTAAAAATTTCG | 1115 | CGAAATTTTAATGCAGGTT | 2884 |
| 2793 | 2815 | CCTGCATTAAAAATTTCGGTTGG | 1116 | CCAACCGAAATTTTTAATGC | 2885 |
| 2821 | 2843 | CCTCGGAGCAGAACCCAACCTCC | 1117 | GGAGGTTGGGTTCTGCTCCG | 2886 |
| 2834 | 2856 | CCCAACCTCCGAGCAGTACATGC | 1118 | GCATGTACTGCTCGGAGGTT | 2887 |
| 2835 | 2857 | CCAACCTCCGAGCAGTACATGCT | 1119 | AGCATGTACTGCTCGGAGGT | 2888 |
| 2839 | 2861 | CCTCCGAGCAGTACATGCTAAGA | 1120 | TCTTAGCATGTACTGCTCGG | 2889 |
| 2842 | 2864 | CCGAGCAGTACATGCTAAGACTT | 1121 | AAGTCTTAGCATGTACTGCT | 2890 |
| 2867 | 2889 | CCAGTCAAAGCGAACTACTATAC | 1122 | GTATAGTAGTTCGCTTTGAC | 2891 |
| 2899 | 2921 | CCAATAACTTGACCAACGGAACA | 1123 | TGTTCCGTTGGTCAAGTTAT | 2892 |
| 2911 | 2933 | CCAACGGAACAAGTTACCCTAGG | 1124 | CCTAGGGTAACTTGTTCCGT | 2893 |
| 2927 | 2949 | CCCTAGGGATAACAGCGCAATCC | 1125 | GGATTGCGCTGTTATCCCTA | 2894 |
| 2928 | 2950 | CCTAGGGATAACAGCGCAATCCT | 1126 | AGGATTGCGCTGTTATCCCT | 2895 |
| 2948 | 2970 | CCTATTCTAGAGTCCATATCAAC | 1127 | GTTGATATGGACTCTAGAAT | 2896 |
| 2961 | 2983 | CCATATCAACAATAGGGTTTACG | 1128 | CGTAAACCCTATTGTTGATA | 2897 |
| 2985 | 3007 | CCTCGATGTTGGATCAGGACATC | 1129 | GATGTCCTGATCCAACATCG | 2898 |
| 3007 | 3029 | CCCGATGGTGCAGCCGCTATTAA | 1130 | TTAATAGCGGCTGCACCATC | 2899 |
| 3008 | 3030 | CCGATGGTGCAGCCGCTATTAAA | 1131 | TTTAATAGCGGCTGCACCAT | 2900 |
| 3020 | 3042 | CCGCTATTAAAGGTTCGTTTGTT | 1132 | AACAAACGAACCTTTAATAG | 2901 |
| 3056 | 3078 | CCTACGTGATCTGAGTTCAGACC | 1133 | GGTCTGAACTCAGATCACGT | 2902 |
| 3077 | 3099 | CCGGAGTAATCCAGGTCGGTTTC | 1134 | GAAACCGACCTGGATTACTC | 2903 |
| 3087 | 3109 | CCAGGTCGGTTTCTATCTACNTT | 1135 | AANGTAGATAGAAACCGACC | 2904 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 3116 | 3138 | CCTCCCTGTACGAAAGGACAAGA | 1136 | TCTTGTCCTTTCGTACAGGG | 2905 |
| 3119 | 3141 | CCCTGTACGAAAGGACAAGAGAA | 1137 | TTCTCTTGTCCTTTCGTACA | 2906 |
| 3120 | 3142 | CCTGTACGAAAGGACAAGAGAAA | 1138 | TTTCTCTTGTCCTTTCGTAC | 2907 |
| 3148 | 3170 | CCTACTTCACAAAGCGCCTTCCC | 1139 | GGGAAGGCGCTTTGTGAAGT | 2908 |
| 3164 | 3186 | CCTTCCCCGTAAATGATATCAT | 1140 | ATGATATCATTTACGGGGA | 2909 |
| 3168 | 3190 | CCCCCGTAAATGATATCATCTCA | 1141 | TGAGATGATATCATTTACGG | 2910 |
| 3169 | 3191 | CCCCGTAAATGATATCATCTCAA | 1142 | TTGAGATGATATCATTTACG | 2911 |
| 3170 | 3192 | CCCGTAAATGATATCATCTCAAC | 1143 | GTTGAGATGATATCATTTAC | 2912 |
| 3171 | 3193 | CCGTAAATGATATCATCTCAACT | 1144 | AGTTGAGATGATATCATTTA | 2913 |
| 3204 | 3226 | CCCACACCCACCCAAGAACAGGG | 1145 | CCCTGTTCTTGGGTGGGTGT | 2914 |
| 3205 | 3227 | CCACACCCACCCAAGAACAGGGT | 1146 | ACCCTGTTCTTGGGTGGGTG | 2915 |
| 3210 | 3232 | CCCACCCAAGAACAGGGTTTGTT | 1147 | AACAAACCCTGTTCTTGGGT | 2916 |
| 3211 | 3233 | CCACCCAAGAACAGGGTTTGTTA | 1148 | TAACAAACCCTGTTCTTGGG | 2917 |
| 3214 | 3236 | CCCAAGAACAGGGTTTGTTAAGA | 1149 | TCTTAACAAACCCTGTTCTT | 2918 |
| 3215 | 3237 | CCAAGAACAGGGTTTGTTAAGAT | 1150 | ATCTTAACAAACCCTGTTCT | 2919 |
| 3245 | 3267 | CCCGGTAATCGCATAAAACTTAA | 1151 | TTAAGTTTTATGCGATTACC | 2920 |
| 3246 | 3268 | CCGGTAATCGCATAAAACTTAAA | 1152 | TTAAGTTTTATGCGATTAC | 2921 |
| 3292 | 3314 | CCTCTTCTTAACAACATACCCAT | 1153 | ATGGGTATGTTGTTAAGAAG | 2922 |
| 3310 | 3332 | CCCATGGCCAACCTCCTACTCCT | 1154 | AGGAGTAGGAGGTTGGCCAT | 2923 |
| 3311 | 3333 | CCATGGCCAACCTCCTACTCCTC | 1155 | GAGGAGTAGGAGGTTGGCCA | 2924 |
| 3317 | 3339 | CCAACCTCCTACTCCTCATTGTA | 1156 | TACAATGAGGAGTAGGAGGT | 2925 |
| 3321 | 3343 | CCTCCTACTCCTCATTGTACCCA | 1157 | TGGGTACAATGAGGAGTAGG | 2926 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 3324 | 3346 | CCTACTCCTCATTGTACCCATTC | 1158 | GAATGGGTACAATGAGGAGT | 2927 |
| 3330 | 3352 | CCTCATTGTACCCATTCTAATCG | 1159 | CGATTAGAATGGGTACAATG | 2928 |
| 3340 | 3362 | CCCATTCTAATCGCAATGGCATT | 1160 | AATGCCATTGCGATTAGAAT | 2929 |
| 3341 | 3363 | CCATTCTAATCGCAATGCATTC | 1161 | GAATGCCATTGCGATTAGAA | 2930 |
| 3363 | 3385 | CCTAATGCTTACCGAACGAAAAA | 1162 | TTTTTCGTTCGGTAAGCATT | 2931 |
| 3374 | 3396 | CCGAACGAAAAATTCTAGGCTAT | 1163 | ATAGCCTAGAATTTTCGTT | 2932 |
| 3414 | 3436 | CCCCAACGTTGTAGGCCCCTACG | 1164 | CGTAGGGGCCTACAACGTTG | 2933 |
| 3415 | 3437 | CCCAACGTTGTAGGCCCCTACGG | 1165 | CCGTAGGGGCCTACAACGTT | 2934 |
| 3416 | 3438 | CCAACGTTGTAGGCCCCTACGGG | 1166 | CCCGTAGGGGCCTACAACGT | 2935 |
| 3429 | 3451 | CCCCTACGGGCTACTACAACCCT | 1167 | AGGGTTGTAGTAGCCCGTAG | 2936 |
| 3430 | 3452 | CCCTACGGGCTACTACAACCCTT | 1168 | AAGGGTTGTAGTAGCCCGTA | 2937 |
| 3431 | 3453 | CCTACGGGCTACTACAACCCTTC | 1169 | GAAGGGTTGTAGTAGCCCGT | 2938 |
| 3448 | 3470 | CCCTTCGCTGACGCCATAAAACT | 1170 | AGTTTTATGGCGTCAGCGAA | 2939 |
| 3449 | 3471 | CCTTCGCTGACGCCATAAAACTC | 1171 | GAGTTTTATGGCGTCAGCGA | 2940 |
| 3461 | 3483 | CCATAAAACTCTTCACCAAAGAG | 1172 | CTCTTTGGTGAAGAGTTTTA | 2941 |
| 3476 | 3498 | CCAAAGAGCCCCTAAAACCCGCC | 1173 | GGCGGGTTTTAGGGGCTCTT | 2942 |
| 3484 | 3506 | CCCCTAAAACCCGCCACATCTAC | 1174 | GTAGATGTGGCGGGTTTTAG | 2943 |
| 3485 | 3507 | CCCTAAAACCCGCCACATCTACC | 1175 | GGTAGATGTGGCGGGTTTTA | 2944 |
| 3486 | 3508 | CCTAAAACCCGCCACATCTACCA | 1176 | TGGTAGATGTGGCGGGTTTT | 2945 |
| 3493 | 3515 | CCCGCCACATCTACCATCACCCT | 1177 | AGGGTGATGGTAGATGTGGC | 2946 |
| 3494 | 3516 | CCGCCACATCTACCATCACCCTC | 1178 | GAGGGTGATGGTAGATGTGG | 2947 |
| 3497 | 3519 | CCACATCTACCATCACCCTCTAC | 1179 | GTAGAGGGTGATGGTAGATG | 2948 |
| 3506 | 3528 | CCATCACCCTCTACATCACCGCC | 1180 | GGCGGTGATGTAGAGGGTGA | 2949 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 3512 | 3534 | CCCTCTACATCACCGCCCCGACC | 1181 | GGTCGGGGCGGTGATGTAGA | 2950 |
| 3513 | 3535 | CCTCTACATCACCGCCCCGACCT | 1182 | AGGTCGGGGCGGTGATGTAG | 2951 |
| 3524 | 3546 | CCGCCCCGACCTTAGCTCTCACC | 1183 | GGTGAGAGCTAAGGTCGGGG | 2952 |
| 3527 | 3549 | CCCCGACCTTAGCTCTCACCATC | 1184 | GATGGTGAGAGCTAAGGTCG | 2953 |
| 3528 | 3550 | CCCGACCTTAGCTCTCACCATCG | 1185 | CGATGGTGAGAGCTAAGGTC | 2954 |
| 3529 | 3551 | CCGACCTTAGCTCTCACCATCGC | 1186 | GCGATGGTGAGAGCTAAGGT | 2955 |
| 3533 | 3555 | CCTTAGCTCTCACCATCGCTCTT | 1187 | AAGAGCGATGGTGAGAGCTA | 2956 |
| 3545 | 3567 | CCATCGCTCTTCTACTATGAACC | 1188 | GGTTCATAGTAGAAGAGCGA | 2957 |
| 3566 | 3588 | CCCCCCTCCCCATACCCAACCCC | 1189 | GGGGTTGGGTATGGGGAGGG | 2958 |
| 3567 | 3589 | CCCCCTCCCCATACCCAACCCCC | 1190 | GGGGGTTGGGTATGGGGAGG | 2959 |
| 3568 | 3590 | CCCCTCCCCATACCCAACCCCCT | 1191 | AGGGGGTTGGGTATGGGGAG | 2960 |
| 3569 | 3591 | CCCTCCCCATACCCAACCCCCTG | 1192 | CAGGGGGTTGGGTATGGGGA | 2961 |
| 3570 | 3592 | CCTCCCCATACCCAACCCCTGG | 1193 | CCAGGGGGTTGGGTATGGGG | 2962 |
| 3573 | 3595 | CCCCATACCCAACCCCCTGGTCA | 1194 | TGACCAGGGGGTTGGGTATG | 2963 |
| 3574 | 3596 | CCCATACCCAACCCCCTGGTCAA | 1195 | TTGACCAGGGGGTTGGGTAT | 2964 |
| 3575 | 3597 | CCATACCCAACCCCCTGGTCAAC | 1196 | GTTGACCAGGGGGTTGGGTA | 2965 |
| 3580 | 3602 | CCCAACCCCCTGGTCAACCTCAA | 1197 | TTGAGGTTGACCAGGGGGTT | 2966 |
| 3581 | 3603 | CCAACCCCCTGGTCAACCTCAAC | 1198 | GTTGAGGTTGACCAGGGGGT | 2967 |
| 3585 | 3607 | CCCCCTGGTCAACCTCAACCTAG | 1199 | CTAGGTTGAGGTTGACCAGG | 2968 |
| 3586 | 3608 | CCCCTGGTCAACCTCAACCTAGG | 1200 | CCTAGGTTGAGGTTGACCAG | 2969 |
| 3587 | 3609 | CCCTGGTCAACCTCAACCTAGGC | 1201 | GCCTAGGTTGAGGTTGACCA | 2970 |
| 3588 | 3610 | CCTGGTCAACCTCAACCTAGGCC | 1202 | GGCCTAGGTTGAGGTTGACC | 2971 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 3597 | 3619 | CCTCAACCTAGGCCTCCTATTTA | 1203 | TAAATAGGAGGCCTAGGTTG | 2972 |
| 3603 | 3625 | CCTAGGCCTCCTATTTATTCTAG | 1204 | CTAGAATAAATAGGAGGCCT | 2973 |
| 3609 | 3631 | CCTCCTATTTATTCTAGCCACCT | 1205 | AGGTGGCTAGAATAAATAGG | 2974 |
| 3612 | 3634 | CCTATTTATTCTAGCCACCTCTA | 1206 | TAGAGGTGGCTAGAATAAAT | 2975 |
| 3626 | 3648 | CCACCTCTAGCCTAGCCGTTTAC | 1207 | GTAAACGGCTAGGCTAGAGG | 2976 |
| 3629 | 3651 | CCTCTAGCCTAGCCGTTTACTCA | 1208 | TGAGTAAACGGCTAGGCTAG | 2977 |
| 3636 | 3658 | CCTAGCCGTTTACTCAATCCTCT | 1209 | AGAGGATTGAGTAAACGGCT | 2978 |
| 3641 | 3663 | CCGTTTACTCAATCCTCTGATCA | 1210 | TGATCAGAGGATTGAGTAAA | 2979 |
| 3654 | 3676 | CCTCTGATCAGGGTGAGCATCAA | 1211 | TTGATGCTCACCCTGATCAG | 2980 |
| 3689 | 3711 | CCCTGATCGGCGCACTGCGAGCA | 1212 | TGCTCGCAGTGCGCCGATCA | 2981 |
| 3690 | 3712 | CCTGATCGGCGCACTGCGAGCAG | 1213 | CTGCTCGCAGTGCGCCGATC | 2982 |
| 3716 | 3738 | CCCAAACAATCTCATATGAAGTC | 1214 | GACTTCATATGAGATTGTTT | 2983 |
| 3717 | 3739 | CCAAACAATCTCATATGAAGTCA | 1215 | TGACTTCATATGAGATTGTT | 2984 |
| 3740 | 3762 | CCCTAGCCATCATTCTACTATCA | 1216 | TGATAGTAGAATGATGGCTA | 2985 |
| 3741 | 3763 | CCTAGCCATCATTCTACTATCAA | 1217 | TTGATAGTAGAATGATGGCT | 2986 |
| 3746 | 3768 | CCATCATTCTACTATCAACATTA | 1218 | TAATGTTGATAGTAGAATGA | 2987 |
| 3782 | 3804 | CCTTTAACCTCTCCACCCTTATC | 1219 | GATAAGGGTGGAGAGGTTAA | 2988 |
| 3789 | 3811 | CCTCTCCACCCTTATCACAACAC | 1220 | GTGTTGTGATAAGGGTGGAG | 2989 |
| 3794 | 3816 | CCACCCTTATCACAACACAAGAA | 1221 | TTCTTGTGTTGTGATAAGGG | 2990 |
| 3797 | 3819 | CCCTTATCACAACACAAGAACAC | 1222 | GTGTTCTTGTGTTGTGATAA | 2991 |
| 3798 | 3820 | CCTTATCACAACACAAGAACACC | 1223 | GGTGTTCTTGTGTTGTGATA | 2992 |
| 3819 | 3841 | CCTCTGATTACTCCTGCCATCAT | 1224 | ATGATGGCAGGAGTAATCAG | 2993 |
| 3831 | 3853 | CCTGCCATCATGACCCTGGCCA | 1225 | TGGCCAGGGTCATGATGGC | 2994 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 3835 | 3857 | CCATCATGACCCTTGGCCATAAT | 1226 | ATTATGGCCAAGGGTCATGA | 2995 |
| 3844 | 3866 | CCCTTGGCCATAATATGATTTAT | 1227 | ATAAATCATATTATGGCCAA | 2996 |
| 3845 | 3867 | CCTTGGCCATAATATGATTTATC | 1228 | GATAAATCATATTATGGCCA | 2997 |
| 3851 | 3873 | CCATAATATGATTTATCTCCACA | 1229 | TGTGGAGATAAATCATATTA | 2998 |
| 3869 | 3891 | CCACACTAGCAGAGACCAACCGA | 1230 | TCGGTTGGTCTCTGCTAGTG | 2999 |
| 3884 | 3906 | CCAACCGAACCCCCTTCGACCTT | 1231 | AAGGTCGAAGGGGGTTCGGT | 3000 |
| 3888 | 3910 | CCGAACCCCCTTCGACCTTGCCG | 1232 | CGGCAAGGTCGAAGGGGGTT | 3001 |
| 3893 | 3915 | CCCCCTTCGACCTTGCCGAAGGG | 1233 | CCCTTCGGCAAGGTCGAAGG | 3002 |
| 3894 | 3916 | CCCCTTCGACCTTGCCGAAGGGG | 1234 | CCCCTTCGGCAAGGTCGAAG | 3003 |
| 3895 | 3917 | CCCTTCGACCTTGCCGAAGGGGA | 1235 | TCCCCTTCGGCAAGGTCGAA | 3004 |
| 3896 | 3918 | CCTTCGACCTTGCCGAAGGGGAG | 1236 | CTCCCCTTCGGCAAGGTCGA | 3005 |
| 3903 | 3925 | CCTTGCCGAAGGGGAGTCCGAAC | 1237 | GTTCGGACTCCCCTTCGGCA | 3006 |
| 3908 | 3930 | CCGAAGGGGAGTCCGAACTAGTC | 1238 | GACTAGTTCGGACTCCCCTT | 3007 |
| 3920 | 3942 | CCGAACTAGTCTCAGGCTTCAAC | 1239 | GTTGAAGCCTGAGACTAGTT | 3008 |
| 3953 | 3975 | CCGCAGGCCCCTTCGCCCTATTC | 1240 | GAATAGGGCGAAGGGCCTG | 3009 |
| 3960 | 3982 | CCCCTTCGCCCTATTCTTCATAG | 1241 | CTATGAAGAATAGGGCGAAG | 3010 |
| 3961 | 3983 | CCCTTCGCCCTATTCTTCATAGC | 1242 | GCTATGAAGAATAGGGCGAA | 3011 |
| 3962 | 3984 | CCTTCGCCCTATTCTTCATAGCC | 1243 | GGCTATGAAGAATAGGGCGA | 3012 |
| 3968 | 3990 | CCCTATTCTTCATAGCCGAATAC | 1244 | GTATTCGGCTATGAAGAATA | 3013 |
| 3969 | 3991 | CCTATTCTTCATAGCCGAATACA | 1245 | TGTATTCGGCTATGAAGAAT | 3014 |
| 3983 | 4005 | CCGAATACACAAACATTATTATA | 1246 | TATAATAATGTTTGTGTATT | 3015 |
| 4013 | 4035 | CCCTCACCACTACAATCTTCCTA | 1247 | TAGGAAGATTGTAGTGGTGA | 3016 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 4014 | 4036 | CCTCACCACTACAATCTTCCTAG | 1248 | CTAGGAAGATTGTAGTGGTG | 3017 |
| 4019 | 4041 | CCACTACAATCTTCCTAGGAACA | 1249 | TGTTCCTAGGAAGATTGTAG | 3018 |
| 4032 | 4054 | CCTAGGAACAACATATGACGCAC | 1250 | GTGCGTCATATGTTGTTCCT | 3019 |
| 4058 | 4080 | CCCCTGAACTCTACACAACATAT | 1251 | ATATGTTGTGTAGAGTTCAG | 3020 |
| 4059 | 4081 | CCCTGAACTCTACACAACATATT | 1252 | AATATGTTGTGTAGAGTTCA | 3021 |
| 4060 | 4082 | CCTGAACTCTACACAACATATTT | 1253 | AAATATGTTGTGTAGAGTTC | 3022 |
| 4088 | 4110 | CCAAGACCCTACTTCTAACCTCC | 1254 | GGAGGTTAGAAGTAGGGTCT | 3023 |
| 4094 | 4116 | CCCTACTTCTAACCTCCCTGTTC | 1255 | GAACAGGGAGGTTAGAAGTA | 3024 |
| 4095 | 4117 | CCTACTTCTAACCTCCCTGTTCT | 1256 | AGAACAGGGAGGTTAGAAGT | 3025 |
| 4106 | 4128 | CCTCCCTGTTCTTATGAATTCGA | 1257 | TCGAATTCATAAGAACAGGG | 3026 |
| 4109 | 4131 | CCCTGTTCTTATGAATTCGAACA | 1258 | TGTTCGAATTCATAAGAACA | 3027 |
| 4110 | 4132 | CCTGTTCTTATGAATTCGAACAG | 1259 | CTGTTCGAATTCATAAGAAC | 3028 |
| 4137 | 4159 | CCCCCGATTCCGCTACGACCAAC | 1260 | GTTGGTCGTAGCGGAATCGG | 3029 |
| 4138 | 4160 | CCCCGATTCCGCTACGACCAACT | 1261 | AGTTGGTCGTAGCGGAATCG | 3030 |
| 4139 | 4161 | CCCGATTCCGCTACGACCAACTC | 1262 | GAGTTGGTCGTAGCGGAATC | 3031 |
| 4140 | 4162 | CCGATTCCGCTACGACCAACTCA | 1263 | TGAGTTGGTCGTAGCGGAAT | 3032 |
| 4146 | 4168 | CCGCTACGACCAACTCATACACC | 1264 | GGTGTATGAGTTGGTCGTAG | 3033 |
| 4155 | 4177 | CCAACTCATACACCTCCTATGAA | 1265 | TTCATAGGAGGTGTATGAGT | 3034 |
| 4167 | 4189 | CCTCCTATGAAAAAACTTCCTAC | 1266 | GTAGGAAGTTTTTTCATAGG | 3035 |
| 4170 | 4192 | CCTATGAAAAAACTTCCTACCAC | 1267 | GTGGTAGGAAGTTTTTTCAT | 3036 |
| 4185 | 4207 | CCTACCACTCACCCTAGCATTAC | 1268 | GTAATGCTAGGGTGAGTGGT | 3037 |
| 4189 | 4211 | CCACTCACCCTAGCATTACTTAT | 1269 | ATAAGTAATGCTAGGGTGAG | 3038 |
| 4196 | 4218 | CCCTAGCATTACTTATATGATAT | 1270 | ATATCATATAAGTAATGCTA | 3039 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 4197 | 4219 | CCTAGCATTACTTATATGATATG | 1271 | CATATCATATAAGTAATGCT | 3040 |
| 4223 | 4245 | CCATACCCATTACAATCTCCAGC | 1272 | GCTGGAGATTGTAATGGGTA | 3041 |
| 4228 | 4250 | CCCATTACAATCTCCAGCATTCC | 1273 | GGAATGCTGGAGATTGTAAT | 3042 |
| 4229 | 4251 | CCATTACAATCTCCAGCATTCCC | 1274 | GGGAATGCTGGAGATTGTAA | 3043 |
| 4241 | 4263 | CCAGCATTCCCCCTCAAACCTAA | 1275 | TTAGGTTTGAGGGGGAATGC | 3044 |
| 4249 | 4271 | CCCCCTCAAACCTAAGAAATATG | 1276 | CATATTTCTTAGGTTTGAGG | 3045 |
| 4250 | 4272 | CCCCTCAAACCTAAGAAATATGT | 1277 | ACATATTTCTTAGGTTTGAG | 3046 |
| 4251 | 4273 | CCCTCAAACCTAAGAAATATGTC | 1278 | GACATATTTCTTAGGTTTGA | 3047 |
| 4252 | 4274 | CCTCAAACCTAAGAAATATGTCT | 1279 | AGACATATTTCTTAGGTTTG | 3048 |
| 4259 | 4281 | CCTAAGAAATATGTCTGATAAAA | 1280 | TTTTATCAGACATATTTCTT | 3049 |
| 4318 | 4340 | CCCCCTTATTTCTAGGACTATGA | 1281 | TCATAGTCCTAGAAATAAGG | 3050 |
| 4319 | 4341 | CCCCTTATTTCTAGGACTATGAG | 1282 | CTCATAGTCCTAGAAATAAG | 3051 |
| 4320 | 4342 | CCCTTATTTCTAGGACTATGAGA | 1283 | TCTCATAGTCCTAGAAATAA | 3052 |
| 4321 | 4343 | CCTTATTTCTAGGACTATGAGAA | 1284 | TTCTCATAGTCCTAGAAATA | 3053 |
| 4349 | 4371 | CCCATCCCTGAGAATCCAAAATT | 1285 | AATTTTGGATTCTCAGGGAT | 3054 |
| 4350 | 4372 | CCATCCCTGAGAATCCAAAATTC | 1286 | GAATTTTGGATTCTCAGGGA | 3055 |
| 4354 | 4376 | CCCTGAGAATCCAAAATTCTCCG | 1287 | CGGAGAATTTTGGATTCTCA | 3056 |
| 4355 | 4377 | CCTGAGAATCCAAAATTCTCCGT | 1288 | ACGGAGAATTTTGGATTCTC | 3057 |
| 4364 | 4386 | CCAAAATTCTCCGTGCCACCTAT | 1289 | ATAGGTGGCACGGAGAATTT | 3058 |
| 4374 | 4396 | CCGTGCCACCTATCACACCCCAT | 1290 | ATGGGGTGTGATAGGTGGCA | 3059 |
| 4379 | 4401 | CCACCTATCACACCCCATCCTAA | 1291 | TTAGGATGGGGTGTGATAGG | 3060 |
| 4382 | 4404 | CCTATCACACCCCATCCTAAAGT | 1292 | ACTTTAGGATGGGGTGTGAT | 3061 |
| 4391 | 4413 | CCCCATCCTAAAGTAAGGTCAGC | 1293 | GCTGACCTTACTTTAGGATG | 3062 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 4392 | 4414 | CCCATCCTAAAGTAAGGTCAGCT | 1294 | AGCTGACCTTACTTTAGGAT | 3063 |
| 4393 | 4415 | CCATCCTAAAGTAAGGTCAGCTA | 1295 | TAGCTGACCTTACTTTAGGA | 3064 |
| 4397 | 4419 | CCTAAAGTAAGGTCAGCTAAATA | 1296 | TATTTAGCTGACCTTACTTT | 3065 |
| 4430 | 4452 | CCCATACCCCGAAAATGTTGGTT | 1297 | AACCAACATTTTCGGGGTAT | 3066 |
| 4431 | 4453 | CCATACCCCGAAAATGTTGGTTA | 1298 | TAACCAACATTTTCGGGGTA | 3067 |
| 4436 | 4458 | CCCCGAAAATGTTGGTTATACCC | 1299 | GGGTATAACCAACATTTTCG | 3068 |
| 4437 | 4459 | CCCGAAAATGTTGGTTATACCCT | 1300 | AGGGTATAACCAACATTTTC | 3069 |
| 4438 | 4460 | CCGAAAATGTTGGTTATACCCTT | 1301 | AAGGGTATAACCAACATTTT | 3070 |
| 4456 | 4478 | CCCTTCCCGTACTAATTAATCCC | 1302 | GGGATTAATTAGTACGGGAA | 3071 |
| 4457 | 4479 | CCTTCCCGTACTAATTAATCCCC | 1303 | GGGGATTAATTAGTACGGGA | 3072 |
| 4461 | 4483 | CCCGTACTAATTAATCCCCTGGC | 1304 | GCCAGGGGATTAATTAGTAC | 3073 |
| 4462 | 4484 | CCGTACTAATTAATCCCCTGGCC | 1305 | GGCCAGGGGATTAATTAGTA | 3074 |
| 4476 | 4498 | CCCCTGGCCCAACCCGTCATCTA | 1306 | TAGATGACGGGTTGGGCCAG | 3075 |
| 4477 | 4499 | CCCTGGCCCAACCCGTCATCTAC | 1307 | GTAGATGACGGGTTGGGCCA | 3076 |
| 4478 | 4500 | CCTGGCCCAACCCGTCATCTACT | 1308 | AGTAGATGACGGGTTGGGCC | 3077 |
| 4483 | 4505 | CCCAACCCGTCATCTACTCTACC | 1309 | GGTAGAGTAGATGACGGGTT | 3078 |
| 4484 | 4506 | CCAACCCGTCATCTACTCTACCA | 1310 | TGGTAGAGTAGATGACGGGT | 3079 |
| 4488 | 4510 | CCCGTCATCTACTCTACCATCTT | 1311 | AAGATGGTAGAGTAGATGAC | 3080 |
| 4489 | 4511 | CCGTCATCTACTCTACCATCTTT | 1312 | AAAGATGGTAGAGTAGATGA | 3081 |
| 4504 | 4526 | CCATCTTTGCAGGCACACTCATC | 1313 | GATGAGTGTGCCTGCAAAGA | 3082 |
| 4555 | 4577 | CCTGAGTAGGCCTAGAAATAAAC | 1314 | GTTTATTTCTAGGCCTACTC | 3083 |
| 4565 | 4587 | CCTAGAAATAAACATGCTAGCTT | 1315 | AAGCTAGCATGTTTATTTCT | 3084 |
| 4593 | 4615 | CCAGTTCTAACCAAAAAATAAA | 1316 | TTTATTTTTTGGTTAGAAC | 3085 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 4603 | 4625 | CCAAAAAATAAACCCTCGTTCC | 1317 | GGAACGAGGGTTTATTTTTT | 3086 |
| 4616 | 4638 | CCCTCGTTCCACAGAAGCTGCCA | 1318 | TGGCAGCTTCTGTGGAACGA | 3087 |
| 4617 | 4639 | CCTCGTTCCACAGAAGCTGCCAT | 1319 | ATGGCAGCTTCTGTGGAACG | 3088 |
| 4624 | 4646 | CCACAGAAGCTGCCATCAAGTAT | 1320 | ATACTTGATGGCAGCTTCTG | 3089 |
| 4636 | 4658 | CCATCAAGTATTTCCTCACGCAA | 1321 | TTGCGTGAGGAAATACTTGA | 3090 |
| 4649 | 4671 | CCTCACGCAAGCAACCGCATCCA | 1322 | TGGATGCGGTTGCTTGCGTG | 3091 |
| 4663 | 4685 | CCGCATCCATAATCCTTCTAATA | 1323 | TATTAGAAGGATTATGGATG | 3092 |
| 4669 | 4691 | CCATAATCCTTCTAATAGCTATC | 1324 | GATAGCTATTAGAAGGATTA | 3093 |
| 4676 | 4698 | CCTTCTAATAGCTATCCTCTTCA | 1325 | TGAAGAGGATAGCTATTAGA | 3094 |
| 4691 | 4713 | CCTCTTCAACAATATACTCTCCG | 1326 | CGGAGAGTATATTGTTGAAG | 3095 |
| 4711 | 4733 | CCGGACAATGAACCATAACCAAT | 1327 | ATTGGTTATGGTTCATTGTC | 3096 |
| 4723 | 4745 | CCATAACCAATACTACCAATCAA | 1328 | TTGATTGGTAGTATTGGTTA | 3097 |
| 4729 | 4751 | CCAATACTACCAATCAATACTCA | 1329 | TGAGTATTGATTGGTAGTAT | 3098 |
| 4738 | 4760 | CCAATCAATACTCATCATTAATA | 1330 | TATTAATGATGAGTATTGAT | 3099 |
| 4795 | 4817 | CCCCCTTTCACTTCTGAGTCCCA | 1331 | TGGGACTCAGAAGTGAAAGG | 3100 |
| 4796 | 4818 | CCCCTTTCACTTCTGAGTCCCAG | 1332 | CTGGGACTCAGAAGTGAAAG | 3101 |
| 4797 | 4819 | CCCTTTCACTTCTGAGTCCCAGA | 1333 | TCTGGGACTCAGAAGTGAAA | 3102 |
| 4798 | 4820 | CCTTTCACTTCTGAGTCCCAGAG | 1334 | CTCTGGGACTCAGAAGTGAA | 3103 |
| 4814 | 4836 | CCCAGAGGTTACCCAAGGCACCC | 1335 | GGGTGCCTTGGGTAACCTCT | 3104 |
| 4815 | 4837 | CCAGAGGTTACCCAAGGCACCCC | 1336 | GGGGTGCCTTGGGTAACCTC | 3105 |
| 4825 | 4847 | CCCAAGGCACCCCTCTGACATCC | 1337 | GGATGTCAGAGGGGTGCCTT | 3106 |
| 4826 | 4848 | CCAAGGCACCCCTCTGACATCCG | 1338 | CGGATGTCAGAGGGGTGCCT | 3107 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 4834 | 4856 | CCCCTCTGACATCCGGCCTGCTT | 1339 | AAGCAGGCCGGATGTCAGAG | 3108 |
| 4835 | 4857 | CCCTCTGACATCCGGCCTGCTTC | 1340 | GAAGCAGGCCGGATGTCAGA | 3109 |
| 4836 | 4858 | CCTCTGACATCCGGCCTGCTTCT | 1341 | AGAAGCAGGCCGGATGTCAG | 3110 |
| 4846 | 4868 | CCGGCCTGCTTCTTCTCACATGA | 1342 | TCATGTGAGAAGAAGCAGGC | 3111 |
| 4850 | 4872 | CCTGCTTCTTCTCACATGACAAA | 1343 | TTTGTCATGTGAGAAGAAGC | 3112 |
| 4879 | 4901 | CCCCCATCTCAATCATATACCAA | 1344 | TTGGTATATGATTGAGATGG | 3113 |
| 4880 | 4902 | CCCCATCTCAATCATATACCAAA | 1345 | TTTGGTATATGATTGAGATG | 3114 |
| 4881 | 4903 | CCCATCTCAATCATATACCAAAT | 1346 | ATTTGGTATATGATTGAGAT | 3115 |
| 4882 | 4904 | CCATCTCAATCATATACCAAATC | 1347 | GATTTGGTATATGATTGAGA | 3116 |
| 4898 | 4920 | CCAAATCTCTCCCTCACTAAACG | 1348 | CGTTTAGTGAGGGAGAGATT | 3117 |
| 4908 | 4930 | CCCTCACTAAACGTAAGCCTTCT | 1349 | AGAAGGCTTACGTTTAGTGA | 3118 |
| 4909 | 4931 | CCTCACTAAACGTAAGCCTTCTC | 1350 | GAGAAGGCTTACGTTTAGTG | 3119 |
| 4925 | 4947 | CCTTCTCCTCACTCTCTCAATCT | 1351 | AGATTGAGAGAGTGAGGAGA | 3120 |
| 4931 | 4953 | CCTCACTCTCTCAATCTTATCCA | 1352 | TGGATAAGATTGAGAGAGTG | 3121 |
| 4951 | 4973 | CCATCATAGCAGGCAGTTGAGGT | 1353 | ACCTCAACTGCCTGCTATGA | 3122 |
| 4982 | 5004 | CCAAACCCAGCTACGCAAAATCT | 1354 | AGATTTTGCGTAGCTGGGTT | 3123 |
| 4987 | 5009 | CCCAGCTACGCAAAATCTTAGCA | 1355 | TGCTAAGATTTTGCGTAGCT | 3124 |
| 4988 | 5010 | CCAGCTACGCAAAATCTTAGCAT | 1356 | ATGCTAAGATTTTGCGTAGC | 3125 |
| 5014 | 5036 | CCTCAATTACCCACATAGGATGA | 1357 | TCATCCTATGTGGGTAATTG | 3126 |
| 5023 | 5045 | CCCACATAGGATGAATAATAGCA | 1358 | TGCTATTATTCATCCTATGT | 3127 |
| 5024 | 5046 | CCACATAGGATGAATAATAGCAG | 1359 | CTGCTATTATTCATCCTATG | 3128 |
| 5052 | 5074 | CCGTACAACCCTAACATAACCAT | 1360 | ATGGTTATGTTAGGGTTGTA | 3129 |
| 5060 | 5082 | CCCTAACATAACCATTCTTAATT | 1361 | AATTAAGAATGGTTATGTTA | 3130 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 5061 | 5083 | CCTAACATAACCATTCTTAATTT | 1362 | AAATTAAGAATGGTTATGTT | 3131 |
| 5071 | 5093 | CCATTCTTAATTTAACTATTTAT | 1363 | ATAAATAGTTAAATTAAGAA | 3132 |
| 5099 | 5121 | CCTAACTACTACCGCATTCCTAC | 1364 | GTAGGAATGCGGTAGTAGTT | 3133 |
| 5110 | 5132 | CCGCATTCCTACTACTCAACTTA | 1365 | TAAGTTGAGTAGTAGGAATG | 3134 |
| 5117 | 5139 | CCTACTACTCAACTTAAACTCCA | 1366 | TGGAGTTTAAGTTGAGTAGT | 3135 |
| 5137 | 5159 | CCAGCACCACGACCCTACTACTA | 1367 | TAGTAGTAGGGTCGTGGTGC | 3136 |
| 5143 | 5165 | CCACGACCCTACTACTATCTCGC | 1368 | GCGAGATAGTAGTAGGGTCG | 3137 |
| 5149 | 5171 | CCCTACTACTATCTCGCACCTGA | 1369 | TCAGGTGCGAGATAGTAGTA | 3138 |
| 5150 | 5172 | CCTACTACTATCTCGCACCTGAA | 1370 | TTCAGGTGCGAGATAGTAGT | 3139 |
| 5167 | 5189 | CCTGAAACAAGCTAACATGACTA | 1371 | TAGTCATGTTAGCTTGTTTC | 3140 |
| 5193 | 5215 | CCCTTAATTCCATCCACCCTCCT | 1372 | AGGAGGGTGGATGGAATTAA | 3141 |
| 5194 | 5216 | CCTTAATTCCATCCACCCTCCTC | 1373 | GAGGAGGGTGGATGGAATTA | 3142 |
| 5202 | 5224 | CCATCCACCCTCCTCTCCCTAGG | 1374 | CCTAGGGAGAGGAGGGTGGA | 3143 |
| 5206 | 5228 | CCACCCTCCTCTCCCTAGGAGGC | 1375 | GCCTCCTAGGGAGAGGAGGG | 3144 |
| 5209 | 5231 | CCCTCCTCTCCCTAGGAGGCCTG | 1376 | CAGGCCTCCTAGGGAGAGGA | 3145 |
| 5210 | 5232 | CCTCCTCTCCCTAGGAGGCCTGC | 1377 | GCAGGCCTCCTAGGGAGAGG | 3146 |
| 5213 | 5235 | CCTCTCCCTAGGAGGCCTGCCCC | 1378 | GGGGCAGGCCTCCTAGGGAG | 3147 |
| 5218 | 5240 | CCCTAGGAGGCCTGCCCCGCTA | 1379 | TAGCGGGGCAGGCCTCCTA | 3148 |
| 5219 | 5241 | CCTAGGAGGCCTGCCCCGCTAA | 1380 | TTAGCGGGGCAGGCCTCCT | 3149 |
| 5228 | 5250 | CCTGCCCCCGCTAACCGGCTTTT | 1381 | AAAAGCCGGTTAGCGGGGC | 3150 |
| 5232 | 5254 | CCCCCGCTAACCGGCTTTTTGCC | 1382 | GGCAAAAAGCCGGTTAGCGG | 3151 |
| 5233 | 5255 | CCCCGCTAACCGGCTTTTTGCCC | 1383 | GGGCAAAAAGCCGGTTAGCG | 3152 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 5234 | 5256 | CCCGCTAACCGGCTTTTTGCCCA | 1384 | TGGGCAAAAGCCGGTTAGC | 3153 |
| 5235 | 5257 | CCGCTAACCGGCTTTTTGCCCAA | 1385 | TTGGGCAAAAGCCGGTTAG | 3154 |
| 5242 | 5264 | CCGGCTTTTTGCCCAAATGGGCC | 1386 | GGCCCATTTGGGCAAAAAGC | 3155 |
| 5253 | 5275 | CCCAAATGGGCCATTATCGAAGA | 1387 | TCTTCGATAATGGCCCATTT | 3156 |
| 5254 | 5276 | CCAAATGGGCCATTATCGAAGAA | 1388 | TTCTTCGATAATGGCCCATT | 3157 |
| 5263 | 5285 | CCATTATCGAAGAATTCACAAAA | 1389 | TTTTGTGAATTCTTCGATAA | 3158 |
| 5294 | 5316 | CCTCATCATCCCCACCATCATAG | 1390 | CTATGATGGTGGGGATGATG | 3159 |
| 5303 | 5325 | CCCCACCATCATAGCCACCATCA | 1391 | TGATGGTGGCTATGATGGTG | 3160 |
| 5304 | 5326 | CCCACCATCATAGCCACCATCAC | 1392 | GTGATGGTGGCTATGATGGT | 3161 |
| 5305 | 5327 | CCACCATCATAGCCACCATCACC | 1393 | GGTGATGGTGGCTATGATGG | 3162 |
| 5308 | 5330 | CCATCATAGCCACCATCACCCTC | 1394 | GAGGGTGATGGTGGCTATGA | 3163 |
| 5317 | 5339 | CCACCATCACCCTCCTTAACCTC | 1395 | GAGGTTAAGGAGGGTGATGG | 3164 |
| 5320 | 5342 | CCATCACCCTCCTTAACCTCTAC | 1396 | GTAGAGGTTAAGGAGGGTGA | 3165 |
| 5326 | 5348 | CCCTCCTTAACCTCTACTTCTAC | 1397 | GTAGAAGTAGAGGTTAAGGA | 3166 |
| 5327 | 5349 | CCTCCTTAACCTCTACTTCTACC | 1398 | GGTAGAAGTAGAGGTTAAGG | 3167 |
| 5330 | 5352 | CCTTAACCTCTACTTCTACCTAC | 1399 | GTAGGTAGAAGTAGAGGTTA | 3168 |
| 5336 | 5358 | CCTCTACTTCTACCTACGCCTAA | 1400 | TTAGGCGTAGGTAGAAGTAG | 3169 |
| 5348 | 5370 | CCTACGCCTAATCTACTCCACCT | 1401 | AGGTGGAGTAGATTAGGCGT | 3170 |
| 5354 | 5376 | CCTAATCTACTCCACCTCAATCA | 1402 | TGATTGAGGTGGAGTAGATT | 3171 |
| 5365 | 5387 | CCACCTCAATCACACTACTCCCC | 1403 | GGGGAGTAGTGTGATTGAGG | 3172 |
| 5368 | 5390 | CCTCAATCACACTACTCCCCATA | 1404 | TATGGGGAGTAGTGTGATTG | 3173 |
| 5384 | 5406 | CCCCATATCTAACAACGTAAAAA | 1405 | TTTTTACGTTGTTAGATATG | 3174 |
| 5385 | 5407 | CCCATATCTAACAACGTAAAAAT | 1406 | ATTTTTACGTTGTTAGATAT | 3175 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 5386 | 5408 | CCATATCTAACAACGTAAAAATA | 1407 | TATTTTTACGTTGTTAGATA | 3176 |
| 5433 | 5455 | CCCACCCCATTCCTCCCCACACT | 1408 | AGTGTGGGGAGGAATGGGGT | 3177 |
| 5434 | 5456 | CCACCCCATTCCTCCCCACACTC | 1409 | GAGTGTGGGGAGGAATGGGG | 3178 |
| 5437 | 5459 | CCCCATTCCTCCCCACACTCATC | 1410 | GATGAGTGTGGGGAGGAATG | 3179 |
| 5438 | 5460 | CCCATTCCTCCCCACACTCATCG | 1411 | CGATGAGTGTGGGGAGGAAT | 3180 |
| 5439 | 5461 | CCATTCCTCCCCACACTCATCGC | 1412 | GCGATGAGTGTGGGGAGGAA | 3181 |
| 5444 | 5466 | CCTCCCCACACTCATCGCCCTTA | 1413 | TAAGGGCGATGAGTGTGGGG | 3182 |
| 5447 | 5469 | CCCCACACTCATCGCCCTTACCA | 1414 | TGGTAAGGGCGATGAGTGTG | 3183 |
| 5448 | 5470 | CCCACACTCATCGCCCTTACCAC | 1415 | GTGGTAAGGGCGATGAGTGT | 3184 |
| 5449 | 5471 | CCACACTCATCGCCCTTACCACG | 1416 | CGTGGTAAGGGCGATGAGTG | 3185 |
| 5461 | 5483 | CCCTTACCACGCTACTCCTACCT | 1417 | AGGTAGGAGTAGCGTGGTAA | 3186 |
| 5462 | 5484 | CCTTACCACGCTACTCCTACCTA | 1418 | TAGGTAGGAGTAGCGTGGTA | 3187 |
| 5467 | 5489 | CCACGCTACTCCTACCTATCTCC | 1419 | GGAGATAGGTAGGAGTAGCG | 3188 |
| 5477 | 5499 | CCTACCTATCTCCCCTTTATAC | 1420 | GTATAAAGGGGAGATAGGT | 3189 |
| 5481 | 5503 | CCTATCTCCCCTTTTATACTAAT | 1421 | ATTAGTATAAAAGGGGAGAT | 3190 |
| 5488 | 5510 | CCCCTTTTATACTAATAATCTTA | 1422 | TAAGATTATTAGTATAAAAG | 3191 |
| 5489 | 5511 | CCCTTTTATACTAATAATCTTAT | 1423 | ATAAGATTATTAGTATAAAA | 3192 |
| 5490 | 5512 | CCTTTTATACTAATAATCTTATA | 1424 | TATAAGATTATTAGTATAAA | 3193 |
| 5534 | 5556 | CCAAGAGCCTTCAAAGCCCTCAG | 1425 | CTGAGGGCTTTGAAGGCTCT | 3194 |
| 5541 | 5563 | CCTTCAAAGCCCTCAGTAAGTTG | 1426 | CAACTTACTGAGGGCTTTGA | 3195 |
| 5550 | 5572 | CCCTCAGTAAGTTGCAATACTTA | 1427 | TAAGTATTGCAACTTACTGA | 3196 |
| 5551 | 5573 | CCTCAGTAAGTTGCAATACTTAA | 1428 | TTAAGTATTGCAACTTACTG | 3197 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 5601 | 5623 | CCCCACTCTGCATCAACTGAACG | 1429 | CGTTCAGTTGATGCAGAGTG | 3198 |
| 5602 | 5624 | CCCACTCTGCATCAACTGAACGC | 1430 | GCGTTCAGTTGATGCAGAGT | 3199 |
| 5603 | 5625 | CCACTCTGCATCAACTGAACGCA | 1431 | TGCGTTCAGTTGATGCAGAG | 3200 |
| 5632 | 5654 | CCACTTTAATTAAGCTAAGCCCT | 1432 | AGGGCTTAGCTTAATTAAAG | 3201 |
| 5651 | 5673 | CCCTTACTAGACCAATGGGACTT | 1433 | AAGTCCCATTGGTCTAGTAA | 3202 |
| 5652 | 5674 | CCTTACTAGACCAATGGGACTTA | 1434 | TAAGTCCCATTGGTCTAGTA | 3203 |
| 5662 | 5684 | CCAATGGGACTTAAACCCACAAA | 1435 | TTTGTGGGTTTAAGTCCCAT | 3204 |
| 5677 | 5699 | CCCACAAACACTTAGTTAACAGC | 1436 | GCTGTTAACTAAGTGTTTGT | 3205 |
| 5678 | 5700 | CCACAAACACTTAGTTAACAGCT | 1437 | AGCTGTTAACTAAGTGTTTG | 3206 |
| 5706 | 5728 | CCCTAATCAACTGGCTTCAATCT | 1438 | AGATTGAAGCCAGTTGATTA | 3207 |
| 5707 | 5729 | CCTAATCAACTGGCTTCAATCTA | 1439 | TAGATTGAAGCCAGTTGATT | 3208 |
| 5735 | 5757 | CCCGCCGCGGGAAAAAAGGCGG | 1440 | CCGCCTTTTTTCCCGGCGGC | 3209 |
| 5736 | 5758 | CCGCCGCGGGAAAAAAGGCGGG | 1441 | CCCGCCTTTTTTCCCGGCGG | 3210 |
| 5739 | 5761 | CCGCCGGGAAAAAAGGCGGGAGA | 1442 | TCTCCCGCCTTTTTTCCCGG | 3211 |
| 5742 | 5764 | CCGGGAAAAAAGGCGGGAGAAGC | 1443 | GCTTCTCCCGCCTTTTTTCC | 3212 |
| 5764 | 5786 | CCCCGGCAGGTTTGAAGCTGCTT | 1444 | AAGCAGCTTCAAACCTGCCG | 3213 |
| 5765 | 5787 | CCCGGCAGGTTTGAAGCTGCTTC | 1445 | GAAGCAGCTTCAAACCTGCC | 3214 |
| 5766 | 5788 | CCGGCAGGTTTGAAGCTGCTTCT | 1446 | AGAAGCAGCTTCAAACCTGC | 3215 |
| 5817 | 5839 | CCTCGGAGCTGGTAAAAAGAGGC | 1447 | GCCTCTTTTTACCAGCTCCG | 3216 |
| 5839 | 5861 | CCTAACCCCTGTCTTTAGATTTA | 1448 | TAAATCTAAAGACAGGGGTT | 3217 |
| 5844 | 5866 | CCCCTGTCTTTAGATTTACAGTC | 1449 | GACTGTAAATCTAAAGACAG | 3218 |
| 5845 | 5867 | CCCTGTCTTTAGATTTACAGTCC | 1450 | GGACTGTAAATCTAAAGACA | 3219 |
| 5846 | 5868 | CCTGTCTTTAGATTTACAGTCCA | 1451 | TGGACTGTAAATCTAAAGAC | 3220 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 5866 | 5888 | CCAATGCTTCACTCAGCCATTTT | 1452 | AAAATGGCTGAGTGAAGCAT | 3221 |
| 5882 | 5904 | CCATTTTACCTCACCCCCACTGA | 1453 | TCAGTGGGGGTGAGGTAAAA | 3222 |
| 5890 | 5912 | CCTCACCCCCACTGATGTTCGCC | 1454 | GGCGAACATCAGTGGGGGTG | 3223 |
| 5895 | 5917 | CCCCCACTGATGTTCGCCGACCG | 1455 | CGGTCGGCGAACATCAGTGG | 3224 |
| 5896 | 5918 | CCCCACTGATGTTCGCCGACCGT | 1456 | ACGGTCGGCGAACATCAGTG | 3225 |
| 5897 | 5919 | CCCACTGATGTTCGCCGACCGTT | 1457 | AACGGTCGGCGAACATCAGT | 3226 |
| 5898 | 5920 | CCACTGATGTTCGCCGACCGTTG | 1458 | CAACGGTCGGCGAACATCAG | 3227 |
| 5911 | 5933 | CCGACCGTTGACTATTCTCTACA | 1459 | TGTAGAGAATAGTCAACGGT | 3228 |
| 5915 | 5937 | CCGTTGACTATTCTCTACAAACC | 1460 | GGTTTGTAGAGAATAGTCAA | 3229 |
| 5936 | 5958 | CCACAAAGACATTGGAACACTAT | 1461 | ATAGTGTTCCAATGTCTTTG | 3230 |
| 5960 | 5982 | CCTATTATTCGGCGCATGAGCTG | 1462 | CAGCTCATGCGCCGAATAAT | 3231 |
| 5987 | 6009 | CCTAGGCACAGCTCTAAGCCTCC | 1463 | GGAGGCTTAGAGCTGTGCCT | 3232 |
| 6005 | 6027 | CCTCCTTATTCGAGCCGAGCTGG | 1464 | CCAGCTCGGCTCGAATAAGG | 3233 |
| 6008 | 6030 | CCTTATTCGAGCCGAGCTGGGCC | 1465 | GGCCCAGCTCGGCTCGAATA | 3234 |
| 6019 | 6041 | CCGAGCTGGGCCAGCCAGGCAAC | 1466 | GTTGCCTGGCTGGCCCAGCT | 3235 |
| 6029 | 6051 | CCAGCCAGGCAACCTTCTAGGTA | 1467 | TACCTAGAAGGTTGCCTGGC | 3236 |
| 6033 | 6055 | CCAGGCAACCTTCTAGGTAACGA | 1468 | TCGTTACCTAGAAGGTTGCC | 3237 |
| 6041 | 6063 | CCTTCTAGGTAACGACCACATCT | 1469 | AGATGTGGTCGTTACCTAGA | 3238 |
| 6056 | 6078 | CCACATCTACAACGTTATCGTCA | 1470 | TGACGATAACGTTGTAGATG | 3239 |
| 6082 | 6104 | CCCATGCATTTGTAATAATCTTC | 1471 | GAAGATTATTACAAATGCAT | 3240 |
| 6083 | 6105 | CCATGCATTTGTAATAATCTTCT | 1472 | AGAAGATTATTACAAATGCA | 3241 |
| 6117 | 6139 | CCCATCATAATCGGAGGCTTTGG | 1473 | CCAAAGCCTCCGATTATGAT | 3242 |
| 6118 | 6140 | CCATCATAATCGGAGGCTTTGGC | 1474 | GCCAAAGCCTCCGATTATGA | 3243 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 6153 | 6175 | CCCCTAATAATCGGTGCCCCCGA | 1475 | TCGGGGGCACCGATTATTAG | 3244 |
| 6154 | 6176 | CCCTAATAATCGGTGCCCCGAT | 1476 | ATCGGGGCACCGATTATTA | 3245 |
| 6155 | 6177 | CCTAATAATCGGTGCCCCGATA | 1477 | TATCGGGGCACCGATTATT | 3246 |
| 6169 | 6191 | CCCCCGATATGGCGTTTCCCCGC | 1478 | GCGGGGAAACGCCATATCGG | 3247 |
| 6170 | 6192 | CCCCGATATGGCGTTTCCCGCA | 1479 | TGCGGGGAAACGCCATATCG | 3248 |
| 6171 | 6193 | CCCGATATGGCGTTTCCCCGCAT | 1480 | ATGCGGGGAAACGCCATATC | 3249 |
| 6172 | 6194 | CCGATATGGCGTTTCCCCGCATA | 1481 | TATGCGGGGAAACGCCATAT | 3250 |
| 6186 | 6208 | CCCCGCATAAACAACATAAGCTT | 1482 | AAGCTTATGTTGTTTATGCG | 3251 |
| 6187 | 6209 | CCCGCATAAACAACATAAGCTTC | 1483 | GAAGCTTATGTTGTTTATGC | 3252 |
| 6188 | 6210 | CCGCATAAACAACATAAGCTTCT | 1484 | AGAAGCTTATGTTGTTTATG | 3253 |
| 6219 | 6241 | CCTCCCTCTCTCCTACTCCTGCT | 1485 | AGCAGGAGTAGGAGAGAGGG | 3254 |
| 6222 | 6244 | CCCTCTCTCCTACTCCTGCTCGC | 1486 | GCGAGCAGGAGTAGGAGAGA | 3255 |
| 6223 | 6245 | CCTCTCTCCTACTCCTGCTCGCA | 1487 | TGCGAGCAGGAGTAGGAGAG | 3256 |
| 6230 | 6252 | CCTACTCCTGCTCGCATCTGCTA | 1488 | TAGCAGATGCGAGCAGGAGT | 3257 |
| 6236 | 6258 | CCTGCTCGCATCTGCTATAGTGG | 1489 | CCACTATAGCAGATGCGAGC | 3258 |
| 6262 | 6284 | CCGGAGCAGGAACAGGTTGAACA | 1490 | TGTTCAACCTGTTCCTGCTC | 3259 |
| 6290 | 6312 | CCCTCCCTTAGCAGGGAACTACT | 1491 | AGTAGTTCCCTGCTAAGGGA | 3260 |
| 6291 | 6313 | CCTCCCTTAGCAGGGAACTACTC | 1492 | GAGTAGTTCCCTGCTAAGGG | 3261 |
| 6294 | 6316 | CCCTTAGCAGGGAACTACTCCCA | 1493 | TGGGAGTAGTTCCCTGCTAA | 3262 |
| 6295 | 6317 | CCTTAGCAGGGAACTACTCCCAC | 1494 | GTGGGAGTAGTTCCCTGCTA | 3263 |
| 6313 | 6335 | CCCACCCTGGAGCCTCCGTAGAC | 1495 | GTCTACGGAGGCTCCAGGGT | 3264 |
| 6314 | 6336 | CCACCCTGGAGCCTCCGTAGACC | 1496 | GGTCTACGGAGGCTCCAGGG | 3265 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 6317 | 6339 | CCCTGGAGCCTCCGTAGACCTAA | 1497 | TTAGGTCTACGGAGGCTCCA | 3266 |
| 6318 | 6340 | CCTGGAGCCTCCGTAGACCTAAC | 1498 | GTTAGGTCTACGGAGGCTCC | 3267 |
| 6325 | 6347 | CCTCCGTAGACCTAACCATCTTC | 1499 | GAAGATGGTTAGGTCTACGG | 3268 |
| 6328 | 6350 | CCGTAGACCTAACCATCTTCTCC | 1500 | GGAGAAGATGGTTAGGTCTA | 3269 |
| 6335 | 6357 | CCTAACCATCTTCTCCTTACACC | 1501 | GGTGTAAGGAGAAGATGGTT | 3270 |
| 6340 | 6362 | CCATCTTCTCCTTACACCTAGCA | 1502 | TGCTAGGTGTAAGGAGAAGA | 3271 |
| 6349 | 6371 | CCTTACACCTAGCAGGTGTCTCC | 1503 | GGAGACACCTGCTAGGTGTA | 3272 |
| 6356 | 6378 | CCTAGCAGGTGTCTCCTCTATCT | 1504 | AGATAGAGGAGACACCTGCT | 3273 |
| 6370 | 6392 | CCTCTATCTTAGGGGCCATCAAT | 1505 | ATTGATGGCCCCTAAGATAG | 3274 |
| 6385 | 6407 | CCATCAATTTCATCACAACAATT | 1506 | AATTGTTGTGATGAAATTGA | 3275 |
| 6420 | 6442 | CCCCCTGCCATAACCCAATACCA | 1507 | TGGTATTGGGTTATGGCAGG | 3276 |
| 6421 | 6443 | CCCCTGCCATAACCCAATACCAA | 1508 | TTGGTATTGGGTTATGGCAG | 3277 |
| 6422 | 6444 | CCCTGCCATAACCCAATACCAAA | 1509 | TTTGGTATTGGGTTATGGCA | 3278 |
| 6423 | 6445 | CCTGCCATAACCCAATACCAAAC | 1510 | GTTTGGTATTGGGTTATGGC | 3279 |
| 6427 | 6449 | CCATAACCCAATACCAAACGCCC | 1511 | GGGCGTTTGGTATTGGGTTA | 3280 |
| 6433 | 6455 | CCCAATACCAAACGCCCCTCTTC | 1512 | GAAGAGGGGCGTTTGGTATT | 3281 |
| 6434 | 6456 | CCAATACCAAACGCCCCTCTTCG | 1513 | CGAAGAGGGGCGTTTGGTAT | 3282 |
| 6440 | 6462 | CCAAACGCCCCTCTTCGTCTGAT | 1514 | ATCAGACGAAGAGGGGCGTT | 3283 |
| 6447 | 6469 | CCCCTCTTCGTCTGATCCGTCCT | 1515 | AGGACGGATCAGACGAAGAG | 3284 |
| 6448 | 6470 | CCCTCTTCGTCTGATCCGTCCTA | 1516 | TAGGACGGATCAGACGAAGA | 3285 |
| 6449 | 6471 | CCTCTTCGTCTGATCCGTCCTAA | 1517 | TTAGGACGGATCAGACGAAG | 3286 |
| 6463 | 6485 | CCGTCCTAATCACAGCAGTCCTA | 1518 | TAGGACTGCTGTGATTAGGA | 3287 |
| 6467 | 6489 | CCTAATCACAGCAGTCCTACTTC | 1519 | GAAGTAGGACTGCTGTGATT | 3288 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 6482 | 6504 | CCTACTTCTCCTATCTCTCCCAG | 1520 | CTGGGAGAGATAGGAGAAGT | 3289 |
| 6491 | 6513 | CCTATCTCTCCCAGTCCTAGCTG | 1521 | CAGCTAGGACTGGGAGAGAT | 3290 |
| 6500 | 6522 | CCCAGTCCTAGCTGCTGGCATCA | 1522 | TGATGCCAGCAGCTAGGACT | 3291 |
| 6501 | 6523 | CCAGTCCTAGCTGCTGGCATCAC | 1523 | GTGATGCCAGCAGCTAGGAC | 3292 |
| 6506 | 6528 | CCTAGCTGCTGGCATCACTATAC | 1524 | GTATAGTGATGCCAGCAGCT | 3293 |
| 6539 | 6561 | CCGCAACCTCAACACCACCTTCT | 1525 | AGAAGGTGGTGTTGAGGTTG | 3294 |
| 6545 | 6567 | CCTCAACACCACCTTCTTCGACC | 1526 | GGTCGAAGAAGGTGGTGTTG | 3295 |
| 6553 | 6575 | CCACCTTCTTCGACCCCGCCGGA | 1527 | TCCGGCGGGGTCGAAGAAGG | 3296 |
| 6556 | 6578 | CCTTCTTCGACCCCGCCGGAGGA | 1528 | TCCTCCGGCGGGGTCGAAGA | 3297 |
| 6566 | 6588 | CCCCGCCGGAGGAGGAGACCCCA | 1529 | TGGGGTCTCCTCCTCCGGCG | 3298 |
| 6567 | 6589 | CCCGCCGGAGGAGGAGACCCCAT | 1530 | ATGGGGTCTCCTCCTCCGGC | 3299 |
| 6568 | 6590 | CCGCCGGAGGAGGAGACCCCATT | 1531 | AATGGGGTCTCCTCCTCCGG | 3300 |
| 6571 | 6593 | CCGGAGGAGGAGACCCCATTCTA | 1532 | TAGAATGGGGTCTCCTCCTC | 3301 |
| 6584 | 6606 | CCCCATTCTATACCAACACCTAT | 1533 | ATAGGTGTTGGTATAGAATG | 3302 |
| 6585 | 6607 | CCCATTCTATACCAACACCTATT | 1534 | AATAGGTGTTGGTATAGAAT | 3303 |
| 6586 | 6608 | CCATTCTATACCAACACCTATTC | 1535 | GAATAGGTGTTGGTATAGAA | 3304 |
| 6596 | 6618 | CCAACACCTATTCTGATTTTCG | 1536 | CGAAAAATCAGAATAGGTGT | 3305 |
| 6602 | 6624 | CCTATTCTGATTTTCGGTCACC | 1537 | GGTGACCGAAAAATCAGAAT | 3306 |
| 6623 | 6645 | CCCTGAAGTTTATATTCTTATCC | 1538 | GGATAAGAATATAAACTTCA | 3307 |
| 6624 | 6646 | CCTGAAGTTTATATTCTTATCCT | 1539 | AGGATAAGAATATAAACTTC | 3308 |
| 6644 | 6666 | CCTACCAGGCTTCGGAATAATCT | 1540 | AGATTATTCCGAAGCCTGGT | 3309 |
| 6648 | 6670 | CCAGGCTTCGGAATAATCTCCCA | 1541 | TGGGAGATTATTCCGAAGCC | 3310 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 6667 | 6689 | CCCATATTGTAACTTACTACTCC | 1542 | GGAGTAGTAAGTTACAATAT | 3311 |
| 6668 | 6690 | CCATATTGTAACTTACTACTCCG | 1543 | CGGAGTAGTAAGTTACAATA | 3312 |
| 6688 | 6710 | CCGGAAAAAAGAACCATTTGGA | 1544 | TCCAAATGGTTCTTTTTTTC | 3313 |
| 6702 | 6724 | CCATTTGGATACATAGGTATGGT | 1545 | ACCATACCTATGTATCCAAA | 3314 |
| 6749 | 6771 | CCTAGGGTTTATCGTGTGAGCAC | 1546 | GTGCTCACACGATAAACCCT | 3315 |
| 6773 | 6795 | CCATATATTTACAGTAGGAATAG | 1547 | CTATTCCTACTGTAAATATA | 3316 |
| 6820 | 6842 | CCTCCGCTACCATAATCATCGCT | 1548 | AGCGATGATTATGGTAGCGG | 3317 |
| 6823 | 6845 | CCGCTACCATAATCATCGCTATC | 1549 | GATAGCGATGATTATGGTAG | 3318 |
| 6829 | 6851 | CCATAATCATCGCTATCCCCACC | 1550 | GGTGGGGATAGCGATGATTA | 3319 |
| 6845 | 6867 | CCCCACCGGCGTCAAAGTATTTA | 1551 | TAAATACTTTGACGCCGGTG | 3320 |
| 6846 | 6868 | CCCACCGGCGTCAAAGTATTTAG | 1552 | CTAAATACTTTGACGCCGGT | 3321 |
| 6847 | 6869 | CCACCGGCGTCAAAGTATTTAGC | 1553 | GCTAAATACTTTGACGCCGG | 3322 |
| 6850 | 6872 | CCGGCGTCAAAGTATTTAGCTGA | 1554 | TCAGCTAAATACTTTGACGC | 3323 |
| 6877 | 6899 | CCACACTCCACGGAAGCAATATG | 1555 | CATATTGCTTCCGTGGAGTG | 3324 |
| 6884 | 6906 | CCACGGAAGCAATATGAAATGAT | 1556 | ATCATTTCATATTGCTTCCG | 3325 |
| 6925 | 6947 | CCCTAGGATTCATCTTTCTTTTC | 1557 | GAAAAGAAAGATGAATCCTA | 3326 |
| 6926 | 6948 | CCTAGGATTCATCTTTCTTTTCA | 1558 | TGAAAAGAAAGATGAATCCT | 3327 |
| 6949 | 6971 | CCGTAGGTGGCCTGACTGGCATT | 1559 | AATGCCAGTCAGGCCACCTA | 3328 |
| 6959 | 6981 | CCTGACTGGCATTGTATTAGCAA | 1560 | TTGCTAATACAATGCCAGTC | 3329 |
| 7027 | 7049 | CCCACTTCCACTATGTCCTATCA | 1561 | TGATAGGACATAGTGGAAGT | 3330 |
| 7028 | 7050 | CCACTTCCACTATGTCCTATCAA | 1562 | TTGATAGGACATAGTGGAAG | 3331 |
| 7034 | 7056 | CCACTATGTCCTATCAATAGGAG | 1563 | CTCCTATTGATAGGACATAG | 3332 |
| 7043 | 7065 | CCTATCAATAGGAGCTGTATTTG | 1564 | CAAATACAGCTCCTATTGAT | 3333 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 7066 | 7088 | CCATCATAGGAGGCTTCATTCAC | 1565 | GTGAATGAAGCCTCCTATGA | 3334 |
| 7095 | 7117 | CCCCTATTCTCAGGCTACACCCT | 1566 | AGGGTGTAGCCTGAGAATAG | 3335 |
| 7096 | 7118 | CCCTATTCTCAGGCTACACCCTA | 1567 | TAGGGTGTAGCCTGAGAATA | 3336 |
| 7097 | 7119 | CCTATTCTCAGGCTACACCCTAG | 1568 | CTAGGGTGTAGCCTGAGAAT | 3337 |
| 7114 | 7136 | CCCTAGACCAAACCTACGCCAAA | 1569 | TTTGGCGTAGGTTTGGTCTA | 3338 |
| 7115 | 7137 | CCTAGACCAAACCTACGCCAAAA | 1570 | TTTTGGCGTAGGTTTGGTCT | 3339 |
| 7121 | 7143 | CCAAACCTACGCCAAAATCCATT | 1571 | AATGGATTTTGGCGTAGGTT | 3340 |
| 7126 | 7148 | CCTACGCCAAAATCCATTTCACT | 1572 | AGTGAAATGGATTTTGGCGT | 3341 |
| 7132 | 7154 | CCAAAATCCATTTCACTATCATA | 1573 | TATGATAGTGAAATGGATTT | 3342 |
| 7139 | 7161 | CCATTTCACTATCATATTCATCG | 1574 | CGATGAATATGATAGTGAAA | 3343 |
| 7181 | 7203 | CCCACAACACTTTCTCGGCCTAT | 1575 | ATAGGCCGAGAAAGTGTTGT | 3344 |
| 7182 | 7204 | CCACAACACTTTCTCGGCCTATC | 1576 | GATAGGCCGAGAAAGTGTTG | 3345 |
| 7199 | 7221 | CCTATCCGGAATGCCCCGACGTT | 1577 | AACGTCGGGGCATTCCGGAT | 3346 |
| 7204 | 7226 | CCGGAATGCCCCGACGTTACTCG | 1578 | CGAGTAACGTCGGGGCATTC | 3347 |
| 7212 | 7234 | CCCCGACGTTACTCGGACTACCC | 1579 | GGGTAGTCCGAGTAACGTCG | 3348 |
| 7213 | 7235 | CCCGACGTTACTCGGACTACCCC | 1580 | GGGGTAGTCCGAGTAACGTC | 3349 |
| 7214 | 7236 | CCGACGTTACTCGGACTACCCCG | 1581 | CGGGGTAGTCCGAGTAACGT | 3350 |
| 7232 | 7254 | CCCCGATGCATACACCACATGAA | 1582 | TTCATGTGGTGTATGCATCG | 3351 |
| 7233 | 7255 | CCCGATGCATACACCACATGAAA | 1583 | TTTCATGTGGTGTATGCATC | 3352 |
| 7234 | 7256 | CCGATGCATACACCACATGAAAC | 1584 | GTTTCATGTGGTGTATGCAT | 3353 |
| 7246 | 7268 | CCACATGAAACATCCTATCATCT | 1585 | AGATGATAGGATGTTTCATG | 3354 |
| 7259 | 7281 | CCTATCATCTGTAGGCTCATTCA | 1586 | TGAATGAGCCTACAGATGAT | 3355 |
| 7327 | 7349 | CCTTCGCTTCGAAGCGAAAAGTC | 1587 | GACTTTTCGCTTCGAAGCGA | 3356 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 7349 | 7371 | CCTAATAGTAGAAGAACCCTCCA | 1588 | TGGAGGGTTCTTCTACTATT | 3357 |
| 7365 | 7387 | CCCTCCATAAACCTGGAGTGACT | 1589 | AGTCACTCCAGGTTTATGGA | 3358 |
| 7366 | 7388 | CCTCCATAAACCTGGAGTGACTA | 1590 | TAGTCACTCCAGGTTTATGG | 3359 |
| 7369 | 7391 | CCATAAACCTGGAGTGACTATAT | 1591 | ATATAGTCACTCCAGGTTTA | 3360 |
| 7376 | 7398 | CCTGGAGTGACTATATGGATGCC | 1592 | GGCATCCATATAGTCACTCC | 3361 |
| 7397 | 7419 | CCCCCCACCCTACCACACATTCG | 1593 | CGAATGTGTGGTAGGGTGGG | 3362 |
| 7398 | 7420 | CCCCCACCCTACCACACATTCGA | 1594 | TCGAATGTGTGGTAGGGTGG | 3363 |
| 7399 | 7421 | CCCCACCCTACCACACATTCGAA | 1595 | TTCGAATGTGTGGTAGGGTG | 3364 |
| 7400 | 7422 | CCCACCCTACCACACATTCGAAG | 1596 | CTTCGAATGTGTGGTAGGGT | 3365 |
| 7401 | 7423 | CCACCCTACCACACATTCGAAGA | 1597 | TCTTCGAATGTGTGGTAGGG | 3366 |
| 7404 | 7426 | CCCTACCACACATTCGAAGAACC | 1598 | GGTTCTTCGAATGTGTGGTA | 3367 |
| 7405 | 7427 | CCTACCACACATTCGAAGAACCC | 1599 | GGGTTCTTCGAATGTGTGGT | 3368 |
| 7409 | 7431 | CCACACATTCGAAGAACCCGTAT | 1600 | ATACGGGTTCTTCGAATGTG | 3369 |
| 7425 | 7447 | CCCGTATACATAAAATCTAGACA | 1601 | TGTCTAGATTTTATGTATAC | 3370 |
| 7426 | 7448 | CCGTATACATAAAATCTAGACAA | 1602 | TTGTCTAGATTTTATGTATA | 3371 |
| 7466 | 7488 | CCCCCCAAAGCTGGTTTCAAGCC | 1603 | GGCTTGAAACCAGCTTTGGG | 3372 |
| 7467 | 7489 | CCCCCAAAGCTGGTTTCAAGCCA | 1604 | TGGCTTGAAACCAGCTTTGG | 3373 |
| 7468 | 7490 | CCCCAAAGCTGGTTTCAAGCCAA | 1605 | TTGGCTTGAAACCAGCTTTG | 3374 |
| 7469 | 7491 | CCCAAAGCTGGTTTCAAGCCAAC | 1606 | GTTGGCTTGAAACCAGCTTT | 3375 |
| 7470 | 7492 | CCAAAGCTGGTTTCAAGCCAACC | 1607 | GGTTGGCTTGAAACCAGCTT | 3376 |
| 7487 | 7509 | CCAACCCCATGGCCTCCATGACT | 1608 | AGTCATGGAGGCCATGGGGT | 3377 |
| 7491 | 7513 | CCCCATGGCCTCCATGACTTTTT | 1609 | AAAAAGTCATGGAGGCCATG | 3378 |
| 7492 | 7514 | CCCATGGCCTCCATGACTTTTTC | 1610 | GAAAAAGTCATGGAGGCCAT | 3379 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 7493 | 7515 | CCATGGCCTCCATGACTTTTTCA | 1611 | TGAAAAAGTCATGGAGGCCA | 3380 |
| 7499 | 7521 | CCTCCATGACTTTTTCAAAAGG | 1612 | CCTTTTTGAAAAAGTCATGG | 3381 |
| 7502 | 7524 | CCATGACTTTTTCAAAAAGGTAT | 1613 | ATACCTTTTTGAAAAAGTCA | 3382 |
| 7533 | 7555 | CCATTTCATAACTTTGTCAAAGT | 1614 | ACTTTGACAAAGTTATGAAA | 3383 |
| 7573 | 7595 | CCTATATATCTTAATGGCACATG | 1615 | CATGTGCCATTAAGATATAT | 3384 |
| 7626 | 7648 | CCCCTATCATAGAAGAGCTTATC | 1616 | GATAAGCTCTTCTATGATAG | 3385 |
| 7627 | 7649 | CCCTATCATAGAAGAGCTTATCA | 1617 | TGATAAGCTCTTCTATGATA | 3386 |
| 7628 | 7650 | CCTATCATAGAAGAGCTTATCAC | 1618 | GTGATAAGCTCTTCTATGAT | 3387 |
| 7650 | 7672 | CCTTTCATGATCACGCCCTCATA | 1619 | TATGAGGGCGTGATCATGAA | 3388 |
| 7665 | 7687 | CCCTCATAATCATTTTCCTTATC | 1620 | GATAAGGAAAATGATTATGA | 3389 |
| 7666 | 7688 | CCTCATAATCATTTTCCTTATCT | 1621 | AGATAAGGAAAATGATTATG | 3390 |
| 7681 | 7703 | CCTTATCTGCTTCCTAGTCCTGT | 1622 | ACAGGACTAGGAAGCAGATA | 3391 |
| 7693 | 7715 | CCTAGTCCTGTATGCCCTTTTCC | 1623 | GGAAAAGGGCATACAGGACT | 3392 |
| 7699 | 7721 | CCTGTATGCCCTTTTCCTAACAC | 1624 | GTGTTAGGAAAAGGGCATAC | 3393 |
| 7707 | 7729 | CCCTTTTCCTAACACTCACAACA | 1625 | TGTTGTGAGTGTTAGGAAAA | 3394 |
| 7708 | 7730 | CCTTTTCCTAACACTCACAACAA | 1626 | TTGTTGTGAGTGTTAGGAAA | 3395 |
| 7714 | 7736 | CCTAACACTCACAACAAAACTAA | 1627 | TTAGTTTTGTTGTGAGTGTT | 3396 |
| 7773 | 7795 | CCGTCTGAACTATCCTGCCCGCC | 1628 | GGCGGGCAGGATAGTTCAGA | 3397 |
| 7786 | 7808 | CCTGCCCGCCATCATCCTAGTCC | 1629 | GGACTAGGATGATGGCGGGC | 3398 |
| 7790 | 7812 | CCCGCCATCATCCTAGTCCTCAT | 1630 | ATGAGGACTAGGATGATGGC | 3399 |
| 7791 | 7813 | CCGCCATCATCCTAGTCCTCATC | 1631 | GATGAGGACTAGGATGATGG | 3400 |
| 7794 | 7816 | CCATCATCCTAGTCCTCATCGCC | 1632 | GGCGATGAGGACTAGGATGA | 3401 |
| 7801 | 7823 | CCTAGTCCTCATCGCCCTCCCAT | 1633 | ATGGGAGGGCGATGAGGACT | 3402 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 7807 | 7829 | CCTCATCGCCCTCCCATCCCTAC | 1634 | GTAGGGATGGGAGGGCGATG | 3403 |
| 7815 | 7837 | CCCTCCCATCCCTACGCATCCTT | 1635 | AAGGATGCGTAGGGATGGGA | 3404 |
| 7816 | 7838 | CCTCCCATCCCTACGCATCCTTT | 1636 | AAAGGATGCGTAGGGATGGG | 3405 |
| 7819 | 7841 | CCCATCCCTACGCATCCTTTACA | 1637 | TGTAAAGGATGCGTAGGGAT | 3406 |
| 7820 | 7842 | CCATCCCTACGCATCCTTTACAT | 1638 | ATGTAAAGGATGCGTAGGGA | 3407 |
| 7824 | 7846 | CCCTACGCATCCTTTACATAACA | 1639 | TGTTATGTAAAGGATGCGTA | 3408 |
| 7825 | 7847 | CCTACGCATCCTTTACATAACAG | 1640 | CTGTTATGTAAAGGATGCGT | 3409 |
| 7834 | 7856 | CCTTTACATAACAGACGAGGTCA | 1641 | TGACCTCGTCTGTTATGTAA | 3410 |
| 7862 | 7884 | CCCTCCCTTACCATCAAATCAAT | 1642 | ATTGATTTGATGGTAAGGGA | 3411 |
| 7863 | 7885 | CCTCCCTTACCATCAAATCAATT | 1643 | AATTGATTTGATGGTAAGGG | 3412 |
| 7866 | 7888 | CCCTTACCATCAAATCAATTGGC | 1644 | GCCAATTGATTTGATGGTAA | 3413 |
| 7867 | 7889 | CCTTACCATCAAATCAATTGGCC | 1645 | GGCCAATTGATTTGATGGTA | 3414 |
| 7872 | 7894 | CCATCAAATCAATTGGCCACCAA | 1646 | TTGGTGGCCAATTGATTTGA | 3415 |
| 7888 | 7910 | CCACCAATGGTACTGAACCTACG | 1647 | CGTAGGTTCAGTACCATTGG | 3416 |
| 7891 | 7913 | CCAATGGTACTGAACCTACGAGT | 1648 | ACTCGTAGGTTCAGTACCAT | 3417 |
| 7905 | 7927 | CCTACGAGTACACCGACTACGGC | 1649 | GCCGTAGTCGGTGTACTCGT | 3418 |
| 7917 | 7939 | CCGACTACGGCGGACTAATCTTC | 1650 | GAAGATTAGTCCGCCGTAGT | 3419 |
| 7944 | 7966 | CCTACATACTTCCCCCATTATTC | 1651 | GAATAATGGGGGAAGTATGT | 3420 |
| 7955 | 7977 | CCCCCATTATTCCTAGAACCAGG | 1652 | CCTGGTTCTAGGAATAATGG | 3421 |
| 7956 | 7978 | CCCCATTATTCCTAGAACCAGGC | 1653 | GCCTGGTTCTAGGAATAATG | 3422 |
| 7957 | 7979 | CCCATTATTCCTAGAACCAGGCG | 1654 | CGCCTGGTTCTAGGAATAAT | 3423 |
| 7958 | 7980 | CCATTATTCCTAGAACCAGGCGA | 1655 | TCGCCTGGTTCTAGGAATAA | 3424 |
| 7966 | 7988 | CCTAGAACCAGGCGACCTGCGAC | 1656 | GTCGCAGGTCGCCTGGTTCT | 3425 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 7973 | 7995 | CCAGGCGACCTGCGACTCCTTGA | 1657 | TCAAGGAGTCGCAGGTCGCC | 3426 |
| 7981 | 8003 | CCTGCGACTCCTTGACGTTGACA | 1658 | TGTCAACGTCAAGGAGTCGC | 3427 |
| 7990 | 8012 | CCTTGACGTTGACAATCGAGTAG | 1659 | CTACTCGATTGTCAACGTCA | 3428 |
| 8017 | 8039 | CCCGATTGAAGCCCCCATTCGTA | 1660 | TACGAATGGGGCTTCAATC | 3429 |
| 8018 | 8040 | CCGATTGAAGCCCCCATTCGTAT | 1661 | ATACGAATGGGGCTTCAAT | 3430 |
| 8028 | 8050 | CCCCCATTCGTATAATAATTACA | 1662 | TGTAATTATTATACGAATGG | 3431 |
| 8029 | 8051 | CCCCATTCGTATAATAATTACAT | 1663 | ATGTAATTATTATACGAATG | 3432 |
| 8030 | 8052 | CCCATTCGTATAATAATTACATC | 1664 | GATGTAATTATTATACGAAT | 3433 |
| 8031 | 8053 | CCATTCGTATAATAATTACATCA | 1665 | TGATGTAATTATTATACGAA | 3434 |
| 8080 | 8102 | CCCCACATTAGGCTTAAAAACAG | 1666 | CTGTTTTAAGCCTAATGTG | 3435 |
| 8081 | 8103 | CCCACATTAGGCTTAAAAACAGA | 1667 | TCTGTTTTAAGCCTAATGT | 3436 |
| 8082 | 8104 | CCACATTAGGCTTAAAAACAGAT | 1668 | ATCTGTTTTAAGCCTAATG | 3437 |
| 8111 | 8133 | CCCGGACGTCTAAACCAAACCAC | 1669 | GTGGTTTGGTTTAGACGTCC | 3438 |
| 8112 | 8134 | CCGGACGTCTAAACCAAACCACT | 1670 | AGTGGTTTGGTTTAGACGTC | 3439 |
| 8125 | 8147 | CCAAACCACTTTCACCGCTACAC | 1671 | GTGTAGCGGTGAAAGTGGTT | 3440 |
| 8130 | 8152 | CCACTTTCACCGCTACACGACCG | 1672 | CGGTCGTGTAGCGGTGAAAG | 3441 |
| 8139 | 8161 | CCGCTACACGACCGGGGTATAC | 1673 | GTATACCCCGGTCGTGTAG | 3442 |
| 8150 | 8172 | CCGGGGTATACTACGGTCAATG | 1674 | CATTGACCGTAGTATACCCC | 3443 |
| 8194 | 8216 | CCACAGTTTCATGCCCATCGTCC | 1675 | GGACGATGGGCATGAAACTG | 3444 |
| 8207 | 8229 | CCCATCGTCCTAGAATTAATTCC | 1676 | GGAATTAATTCTAGGACGAT | 3445 |
| 8208 | 8230 | CCATCGTCCTAGAATTAATTCCC | 1677 | GGGAATTAATTCTAGGACGA | 3446 |
| 8215 | 8237 | CCTAGAATTAATTCCCCTAAAAA | 1678 | TTTTTAGGGGAATTAATTCT | 3447 |
| 8228 | 8250 | CCCCTAAAAATCTTTGAAATAGG | 1679 | CCTATTTCAAAGATTTTTAG | 3448 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 8229 | 8251 | CCCTAAAAATCTTTGAAATAGGG | 1680 | CCCTATTTCAAAGATTTTTA | 3449 |
| 8230 | 8252 | CCTAAAAATCTTTGAAATAGGGC | 1681 | GCCCTATTTCAAAGATTTTT | 3450 |
| 8252 | 8274 | CCCGTATTTACCCTATAGCACCC | 1682 | GGGTGCTATAGGGTAAATAC | 3451 |
| 8253 | 8275 | CCGTATTTACCCTATAGCACCCC | 1683 | GGGGTGCTATAGGGTAAATA | 3452 |
| 8262 | 8284 | CCCTATAGCACCCCCTCTACCCC | 1684 | GGGGTAGAGGGGGTGCTATA | 3453 |
| 8263 | 8285 | CCTATAGCACCCCCTCTACCCCC | 1685 | GGGGGTAGAGGGGGTGCTAT | 3454 |
| 8272 | 8294 | CCCCCTCTACCCCCTCTAGAGCC | 1686 | GGCTCTAGAGGGGTAGAGG | 3455 |
| 8273 | 8295 | CCCCTCTACCCCCTCTAGAGCCC | 1687 | GGGCTCTAGAGGGGGTAGAG | 3456 |
| 8274 | 8296 | CCCTCTACCCCCTCTAGAGCCCA | 1688 | TGGGCTCTAGAGGGGGTAGA | 3457 |
| 8275 | 8297 | CCTCTACCCCCTCTAGAGCCCAC | 1689 | GTGGGCTCTAGAGGGGGTAG | 3458 |
| 8281 | 8303 | CCCCCTCTAGAGCCCACTGTAAA | 1690 | TTTACAGTGGGCTCTAGAGG | 3459 |
| 8282 | 8304 | CCCCTCTAGAGCCCACTGTAAAG | 1691 | CTTTACAGTGGGCTCTAGAG | 3460 |
| 8283 | 8305 | CCCTCTAGAGCCCACTGTAAAGC | 1692 | GCTTTACAGTGGGCTCTAGA | 3461 |
| 8284 | 8306 | CCTCTAGAGCCCACTGTAAAGCT | 1693 | AGCTTTACAGTGGGCTCTAG | 3462 |
| 8293 | 8315 | CCCACTGTAAAGCTAACTTAGCA | 1694 | TGCTAAGTTAGCTTTACAGT | 3463 |
| 8294 | 8316 | CCACTGTAAAGCTAACTTAGCAT | 1695 | ATGCTAAGTTAGCTTTACAG | 3464 |
| 8320 | 8342 | CCTTTTAAGTTAAAGATTAAGAG | 1696 | CTCTTAATCTTTAACTTAAA | 3465 |
| 8345 | 8367 | CCAACACCTCTTTACAGTGAAAT | 1697 | ATTTCACTGTAAAGAGGTGT | 3466 |
| 8351 | 8373 | CCTCTTTACAGTGAAATGCCCCA | 1698 | TGGGGCATTTCACTGTAAAG | 3467 |
| 8369 | 8391 | CCCCAACTAAATACTACCGTATG | 1699 | CATACGGTAGTATTTAGTTG | 3468 |
| 8370 | 8392 | CCCAACTAAATACTACCGTATGG | 1700 | CCATACGGTAGTATTTAGTT | 3469 |
| 8371 | 8393 | CCAACTAAATACTACCGTATGGC | 1701 | GCCATACGGTAGTATTTAGT | 3470 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 8385 | 8407 | CCGTATGGCCCACCATAATTACC | 1702 | GGTAATTATGGTGGGCCATA | 3471 |
| 8393 | 8415 | CCCACCATAATTACCCCCATACT | 1703 | AGTATGGGGGTAATTATGGT | 3472 |
| 8394 | 8416 | CCACCATAATTACCCCCATACTC | 1704 | GAGTATGGGGTAATTATGG | 3473 |
| 8397 | 8419 | CCATAATTACCCCCATACTCCTT | 1705 | AAGGAGTATGGGGGTAATTA | 3474 |
| 8406 | 8428 | CCCCCATACTCCTTACACTATTC | 1706 | GAATAGTGTAAGGAGTATGG | 3475 |
| 8407 | 8429 | CCCCATACTCCTTACACTATTCC | 1707 | GGAATAGTGTAAGGAGTATG | 3476 |
| 8408 | 8430 | CCCATACTCCTTACACTATTCCT | 1708 | AGGAATAGTGTAAGGAGTAT | 3477 |
| 8409 | 8431 | CCATACTCCTTACACTATTCCTC | 1709 | GAGGAATAGTGTAAGGAGTA | 3478 |
| 8416 | 8438 | CCTTACACTATTCCTCATCACCC | 1710 | GGGTGATGAGGAATAGTGTA | 3479 |
| 8428 | 8450 | CCTCATCACCCAACTAAAATAT | 1711 | ATATTTTAGTTGGGTGATG | 3480 |
| 8436 | 8458 | CCCAACTAAAAATATTAAACACA | 1712 | TGTGTTTAATATTTTAGTT | 3481 |
| 8437 | 8459 | CCAACTAAAAATATTAAACACAA | 1713 | TTGTGTTTAATATTTTTAGT | 3482 |
| 8464 | 8486 | CCACCTACCTCCCTCACCAAAGC | 1714 | GCTTTGGTGAGGGAGGTAGG | 3483 |
| 8467 | 8489 | CCTACCTCCCTCACCAAAGCCCA | 1715 | TGGGCTTTGGTGAGGGAGGT | 3484 |
| 8471 | 8493 | CCTCCCTCACCAAAGCCCATAAA | 1716 | TTTATGGGCTTTGGTGAGGG | 3485 |
| 8474 | 8496 | CCCTCACCAAAGCCCATAAAAAT | 1717 | ATTTTTATGGGCTTTGGTGA | 3486 |
| 8475 | 8497 | CCTCACCAAAGCCCATAAAATA | 1718 | TATTTTTATGGGCTTTGGTG | 3487 |
| 8480 | 8502 | CCAAAGCCCATAAAAATAAAAAA | 1719 | TTTTTATTTTTATGGGCTT | 3488 |
| 8486 | 8508 | CCCATAAAAATAAAAATTATAA | 1720 | TTATAATTTTTATTTTTAT | 3489 |
| 8487 | 8509 | CCATAAAAATAAAAATTATAAC | 1721 | GTTATAATTTTTATTTTTA | 3490 |
| 8513 | 8535 | CCCTGAGAACCAAAATGAACGAA | 1722 | TTCGTTCATTTTGGTTCTCA | 3491 |
| 8514 | 8536 | CCTGAGAACCAAAATGAACGAAA | 1723 | TTTCGTTCATTTTGGTTCTC | 3492 |
| 8522 | 8544 | CCAAAATGAACGAAAATCTGTTC | 1724 | GAACAGATTTTCGTTCATTT | 3493 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 8558 | 8580 | CCCCCACAATCCTAGGCCTACCC | 1725 | GGGTAGGCCTAGGATTGTGG | 3494 |
| 8559 | 8581 | CCCCACAATCCTAGGCCTACCCG | 1726 | CGGGTAGGCCTAGGATTGTG | 3495 |
| 8560 | 8582 | CCCACAATCCTAGGCCTACCCGC | 1727 | GCGGGTAGGCCTAGGATTGT | 3496 |
| 8561 | 8583 | CCACAATCCTAGGCCTACCCGCC | 1728 | GGCGGGTAGGCCTAGGATTG | 3497 |
| 8568 | 8590 | CCTAGGCCTACCCGCCGCAGTAC | 1729 | GTACTGCGGCGGGTAGGCCT | 3498 |
| 8574 | 8596 | CCTACCCGCCGCAGTACTGATCA | 1730 | TGATCAGTACTGCGGCGGGT | 3499 |
| 8578 | 8600 | CCCGCCGCAGTACTGATCATTCT | 1731 | AGAATGATCAGTACTGCGGC | 3500 |
| 8579 | 8601 | CCGCCGCAGTACTGATCATTCTA | 1732 | TAGAATGATCAGTACTGCGG | 3501 |
| 8582 | 8604 | CCGCAGTACTGATCATTCTATTT | 1733 | AAATAGAATGATCAGTACTG | 3502 |
| 8605 | 8627 | CCCCCTCTATTGATCCCCACCTC | 1734 | GAGGTGGGGATCAATAGAGG | 3503 |
| 8606 | 8628 | CCCCTCTATTGATCCCCACCTCC | 1735 | GGAGGTGGGGATCAATAGAG | 3504 |
| 8607 | 8629 | CCCTCTATTGATCCCCACCTCCA | 1736 | TGGAGGTGGGGATCAATAGA | 3505 |
| 8608 | 8630 | CCTCTATTGATCCCCACCTCCAA | 1737 | TTGGAGGTGGGGATCAATAG | 3506 |
| 8619 | 8641 | CCCCACCTCCAAATATCTCATCA | 1738 | TGATGAGATATTTGGAGGTG | 3507 |
| 8620 | 8642 | CCCACCTCCAAATATCTCATCAA | 1739 | TTGATGAGATATTTGGAGGT | 3508 |
| 8621 | 8643 | CCACCTCCAAATATCTCATCAAC | 1740 | GTTGATGAGATATTTGGAGG | 3509 |
| 8624 | 8646 | CCTCCAAATATCTCATCAACAAC | 1741 | GTTGTTGATGAGATATTTGG | 3510 |
| 8627 | 8649 | CCAAATATCTCATCAACAACCGA | 1742 | TCGGTTGTTGATGAGATATT | 3511 |
| 8646 | 8668 | CCGACTAATCACCACCCAACAAT | 1743 | ATTGTTGGGTGGTGATTAGT | 3512 |
| 8657 | 8679 | CCACCCAACAATGACTAATCAAA | 1744 | TTTGATTAGTCATTGTTGGG | 3513 |
| 8660 | 8682 | CCCAACAATGACTAATCAAACTA | 1745 | TAGTTTGATTAGTCATTGTT | 3514 |
| 8661 | 8683 | CCAACAATGACTAATCAAACTAA | 1746 | TTAGTTTGATTAGTCATTGT | 3515 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 8684 | 8706 | CCTCAAAACAAATGATAACCATA | 1747 | TATGGTTATCATTTGTTTTG | 3516 |
| 8702 | 8724 | CCATACACAACACTAAAGGACGA | 1748 | TCGTCCTTTAGTGTTGTGTA | 3517 |
| 8726 | 8748 | CCTGATCTCTTATACTAGTATCC | 1749 | GGATACTAGTATAAGAGATC | 3518 |
| 8747 | 8769 | CCTTAATCATTTTTATTGCCACA | 1750 | TGTGGCAATAAAAATGATTA | 3519 |
| 8765 | 8787 | CCACAACTAACCTCCTCGGACTC | 1751 | GAGTCCGAGGAGGTTAGTTG | 3520 |
| 8775 | 8797 | CCTCCTCGGACTCCTGCCTCACT | 1752 | AGTGAGGCAGGAGTCCGAGG | 3521 |
| 8778 | 8800 | CCTCGGACTCCTGCCTCACTCAT | 1753 | ATGAGTGAGGCAGGAGTCCG | 3522 |
| 8787 | 8809 | CCTGCCTCACTCATTTACACCAA | 1754 | TTGGTGTAAATGAGTGAGGC | 3523 |
| 8791 | 8813 | CCTCACTCATTTACACCAACCAC | 1755 | GTGGTTGGTGTAAATGAGTG | 3524 |
| 8806 | 8828 | CCAACCACCCAACTATCTATAAA | 1756 | TTTATAGATAGTTGGGTGGT | 3525 |
| 8810 | 8832 | CCACCCAACTATCTATAAACCTA | 1757 | TAGGTTTATAGATAGTTGGG | 3526 |
| 8813 | 8835 | CCCAACTATCTATAAACCTAGCC | 1758 | GGCTAGGTTTATAGATAGTT | 3527 |
| 8814 | 8836 | CCAACTATCTATAAACCTAGCCA | 1759 | TGGCTAGGTTTATAGATAGT | 3528 |
| 8829 | 8851 | CCTAGCCATGGCCATCCCCTTAT | 1760 | ATAAGGGGATGGCCATGGCT | 3529 |
| 8834 | 8856 | CCATGGCCATCCCCTTATGAGCG | 1761 | CGCTCATAAGGGGATGGCCA | 3530 |
| 8840 | 8862 | CCATCCCCTTATGAGCGGGCACA | 1762 | TGTGCCCGCTCATAAGGGGA | 3531 |
| 8844 | 8866 | CCCCTTATGAGCGGGCACAGTGA | 1763 | TCACTGTGCCCGCTCATAAG | 3532 |
| 8845 | 8867 | CCCTTATGAGCGGGCACAGTGAT | 1764 | ATCACTGTGCCCGCTCATAA | 3533 |
| 8846 | 8868 | CCTTATGAGCGGGCACAGTGATT | 1765 | AATCACTGTGCCCGCTCATA | 3534 |
| 8897 | 8919 | CCCTAGCCCACTTCTTACCACAA | 1766 | TTGTGGTAAGAAGTGGGCTA | 3535 |
| 8898 | 8920 | CCTAGCCCACTTCTTACCACAAG | 1767 | CTTGTGGTAAGAAGTGGGCT | 3536 |
| 8903 | 8925 | CCCACTTCTTACCACAAGGCACA | 1768 | TGTGCCTTGTGGTAAGAAGT | 3537 |
| 8904 | 8926 | CCACTTCTTACCACAAGGCACAC | 1769 | GTGTGCCTTGTGGTAAGAAG | 3538 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 8914 | 8936 | CCACAAGGCACACCTACACCCCT | 1770 | AGGGGTGTAGGTGTGCCTTG | 3539 |
| 8926 | 8948 | CCTACACCCCTTATCCCCATACT | 1771 | AGTATGGGGATAAGGGGTGT | 3540 |
| 8932 | 8954 | CCCCTTATCCCCATACTAGTTAT | 1772 | ATAACTAGTATGGGGATAAG | 3541 |
| 8933 | 8955 | CCCTTATCCCCATACTAGTTATT | 1773 | AATAACTAGTATGGGGATAA | 3542 |
| 8934 | 8956 | CCTTATCCCCATACTAGTTATTA | 1774 | TAATAACTAGTATGGGGATA | 3543 |
| 8940 | 8962 | CCCCATACTAGTTATTATCGAAA | 1775 | TTTCGATAATAACTAGTATG | 3544 |
| 8941 | 8963 | CCCATACTAGTTATTATCGAAAC | 1776 | GTTTCGATAATAACTAGTAT | 3545 |
| 8942 | 8964 | CCATACTAGTTATTATCGAAACC | 1777 | GGTTTCGATAATAACTAGTA | 3546 |
| 8963 | 8985 | CCATCAGCCTACTCATTCAACCA | 1778 | TGGTTGAATGAGTAGGCTGA | 3547 |
| 8970 | 8992 | CCTACTCATTCAACCAATAGCCC | 1779 | GGGCTATTGGTTGAATGAGT | 3548 |
| 8983 | 9005 | CCAATAGCCCTGGCCGTACGCCT | 1780 | AGGCGTACGGCCAGGGCTAT | 3549 |
| 8990 | 9012 | CCCTGGCCGTACGCCTAACCGCT | 1781 | AGCGGTTAGGCGTACGGCCA | 3550 |
| 8991 | 9013 | CCTGGCCGTACGCCTAACCGCTA | 1782 | TAGCGGTTAGGCGTACGGCC | 3551 |
| 8996 | 9018 | CCGTACGCCTAACCGCTAACATT | 1783 | AATGTTAGCGGTTAGGCGTA | 3552 |
| 9003 | 9025 | CCTAACCGCTAACATTACTGCAG | 1784 | CTGCAGTAATGTTAGCGGTT | 3553 |
| 9008 | 9030 | CCGCTAACATTACTGCAGGCCAC | 1785 | GTGGCCTGCAGTAATGTTAG | 3554 |
| 9027 | 9049 | CCACCTACTCATGCACCTAATTG | 1786 | CAATTAGGTGCATGAGTAGG | 3555 |
| 9030 | 9052 | CCTACTCATGCACCTAATTGGAA | 1787 | TTCCAATTAGGTGCATGAGT | 3556 |
| 9042 | 9064 | CCTAATTGGAAGCGCCACCCTAG | 1788 | CTAGGGTGGCGCTTCCAATT | 3557 |
| 9056 | 9078 | CCACCCTAGCAATATCAACCATT | 1789 | AATGGTTGATATTGCTAGGG | 3558 |
| 9059 | 9081 | CCCTAGCAATATCAACCATTAAC | 1790 | GTTAATGGTTGATATTGCTA | 3559 |
| 9060 | 9082 | CCTAGCAATATCAACCATTAACC | 1791 | GGTTAATGGTTGATATTGCT | 3560 |
| 9074 | 9096 | CCATTAACCTTCCCTCTACACTT | 1792 | AAGTGTAGAGGGAAGGTTAA | 3561 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 9081 | 9103 | CCTTCCCTCTACACTTATCATCT | 1793 | AGATGATAAGTGTAGAGGGA | 3562 |
| 9085 | 9107 | CCCTCTACACTTATCATCTTCAC | 1794 | GTGAAGATGATAAGTGTAGA | 3563 |
| 9086 | 9108 | CCTCTACACTTATCATCTTCACA | 1795 | TGTGAAGATGATAAGTGTAG | 3564 |
| 9129 | 9151 | CCTAGAAATCGCTGTCGCCTTAA | 1796 | TTAAGGCGACAGCGATTTCT | 3565 |
| 9146 | 9168 | CCTTAATCCAAGCCTACGTTTTC | 1797 | GAAAACGTAGGCTTGGATTA | 3566 |
| 9153 | 9175 | CCAAGCCTACGTTTTCACACTTC | 1798 | GAAGTGTGAAAACGTAGGCT | 3567 |
| 9158 | 9180 | CCTACGTTTTCACACTTCTAGTA | 1799 | TACTAGAAGTGTGAAAACGT | 3568 |
| 9183 | 9205 | CCTCTACCTGCACGACAACACAT | 1800 | ATGTGTTGTCGTGCAGGTAG | 3569 |
| 9189 | 9211 | CCTGCACGACAACACATAATGAC | 1801 | GTCATTATGTGTTGTCGTGC | 3570 |
| 9211 | 9233 | CCCACCAATCACATGCCTATCAT | 1802 | ATGATAGGCATGTGATTGGT | 3571 |
| 9212 | 9234 | CCACCAATCACATGCCTATCATA | 1803 | TATGATAGGCATGTGATTGG | 3572 |
| 9215 | 9237 | CCAATCACATGCCTATCATATAG | 1804 | CTATATGATAGGCATGTGAT | 3573 |
| 9226 | 9248 | CCTATCATATAGTAAAACCCAGC | 1805 | GCTGGGTTTTACTATATGAT | 3574 |
| 9243 | 9265 | CCCAGCCCATGACCCCTAACAGG | 1806 | CCTGTTAGGGGTCATGGGCT | 3575 |
| 9244 | 9266 | CCAGCCCATGACCCCTAACAGGG | 1807 | CCCTGTTAGGGGTCATGGGC | 3576 |
| 9248 | 9270 | CCCATGACCCCTAACAGGGGCCC | 1808 | GGGCCCCTGTTAGGGGTCAT | 3577 |
| 9249 | 9271 | CCATGACCCCTAACAGGGGCCCT | 1809 | AGGGCCCCTGTTAGGGGTCA | 3578 |
| 9255 | 9277 | CCCCTAACAGGGGCCCTCTCAGC | 1810 | GCTGAGAGGGCCCCTGTTAG | 3579 |
| 9256 | 9278 | CCCTAACAGGGGCCCTCTCAGCC | 1811 | GGCTGAGAGGGCCCCTGTTA | 3580 |
| 9257 | 9279 | CCTAACAGGGGCCCTCTCAGCCC | 1812 | GGGCTGAGAGGGCCCCTGTT | 3581 |
| 9268 | 9290 | CCCTCTCAGCCCTCCTAATGACC | 1813 | GGTCATTAGGAGGGCTGAGA | 3582 |
| 9269 | 9291 | CCTCTCAGCCCTCCTAATGACCT | 1814 | AGGTCATTAGGAGGGCTGAG | 3583 |
| 9277 | 9299 | CCCTCCTAATGACCTCCGGCCTA | 1815 | TAGGCCGGAGGTCATTAGGA | 3584 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 9278 | 9300 | CCTCCTAATGACCTCCGGCCTAG | 1816 | CTAGGCCGGAGGTCATTAGG | 3585 |
| 9281 | 9303 | CCTAATGACCTCCGGCCTAGCCA | 1817 | TGGCTAGGCCGGAGGTCATT | 3586 |
| 9289 | 9311 | CCTCCGGCCTAGCCATGTGATTT | 1818 | AAATCACATGGCTAGGCCGG | 3587 |
| 9292 | 9314 | CCGGCCTAGCCATGTGATTTCAC | 1819 | GTGAAATCACATGGCTAGGC | 3588 |
| 9296 | 9318 | CCTAGCCATGTGATTTCACTTCC | 1820 | GGAAGTGAAATCACATGGCT | 3589 |
| 9301 | 9323 | CCATGTGATTTCACTTCCACTCC | 1821 | GGAGTGGAAGTGAAATCACA | 3590 |
| 9317 | 9339 | CCACTCCATAACGCTCCTCATAC | 1822 | GTATGAGGAGCGTTATGGAG | 3591 |
| 9322 | 9344 | CCATAACGCTCCTCATACTAGGC | 1823 | GCCTAGTATGAGGAGCGTTA | 3592 |
| 9332 | 9354 | CCTCATACTAGGCCTACTAACCA | 1824 | TGGTTAGTAGGCCTAGTATG | 3593 |
| 9344 | 9366 | CCTACTAACCAACACACTAACCA | 1825 | TGGTTAGTGTGTTGGTTAGT | 3594 |
| 9352 | 9374 | CCAACACACTAACCATATACCAA | 1826 | TTGGTATATGGTTAGTGTGT | 3595 |
| 9364 | 9386 | CCATATACCAATGATGGCGCGAT | 1827 | ATCGCGCCATCATTGGTATA | 3596 |
| 9371 | 9393 | CCAATGATGGCGCGATGTAACAC | 1828 | GTGTTACATCGCGCCATCAT | 3597 |
| 9407 | 9429 | CCAAGGCCACCACACACCACCTG | 1829 | CAGGTGGTGTGTGGTGGCCT | 3598 |
| 9413 | 9435 | CCACCACACACCACCTGTCCAAA | 1830 | TTTGGACAGGTGGTGTGTGG | 3599 |
| 9416 | 9438 | CCACACACCACCTGTCCAAAAAG | 1831 | CTTTTTGGACAGGTGGTGTG | 3600 |
| 9423 | 9445 | CCACCTGTCCAAAAAGGCCTTCG | 1832 | CGAAGGCCTTTTTGGACAGG | 3601 |
| 9426 | 9448 | CCTGTCCAAAAAGGCCTTCGATA | 1833 | TATCGAAGGCCTTTTTGGAC | 3602 |
| 9431 | 9453 | CCAAAAAGGCCTTCGATACGGGA | 1834 | TCCCGTATCGAAGGCCTTTT | 3603 |
| 9440 | 9462 | CCTTCGATACGGGATAATCCTAT | 1835 | ATAGGATTATCCCGTATCGA | 3604 |
| 9458 | 9480 | CCTATTTATTACCTCAGAAGTTT | 1836 | AAACTTCTGAGGTAATAAAT | 3605 |
| 9469 | 9491 | CCTCAGAAGTTTTTTTCTTCGCA | 1837 | TGCGAAGAAAAAACTTCTG | 3606 |
| 9505 | 9527 | CCTTTTACCACTCCAGCCTAGCC | 1838 | GGCTAGGCTGGAGTGGTAAA | 3607 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 9512 | 9534 | CCACTCCAGCCTAGCCCCTACCC | 1839 | GGGTAGGGGCTAGGCTGGAG | 3608 |
| 9517 | 9539 | CCAGCCTAGCCCCTACCCCCCAA | 1840 | TTGGGGGGTAGGGCTAGGC | 3609 |
| 9521 | 9543 | CCTAGCCCCTACCCCCCAATTAG | 1841 | CTAATTGGGGGTAGGGGCT | 3610 |
| 9526 | 9548 | CCCCTACCCCCCAATTAGGAGGG | 1842 | CCCTCCTAATTGGGGGTAG | 3611 |
| 9527 | 9549 | CCCTACCCCCCAATTAGGAGGGC | 1843 | GCCCTCCTAATTGGGGGGTA | 3612 |
| 9528 | 9550 | CCTACCCCCCAATTAGGAGGGCA | 1844 | TGCCCTCCTAATTGGGGGGT | 3613 |
| 9532 | 9554 | CCCCCCAATTAGGAGGGCACTGG | 1845 | CCAGTGCCCTCCTAATTGGG | 3614 |
| 9533 | 9555 | CCCCCAATTAGGAGGGCACTGGC | 1846 | GCCAGTGCCCTCCTAATTGG | 3615 |
| 9534 | 9556 | CCCCAATTAGGAGGGCACTGGCC | 1847 | GGCCAGTGCCCTCCTAATTG | 3616 |
| 9535 | 9557 | CCCAATTAGGAGGGCACTGGCCC | 1848 | GGGCCAGTGCCCTCCTAATT | 3617 |
| 9536 | 9558 | CCAATTAGGAGGGCACTGGCCCC | 1849 | GGGGCCAGTGCCCTCCTAAT | 3618 |
| 9555 | 9577 | CCCCCAACAGGCATCACCCCGCT | 1850 | AGCGGGGTGATGCCTGTTGG | 3619 |
| 9556 | 9578 | CCCCAACAGGCATCACCCCGCTA | 1851 | TAGCGGGGTGATGCCTGTTG | 3620 |
| 9557 | 9579 | CCCAACAGGCATCACCCCGCTAA | 1852 | TTAGCGGGGTGATGCCTGTT | 3621 |
| 9558 | 9580 | CCAACAGGCATCACCCCGCTAAA | 1853 | TTTAGCGGGGTGATGCCTGT | 3622 |
| 9571 | 9593 | CCCCGCTAAATCCCCTAGAAGTC | 1854 | GACTTCTAGGGGATTTAGCG | 3623 |
| 9572 | 9594 | CCCGCTAAATCCCCTAGAAGTCC | 1855 | GGACTTCTAGGGGATTTAGC | 3624 |
| 9573 | 9595 | CCGCTAAATCCCCTAGAAGTCCC | 1856 | GGGACTTCTAGGGGATTTAG | 3625 |
| 9582 | 9604 | CCCCTAGAAGTCCCACTCCTAAA | 1857 | TTTAGGAGTGGGACTTCTAG | 3626 |
| 9583 | 9605 | CCCTAGAAGTCCCACTCCTAAAC | 1858 | GTTTAGGAGTGGGACTTCTA | 3627 |
| 9584 | 9606 | CCTAGAAGTCCCACTCCTAAACA | 1859 | TGTTTAGGAGTGGGACTTCT | 3628 |
| 9593 | 9615 | CCCACTCCTAAACACATCCGTAT | 1860 | ATACGGATGTGTTTAGGAGT | 3629 |
| 9594 | 9616 | CCACTCCTAAACACATCCGTATT | 1861 | AATACGGATGTGTTTAGGAG | 3630 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 9599 | 9621 | CCTAAACACATCCGTATTACTCG | 1862 | CGAGTAATACGGATGTGTTT | 3631 |
| 9610 | 9632 | CCGTATTACTCGCATCAGGAGTA | 1863 | TACTCCTGATGCGAGTAATA | 3632 |
| 9640 | 9662 | CCTGAGCTCACCATAGTCTAATA | 1864 | TATTAGACTATGGTGAGCTC | 3633 |
| 9650 | 9672 | CCATAGTCTAATAGAAACAACC | 1865 | GGTTGTTTTCTATTAGACTA | 3634 |
| 9671 | 9693 | CCGAAACCAAATAATTCAAGCAC | 1866 | GTGCTTGAATTATTTGGTTT | 3635 |
| 9677 | 9699 | CCAAATAATTCAAGCACTGCTTA | 1867 | TAAGCAGTGCTTGAATTATT | 3636 |
| 9727 | 9749 | CCCTCCTACAAGCCTCAGAGTAC | 1868 | GTACTCTGAGGCTTGTAGGA | 3637 |
| 9728 | 9750 | CCTCCTACAAGCCTCAGAGTACT | 1869 | AGTACTCTGAGGCTTGTAGG | 3638 |
| 9731 | 9753 | CCTACAAGCCTCAGAGTACTTCG | 1870 | CGAAGTACTCTGAGGCTTGT | 3639 |
| 9739 | 9761 | CCTCAGAGTACTTCGAGTCTCCC | 1871 | GGGAGACTCGAAGTACTCTG | 3640 |
| 9759 | 9781 | CCCTTCACCATTTCCGACGGCAT | 1872 | ATGCCGTCGGAAATGGTGAA | 3641 |
| 9760 | 9782 | CCTTCACCATTTCCGACGGCATC | 1873 | GATGCCGTCGGAAATGGTGA | 3642 |
| 9766 | 9788 | CCATTTCCGACGGCATCTACGGC | 1874 | GCCGTAGATGCCGTCGGAAA | 3643 |
| 9772 | 9794 | CCGACGGCATCTACGGCTCAACA | 1875 | TGTTGAGCCGTAGATGCCGT | 3644 |
| 9805 | 9827 | CCACAGGCTTCCACGGACTTCAC | 1876 | GTGAAGTCCGTGGAAGCCTG | 3645 |
| 9815 | 9837 | CCACGGACTTCACGTCATTATTG | 1877 | CAATAATGACGTGAAGTCCG | 3646 |
| 9848 | 9870 | CCTCACTATCTGCTTCATCCGCC | 1878 | GGCGGATGAAGCAGATAGTG | 3647 |
| 9866 | 9888 | CCGCCAACTAATATTTCACTTTA | 1879 | TAAAGTGAAATATTAGTTGG | 3648 |
| 9869 | 9891 | CCAACTAATATTTCACTTTACAT | 1880 | ATGTAAAGTGAAATATTAGT | 3649 |
| 9892 | 9914 | CCAAACATCACTTTGGCTTCGAA | 1881 | TTCGAAGCCAAAGTGATGTT | 3650 |
| 9916 | 9938 | CCGCCGCTGATACTGGCATTTT | 1882 | AAAATGCCAGTATCAGGCGG | 3651 |
| 9919 | 9941 | CCGCCTGATACTGGCATTTTGTA | 1883 | TACAAAATGCCAGTATCAGG | 3652 |
| 9922 | 9944 | CCTGATACTGGCATTTTGTAGAT | 1884 | ATCTACAAAATGCCAGTATC | 3653 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 9970 | 9992 | CCATCTATTGATGAGGGTCTTAC | 1885 | GTAAGACCCTCATCAATAGA | 3654 |
| 10012 | 10034 | CCGTTAACTTCCAATTAACTAGT | 1886 | ACTAGTTAATTGGAAGTTAA | 3655 |
| 10022 | 10044 | CCAATTAACTAGTTTTGACAACA | 1887 | TGTTGTCAAAACTAGTTAAT | 3656 |
| 10069 | 10091 | CCTTAATTTTAATAATCAACACC | 1888 | GGTGTTGATTATTAAAATTA | 3657 |
| 10090 | 10112 | CCCTCCTAGCCTTACTACTAATA | 1889 | TATTAGTAGTAAGGCTAGGA | 3658 |
| 10091 | 10113 | CCTCCTAGCCTTACTACTAATAA | 1890 | TTATTAGTAGTAAGGCTAGG | 3659 |
| 10094 | 10116 | CCTAGCCTTACTACTAATAATTA | 1891 | TAATTATTAGTAGTAAGGCT | 3660 |
| 10099 | 10121 | CCTTACTACTAATAATTATTACA | 1892 | TGTAATAATTATTAGTAGTA | 3661 |
| 10131 | 10153 | CCACAACTCAACGGCTACATAGA | 1893 | TCTATGTAGCCGTTGAGTTG | 3662 |
| 10159 | 10181 | CCACCCCTTACGAGTGCGGCTTC | 1894 | GAAGCCGCACTCGTAAGGGG | 3663 |
| 10162 | 10184 | CCCCTTACGAGTGCGGCTTCGAC | 1895 | GTCGAAGCCGCACTCGTAAG | 3664 |
| 10163 | 10185 | CCCTTACGAGTGCGGCTTCGACC | 1896 | GGTCGAAGCCGCACTCGTAA | 3665 |
| 10164 | 10186 | CCTTACGAGTGCGGCTTCGACCC | 1897 | GGGTCGAAGCCGCACTCGTA | 3666 |
| 10184 | 10206 | CCCTATATCCCCCGCCCGCGTCC | 1898 | GGACGCGGGCGGGGATATA | 3667 |
| 10185 | 10207 | CCTATATCCCCCGCCCGCGTCCC | 1899 | GGGACGCGGGCGGGGATAT | 3668 |
| 10192 | 10214 | CCCCCGCCCGCGTCCCTTCTCC | 1900 | GGAGAAAGGGACGCGGGCGG | 3669 |
| 10193 | 10215 | CCCCGCCCGCGTCCCTTTCTCCA | 1901 | TGGAGAAAGGGACGCGGGCG | 3670 |
| 10194 | 10216 | CCCGCCCGCGTCCCTTTCTCCAT | 1902 | ATGGAGAAAGGGACGCGGGC | 3671 |
| 10195 | 10217 | CCGCCCGCGTCCCTTTCTCCATA | 1903 | TATGGAGAAAGGGACGCGGG | 3672 |
| 10198 | 10220 | CCCGCGTCCCTTTCTCCATAAAA | 1904 | TTTTATGGAGAAAGGGACGC | 3673 |
| 10199 | 10221 | CCGCGTCCCTTTCTCCATAAAAT | 1905 | ATTTTATGGAGAAAGGGACG | 3674 |
| 10205 | 10227 | CCCTTTCTCCATAAAATTCTTCT | 1906 | AGAAGAATTTTATGGAGAAA | 3675 |
| 10206 | 10228 | CCTTTCTCCATAAAATTCTTCTT | 1907 | AAGAAGAATTTTATGGAGAA | 3676 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 10213 | 10235 | CCATAAAATTCTTCTTAGTAGCT | 1908 | AGCTACTAAGAAGAATTTTA | 3677 |
| 10240 | 10262 | CCTTCTTATTATTTGATCTAGAA | 1909 | TTCTAGATCAAATAATAAGA | 3678 |
| 10267 | 10289 | CCCTCCTTTTACCCCTACCATGA | 1910 | TCATGGTAGGGGTAAAAGGA | 3679 |
| 10268 | 10290 | CCTCCTTTTACCCCTACCATGAG | 1911 | CTCATGGTAGGGGTAAAAGG | 3680 |
| 10271 | 10293 | CCTTTTACCCCTACCATGAGCCC | 1912 | GGGCTCATGGTAGGGGTAAA | 3681 |
| 10278 | 10300 | CCCCTACCATGAGCCCTACAAAC | 1913 | GTTTGTAGGGCTCATGGTAG | 3682 |
| 10279 | 10301 | CCCTACCATGAGCCCTACAAACA | 1914 | TGTTTGTAGGGCTCATGGTA | 3683 |
| 10280 | 10302 | CCTACCATGAGCCCTACAAACAA | 1915 | TTGTTTGTAGGGCTCATGGT | 3684 |
| 10284 | 10306 | CCATGAGCCCTACAAACAACTAA | 1916 | TTAGTTGTTTGTAGGGCTCA | 3685 |
| 10291 | 10313 | CCCTACAAACAACTAACCTGCCA | 1917 | TGGCAGGTTAGTTGTTTGTA | 3686 |
| 10292 | 10314 | CCTACAAACAACTAACCTGCCAC | 1918 | GTGGCAGGTTAGTTGTTTGT | 3687 |
| 10307 | 10329 | CCTGCCACTAATAGTTATGTCAT | 1919 | ATGACATAACTATTAGTGGC | 3688 |
| 10311 | 10333 | CCACTAATAGTTATGTCATCCCT | 1920 | AGGGATGACATAACTATTAG | 3689 |
| 10330 | 10352 | CCCTCTTATTAATCATCATCCTA | 1921 | TAGGATGATGATTAATAAGA | 3690 |
| 10331 | 10353 | CCTCTTATTAATCATCATCCTAG | 1922 | CTAGGATGATGATTAATAAG | 3691 |
| 10349 | 10371 | CCTAGCCCTAAGTCTGGCCTATG | 1923 | CATAGGCCAGACTTAGGGCT | 3692 |
| 10354 | 10376 | CCCTAAGTCTGGCCTATGAGTGA | 1924 | TCACTCATAGGCCAGACTTA | 3693 |
| 10355 | 10377 | CCTAAGTCTGGCCTATGAGTGAC | 1925 | GTCACTCATAGGCCAGACTT | 3694 |
| 10366 | 10388 | CCTATGAGTGACTACAAAAAGGA | 1926 | TCCTTTTTGTAGTCACTCAT | 3695 |
| 10399 | 10421 | CCGAATTGGTATATAGTTTAAAC | 1927 | GTTTAAACTATATACCAATT | 3696 |
| 10466 | 10488 | CCAAATGCCCCTCATTTACATAA | 1928 | TTATGTAAATGAGGGGCATT | 3697 |
| 10473 | 10495 | CCCCTCATTTACATAAATATTAT | 1929 | ATAATATTTATGTAAATGAG | 3698 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 10474 | 10496 | CCCTCATTTACATAAATATTATA | 1930 | TATAATATTTATGTAAATGA | 3699 |
| 10475 | 10497 | CCTCATTTACATAAATATTATAC | 1931 | GTATAATATTTATGTAAATG | 3700 |
| 10507 | 10529 | CCATCTCACTTCTAGGAATACTA | 1932 | TAGTATTCCTAGAAGTGAGA | 3701 |
| 10544 | 10566 | CCTCATATCCTCCCTACTATGCC | 1933 | GGCATAGTAGGGAGGATATG | 3702 |
| 10552 | 10574 | CCTCCCTACTATGCCTAGAAGGA | 1934 | TCCTTCTAGGCATAGTAGGG | 3703 |
| 10555 | 10577 | CCCTACTATGCCTAGAAGGAATA | 1935 | TATTCCTTCTAGGCATAGTA | 3704 |
| 10556 | 10578 | CCTACTATGCCTAGAAGGAATAA | 1936 | TTATTCCTTCTAGGCATAGT | 3705 |
| 10565 | 10587 | CCTAGAAGGAATAATACTATCGC | 1937 | GCGATAGTATTATTCCTTCT | 3706 |
| 10612 | 10634 | CCCTCAACACCCACTCCCTCTTA | 1938 | TAAGAGGGAGTGGGTGTTGA | 3707 |
| 10613 | 10635 | CCTCAACACCCACTCCCTCTTAG | 1939 | CTAAGAGGGAGTGGGTGTTG | 3708 |
| 10621 | 10643 | CCCACTCCCTCTTAGCCAATATT | 1940 | AATATTGGCTAAGAGGGAGT | 3709 |
| 10622 | 10644 | CCACTCCCTCTTAGCCAATATTG | 1941 | CAATATTGGCTAAGAGGGAG | 3710 |
| 10627 | 10649 | CCCTCTTAGCCAATATTGTGCCT | 1942 | AGGCACAATATTGGCTAAGA | 3711 |
| 10628 | 10650 | CCTCTTAGCCAATATTGTGCCTA | 1943 | TAGGCACAATATTGGCTAAG | 3712 |
| 10636 | 10658 | CCAATATTGTGCCTATTGCCATA | 1944 | TATGGCAATAGGCACAATAT | 3713 |
| 10647 | 10669 | CCTATTGCCATACTAGTCTTTGC | 1945 | GCAAAGACTAGTATGGCAAT | 3714 |
| 10654 | 10676 | CCATACTAGTCTTTGCCGCTGC | 1946 | GCAGGCGGCAAAGACTAGTA | 3715 |
| 10669 | 10691 | CCGCCTGCGAAGCAGCGGTGGGC | 1947 | GCCCACCGCTGCTTCGCAGG | 3716 |
| 10672 | 10694 | CCTGCGAAGCAGCGGTGGGCCTA | 1948 | TAGGCCCACCGCTGCTTCGC | 3717 |
| 10691 | 10713 | CCTAGCCCTACTAGTCTCAATCT | 1949 | AGATTGAGACTAGTAGGGCT | 3718 |
| 10696 | 10718 | CCCTACTAGTCTCAATCTCCAAC | 1950 | GTTGGAGATTGAGACTAGTA | 3719 |
| 10697 | 10719 | CCTACTAGTCTCAATCTCCAACA | 1951 | TGTTGGAGATTGAGACTAGT | 3720 |
| 10714 | 10736 | CCAACACATATGGCCTAGACTAC | 1952 | GTAGTCTAGGCCATATGTGT | 3721 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 10727 | 10749 | CCTAGACTACGTACATAACCTAA | 1953 | TTAGGTTATGTACGTAGTCT | 3722 |
| 10745 | 10767 | CCTAAACCTACTCCAATGCTAAA | 1954 | TTTAGCATTGGAGTAGGTTT | 3723 |
| 10751 | 10773 | CCTACTCCAATGCTAAAACTAAT | 1955 | ATTAGTTTTAGCATTGGAGT | 3724 |
| 10757 | 10779 | CCAATGCTAAAACTAATCGTCCC | 1956 | GGGACGATTAGTTTTAGCAT | 3725 |
| 10777 | 10799 | CCCAACAATTATATTACTACCAC | 1957 | GTGGTAGTAATATAATTGTT | 3726 |
| 10778 | 10800 | CCAACAATTATATTACTACCACT | 1958 | AGTGGTAGTAATATAATTGT | 3727 |
| 10796 | 10818 | CCACTGACATGACTTTCCAAAAA | 1959 | TTTTTGGAAAGTCATGTCAG | 3728 |
| 10812 | 10834 | CCAAAAAACACATAATTTGAATC | 1960 | GATTCAAATTATGTGTTTTT | 3729 |
| 10842 | 10864 | CCACCCACAGCCTAATTATTAGC | 1961 | GCTAATAATTAGGCTGTGGG | 3730 |
| 10845 | 10867 | CCCACAGCCTAATTATTAGCATC | 1962 | GATGCTAATAATTAGGCTGT | 3731 |
| 10846 | 10868 | CCACAGCCTAATTATTAGCATCA | 1963 | TGATGCTAATAATTAGGCTG | 3732 |
| 10852 | 10874 | CCTAATTATTAGCATCATCCCTC | 1964 | GAGGGATGATGCTAATAATT | 3733 |
| 10870 | 10892 | CCCTCTACTATTTTTAACCAAA | 1965 | TTTGGTTAAAAAATAGTAGA | 3734 |
| 10871 | 10893 | CCTCTACTATTTTTAACCAAAT | 1966 | ATTTGGTTAAAAAATAGTAG | 3735 |
| 10888 | 10910 | CCAAATCAACAACAACCTATTTA | 1967 | TAAATAGGTTGTTGTTGATT | 3736 |
| 10903 | 10925 | CCTATTTAGCTGTTCCCCAACCT | 1968 | AGGTTGGGGAACAGCTAAAT | 3737 |
| 10917 | 10939 | CCCCAACCTTTTCCTCCGACCCC | 1969 | GGGGTCGGAGGAAAAGGTTG | 3738 |
| 10918 | 10940 | CCCAACCTTTTCCTCCGACCCCC | 1970 | GGGGGTCGGAGGAAAAGGTT | 3739 |
| 10919 | 10941 | CCAACCTTTTCCTCCGACCCCCT | 1971 | AGGGGGTCGGAGGAAAAGGT | 3740 |
| 10923 | 10945 | CCTTTTCCTCCGACCCCCTAACA | 1972 | TGTTAGGGGGTCGGAGGAAA | 3741 |
| 10929 | 10951 | CCTCCGACCCCCTAACAACCCCC | 1973 | GGGGGTTGTTAGGGGGTCGG | 3742 |
| 10932 | 10954 | CCGACCCCCTAACAACCCCCTC | 1974 | GAGGGGGGTTGTTAGGGGGT | 3743 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 10936 | 10958 | CCCCCTAACAACCCCCCTCCTAA | 1975 | TTAGGAGGGGGGTTGTTAGG | 3744 |
| 10937 | 10959 | CCCCTAACAACCCCCCTCCTAAT | 1976 | ATTAGGAGGGGGGTTGTTAG | 3745 |
| 10938 | 10960 | CCCTAACAACCCCCCTCCTAATA | 1977 | TATTAGGAGGGGGGTTGTTA | 3746 |
| 10939 | 10961 | CCTAACAACCCCCCTCCTAATAC | 1978 | GTATTAGGAGGGGGGTTGTT | 3747 |
| 10947 | 10969 | CCCCCCTCCTAATACTAACTACC | 1979 | GGTAGTTAGTATTAGGAGGG | 3748 |
| 10948 | 10970 | CCCCCTCCTAATACTAACTACCT | 1980 | AGGTAGTTAGTATTAGGAGG | 3749 |
| 10949 | 10971 | CCCCTCCTAATACTAACTACCTG | 1981 | CAGGTAGTTAGTATTAGGAG | 3750 |
| 10950 | 10972 | CCCTCCTAATACTAACTACCTGA | 1982 | TCAGGTAGTTAGTATTAGGA | 3751 |
| 10951 | 10973 | CCTCCTAATACTAACTACCTGAC | 1983 | GTCAGGTAGTTAGTATTAGG | 3752 |
| 10954 | 10976 | CCTAATACTAACTACCTGACTCC | 1984 | GGAGTCAGGTAGTTAGTATT | 3753 |
| 10968 | 10990 | CCTGACTCCTACCCCTCACAATC | 1985 | GATTGTGAGGGGTAGGAGTC | 3754 |
| 10975 | 10997 | CCTACCCCTCACAATCATGGCAA | 1986 | TTGCCATGATTGTGAGGGGT | 3755 |
| 10979 | 11001 | CCCCTCACAATCATGGCAAGCCA | 1987 | TGGCTTGCCATGATTGTGAG | 3756 |
| 10980 | 11002 | CCCTCACAATCATGGCAAGCCAA | 1988 | TTGGCTTGCCATGATTGTGA | 3757 |
| 10981 | 11003 | CCTCACAATCATGGCAAGCCAAC | 1989 | GTTGGCTTGCCATGATTGTG | 3758 |
| 10999 | 11021 | CCAACGCCACTTATCCAGTGAAC | 1990 | GTTCACTGGATAAGTGGCGT | 3759 |
| 11005 | 11027 | CCACTTATCCAGTGAACCACTAT | 1991 | ATAGTGGTTCACTGGATAAG | 3760 |
| 11013 | 11035 | CCAGTGAACCACTATCACGAAAA | 1992 | TTTTCGTGATAGTGGTTCAC | 3761 |
| 11021 | 11043 | CCACTATCACGAAAAAAACTCTA | 1993 | TAGAGTTTTTTTCGTGATAG | 3762 |
| 11044 | 11066 | CCTCTCTATACTAATCTCCCTAC | 1994 | GTAGGGAGATTAGTATAGAG | 3763 |
| 11061 | 11083 | CCCTACAAATCTCCTTAATTATA | 1995 | TATAATTAAGGAGATTTGTA | 3764 |
| 11062 | 11084 | CCTACAAATCTCCTTAATTATAA | 1996 | TTATAATTAAGGAGATTTGT | 3765 |
| 11073 | 11095 | CCTTAATTATAACATTCACAGCC | 1997 | GGCTGTGAATGTTATAATTA | 3766 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 11094 | 11116 | CCACAGAACTAATCATATTTTAT | 1998 | ATAAAATATGATTAGTTCTG | 3767 |
| 11130 | 11152 | CCACACTTATCCCCACCTTGGCT | 1999 | AGCCAAGGTGGGGATAAGTG | 3768 |
| 11140 | 11162 | CCCCACCTTGGCTATCATCACCC | 2000 | GGGTGATGATAGCCAAGGTG | 3769 |
| 11141 | 11163 | CCCACCTTGGCTATCATCACCCG | 2001 | CGGGTGATGATAGCCAAGGT | 3770 |
| 11142 | 11164 | CCACCTTGGCTATCATCACCCGA | 2002 | TCGGGTGATGATAGCCAAGG | 3771 |
| 11145 | 11167 | CCTTGGCTATCATCACCCGATGA | 2003 | TCATCGGGTGATGATAGCCA | 3772 |
| 11160 | 11182 | CCCGATGAGGCAACCAGCCAGAA | 2004 | TTCTGGCTGGTTGCCTCATC | 3773 |
| 11161 | 11183 | CCGATGAGGCAACCAGCCAGAAC | 2005 | GTTCTGGCTGGTTGCCTCAT | 3774 |
| 11173 | 11195 | CCAGCCAGAACGCCTGAACGCAG | 2006 | CTGCGTTCAGGCGTTCTGGC | 3775 |
| 11177 | 11199 | CCAGAACGCCTGAACGCAGGCAC | 2007 | GTGCCTGCGTTCAGGCGTTC | 3776 |
| 11185 | 11207 | CCTGAACGCAGGCACATACTTCC | 2008 | GGAAGTATGTGCCTGCGTTC | 3777 |
| 11206 | 11228 | CCTATTCTACACCCTAGTAGGCT | 2009 | AGCCTACTAGGGTGTAGAAT | 3778 |
| 11217 | 11239 | CCCTAGTAGGCTCCCTTCCCCTA | 2010 | TAGGGGAAGGGAGCCTACTA | 3779 |
| 11218 | 11240 | CCTAGTAGGCTCCCTTCCCTAC | 2011 | GTAGGGGAAGGGAGCCTACT | 3780 |
| 11229 | 11251 | CCCTTCCCCTACTCATCGCACTA | 2012 | TAGTGCGATGAGTAGGGGAA | 3781 |
| 11230 | 11252 | CCTTCCCCTACTCATCGCACTAA | 2013 | TTAGTGCGATGAGTAGGGGA | 3782 |
| 11234 | 11256 | CCCCTACTCATCGCACTAATTTA | 2014 | TAAATTAGTGCGATGAGTAG | 3783 |
| 11235 | 11257 | CCCTACTCATCGCACTAATTTAC | 2015 | GTAAATTAGTGCGATGAGTA | 3784 |
| 11236 | 11258 | CCTACTCATCGCACTAATTTACA | 2016 | TGTAAATTAGTGCGATGAGT | 3785 |
| 11268 | 11290 | CCCTAGGCTCACTAAACATTCTA | 2017 | TAGAATGTTTAGTGAGCCTA | 3786 |
| 11269 | 11291 | CCTAGGCTCACTAAACATTCTAC | 2018 | GTAGAATGTTTAGTGAGCCT | 3787 |
| 11307 | 11329 | CCCAAGAACTATCAAACTCCTGA | 2019 | TCAGGAGTTTGATAGTTCTT | 3788 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 11308 | 11330 | CCAAGAACTATCAAACTCCTGAG | 2020 | CTCAGGAGTTTGATAGTTCT | 3789 |
| 11325 | 11347 | CCTGAGCCAACAACTTAATATGA | 2021 | TCATATTAAGTTGTTGGCTC | 3790 |
| 11331 | 11353 | CCAACAACTTAATATGACTAGCT | 2022 | AGCTAGTCATATTAAGTTGT | 3791 |
| 11381 | 11403 | CCTCTTTACGGACTCCACTTATG | 2023 | CATAAGTGGAGTCCGTAAAG | 3792 |
| 11395 | 11417 | CCACTTATGACTCCCTAAAGCCC | 2024 | GGGCTTTAGGGAGTCATAAG | 3793 |
| 11407 | 11429 | CCCTAAAGCCCATGTCGAAGCCC | 2025 | GGGCTTCGACATGGGCTTTA | 3794 |
| 11408 | 11430 | CCTAAAGCCCATGTCGAAGCCCC | 2026 | GGGGCTTCGACATGGGCTTT | 3795 |
| 11415 | 11437 | CCCATGTCGAAGCCCCCATCGCT | 2027 | AGCGATGGGGGCTTCGACAT | 3796 |
| 11416 | 11438 | CCATGTCGAAGCCCCCATCGCTG | 2028 | CAGCGATGGGGGCTTCGACA | 3797 |
| 11427 | 11449 | CCCCCATCGCTGGGTCAATAGTA | 2029 | TACTATTGACCCAGCGATGG | 3798 |
| 11428 | 11450 | CCCCATCGCTGGGTCAATAGTAC | 2030 | GTACTATTGACCCAGCGATG | 3799 |
| 11429 | 11451 | CCCATCGCTGGGTCAATAGTACT | 2031 | AGTACTATTGACCCAGCGAT | 3800 |
| 11430 | 11452 | CCATCGCTGGGTCAATAGTACTT | 2032 | AAGTACTATTGACCCAGCGA | 3801 |
| 11454 | 11476 | CCGCAGTACTCTTAAAACTAGGC | 2033 | GCCTAGTTTTAAGAGTACTG | 3802 |
| 11494 | 11516 | CCTCACACTCATTCTCAACCCCC | 2034 | GGGGGTTGAGAATGAGTGTG | 3803 |
| 11512 | 11534 | CCCCCTGACAAAACACATAGCCT | 2035 | AGGCTATGTGTTTTGTCAGG | 3804 |
| 11513 | 11535 | CCCCTGACAAAACACATAGCCTA | 2036 | TAGGCTATGTGTTTTGTCAG | 3805 |
| 11514 | 11536 | CCCTGACAAAACACATAGCCTAC | 2037 | GTAGGCTATGTGTTTTGTCA | 3806 |
| 11515 | 11537 | CCTGACAAAACACATAGCCTACC | 2038 | GGTAGGCTATGTGTTTTGTC | 3807 |
| 11532 | 11554 | CCTACCCCTTCCTTGTACTATCC | 2039 | GGATAGTACAAGGAAGGGGT | 3808 |
| 11536 | 11558 | CCCCTTCCTTGTACTATCCCTAT | 2040 | ATAGGGATAGTACAAGGAAG | 3809 |
| 11537 | 11559 | CCCTTCCTTGTACTATCCCTATG | 2041 | CATAGGGATAGTACAAGGAA | 3810 |
| 11538 | 11560 | CCTTCCTTGTACTATCCCTATGA | 2042 | TCATAGGGATAGTACAAGGA | 3811 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 11542 | 11564 | CCTTGTACTATCCCTATGAGGCA | 2043 | TGCCTCATAGGGATAGTACA | 3812 |
| 11553 | 11575 | CCCTATGAGGCATAATTATAACA | 2044 | TGTTATAATTATGCCTCATA | 3813 |
| 11554 | 11576 | CCTATGAGGCATAATTATAACAA | 2045 | TTGTTATAATTATGCCTCAT | 3814 |
| 11580 | 11602 | CCATCTGCCTACGACAAACAGAC | 2046 | GTCTGTTTGTCGTAGGCAGA | 3815 |
| 11587 | 11609 | CCTACGACAAACAGACCTAAAAT | 2047 | ATTTTAGGTCTGTTTGTCGT | 3816 |
| 11602 | 11624 | CCTAAAATCGCTCATTGCATACT | 2048 | AGTATGCAATGAGCGATTTT | 3817 |
| 11635 | 11657 | CCACATAGCCCTCGTAGTAACAG | 2049 | CTGTTACTACGAGGGCTATG | 3818 |
| 11643 | 11665 | CCCTCGTAGTAACAGCCATTCTC | 2050 | GAGAATGGCTGTTACTACGA | 3819 |
| 11644 | 11666 | CCTCGTAGTAACAGCCATTCTCA | 2051 | TGAGAATGGCTGTTACTACG | 3820 |
| 11658 | 11680 | CCATTCTCATCCAAACCCCTGA | 2052 | TCAGGGGTTTGGATGAGAA | 3821 |
| 11668 | 11690 | CCAAACCCCTGAAGCTTCACCG | 2053 | CGGTGAAGCTTCAGGGGGTT | 3822 |
| 11673 | 11695 | CCCCCTGAAGCTTCACCGGCGCA | 2054 | TGCGCCGGTGAAGCTTCAGG | 3823 |
| 11674 | 11696 | CCCCTGAAGCTTCACCGGCGCAG | 2055 | CTGCGCCGGTGAAGCTTCAG | 3824 |
| 11675 | 11697 | CCCTGAAGCTTCACCGGCGCAGT | 2056 | ACTGCGCCGGTGAAGCTTCA | 3825 |
| 11676 | 11698 | CCTGAAGCTTCACCGGCGCAGTC | 2057 | GACTGCGCCGGTGAAGCTTC | 3826 |
| 11688 | 11710 | CCGGCGCAGTCATTCTCATAATC | 2058 | GATTATGAGAATGACTGCGC | 3827 |
| 11712 | 11734 | CCCACGGGCTTACATCCTCATTA | 2059 | TAATGAGGATGTAAGCCCGT | 3828 |
| 11713 | 11735 | CCACGGGCTTACATCCTCATTAC | 2060 | GTAATGAGGATGTAAGCCCG | 3829 |
| 11727 | 11749 | CCTCATTACTATTCTGCCTAGCA | 2061 | TGCTAGGCAGAATAGTAATG | 3830 |
| 11743 | 11765 | CCTAGCAAACTCAAACTACGAAC | 2062 | GTTCGTAGTTTGAGTTTGCT | 3831 |
| 11788 | 11810 | CCTCTCTCAAGGACTTCAAACTC | 2063 | GAGTTTGAAGTCCTTGAGAG | 3832 |
| 11815 | 11837 | CCCACTAATAGCTTTTTGATGAC | 2064 | GTCATCAAAAGCTATTAGT | 3833 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 11816 | 11838 | CCACTAATAGCTTTTGATGACT | 2065 | AGTCATCAAAAAGCTATTAG | 3834 |
| 11848 | 11870 | CCTCGCTAACCTCGCCTTACCCC | 2066 | GGGGTAAGGCGAGGTTAGCG | 3835 |
| 11857 | 11879 | CCTCGCCTTACCCCCACTATTA | 2067 | TAATAGTGGGGGTAAGGCG | 3836 |
| 11862 | 11884 | CCTTACCCCCACTATTAACCTA | 2068 | TAGGTTAATAGTGGGGGTA | 3837 |
| 11867 | 11889 | CCCCCACTATTAACCTACTGGG | 2069 | CCCAGTAGGTTAATAGTGGG | 3838 |
| 11868 | 11890 | CCCCACTATTAACCTACTGGGA | 2070 | TCCCAGTAGGTTAATAGTGG | 3839 |
| 11869 | 11891 | CCCCACTATTAACCTACTGGGAG | 2071 | CTCCCAGTAGGTTAATAGTG | 3840 |
| 11870 | 11892 | CCCACTATTAACCTACTGGGAGA | 2072 | TCTCCCAGTAGGTTAATAGT | 3841 |
| 11871 | 11893 | CCACTATTAACCTACTGGGAGAA | 2073 | TTCTCCCAGTAGGTTAATAG | 3842 |
| 11881 | 11903 | CCTACTGGGAGAACTCTCTGTGC | 2074 | GCACAGAGAGTTCTCCCAGT | 3843 |
| 11910 | 11932 | CCACGTTCTCCTGATCAAATATC | 2075 | GATATTTGATCAGGAGAACG | 3844 |
| 11919 | 11941 | CCTGATCAAATATCACTCTCCTA | 2076 | TAGGAGAGTGATATTTGATC | 3845 |
| 11938 | 11960 | CCTACTTACAGGACTCAACATAC | 2077 | GTATGTTGAGTCCTGTAAGT | 3846 |
| 11970 | 11992 | CCCTATACTCCCTCTACATATTT | 2078 | AAATATGTAGAGGGAGTATA | 3847 |
| 11971 | 11993 | CCTATACTCCCTCTACATATTTA | 2079 | TAAATATGTAGAGGGAGTAT | 3848 |
| 11979 | 12001 | CCCTCTACATATTTACCACAACA | 2080 | TGTTGTGGTAAATATGTAGA | 3849 |
| 11980 | 12002 | CCTCTACATATTTACCACAACAC | 2081 | GTGTTGTGGTAAATATGTAG | 3850 |
| 11994 | 12016 | CCACAACACAATGGGCTCACTC | 2082 | GAGTGAGCCCCATTGTGTTG | 3851 |
| 12018 | 12040 | CCCACCACATTAACAACATAAAA | 2083 | TTTTATGTTGTTAATGTGGT | 3852 |
| 12019 | 12041 | CCACCACATTAACAACATAAAAC | 2084 | GTTTTATGTTGTTAATGTGG | 3853 |
| 12022 | 12044 | CCACATTAACAACATAAACCCT | 2085 | AGGGTTTTATGTTGTTAATG | 3854 |
| 12041 | 12063 | CCCTCATTCACACGAGAAAACAC | 2086 | GTGTTTTCTCGTGTGAATGA | 3855 |
| 12042 | 12064 | CCTCATTCACACGAGAAAACACC | 2087 | GGTGTTTTCTCGTGTGAATG | 3856 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 12063 | 12085 | CCCTCATGTTCATACACCTATCC | 2088 | GGATAGGTGTATGAACATGA | 3857 |
| 12064 | 12086 | CCTCATGTTCATACACCTATCCC | 2089 | GGGATAGGTGTATGAACATG | 3858 |
| 12079 | 12101 | CCTATCCCCCATTCTCCTCCTAT | 2090 | ATAGGAGGAGAATGGGGGAT | 3859 |
| 12084 | 12106 | CCCCCATTCTCCTCCTATCCCTC | 2091 | GAGGGATAGGAGGAGAATGG | 3860 |
| 12085 | 12107 | CCCCATTCTCCTCCTATCCCTCA | 2092 | TGAGGGATAGGAGGAGAATG | 3861 |
| 12086 | 12108 | CCCATTCTCCTCCTATCCCTCAA | 2093 | TTGAGGGATAGGAGGAGAAT | 3862 |
| 12087 | 12109 | CCATTCTCCTCCTATCCCTCAAC | 2094 | GTTGAGGGATAGGAGGAGAA | 3863 |
| 12094 | 12116 | CCTCCTATCCCTCAACCCCGACA | 2095 | TGTCGGGGTTGAGGGATAGG | 3864 |
| 12097 | 12119 | CCTATCCCTCAACCCCGACATCA | 2096 | TGATGTCGGGGTTGAGGGAT | 3865 |
| 12102 | 12124 | CCCTCAACCCCGACATCATTACC | 2097 | GGTAATGATGTCGGGGTTGA | 3866 |
| 12103 | 12125 | CCTCAACCCCGACATCATTACCG | 2098 | CGGTAATGATGTCGGGGTTG | 3867 |
| 12109 | 12131 | CCCCGACATCATTACCGGGTTTT | 2099 | AAAACCCGGTAATGATGTCG | 3868 |
| 12110 | 12132 | CCCGACATCATTACCGGGTTTTC | 2100 | GAAAACCCGGTAATGATGTC | 3869 |
| 12111 | 12133 | CCGACATCATTACCGGGTTTTCC | 2101 | GGAAAACCCGGTAATGATGT | 3870 |
| 12123 | 12145 | CCGGGTTTTCCTCTTGTAAATAT | 2102 | ATATTTACAAGAGGAAAACC | 3871 |
| 12132 | 12154 | CCTCTTGTAAATATAGTTTAACC | 2103 | GGTTAAACTATATTTACAAG | 3872 |
| 12153 | 12175 | CCAAAACATCAGATTGTGAATCT | 2104 | AGATTCACAATCTGATGTTT | 3873 |
| 12194 | 12216 | CCCCTTATTTACCGAGAAAGCTC | 2105 | GAGCTTTCTCGGTAAATAAG | 3874 |
| 12195 | 12217 | CCCTTATTTACCGAGAAAGCTCA | 2106 | TGAGCTTTCTCGGTAAATAA | 3875 |
| 12196 | 12218 | CCTTATTTACCGAGAAAGCTCAC | 2107 | GTGAGCTTTCTCGGTAAATA | 3876 |
| 12205 | 12227 | CCGAGAAAGCTCACAAGAACTGC | 2108 | GCAGTTCTTGTGAGCTTTCT | 3877 |
| 12237 | 12259 | CCCCCATGTCTAACAACATGGCT | 2109 | AGCCATGTTGTTAGACATGG | 3878 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 12238 | 12260 | CCCCATGTCTAACAACATGGCTT | 2110 | AAGCCATGTTGTTAGACATG | 3879 |
| 12239 | 12261 | CCCATGTCTAACAACATGGCTTT | 2111 | AAAGCCATGTTGTTAGACAT | 3880 |
| 12240 | 12262 | CCATGTCTAACAACATGGCTTTC | 2112 | GAAAGCCATGTTGTTAGACA | 3881 |
| 12288 | 12310 | CCATTGGTCTTAGGCCCCAAAAA | 2113 | TTTTTGGGGCCTAAGACCAA | 3882 |
| 12302 | 12324 | CCCCAAAAATTTTGGTGCAACTC | 2114 | GAGTTGCACCAAAATTTTTG | 3883 |
| 12303 | 12325 | CCCAAAAATTTTGGTGCAACTCC | 2115 | GGAGTTGCACCAAAATTTTT | 3884 |
| 12304 | 12326 | CCAAAAATTTTGGTGCAACTCCA | 2116 | TGGAGTTGCACCAAAATTTT | 3885 |
| 12324 | 12346 | CCAAATAAAGTAATAACCATGC | 2117 | GCATGGTTATTACTTTTATT | 3886 |
| 12341 | 12363 | CCATGCACACTACTATAACCACC | 2118 | GGTGGTTATAGTAGTGTGCA | 3887 |
| 12359 | 12381 | CCACCCTAACCCTGACTTCCCTA | 2119 | TAGGGAAGTCAGGGTTAGGG | 3888 |
| 12362 | 12384 | CCCTAACCCTGACTTCCCTAATT | 2120 | AATTAGGGAAGTCAGGGTTA | 3889 |
| 12363 | 12385 | CCTAACCCTGACTTCCCTAATTC | 2121 | GAATTAGGGAAGTCAGGGTT | 3890 |
| 12368 | 12390 | CCCTGACTTCCCTAATTCCCCCC | 2122 | GGGGGGAATTAGGGAAGTCA | 3891 |
| 12369 | 12391 | CCTGACTTCCCTAATTCCCCCA | 2123 | TGGGGGGAATTAGGGAAGTC | 3892 |
| 12377 | 12399 | CCCTAATTCCCCCCATCCTTACC | 2124 | GGTAAGGATGGGGGGAATTA | 3893 |
| 12378 | 12400 | CCTAATTCCCCCCATCCTTACCA | 2125 | TGGTAAGGATGGGGGGAATT | 3894 |
| 12385 | 12407 | CCCCCCATCCTTACCACCCTCGT | 2126 | ACGAGGGTGGTAAGGATGGG | 3895 |
| 12386 | 12408 | CCCCCATCCTTACCACCCTCGTT | 2127 | AACGAGGGTGGTAAGGATGG | 3896 |
| 12387 | 12409 | CCCCATCCTTACCACCCTCGTTA | 2128 | TAACGAGGGTGGTAAGGATG | 3897 |
| 12388 | 12410 | CCCATCCTTACCACCCTCGTTAA | 2129 | TTAACGAGGGTGGTAAGGAT | 3898 |
| 12389 | 12411 | CCATCCTTACCACCCTCGTTAAC | 2130 | GTTAACGAGGGTGGTAAGGA | 3899 |
| 12393 | 12415 | CCTTACCACCCTCGTTAACCCTA | 2131 | TAGGGTTAACGAGGGTGGTA | 3900 |
| 12398 | 12420 | CCACCCTCGTTAACCCTAACAAA | 2132 | TTTGTTAGGGTTAACGAGGG | 3901 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 12401 | 12423 | CCCTCGTTAACCCTAACAAAAAA | 2133 | TTTTTTGTTAGGGTTAACGA | 3902 |
| 12402 | 12424 | CCTCGTTAACCCTAACAAAAAA | 2134 | TTTTTTTGTTAGGGTTAACG | 3903 |
| 12411 | 12433 | CCCTAACAAAAAAACTCATACC | 2135 | GGTATGAGTTTTTTTGTTA | 3904 |
| 12412 | 12434 | CCTAACAAAAAAACTCATACCC | 2136 | GGGTATGAGTTTTTTTGTT | 3905 |
| 12432 | 12454 | CCCCCATTATGTAAAATCCATTG | 2137 | CAATGGATTTTACATAATGG | 3906 |
| 12433 | 12455 | CCCCATTATGTAAAATCCATTGT | 2138 | ACAATGGATTTTACATAATG | 3907 |
| 12434 | 12456 | CCCATTATGTAAAATCCATTGTC | 2139 | GACAATGGATTTTACATAAT | 3908 |
| 12435 | 12457 | CCATTATGTAAAATCCATTGTCG | 2140 | CGACAATGGATTTTACATAA | 3909 |
| 12449 | 12471 | CCATTGTCGCATCCACCTTTATT | 2141 | AATAAAGGTGGATGCGACAA | 3910 |
| 12461 | 12483 | CCACCTTTATTATCAGTCTCTTC | 2142 | GAAGAGACTGATAATAAAGG | 3911 |
| 12464 | 12486 | CCTTTATTATCAGTCTCTTCCCC | 2143 | GGGGAAGAGACTGATAATAA | 3912 |
| 12483 | 12505 | CCCCACAACAATATTCATGTGCC | 2144 | GGCACATGAATATTGTTGTG | 3913 |
| 12484 | 12506 | CCCACAACAATATTCATGTGCCT | 2145 | AGGCACATGAATATTGTTGT | 3914 |
| 12485 | 12507 | CCACAACAATATTCATGTGCCTA | 2146 | TAGGCACATGAATATTGTTG | 3915 |
| 12504 | 12526 | CCTAGACCAAGAAGTTATTATCT | 2147 | AGATAATAACTTCTTGGTCT | 3916 |
| 12510 | 12532 | CCAAGAAGTTATTATCTCGAACT | 2148 | AGTTCGAGATAATAACTTCT | 3917 |
| 12542 | 12564 | CCACAACCCAAACAACCCAGCTC | 2149 | GAGCTGGGTTGTTTGGGTTG | 3918 |
| 12548 | 12570 | CCCAAACAACCCAGCTCTCCCTA | 2150 | TAGGGAGAGCTGGGTTGTTT | 3919 |
| 12549 | 12571 | CCAAACAACCCAGCTCTCCCTAA | 2151 | TTAGGGAGAGCTGGGTTGTT | 3920 |
| 12557 | 12579 | CCCAGCTCTCCCTAAGCTTCAAA | 2152 | TTTGAAGCTTAGGGAGAGCT | 3921 |
| 12558 | 12580 | CCAGCTCTCCCTAAGCTTCAAAC | 2153 | GTTTGAAGCTTAGGGAGAGC | 3922 |
| 12566 | 12588 | CCCTAAGCTTCAAACTAGACTAC | 2154 | GTAGTCTAGTTTGAAGCTTA | 3923 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 12567 | 12589 | CCTAAGCTTCAAACTAGACTACT | 2155 | AGTAGTCTAGTTTGAAGCTT | 3924 |
| 12593 | 12615 | CCATAATATTCATCCCTGTAGCA | 2156 | TGCTACAGGGATGAATATTA | 3925 |
| 12606 | 12628 | CCCTGTAGCATTGTTCGTTACAT | 2157 | ATGTAACGAACAATGCTACA | 3926 |
| 12607 | 12629 | CCTGTAGCATTGTTCGTTACATG | 2158 | CATGTAACGAACAATGCTAC | 3927 |
| 12632 | 12654 | CCATCATAGAATTCTCACTGTGA | 2159 | TCACAGTGAGAATTCTATGA | 3928 |
| 12669 | 12691 | CCCAAACATTAATCAGTTCTTCA | 2160 | TGAAGAACTGATTAATGTTT | 3929 |
| 12670 | 12692 | CCAAACATTAATCAGTTCTTCAA | 2161 | TTGAAGAACTGATTAATGTT | 3930 |
| 12708 | 12730 | CCTAATTACCATACTAATCTTAG | 2162 | CTAAGATTAGTATGGTAATT | 3931 |
| 12716 | 12738 | CCATACTAATCTTAGTTACCGCT | 2163 | AGCGGTAACTAAGATTAGTA | 3932 |
| 12734 | 12756 | CCGCTAACAACCTATTCAACTG | 2164 | CAGTTGGAATAGGTTGTTAG | 3933 |
| 12744 | 12766 | CCTATTCCAACTGTTCATCGGCT | 2165 | AGCCGATGAACAGTTGGAAT | 3934 |
| 12750 | 12772 | CCAACTGTTCATCGGCTGAGAGG | 2166 | CCTCTCAGCCGATGAACAGT | 3935 |
| 12788 | 12810 | CCTTCTTGCTCATCAGTTGATGA | 2167 | TCATCAACTGATGAGCAAGA | 3936 |
| 12815 | 12837 | CCCGAGCAGATGCCAACACAGCA | 2168 | TGCTGTGTTGGCATCTGCTC | 3937 |
| 12816 | 12838 | CCGAGCAGATGCCAACACAGCAG | 2169 | CTGCTGTGTTGGCATCTGCT | 3938 |
| 12827 | 12849 | CCAACACAGCAGCCATTCAAGCA | 2170 | TGCTTGAATGGCTGCTGTGT | 3939 |
| 12839 | 12861 | CCATTCAAGCAATCCTATACAAC | 2171 | GTTGTATAGGATTGCTTGAA | 3940 |
| 12852 | 12874 | CCTATACAACCGTATCGGCGATA | 2172 | TATCGCCGATACGGTTGTAT | 3941 |
| 12861 | 12883 | CCGTATCGGCGATATCGGTTTCA | 2173 | TGAAACCGATATCGCCGATA | 3942 |
| 12885 | 12907 | CCTCGCCTTAGCATGATTTATCC | 2174 | GGATAAATCATGCTAAGGCG | 3943 |
| 12890 | 12912 | CCTTAGCATGATTTATCCTACAC | 2175 | GTGTAGGATAAATCATGCTA | 3944 |
| 12906 | 12928 | CCTACACTCCAACTCATGAGACC | 2176 | GGTCTCATGAGTTGGAGTGT | 3945 |
| 12914 | 12936 | CCAACTCATGAGACCCACAACAA | 2177 | TTGTTGTGGGTCTCATGAGT | 3946 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 12927 | 12949 | CCCACAACAAATAGCCCTTCTAA | 2178 | TTAGAAGGGCTATTTGTTGT | 3947 |
| 12928 | 12950 | CCACAACAAATAGCCCTTCTAAA | 2179 | TTTAGAAGGGCTATTTGTTG | 3948 |
| 12941 | 12963 | CCCTTCTAAACGCTAATCCAAGC | 2180 | GCTTGGATTAGCGTTTAGAA | 3949 |
| 12942 | 12964 | CCTTCTAAACGCTAATCCAAGCC | 2181 | GGCTTGGATTAGCGTTTAGA | 3950 |
| 12958 | 12980 | CCAAGCCTCACCCCACTACTAGG | 2182 | CCTAGTAGTGGGGTGAGGCT | 3951 |
| 12963 | 12985 | CCTCACCCCACTACTAGGCCTCC | 2183 | GGAGGCCTAGTAGTGGGGTG | 3952 |
| 12968 | 12990 | CCCCACTACTAGGCCTCCTCCTA | 2184 | TAGGAGGAGGCCTAGTAGTG | 3953 |
| 12969 | 12991 | CCCACTACTAGGCCTCCTCCTAG | 2185 | CTAGGAGGAGGCCTAGTAGT | 3954 |
| 12970 | 12992 | CCACTACTAGGCCTCCTCCTAGC | 2186 | GCTAGGAGGAGGCCTAGTAG | 3955 |
| 12981 | 13003 | CCTCCTCCTAGCAGCAGCAGGCA | 2187 | TGCCTGCTGCTGCTAGGAGG | 3956 |
| 12984 | 13006 | CCTCCTAGCAGCAGCAGGCAAAT | 2188 | ATTTGCCTGCTGCTGCTAGG | 3957 |
| 12987 | 13009 | CCTAGCAGCAGCAGGCAAATCAG | 2189 | CTGATTTGCCTGCTGCTGCT | 3958 |
| 13010 | 13032 | CCCAATTAGGTCTCCACCCCTGA | 2190 | TCAGGGGTGGAGACCTAATT | 3959 |
| 13011 | 13033 | CCAATTAGGTCTCCACCCCTGAC | 2191 | GTCAGGGGTGGAGACCTAAT | 3960 |
| 13023 | 13045 | CCACCCCTGACTCCCCTCAGCCA | 2192 | TGGCTGAGGGGAGTCAGGGG | 3961 |
| 13026 | 13048 | CCCCTGACTCCCCTCAGCCATAG | 2193 | CTATGGCTGAGGGGAGTCAG | 3962 |
| 13027 | 13049 | CCCTGACTCCCCTCAGCCATAGA | 2194 | TCTATGGCTGAGGGGAGTCA | 3963 |
| 13028 | 13050 | CCTGACTCCCCTCAGCCATAGAA | 2195 | TTCTATGGCTGAGGGGAGTC | 3964 |
| 13035 | 13057 | CCCCTCAGCCATAGAAGGCCCCA | 2196 | TGGGGCCTTCTATGGCTGAG | 3965 |
| 13036 | 13058 | CCCTCAGCCATAGAAGGCCCCAC | 2197 | GTGGGGCCTTCTATGGCTGA | 3966 |
| 13037 | 13059 | CCTCAGCCATAGAAGGCCCCACC | 2198 | GGTGGGGCCTTCTATGGCTG | 3967 |
| 13043 | 13065 | CCATAGAAGGCCCCACCCCAGTC | 2199 | GACTGGGGTGGGGCCTTCTA | 3968 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 13053 | 13075 | CCCCACCCCAGTCTCAGCCCTAC | 2200 | GTAGGGCTGAGACTGGGGTG | 3969 |
| 13054 | 13076 | CCCACCCCAGTCTCAGCCTACT | 2201 | AGTAGGGCTGAGACTGGGGT | 3970 |
| 13055 | 13077 | CCACCCCAGTCTCAGCCCTACTC | 2202 | GAGTAGGGCTGAGACTGGGG | 3971 |
| 13058 | 13080 | CCCCAGTCTCAGCCCTACTCCAC | 2203 | GTGGAGTAGGGCTGAGACTG | 3972 |
| 13059 | 13081 | CCCAGTCTCAGCCCTACTCCACT | 2204 | AGTGGAGTAGGGCTGAGACT | 3973 |
| 13060 | 13082 | CCAGTCTCAGCCCTACTCCACTC | 2205 | GAGTGGAGTAGGGCTGAGAC | 3974 |
| 13070 | 13092 | CCCTACTCCACTCAAGCACTATA | 2206 | TATAGTGCTTGAGTGGAGTA | 3975 |
| 13071 | 13093 | CCTACTCCACTCAAGCACTATAG | 2207 | CTATAGTGCTTGAGTGGAGT | 3976 |
| 13077 | 13099 | CCACTCAAGCACTATAGTTGTAG | 2208 | CTACAACTATAGTGCTTGAG | 3977 |
| 13119 | 13141 | CCGCTTCCACCCCCTAGCAGAAA | 2209 | TTTCTGCTAGGGGGTGGAAG | 3978 |
| 13125 | 13147 | CCACCCCCTAGCAGAAAATAGCC | 2210 | GGCTATTTTCTGCTAGGGGG | 3979 |
| 13128 | 13150 | CCCCCTAGCAGAAAATAGCCCAC | 2211 | GTGGGCTATTTTCTGCTAGG | 3980 |
| 13129 | 13151 | CCCCTAGCAGAAAATAGCCCACT | 2212 | AGTGGGCTATTTTCTGCTAG | 3981 |
| 13130 | 13152 | CCCTAGCAGAAAATAGCCCACTA | 2213 | TAGTGGGCTATTTTCTGCTA | 3982 |
| 13131 | 13153 | CCTAGCAGAAAATAGCCCACTAA | 2214 | TTAGTGGGCTATTTTCTGCT | 3983 |
| 13146 | 13168 | CCCACTAATCCAAACTCTAACAC | 2215 | GTGTTAGAGTTTGGATTAGT | 3984 |
| 13147 | 13169 | CCACTAATCCAAACTCTAACACT | 2216 | AGTGTTAGAGTTTGGATTAG | 3985 |
| 13155 | 13177 | CCAAACTCTAACACTATGCTTAG | 2217 | CTAAGCATAGTGTTAGAGTT | 3986 |
| 13187 | 13209 | CCACTCTGTTCGCAGCAGTCTGC | 2218 | GCAGACTGCTGCGAACAGAG | 3987 |
| 13211 | 13233 | CCCTTACACAAAATGACATCAAA | 2219 | TTTGATGTCATTTTGTGTAA | 3988 |
| 13212 | 13234 | CCTTACACAAAATGACATCAAAA | 2220 | TTTTGATGTCATTTTGTGTA | 3989 |
| 13244 | 13266 | CCTTCTCCACTTCAAGTCAACTA | 2221 | TAGTTGACTTGAAGTGGAGA | 3990 |
| 13250 | 13272 | CCACTTCAAGTCAACTAGGACTC | 2222 | GAGTCCTAGTTGACTTGAAG | 3991 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 13296 | 13318 | CCAACCACACCTAGCATTCCTGC | 2223 | GCAGGAATGCTAGGTGTGGT | 3992 |
| 13300 | 13322 | CCACACCTAGCATTCCTGCACAT | 2224 | ATGTGCAGGAATGCTAGGTG | 3993 |
| 13305 | 13327 | CCTAGCATTCCTGCACATCTGTA | 2225 | TACAGATGTGCAGGAATGCT | 3994 |
| 13314 | 13336 | CCTGCACATCTGTACCCACGCCT | 2226 | AGGCGTGGGTACAGATGTGC | 3995 |
| 13328 | 13350 | CCCACGCCTTCTTCAAAGCCATA | 2227 | TATGGCTTTGAAGAAGGCGT | 3996 |
| 13329 | 13351 | CCACGCCTTCTTCAAAGCCATAC | 2228 | GTATGGCTTTGAAGAAGGCG | 3997 |
| 13334 | 13356 | CCTTCTTCAAAGCCATACTATTT | 2229 | AAATAGTATGGCTTTGAAGA | 3998 |
| 13346 | 13368 | CCATACTATTTATGTGCTCCGGG | 2230 | CCCGGAGCACATAAATAGTA | 3999 |
| 13364 | 13386 | CCGGGTCCATCATCCACAACCTT | 2231 | AAGGTTGTGGATGATGGACC | 4000 |
| 13370 | 13392 | CCATCATCCACAACCTTAACAAT | 2232 | ATTGTTAAGGTTGTGGATGA | 4001 |
| 13377 | 13399 | CCACAACCTTAACAATGAACAAG | 2233 | CTTGTTCATTGTTAAGGTTG | 4002 |
| 13383 | 13405 | CCTTAACAATGAACAAGATATTC | 2234 | GAATATCTTGTTCATTGTTA | 4003 |
| 13430 | 13452 | CCATACCTCTCACTTCAACCTCC | 2235 | GGAGGTTGAAGTGAGAGGTA | 4004 |
| 13435 | 13457 | CCTCTCACTTCAACCTCCCTCAC | 2236 | GTGAGGGAGGTTGAAGTGAG | 4005 |
| 13448 | 13470 | CCTCCCTCACCATTGGCAGCCTA | 2237 | TAGGCTGCCAATGGTGAGGG | 4006 |
| 13451 | 13473 | CCCTCACCATTGGCAGCCTAGCA | 2238 | TGCTAGGCTGCCAATGGTGA | 4007 |
| 13452 | 13474 | CCTCACCATTGGCAGCCTAGCAT | 2239 | ATGCTAGGCTGCCAATGGTG | 4008 |
| 13457 | 13479 | CCATTGGCAGCCTAGCATTAGCA | 2240 | TGCTAATGCTAGGCTGCCAA | 4009 |
| 13467 | 13489 | CCTAGCATTAGCAGGAATACCTT | 2241 | AAGGTATTCCTGCTAATGCT | 4010 |
| 13486 | 13508 | CCTTTCCTCACAGGTTTCTACTC | 2242 | GAGTAGAAACCTGTGAGGAA | 4011 |
| 13491 | 13513 | CCTCACAGGTTTCTACTCCAAAG | 2243 | CTTTGGAGTAGAAACCTGTG | 4012 |
| 13508 | 13530 | CCAAAGACCACATCATCGAAACC | 2244 | GGTTTCGATGATGTGGTCTT | 4013 |
| 13515 | 13537 | CCACATCATCGAAACCGCAAACA | 2245 | TGTTTGCGGTTTCGATGATG | 4014 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 13529 | 13551 | CCGCAAACATATCATACACAAAC | 2246 | GTTTGTGTATGATATGTTTG | 4015 |
| 13553 | 13575 | CCTGAGCCCTATCTATTACTCTC | 2247 | GAGAGTAATAGATAGGGCTC | 4016 |
| 13559 | 13581 | CCCTATCTATTACTCTCATCGCT | 2248 | AGCGATGAGAGTAATAGATA | 4017 |
| 13560 | 13582 | CCTATCTATTACTCTCATCGCTA | 2249 | TAGCGATGAGAGTAATAGAT | 4018 |
| 13583 | 13605 | CCTCCCTGACAAGCGCCTATAGC | 2250 | GCTATAGGCGCTTGTCAGGG | 4019 |
| 13586 | 13608 | CCCTGACAAGCGCCTATAGCACT | 2251 | AGTGCTATAGGCGCTTGTCA | 4020 |
| 13587 | 13609 | CCTGACAAGCGCCTATAGCACTC | 2252 | GAGTGCTATAGGCGCTTGTC | 4021 |
| 13598 | 13620 | CCTATAGCACTCGAATAATTCTT | 2253 | AAGAATTATTCGAGTGCTAT | 4022 |
| 13625 | 13647 | CCCTAACAGGTCAACCTCGCTTC | 2254 | GAAGCGAGGTTGACCTGTTA | 4023 |
| 13626 | 13648 | CCTAACAGGTCAACCTCGCTTCC | 2255 | GGAAGCGAGGTTGACCTGTT | 4024 |
| 13639 | 13661 | CCTCGCTTCCCCACCCTTACTAA | 2256 | TTAGTAAGGGTGGGGAAGCG | 4025 |
| 13647 | 13669 | CCCCACCCTTACTAACATTAACG | 2257 | CGTTAATGTTAGTAAGGGTG | 4026 |
| 13648 | 13670 | CCCACCCTTACTAACATTAACGA | 2258 | TCGTTAATGTTAGTAAGGGT | 4027 |
| 13649 | 13671 | CCACCCTTACTAACATTAACGAA | 2259 | TTCGTTAATGTTAGTAAGGG | 4028 |
| 13652 | 13674 | CCCTTACTAACATTAACGAAAAT | 2260 | ATTTTCGTTAATGTTAGTAA | 4029 |
| 13653 | 13675 | CCTTACTAACATTAACGAAAATA | 2261 | TATTTTCGTTAATGTTAGTA | 4030 |
| 13677 | 13699 | CCCCACCCTACTAAACCCCATTA | 2262 | TAATGGGGTTTAGTAGGGTG | 4031 |
| 13678 | 13700 | CCCACCCTACTAAACCCCATTAA | 2263 | TTAATGGGGTTTAGTAGGGT | 4032 |
| 13679 | 13701 | CCACCCTACTAAACCCCATTAAA | 2264 | TTTAATGGGGTTTAGTAGGG | 4033 |
| 13682 | 13704 | CCCTACTAAACCCCATTAAACGC | 2265 | GCGTTTAATGGGGTTTAGTA | 4034 |
| 13683 | 13705 | CCTACTAAACCCCATTAAACGCC | 2266 | GGCGTTTAATGGGGTTTAGT | 4035 |
| 13692 | 13714 | CCCCATTAAACGCCTGGCAGCCG | 2267 | CGGCTGCCAGGCGTTTAATG | 4036 |
| 13693 | 13715 | CCCATTAAACGCCTGGCAGCCGG | 2268 | CCGGCTGCCAGGCGTTTAAT | 4037 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 13694 | 13716 | CCATTAAACGCCTGGCAGCCGGA | 2269 | TCCGGCTGCCAGGCGTTTAA | 4038 |
| 13704 | 13726 | CCTGGCAGCCGGAAGCCTATTCG | 2270 | CGAATAGGCTTCCGGCTGCC | 4039 |
| 13712 | 13734 | CCGGAAGCCTATTCGCAGGATTT | 2271 | AAATCCTGCGAATAGGCTTC | 4040 |
| 13719 | 13741 | CCTATTCGCAGGATTTCTCATTA | 2272 | TAATGAGAAATCCTGCGAAT | 4041 |
| 13754 | 13776 | CCCCCGCATCCCCCTTCCAAACA | 2273 | TGTTTGGAAGGGGGATGCGG | 4042 |
| 13755 | 13777 | CCCCGCATCCCCCTTCCAAACAA | 2274 | TTGTTTGGAAGGGGGATGCG | 4043 |
| 13756 | 13778 | CCCGCATCCCCCTTCCAAACAAC | 2275 | GTTGTTTGGAAGGGGGATGC | 4044 |
| 13757 | 13779 | CCGCATCCCCCTTCCAAACAACA | 2276 | TGTTGTTTGGAAGGGGGATG | 4045 |
| 13763 | 13785 | CCCCCTTCCAAACAACAATCCCC | 2277 | GGGGATTGTTGTTTGGAAGG | 4046 |
| 13764 | 13786 | CCCCTTCCAAACAACAATCCCCC | 2278 | GGGGGATTGTTGTTTGGAAG | 4047 |
| 13765 | 13787 | CCCTTCCAAACAACAATCCCCCT | 2279 | AGGGGGATTGTTGTTTGGAA | 4048 |
| 13766 | 13788 | CCTTCCAAACAACAATCCCCCTC | 2280 | GAGGGGGATTGTTGTTTGGA | 4049 |
| 13770 | 13792 | CCAAACAACAATCCCCCTCTACC | 2281 | GGTAGAGGGGGATTGTTGTT | 4050 |
| 13782 | 13804 | CCCCCTCTACCTAAAACTCACAG | 2282 | CTGTGAGTTTTAGGTAGAGG | 4051 |
| 13783 | 13805 | CCCCTCTACCTAAAACTCACAGC | 2283 | GCTGTGAGTTTTAGGTAGAG | 4052 |
| 13784 | 13806 | CCCTCTACCTAAAACTCACAGCC | 2284 | GGCTGTGAGTTTTAGGTAGA | 4053 |
| 13785 | 13807 | CCTCTACCTAAAACTCACAGCCC | 2285 | GGGCTGTGAGTTTTAGGTAG | 4054 |
| 13791 | 13813 | CCTAAAACTCACAGCCCTCGCTG | 2286 | CAGCGAGGGCTGTGAGTTTT | 4055 |
| 13805 | 13827 | CCCTCGCTGTCACTTTCCTAGGA | 2287 | TCCTAGGAAAGTGACAGCGA | 4056 |
| 13806 | 13828 | CCTCGCTGTCACTTTCCTAGGAC | 2288 | GTCCTAGGAAAGTGACAGCG | 4057 |
| 13821 | 13843 | CCTAGGACTTCTAACAGCCCTAG | 2289 | CTAGGGCTGTTAGAAGTCCT | 4058 |
| 13838 | 13860 | CCCTAGACCTCAACTACCTAACC | 2290 | GGTTAGGTAGTTGAGGTCTA | 4059 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 13839 | 13861 | CCTAGACCTCAACTACCTAACCA | 2291 | TGGTTAGGTAGTTGAGGTCT | 4060 |
| 13845 | 13867 | CCTCAACTACCTAACCAACAAAC | 2292 | GTTTGTTGGTTAGGTAGTTG | 4061 |
| 13854 | 13876 | CCTAACCAACAAACTTAAAATAA | 2293 | TTATTTTAAGTTTGTTGGTT | 4062 |
| 13859 | 13881 | CCAACAAACTTAAAATAAAATCC | 2294 | GGATTTTATTTTAAGTTTGT | 4063 |
| 13880 | 13902 | CCCCACTATGCACATTTTATTTC | 2295 | GAAATAAAATGTGCATAGTG | 4064 |
| 13881 | 13903 | CCCACTATGCACATTTTATTTCT | 2296 | AGAAATAAAATGTGCATAGT | 4065 |
| 13882 | 13904 | CCACTATGCACATTTTATTTCTC | 2297 | GAGAAATAAAATGTGCATAG | 4066 |
| 13904 | 13926 | CCAACATACTCGGATTCTACCCT | 2298 | AGGGTAGAATCCGAGTATGT | 4067 |
| 13923 | 13945 | CCCTAGCATCACACACCGCACAA | 2299 | TTGTGCGGTGTGTGATGCTA | 4068 |
| 13924 | 13946 | CCTAGCATCACACACCGCACAAT | 2300 | ATTGTGCGGTGTGTGATGCT | 4069 |
| 13938 | 13960 | CCGCACAATCCCCTATCTAGGCC | 2301 | GGCCTAGATAGGGGATTGTG | 4070 |
| 13947 | 13969 | CCCCTATCTAGGCCTTCTTACGA | 2302 | TCGTAAGAAGGCCTAGATAG | 4071 |
| 13948 | 13970 | CCCTATCTAGGCCTTCTTACGAG | 2303 | CTCGTAAGAAGGCCTAGATA | 4072 |
| 13949 | 13971 | CCTATCTAGGCCTTCTTACGAGC | 2304 | GCTCGTAAGAAGGCCTAGAT | 4073 |
| 13959 | 13981 | CCTTCTTACGAGCCAAAACCTGC | 2305 | GCAGGTTTTGGCTCGTAAGA | 4074 |
| 13971 | 13993 | CCAAAACCTGCCCCTACTCCTCC | 2306 | GGAGGAGTAGGGGCAGGTTT | 4075 |
| 13977 | 13999 | CCTGCCCCTACTCCTCCTAGACC | 2307 | GGTCTAGGAGGAGTAGGGGC | 4076 |
| 13981 | 14003 | CCCCTACTCCTCCTAGACCTAAC | 2308 | GTTAGGTCTAGGAGGAGTAG | 4077 |
| 13982 | 14004 | CCCTACTCCTCCTAGACCTAACC | 2309 | GGTTAGGTCTAGGAGGAGTA | 4078 |
| 13983 | 14005 | CCTACTCCTCCTAGACCTAACCT | 2310 | AGGTTAGGTCTAGGAGGAGT | 4079 |
| 13989 | 14011 | CCTCCTAGACCTAACCTGACTAG | 2311 | CTAGTCAGGTTAGGTCTAGG | 4080 |
| 13992 | 14014 | CCTAGACCTAACCTGACTAGAAA | 2312 | TTTCTAGTCAGGTTAGGTCT | 4081 |
| 13998 | 14020 | CCTAACCTGACTAGAAAAGCTAT | 2313 | ATAGCTTTTCTAGTCAGGTT | 4082 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 14003 | 14025 | CCTGACTAGAAAAGCTATTACCT | 2314 | AGGTAATAGCTTTTCTAGTC | 4083 |
| 14023 | 14045 | CCTAAAACAATTTCACAGCACCA | 2315 | TGGTGCTGTGAAATTGTTTT | 4084 |
| 14043 | 14065 | CCAAATCTCCACCTCCATCATCA | 2316 | TGATGATGGAGGTGGAGATT | 4085 |
| 14051 | 14073 | CCACCTCCATCATCACCTCAACC | 2317 | GGTTGAGGTGATGATGGAGG | 4086 |
| 14054 | 14076 | CCTCCATCATCACCTCAACCCAA | 2318 | TTGGGTTGAGGTGATGATGG | 4087 |
| 14057 | 14079 | CCATCATCACCTCAACCCAAAAA | 2319 | TTTTTGGGTTGAGGTGATGA | 4088 |
| 14066 | 14088 | CCTCAACCCAAAAGGCATAATT | 2320 | AATTATGCCTTTTTGGGTTG | 4089 |
| 14072 | 14094 | CCCAAAAGGCATAATTAAACTT | 2321 | AAGTTTAATTATGCCTTTTT | 4090 |
| 14073 | 14095 | CCAAAAGGCATAATTAAACTTT | 2322 | AAAGTTTAATTATGCCTTTT | 4091 |
| 14100 | 14122 | CCTCTCTTTCTTCTTCCCACTCA | 2323 | TGAGTGGGAAGAAGAAAGAG | 4092 |
| 14115 | 14137 | CCCACTCATCCTAACCCTACTCC | 2324 | GGAGTAGGGTTAGGATGAGT | 4093 |
| 14116 | 14138 | CCACTCATCCTAACCCTACTCCT | 2325 | AGGAGTAGGGTTAGGATGAG | 4094 |
| 14124 | 14146 | CCTAACCCTACTCCTAATCACAT | 2326 | ATGTGATTAGGAGTAGGGTT | 4095 |
| 14129 | 14151 | CCCTACTCCTAATCACATAACCT | 2327 | AGGTTATGTGATTAGGAGTA | 4096 |
| 14130 | 14152 | CCTACTCCTAATCACATAACCTA | 2328 | TAGGTTATGTGATTAGGAGT | 4097 |
| 14136 | 14158 | CCTAATCACATAACCTATTCCCC | 2329 | GGGGAATAGGTTATGTGATT | 4098 |
| 14149 | 14171 | CCTATTCCCCCGAGCAATCTCAA | 2330 | TTGAGATTGCTCGGGGGAAT | 4099 |
| 14155 | 14177 | CCCCCGAGCAATCTCAATTACAA | 2331 | TTGTAATTGAGATTGCTCGG | 4100 |
| 14156 | 14178 | CCCCGAGCAATCTCAATTACAAT | 2332 | ATTGTAATTGAGATTGCTCG | 4101 |
| 14157 | 14179 | CCCGAGCAATCTCAATTACAATA | 2333 | TATTGTAATTGAGATTGCTC | 4102 |
| 14158 | 14180 | CCGAGCAATCTCAATTACAATAT | 2334 | ATATTGTAATTGAGATTGCT | 4103 |
| 14186 | 14208 | CCAACAAACAATGTTCAACCAGT | 2335 | ACTGGTTGAACATTGTTTGT | 4104 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 14204 | 14226 | CCAGTAACTACTACTAATCAACG | 2336 | CGTTGATTAGTAGTAGTTAC | 4105 |
| 14227 | 14249 | CCCATAATCATACAAAGCCCCCG | 2337 | CGGGGGCTTTGTATGATTAT | 4106 |
| 14228 | 14250 | CCATAATCATACAAAGCCCCGC | 2338 | GCGGGGCTTTGTATGATTA | 4107 |
| 14244 | 14266 | CCCCCGCACCAATAGGATCCTCC | 2339 | GGAGGATCCTATTGGTGCGG | 4108 |
| 14245 | 14267 | CCCCGCACCAATAGGATCCTCCC | 2340 | GGGAGGATCCTATTGGTGCG | 4109 |
| 14246 | 14268 | CCCGCACCAATAGGATCCTCCCG | 2341 | CGGGAGGATCCTATTGGTGC | 4110 |
| 14247 | 14269 | CCGCACCAATAGGATCCTCCCGA | 2342 | TCGGGAGGATCCTATTGGTG | 4111 |
| 14252 | 14274 | CCAATAGGATCCTCCCGAATCAA | 2343 | TTGATTCGGGAGGATCCTAT | 4112 |
| 14262 | 14284 | CCTCCCGAATCAACCCTGACCCC | 2344 | GGGGTCAGGGTTGATTCGGG | 4113 |
| 14265 | 14287 | CCCGAATCAACCCTGACCCCTCT | 2345 | AGAGGGGTCAGGGTTGATTC | 4114 |
| 14266 | 14288 | CCGAATCAACCCTGACCCCTCTC | 2346 | GAGAGGGGTCAGGGTTGATT | 4115 |
| 14275 | 14297 | CCCTGACCCCTCTCCTTCATAAA | 2347 | TTTATGAAGGAGAGGGGTCA | 4116 |
| 14276 | 14298 | CCTGACCCCTCTCCTTCATAAAT | 2348 | ATTTATGAAGGAGAGGGGTC | 4117 |
| 14281 | 14303 | CCCCTCTCCTTCATAAATTATTC | 2349 | GAATAATTTATGAAGGAGAG | 4118 |
| 14282 | 14304 | CCCTCTCCTTCATAAATTATTCA | 2350 | TGAATAATTTATGAAGGAGA | 4119 |
| 14283 | 14305 | CCTCTCCTTCATAAATTATTCAG | 2351 | CTGAATAATTTATGAAGGAG | 4120 |
| 14288 | 14310 | CCTTCATAAATTATTCAGCTTCC | 2352 | GGAAGCTGAATAATTTATGA | 4121 |
| 14309 | 14331 | CCTACACTATTAAAGTTTACCAC | 2353 | GTGGTAAACTTTAATAGTGT | 4122 |
| 14328 | 14350 | CCACAACCACCACCCCATCATAC | 2354 | GTATGATGGGTGGTGGTTG | 4123 |
| 14334 | 14356 | CCACCACCCCATCATACTCTTTC | 2355 | GAAAGAGTATGATGGGGTGG | 4124 |
| 14337 | 14359 | CCACCCCATCATACTCTTTCACC | 2356 | GGTGAAAGAGTATGATGGGG | 4125 |
| 14340 | 14362 | CCCCATCATACTCTTTCACCCAC | 2357 | GTGGGTGAAAGAGTATGATG | 4126 |
| 14341 | 14363 | CCCATCATACTCTTTCACCCACA | 2358 | TGTGGGTGAAAGAGTATGAT | 4127 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 14342 | 14364 | CCATCATACTCTTTCACCCACAG | 2359 | CTGTGGGTGAAAGAGTATGA | 4128 |
| 14358 | 14380 | CCCACAGCACCAATCCTACCTCC | 2360 | GGAGGTAGGATTGGTGCTGT | 4129 |
| 14359 | 14381 | CCACAGCACCAATCCTACCTCCA | 2361 | TGGAGGTAGGATTGGTGCTG | 4130 |
| 14367 | 14389 | CCAATCCTACCTCCATCGCTAAC | 2362 | GTTAGCGATGGAGGTAGGAT | 4131 |
| 14372 | 14394 | CCTACCTCCATCGCTAACCCCAC | 2363 | GTGGGGTTAGCGATGGAGGT | 4132 |
| 14376 | 14398 | CCTCCATCGCTAACCCCACTAAA | 2364 | TTTAGTGGGGTTAGCGATGG | 4133 |
| 14379 | 14401 | CCATCGCTAACCCCACTAAAACA | 2365 | TGTTTTAGTGGGGTTAGCGA | 4134 |
| 14389 | 14411 | CCCCACTAAAACACTCACCAAGA | 2366 | TCTTGGTGAGTGTTTTAGTG | 4135 |
| 14390 | 14412 | CCCACTAAAACACTCACCAAGAC | 2367 | GTCTTGGTGAGTGTTTTAGT | 4136 |
| 14391 | 14413 | CCACTAAAACACTCACCAAGACC | 2368 | GGTCTTGGTGAGTGTTTTAG | 4137 |
| 14406 | 14428 | CCAAGACCTCAACCCCTGACCCC | 2369 | GGGGTCAGGGGTTGAGGTCT | 4138 |
| 14412 | 14434 | CCTCAACCCCTGACCCCCATGCC | 2370 | GGCATGGGGGTCAGGGGTTG | 4139 |
| 14418 | 14440 | CCCCTGACCCCCATGCCTCAGGA | 2371 | TCCTGAGGCATGGGGGTCAG | 4140 |
| 14419 | 14441 | CCCTGACCCCCATGCCTCAGGAT | 2372 | ATCCTGAGGCATGGGGGTCA | 4141 |
| 14420 | 14442 | CCTGACCCCCATGCCTCAGGATA | 2373 | TATCCTGAGGCATGGGGGTC | 4142 |
| 14425 | 14447 | CCCCCATGCCTCAGGATACTCCT | 2374 | AGGAGTATCCTGAGGCATGG | 4143 |
| 14426 | 14448 | CCCCATGCCTCAGGATACTCCTC | 2375 | GAGGAGTATCCTGAGGCATG | 4144 |
| 14427 | 14449 | CCCATGCCTCAGGATACTCCTCA | 2376 | TGAGGAGTATCCTGAGGCAT | 4145 |
| 14428 | 14450 | CCATGCCTCAGGATACTCCTCAA | 2377 | TTGAGGAGTATCCTGAGGCA | 4146 |
| 14433 | 14455 | CCTCAGGATACTCCTCAATAGCC | 2378 | GGCTATTGAGGAGTATCCTG | 4147 |
| 14445 | 14467 | CCTCAATAGCCATCGCTGTAGTA | 2379 | TACTACAGCGATGGCTATTG | 4148 |
| 14454 | 14476 | CCATCGCTGTAGTATATCCAAAG | 2380 | CTTTGGATATACTACAGCGA | 4149 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 14471 | 14493 | CCAAAGACAACCATCATTCCCCC | 2381 | GGGGGAATGATGGTTGTCTT | 4150 |
| 14481 | 14503 | CCATCATTCCCCCTAAATAAATT | 2382 | AATTTATTTAGGGGGAATGA | 4151 |
| 14489 | 14511 | CCCCCTAAATAAATTAAAAAAC | 2383 | GTTTTTTTAATTTATTTAGG | 4152 |
| 14490 | 14512 | CCCCTAAATAAATTAAAAAACT | 2384 | AGTTTTTTTAATTTATTTAG | 4153 |
| 14491 | 14513 | CCCTAAATAAATTAAAAAACTA | 2385 | TAGTTTTTTTAATTTATTTA | 4154 |
| 14492 | 14514 | CCTAAATAAATTAAAAAACTAT | 2386 | ATAGTTTTTTTAATTTATTT | 4155 |
| 14519 | 14541 | CCCATATAACCTCCCCCAAAATT | 2387 | AATTTTGGGGGAGGTTATAT | 4156 |
| 14520 | 14542 | CCATATAACCTCCCCCAAAATTC | 2388 | GAATTTTGGGGGAGGTTATA | 4157 |
| 14528 | 14550 | CCTCCCCCAAAATTCAGAATAAT | 2389 | ATTATTCTGAATTTTGGGG | 4158 |
| 14531 | 14553 | CCCCCAAAATTCAGAATAATAAC | 2390 | GTTATTATTCTGAATTTTGG | 4159 |
| 14532 | 14554 | CCCCAAAATTCAGAATAATAACA | 2391 | TGTTATTATTCTGAATTTTG | 4160 |
| 14533 | 14555 | CCCAAAATTCAGAATAATAACAC | 2392 | GTGTTATTATTCTGAATTTT | 4161 |
| 14534 | 14556 | CCAAAATTCAGAATAATAACACA | 2393 | TGTGTTATTATTCTGAATTT | 4162 |
| 14557 | 14579 | CCCGACCACACCGCTAACAATCA | 2394 | TGATTGTTAGCGGTGTGGTC | 4163 |
| 14558 | 14580 | CCGACCACACCGCTAACAATCAA | 2395 | TTGATTGTTAGCGGTGTGGT | 4164 |
| 14562 | 14584 | CCACACCGCTAACAATCAATACT | 2396 | AGTATTGATTGTTAGCGGTG | 4165 |
| 14567 | 14589 | CCGCTAACAATCAATACTAAACC | 2397 | GGTTTAGTATTGATTGTTAG | 4166 |
| 14588 | 14610 | CCCCCATAAATAGGAGAAGGCTT | 2398 | AAGCCTTCTCCTATTTATGG | 4167 |
| 14589 | 14611 | CCCCATAAATAGGAGAAGGCTTA | 2399 | TAAGCCTTCTCCTATTTATG | 4168 |
| 14590 | 14612 | CCCATAAATAGGAGAAGGCTTAG | 2400 | CTAAGCCTTCTCCTATTTAT | 4169 |
| 14591 | 14613 | CCATAAATAGGAGAAGGCTTAGA | 2401 | TCTAAGCCTTCTCCTATTTA | 4170 |
| 14620 | 14642 | CCCCACAAACCCCATTACTAAAC | 2402 | GTTTAGTAATGGGGTTTGTG | 4171 |
| 14621 | 14643 | CCCACAAACCCCATTACTAAACC | 2403 | GGTTTAGTAATGGGGTTTGT | 4172 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 14622 | 14644 | CCACAAACCCCATTACTAAACCC | 2404 | GGGTTTAGTAATGGGGTTTG | 4173 |
| 14629 | 14651 | CCCCATTACTAAACCCACACTCA | 2405 | TGAGTGTGGGTTTAGTAATG | 4174 |
| 14630 | 14652 | CCCATTACTAAACCCACACTCAA | 2406 | TTGAGTGTGGGTTTAGTAAT | 4175 |
| 14631 | 14653 | CCATTACTAAACCCACACTCAAC | 2407 | GTTGAGTGTGGGTTTAGTAA | 4176 |
| 14642 | 14664 | CCCACACTCAACAGAAACAAAGC | 2408 | GCTTTGTTTCTGTTGAGTGT | 4177 |
| 14643 | 14665 | CCACACTCAACAGAAACAAAGCA | 2409 | TGCTTTGTTTCTGTTGAGTG | 4178 |
| 14694 | 14716 | CCACGACCAATGATATGAAAAAC | 2410 | GTTTTTCATATCATTGGTCG | 4179 |
| 14700 | 14722 | CCAATGATATGAAAAACCATCGT | 2411 | ACGATGGTTTTTCATATCAT | 4180 |
| 14716 | 14738 | CCATCGTTGTATTTCAACTACAA | 2412 | TTGTAGTTGAAATACAACGA | 4181 |
| 14744 | 14766 | CCAATGACCCCAATACGCAAAAC | 2413 | GTTTTGCGTATTGGGGTCAT | 4182 |
| 14751 | 14773 | CCCCAATACGCAAAACTAACCCC | 2414 | GGGGTTAGTTTTGCGTATTG | 4183 |
| 14752 | 14774 | CCCAATACGCAAAACTAACCCCC | 2415 | GGGGGTTAGTTTTGCGTATT | 4184 |
| 14753 | 14775 | CCAATACGCAAAACTAACCCCCT | 2416 | AGGGGGTTAGTTTTGCGTAT | 4185 |
| 14770 | 14792 | CCCCTAATAAAATTAATTAACC | 2417 | GGTTAATTAATTTTATTAGG | 4186 |
| 14771 | 14793 | CCCTAATAAAATTAATTAACCA | 2418 | TGGTTAATTAATTTTATTAG | 4187 |
| 14772 | 14794 | CCCTAATAAAATTAATTAACCAC | 2419 | GTGGTTAATTAATTTTATTA | 4188 |
| 14773 | 14795 | CCTAATAAAATTAATTAACCACT | 2420 | AGTGGTTAATTAATTTTATT | 4189 |
| 14791 | 14813 | CCACTCATTCATCGACCTCCCCA | 2421 | TGGGGAGGTCGATGAATGAG | 4190 |
| 14806 | 14828 | CCTCCCCACCCCATCCAACATCT | 2422 | AGATGTTGGATGGGGTGGGG | 4191 |
| 14809 | 14831 | CCCCACCCCATCCAACATCTCCG | 2423 | CGGAGATGTTGGATGGGGTG | 4192 |
| 14810 | 14832 | CCCACCCCATCCAACATCTCCGC | 2424 | GCGGAGATGTTGGATGGGGT | 4193 |
| 14811 | 14833 | CCACCCCATCCAACATCTCCGCA | 2425 | TGCGGAGATGTTGGATGGGG | 4194 |
| 14814 | 14836 | CCCCATCCAACATCTCCGCATGA | 2426 | TCATGCGGAGATGTTGGATG | 4195 |

TABLE 4-continued gRNA target sequence for human mtDNA carrying NGG sequence on the (−) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 14815 | 14837 | CCCATCCAACATCTCCGCATGAT | 2427 | ATCATGCGGAGATGTTGGAT | 4196 |
| 14816 | 14838 | CCATCCAACATCTCCGCATGATG | 2428 | CATCATGCGGAGATGTTGGA | 4197 |
| 14820 | 14842 | CCAACATCTCCGCATGATGAAAC | 2429 | GTTTCATCATGCGGAGATGT | 4198 |
| 14829 | 14851 | CCGCATGATGAAACTTCGGCTCA | 2430 | TGAGCCGAAGTTTCATCATG | 4199 |
| 14854 | 14876 | CCTTGGCGCCTGCCTGATCCTCC | 2431 | GGAGGATCAGGCAGGCGCCA | 4200 |
| 14862 | 14884 | CCTGCCTGATCCTCCAAATCACC | 2432 | GGTGATTTGGAGGATCAGGC | 4201 |
| 14866 | 14888 | CCTGATCCTCCAAATCACCACAG | 2433 | CTGTGGTGATTTGGAGGATC | 4202 |
| 14872 | 14894 | CCTCCAAATCACCACAGGACTAT | 2434 | ATAGTCCTGTGGTGATTTGG | 4203 |
| 14875 | 14897 | CCAAATCACCACAGGACTATTCC | 2435 | GGAATAGTCCTGTGGTGATT | 4204 |
| 14883 | 14905 | CCACAGGACTATTCCTAGCCATG | 2436 | CATGGCTAGGAATAGTCCTG | 4205 |
| 14896 | 14918 | CCTAGCCATGCACTACTCACCAG | 2437 | CTGGTGAGTAGTGCATGGCT | 4206 |
| 14901 | 14923 | CCATGCACTACTCACCAGACGCC | 2438 | GGCGTCTGGTGAGTAGTGCA | 4207 |
| 14915 | 14937 | CCAGACGCCTCAACCGCCTTTTC | 2439 | GAAAAGGCGGTTGAGGCGTC | 4208 |
| 14922 | 14944 | CCTCAACCGCCTTTTCATCAATC | 2440 | GATTGATGAAAAGGCGGTTG | 4209 |
| 14928 | 14950 | CCGCCTTTTCATCAATCGCCCAC | 2441 | GTGGGCGATTGATGAAAAGG | 4210 |
| 14931 | 14953 | CCTTTTCATCAATCGCCCACATC | 2442 | GATGTGGGCGATTGATGAAA | 4211 |
| 14946 | 14968 | CCCACATCACTCGAGACGTAAAT | 2443 | ATTTACGTCTCGAGTGATGT | 4212 |
| 14947 | 14969 | CCACATCACTCGAGACGTAAATT | 2444 | AATTTACGTCTCGAGTGATG | 4213 |
| 14983 | 15005 | CCGCTACCTTCACGCCAATGGCG | 2445 | CGCCATTGGCGTGAAGGTAG | 4214 |
| 14989 | 15011 | CCTTCACGCCAATGGCGCCTCAA | 2446 | TTGAGGCGCCATTGGCGTGA | 4215 |
| 14997 | 15019 | CCAATGGCGCCTCAATATTCTTT | 2447 | AAAGAATATTGAGGCGCCAT | 4216 |
| 15006 | 15028 | CCTCAATATTCTTTATCTGCCTC | 2448 | GAGGCAGATAAAGAATATTG | 4217 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 15025 | 15047 | CCTCTTCCTACACATCGGGCGAG | 2449 | CTCGCCCGATGTGTAGGAAG | 4218 |
| 15031 | 15053 | CCTACACATCGGGCGAGGCCTAT | 2450 | ATAGGCCTCGCCCGATGTGT | 4219 |
| 15049 | 15071 | CCTATATTACGGATCATTTCTCT | 2451 | AGAGAAATGATCCGTAATAT | 4220 |
| 15081 | 15103 | CCTGAAACATCGGCATTATCCTC | 2452 | GAGGATAATGCCGATGTTTC | 4221 |
| 15100 | 15122 | CCTCCTGCTTGCAACTATAGCAA | 2453 | TTGCTATAGTTGCAAGCAGG | 4222 |
| 15103 | 15125 | CCTGCTTGCAACTATAGCAACAG | 2454 | CTGTTGCTATAGTTGCAAGC | 4223 |
| 15126 | 15148 | CCTTCATAGGCTATGTCCTCCCG | 2455 | CGGGAGGACATAGCCTATGA | 4224 |
| 15142 | 15164 | CCTCCCGTGAGGCCAAATATCAT | 2456 | ATGATATTTGGCCTCACGGG | 4225 |
| 15145 | 15167 | CCCGTGAGGCCAAATATCATTCT | 2457 | AGAATGATATTTGGCCTCAC | 4226 |
| 15146 | 15168 | CCGTGAGGCCAAATATCATTCTG | 2458 | CAGAATGATATTTGGCCTCA | 4227 |
| 15154 | 15176 | CCAAATATCATTCTGAGGGGCCA | 2459 | TGGCCCCTCAGAATGATATT | 4228 |
| 15174 | 15196 | CCACAGTAATTACAAACTTACTA | 2460 | TAGTAAGTTTGTAATTACTG | 4229 |
| 15198 | 15220 | CCGCCATCCCATACATTGGGACA | 2461 | TGTCCCAATGTATGGGATGG | 4230 |
| 15201 | 15223 | CCATCCCATACATTGGGACAGAC | 2462 | GTCTGTCCCAATGTATGGGA | 4231 |
| 15205 | 15227 | CCCATACATTGGGACAGACCTAG | 2463 | CTAGGTCTGTCCCAATGTAT | 4232 |
| 15206 | 15228 | CCATACATTGGGACAGACCTAGT | 2464 | ACTAGGTCTGTCCCAATGTA | 4233 |
| 15223 | 15245 | CCTAGTTCAATGAATCTGAGGAG | 2465 | CTCCTCAGATTCATTGAACT | 4234 |
| 15263 | 15285 | CCCACCCTCACACGATTCTTTAC | 2466 | GTAAAGAATCGTGTGAGGGT | 4235 |
| 15264 | 15286 | CCACCCTCACACGATTCTTTACC | 2467 | GGTAAAGAATCGTGTGAGGG | 4236 |
| 15267 | 15289 | CCCTCACACGATTCTTTACCTTT | 2468 | AAAGGTAAAGAATCGTGTGA | 4237 |
| 15268 | 15290 | CCTCACACGATTCTTTACCTTTC | 2469 | GAAAGGTAAAGAATCGTGTG | 4238 |
| 15285 | 15307 | CCTTTCACTTCATCTTGCCCTTC | 2470 | GAAGGGCAAGATGAAGTGAA | 4239 |
| 15302 | 15324 | CCCTTCATTATTGCAGCCCTAGC | 2471 | GCTAGGGCTGCAATAATGAA | 4240 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 15303 | 15325 | CCTTCATTATTGCAGCCCTAGCA | 2472 | TGCTAGGGCTGCAATAATGA | 4241 |
| 15318 | 15340 | CCCTAGCAACACTCCACCTCCTA | 2473 | TAGGAGGTGGAGTGTTGCTA | 4242 |
| 15319 | 15341 | CCTAGCAACACTCCACCTCCTAT | 2474 | ATAGGAGGTGGAGTGTTGCT | 4243 |
| 15331 | 15353 | CCACCTCCTATTCTTGCACGAAA | 2475 | TTTCGTGCAAGAATAGGAGG | 4244 |
| 15334 | 15356 | CCTCCTATTCTTGCACGAAACGG | 2476 | CCGTTTCGTGCAAGAATAGG | 4245 |
| 15337 | 15359 | CCTATTCTTGCACGAAACGGGAT | 2477 | ATCCCGTTTCGTGCAAGAAT | 4246 |
| 15367 | 15389 | CCCCCTAGGAATCACCTCCCATT | 2478 | AATGGGAGGTGATTCCTAGG | 4247 |
| 15368 | 15390 | CCCCTAGGAATCACCTCCCATTC | 2479 | GAATGGGAGGTGATTCCTAG | 4248 |
| 15369 | 15391 | CCCTAGGAATCACCTCCCATTCC | 2480 | GGAATGGGAGGTGATTCCTA | 4249 |
| 15370 | 15392 | CCTAGGAATCACCTCCCATTCCG | 2481 | CGGAATGGGAGGTGATTCCT | 4250 |
| 15381 | 15403 | CCTCCCATTCCGATAAAATCACC | 2482 | GGTGATTTTATCGGAATGGG | 4251 |
| 15384 | 15406 | CCCATTCCGATAAAATCACCTTC | 2483 | GAAGGTGATTTTATCGGAAT | 4252 |
| 15385 | 15407 | CCATTCCGATAAAATCACCTTCC | 2484 | GGAAGGTGATTTTATCGGAA | 4253 |
| 15390 | 15412 | CCGATAAAATCACCTTCCACCCT | 2485 | AGGGTGGAAGGTGATTTTAT | 4254 |
| 15402 | 15424 | CCTTCCACCCTTACTACACAATC | 2486 | GATTGTGTAGTAAGGGTGGA | 4255 |
| 15406 | 15428 | CCACCCTTACTACACAATCAAAG | 2487 | CTTTGATTGTGTAGTAAGGG | 4256 |
| 15409 | 15431 | CCCTTACTACACAATCAAAGACG | 2488 | CGTCTTTGATTGTGTAGTAA | 4257 |
| 15410 | 15432 | CCTTACTACACAATCAAAGACGC | 2489 | GCGTCTTTGATTGTGTAGTA | 4258 |
| 15432 | 15454 | CCCTCGGCTTACTTCTCTTCCTT | 2490 | AAGGAAGAGAAGTAAGCCGA | 4259 |
| 15433 | 15455 | CCTCGGCTTACTTCTCTTCCTTC | 2491 | GAAGGAAGAGAAGTAAGCCG | 4260 |
| 15451 | 15473 | CCTTCTCTCCTTAATGACATTAA | 2492 | TTAATGTCATTAAGGAGAGA | 4261 |
| 15459 | 15481 | CCTTAATGACATTAACCTATTC | 2493 | GAATAGTGTTAATGTCATTA | 4262 |
| 15485 | 15507 | CCAGACCTCCTAGGCGACCCAGA | 2494 | TCTGGGTCGCCTAGGAGGTC | 4263 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 15490 | 15512 | CCTCCTAGGCGACCCAGACAATT | 2495 | AATTGTCTGGGTCGCCTAGG | 4264 |
| 15493 | 15515 | CCTAGGCGACCCAGACAATTATA | 2496 | TATAATTGTCTGGGTCGCCT | 4265 |
| 15502 | 15524 | CCCAGACAATTATACCCTAGCCA | 2497 | TGGCTAGGGTATAATTGTCT | 4266 |
| 15503 | 15525 | CCAGACAATTATACCCTAGCCAA | 2498 | TTGGCTAGGGTATAATTGTC | 4267 |
| 15516 | 15538 | CCCTAGCCAACCCCTTAAACACC | 2499 | GGTGTTTAAGGGGTTGGCTA | 4268 |
| 15517 | 15539 | CCTAGCCAACCCCTTAAACACCC | 2500 | GGGTGTTTAAGGGGTTGGCT | 4269 |
| 15522 | 15544 | CCAACCCCTTAAACACCCTCCC | 2501 | GGGAGGGGTGTTTAAGGGGT | 4270 |
| 15526 | 15548 | CCCCTTAAACACCCCTCCCACA | 2502 | TGTGGGGAGGGGTGTTTAAG | 4271 |
| 15527 | 15549 | CCCTTAAACACCCCTCCCACAT | 2503 | ATGTGGGGAGGGGTGTTTAA | 4272 |
| 15528 | 15550 | CCTTAAACACCCCTCCCCACATC | 2504 | GATGTGGGGAGGGGTGTTTA | 4273 |
| 15537 | 15559 | CCCCTCCCCACATCAAGCCCGAA | 2505 | TTCGGGCTTGATGTGGGGAG | 4274 |
| 15538 | 15560 | CCCTCCCCACATCAAGCCCGAAT | 2506 | ATTCGGGCTTGATGTGGGGA | 4275 |
| 15539 | 15561 | CCTCCCCACATCAAGCCCGAATG | 2507 | CATTCGGGCTTGATGTGGGG | 4276 |
| 15542 | 15564 | CCCCACATCAAGCCCGAATGATA | 2508 | TATCATTCGGGCTTGATGTG | 4277 |
| 15543 | 15565 | CCCACATCAAGCCCGAATGATAT | 2509 | ATATCATTCGGGCTTGATGT | 4278 |
| 15544 | 15566 | CCACATCAAGCCCGAATGATATT | 2510 | AATATCATTCGGGCTTGATG | 4279 |
| 15554 | 15576 | CCCGAATGATATTTCCTATTCGC | 2511 | GCGAATAGGAAATATCATTC | 4280 |
| 15555 | 15577 | CCGAATGATATTTCCTATTCGCC | 2512 | GGCGAATAGGAAATATCATT | 4281 |
| 15568 | 15590 | CCTATTCGCCTACACAATTCTCC | 2513 | GGAGAATTGTGTAGGCGAAT | 4282 |
| 15576 | 15598 | CCTACACAATTCTCCGATCCGTC | 2514 | GACGGATCGGAGAATTGTGT | 4283 |
| 15589 | 15611 | CCGATCCGTCCCTAACAAACTAG | 2515 | CTAGTTTGTTAGGGACGGAT | 4284 |
| 15594 | 15616 | CCGTCCCTAACAAACTAGGAGGC | 2516 | GCCTCCTAGTTTGTTAGGGA | 4285 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 15598 | 15620 | CCCTAACAAACTAGGAGGCGTCC | 2517 | GGACGCCTCCTAGTTTGTTA | 4286 |
| 15599 | 15621 | CCTAACAAACTAGGAGGCGTCCT | 2518 | AGGACGCCTCCTAGTTTGTT | 4287 |
| 15619 | 15641 | CCTTGCCCTATTACTATCCATCC | 2519 | GGATGGATAGTAATAGGGCA | 4288 |
| 15624 | 15646 | CCCTATTACTATCCATCCTCATC | 2520 | GATGAGGATGGATAGTAATA | 4289 |
| 15625 | 15647 | CCTATTACTATCCATCCTCATCC | 2521 | GGATGAGGATGGATAGTAAT | 4290 |
| 15636 | 15658 | CCATCCTCATCCTAGCAATAATC | 2522 | GATTATTGCTAGGATGAGGA | 4291 |
| 15640 | 15662 | CCTCATCCTAGCAATAATCCCCA | 2523 | TGGGGATTATTGCTAGGATG | 4292 |
| 15646 | 15668 | CCTAGCAATAATCCCCATCCTCC | 2524 | GGAGGATGGGGATTATTGCT | 4293 |
| 15658 | 15680 | CCCCATCCTCCATATATCCAAAC | 2525 | GTTTGGATATATGGAGGATG | 4294 |
| 15659 | 15681 | CCCATCCTCCATATATCCAAACA | 2526 | TGTTTGGATATATGGAGGAT | 4295 |
| 15660 | 15682 | CCATCCTCCATATATCCAAACAA | 2527 | TTGTTTGGATATATGGAGGA | 4296 |
| 15664 | 15686 | CCTCCATATATCCAAACAACAAA | 2528 | TTTGTTGTTTGGATATATGG | 4297 |
| 15667 | 15689 | CCATATATCCAAACAACAAAGCA | 2529 | TGCTTTGTTGTTTGGATATA | 4298 |
| 15675 | 15697 | CCAAACAACAAAGCATAATATTT | 2530 | AAATATTATGCTTTGTTGTT | 4299 |
| 15700 | 15722 | CCCACTAAGCCAATCACTTTATT | 2531 | AATAAAGTGATTGGCTTAGT | 4300 |
| 15701 | 15723 | CCACTAAGCCAATCACTTTATTG | 2532 | CAATAAAGTGATTGGCTTAG | 4301 |
| 15709 | 15731 | CCAATCACTTTATTGACTCCTAG | 2533 | CTAGGAGTCAATAAAGTGAT | 4302 |
| 15727 | 15749 | CCTAGCCGCAGACCTCCTCATTC | 2534 | GAATGAGGAGGTCTGCGGCT | 4303 |
| 15732 | 15754 | CCGCAGACCTCCTCATTCTAACC | 2535 | GGTTAGAATGAGGAGGTCTG | 4304 |
| 15739 | 15761 | CCTCCTCATTCTAACCTGAATCG | 2536 | CGATTCAGGTTAGAATGAGG | 4305 |
| 15742 | 15764 | CCTCATTCTAACCTGAATCGGAG | 2537 | CTCCGATTCAGGTTAGAATG | 4306 |
| 15753 | 15775 | CCTGAATCGGAGGACAACCAGTA | 2538 | TACTGGTTGTCCTCCGATTC | 4307 |
| 15770 | 15792 | CCAGTAAGCTACCCTTTTACCAT | 2539 | ATGGTAAAAGGGTAGCTTAC | 4308 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 15781 | 15803 | CCCTTTTACCATCATTGGACAAG | 2540 | CTTGTCCAATGATGGTAAAA | 4309 |
| 15782 | 15804 | CCTTTTACCATCATTGGACAAGT | 2541 | ACTTGTCCAATGATGGTAAA | 4310 |
| 15789 | 15811 | CCATCATTGGACAAGTAGCATCC | 2542 | GGATGCTACTTGTCCAATGA | 4311 |
| 15810 | 15832 | CCGTACTATACTTCACAACAATC | 2543 | GATTGTTGTGAAGTATAGTA | 4312 |
| 15832 | 15854 | CCTAATCCTAATACCAACTATCT | 2544 | AGATAGTTGGTATTAGGATT | 4313 |
| 15838 | 15860 | CCTAATACCAACTATCTCCCTAA | 2545 | TTAGGGAGATAGTTGGTATT | 4314 |
| 15845 | 15867 | CCAACTATCTCCCTAATGAAAA | 2546 | TTTTCAATTAGGGAGATAGT | 4315 |
| 15855 | 15877 | CCCTAATTGAAAACAAAATACTC | 2547 | GAGTATTTTGTTTTCAATTA | 4316 |
| 15856 | 15878 | CCTAATTGAAAACAAAATACTCA | 2548 | TGAGTATTTTGTTTTCAATT | 4317 |
| 15885 | 15907 | CCTGTCCTTGTAGTATAAACTAA | 2549 | TTAGTTTATACTACAAGGAC | 4318 |
| 15890 | 15912 | CCTTGTAGTATAAACTAATACAC | 2550 | GTGTATTAGTTTATACTACA | 4319 |
| 15912 | 15934 | CCAGTCTTGTAAACCGGAGATGA | 2551 | TCATCTCCGGTTTACAAGAC | 4320 |
| 15925 | 15947 | CCGGAGATGAAAACCTTTTTCCA | 2552 | TGGAAAAAGGTTTTCATCTC | 4321 |
| 15938 | 15960 | CCTTTTTCCAAGGACAAATCAGA | 2553 | TCTGATTTGTCCTTGGAAAA | 4322 |
| 15945 | 15967 | CCAAGGACAAATCAGAGAAAAAG | 2554 | CTTTTTCTCTGATTTGTCCT | 4323 |
| 15977 | 15999 | CCACCATTAGCACCCAAAGCTAA | 2555 | TTAGCTTTGGGTGCTAATGG | 4324 |
| 15980 | 16002 | CCATTAGCACCCAAAGCTAAGAT | 2556 | ATCTTAGCTTTGGGTGCTAA | 4325 |
| 15989 | 16011 | CCCAAAGCTAAGATTCTAATTTA | 2557 | TAAATTAGAATCTTAGCTTT | 4326 |
| 15990 | 16012 | CCAAAGCTAAGATTCTAATTTAA | 2558 | TTAAATTAGAATCTTAGCTT | 4327 |
| 16052 | 16074 | CCACCCAAGTATTGACTCACCCA | 2559 | TGGGTGAGTCAATACTTGGG | 4328 |
| 16055 | 16077 | CCCAAGTATTGACTCACCCATCA | 2560 | TGATGGGTGAGTCAATACTT | 4329 |
| 16056 | 16078 | CCAAGTATTGACTCACCCATCAA | 2561 | TTGATGGGTGAGTCAATACT | 4330 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 16071 | 16093 | CCCATCAACAACCGCTATGTATT | 2562 | AATACATAGCGGTTGTTGAT | 4331 |
| 16072 | 16094 | CCATCAACAACCGCTATGTATTT | 2563 | AAATACATAGCGGTTGTTGA | 4332 |
| 16082 | 16104 | CCGCTATGTATTTCGTACATTAC | 2564 | GTAATGTACGAAATACATAG | 4333 |
| 16107 | 16129 | CCAGCCACCATGAATATTGTACG | 2565 | CGTACAATATTCATGGTGGC | 4334 |
| 16111 | 16133 | CCACCATGAATATTGTACGGTAC | 2566 | GTACCGTACAATATTCATGG | 4335 |
| 16114 | 16136 | CCATGAATATTGTACGGTACCAT | 2567 | ATGGTACCGTACAATATTCA | 4336 |
| 16133 | 16155 | CCATAAATACTTGACCACCTGTA | 2568 | TACAGGTGGTCAAGTATTTA | 4337 |
| 16147 | 16169 | CCACCTGTAGTACATAAAAACCC | 2569 | GGGTTTTTATGTACTACAGG | 4338 |
| 16150 | 16172 | CCTGTAGTACATAAAAACCCAAT | 2570 | ATTGGGTTTTTATGTACTAC | 4339 |
| 16167 | 16189 | CCCAATCCACATCAAAACCCCCT | 2571 | AGGGGGTTTTGATGTGGATT | 4340 |
| 16168 | 16190 | CCAATCCACATCAAAACCCCCTC | 2572 | GAGGGGGTTTTGATGTGGAT | 4341 |
| 16173 | 16195 | CCACATCAAAACCCCCTCCCCAT | 2573 | ATGGGGAGGGGGTTTTGATG | 4342 |
| 16184 | 16206 | CCCCCTCCCCATGCTTACAAGCA | 2574 | TGCTTGTAAGCATGGGGAGG | 4343 |
| 16185 | 16207 | CCCCTCCCCATGCTTACAAGCAA | 2575 | TTGCTTGTAAGCATGGGGAG | 4344 |
| 16186 | 16208 | CCCTCCCCATGCTTACAAGCAAG | 2576 | CTTGCTTGTAAGCATGGGGA | 4345 |
| 16187 | 16209 | CCTCCCCATGCTTACAAGCAAGT | 2577 | ACTTGCTTGTAAGCATGGGG | 4346 |
| 16190 | 16212 | CCCCATGCTTACAAGCAAGTACA | 2578 | TGTACTTGCTTGTAAGCATG | 4347 |
| 16191 | 16213 | CCCATGCTTACAAGCAAGTACAG | 2579 | CTGTACTTGCTTGTAAGCAT | 4348 |
| 16192 | 16214 | CCATGCTTACAAGCAAGTACAGC | 2580 | GCTGTACTTGCTTGTAAGCA | 4349 |
| 16221 | 16243 | CCCTCAACTATCACACATCAACT | 2581 | AGTTGATGTGTGATAGTTGA | 4350 |
| 16222 | 16244 | CCTCAACTATCACACATCAACTG | 2582 | CAGTTGATGTGTGATAGTTG | 4351 |
| 16250 | 16272 | CCAAAGCCACCCCTCACCCACTA | 2583 | TAGTGGGTGAGGGGTGGCTT | 4352 |
| 16256 | 16278 | CCACCCCTCACCCACTAGGATAC | 2584 | GTATCCTAGTGGGTGAGGGG | 4353 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 16259 | 16281 | CCCCTCACCCACTAGGATACCAA | 2585 | TTGGTATCCTAGTGGGTGAG | 4354 |
| 16260 | 16282 | CCCTCACCCACTAGGATACCAAC | 2586 | GTTGGTATCCTAGTGGGTGA | 4355 |
| 16261 | 16283 | CCTCACCCACTAGGATACCAACA | 2587 | TGTTGGTATCCTAGTGGGTG | 4356 |
| 16266 | 16288 | CCCACTAGGATACCAACAAACCT | 2588 | AGGTTTGTTGGTATCCTAGT | 4357 |
| 16267 | 16289 | CCACTAGGATACCAACAAACCTA | 2589 | TAGGTTTGTTGGTATCCTAG | 4358 |
| 16278 | 16300 | CCAACAAACCTACCCACCCTTAA | 2590 | TTAAGGGTGGGTAGGTTTGT | 4359 |
| 16286 | 16308 | CCTACCCACCCTTAACAGTACAT | 2591 | ATGTACTGTTAAGGGTGGGT | 4360 |
| 16290 | 16312 | CCCACCCTTAACAGTACATAGTA | 2592 | TACTATGTACTGTTAAGGGT | 4361 |
| 16291 | 16313 | CCACCCTTAACAGTACATAGTAC | 2593 | GTACTATGTACTGTTAAGGG | 4362 |
| 16294 | 16316 | CCCTTAACAGTACATAGTACATA | 2594 | TATGTACTATGTACTGTTAA | 4363 |
| 16295 | 16317 | CCTTAACAGTACATAGTACATAA | 2595 | TTATGTACTATGTACTGTTA | 4364 |
| 16320 | 16342 | CCATTTACCGTACATAGCACATT | 2596 | AATGTGCTATGTACGGTAAA | 4365 |
| 16327 | 16349 | CCGTACATAGCACATTACAGTCA | 2597 | TGACTGTAATGTGCTATGTA | 4366 |
| 16353 | 16375 | CCCTTCTCGTCCCCATGGATGAC | 2598 | GTCATCCATGGGGACGAGAA | 4367 |
| 16354 | 16376 | CCTTCTCGTCCCCATGGATGACC | 2599 | GGTCATCCATGGGGACGAGA | 4368 |
| 16363 | 16385 | CCCCATGGATGACCCCCCTCAGA | 2600 | TCTGAGGGGGGTCATCCATG | 4369 |
| 16364 | 16386 | CCCATGGATGACCCCCCTCAGAT | 2601 | ATCTGAGGGGGGTCATCCAT | 4370 |
| 16365 | 16387 | CCATGGATGACCCCCCTCAGATA | 2602 | TATCTGAGGGGGGTCATCCA | 4371 |
| 16375 | 16397 | CCCCCTCAGATAGGGGTCCCTT | 2603 | AAGGGACCCCTATCTGAGGG | 4372 |
| 16376 | 16398 | CCCCCTCAGATAGGGGTCCCTTG | 2604 | CAAGGGACCCCTATCTGAGG | 4373 |
| 16377 | 16399 | CCCCTCAGATAGGGGTCCCTTGA | 2605 | TCAAGGGACCCCTATCTGAG | 4374 |
| 16378 | 16400 | CCCTCAGATAGGGGTCCCTTGAC | 2606 | GTCAAGGGACCCCTATCTGA | 4375 |

TABLE 4-continued gRNA target sequence for human mtDNA carrying NGG sequence on the (-) strand.

| Chr start position (+ strand) | Chr end position (+ strand) | nt sequence on the (+) strand containing CCN sequence followed by the reverse complementary sequence of gRNA target sequence | SEQ ID NO | 20 nt gRNA target sequence (will encode the gRNA targeting sequence) | SEQ ID NO |
|---|---|---|---|---|---|
| 16379 | 16401 | CCTCAGATAGGGGTCCCTTGACC | 2607 | GGTCAAGGGACCCCTATCTG | 4376 |
| 16393 | 16415 | CCCTTGACCACCATCCTCCGTGA | 2608 | TCACGGAGGATGGTGGTCAA | 4377 |
| 16394 | 16416 | CCTTGACCACCATCCTCCGTGAA | 2609 | TTCACGGAGGATGGTGGTCA | 4378 |
| 16400 | 16422 | CCACCATCCTCCGTGAAATCAAT | 2610 | ATTGATTTCACGGAGGATGG | 4379 |
| 16403 | 16425 | CCATCCTCCGTGAAATCAATATC | 2611 | GATATTGATTTCACGGAGGA | 4380 |
| 16407 | 16429 | CCTCCGTGAAATCAATATCCCGC | 2612 | GCGGGATATTGATTTCACGG | 4381 |
| 16410 | 16432 | CCGTGAAATCAATATCCCGCACA | 2613 | TGTGCGGGATATTGATTTCA | 4382 |
| 16425 | 16447 | CCCGCACAAGAGTGCTACTCTCC | 2614 | GGAGAGTAGCACTCTTGTGC | 4383 |
| 16426 | 16448 | CCGCACAAGAGTGCTACTCTCCT | 2615 | AGGAGAGTAGCACTCTTGTG | 4384 |
| 16446 | 16468 | CCTCGCTCCGGGCCCATAACACT | 2616 | AGTGTTATGGGCCCGGAGCG | 4385 |
| 16453 | 16475 | CCGGGCCCATAACACTTGGGGGT | 2617 | ACCCCCAAGTGTTATGGGCC | 4386 |
| 16458 | 16480 | CCCATAACACTTGGGGGTAGCTA | 2618 | TAGCTACCCCCAAGTGTTAT | 4387 |
| 16459 | 16481 | CCATAACACTTGGGGGTAGCTAA | 2619 | TTAGCTACCCCCAAGTGTTA | 4388 |
| 16494 | 16516 | CCGACATCTGGTTCCTACTTCAG | 2620 | CTGAAGTAGGAACCAGATGT | 4389 |
| 16507 | 16529 | CCTACTTCAGGGTCATAAAGCCT | 2621 | AGGCTTTATGACCCTGAAGT | 4390 |
| 16527 | 16549 | CCTAAATAGCCCACACGTTCCCC | 2622 | GGGGAACGTGTGGGCTATTT | 4391 |
| 16536 | 16558 | CCCACACGTTCCCCTTAAATAAG | 2623 | CTTATTTAAGGGGAACGTGT | 4392 |
| 16537 | 16559 | CCACACGTTCCCCTTAAATAAGA | 2624 | TCTTATTTAAGGGGAACGTG | 4393 |
| 16546 | 16568 | CCCCTTAAATAAGACATCACGAT | 2625 | ATCGTGATGTCTTATTTAAG | 4394 |
| 16547 | 16569 | CCCTTAAATAAGACATCACGATG | 2626 | CATCGTGATGTCTTATTTAA | 4395 |
| 16548 | 16570 | CCTTAAATAAGACATCACGATGG | 2627 | CCATCGTGATGTCTTATTTA | 4396 |

Applications

The gNAs (e.g., gRNAs) and collections of gNAs (e.g., gRNAs) provided herein are useful for a variety of applications, including depletion, partitioning, capture, or enrichment of target sequences of interest; genome-wide labeling; genome-wide editing; genome-wide function screens; and genome-wide regulation.

In one embodiment, the gNAs are selective for host nucleic acids in a biological sample from a host, but are not selective for non-host nucleic acids in the sample from a host. In one embodiment, the gNAs are selective for non-host nucleic acids from a biological sample from a host but are not selective for the host nucleic acids in the sample. In one embodiment, the gNAs are selective for both host nucleic acids and a subset of the non-host nucleic acids in a biological sample from a host. For example, where a complex biological sample comprises host nucleic acids and nucleic acids from more than one non-host organisms, the gRNAs may be selective for more than one of the non-host species. In such embodiments, the gNAs are used to serially deplete or partition the sequences that are not of interest. For example, saliva from a human contains human DNA, as well as the DNA of more than one bacterial species, but may also contain the genomic material of an unknown pathogenic organism. In such an embodiment, gNAs directed at the human DNA and the known bacteria can be used to serially deplete the human DNA, and the DNA of the known bacterial, thus resulting in a sample comprising the genomic material of the unknown pathogenic organism.

In an exemplary embodiment, the gNAs are selective for human host DNA obtained from a biological sample from the host, but do not hybridize with DNA from an unknown pathogen(s) also obtained from the sample.

In some embodiments, the gNAs are useful for depleting and partitioning of targeted sequences in a sample, enriching a sample for non-host nucleic acids, or serially depleting targeted nucleic acids in a sample comprising: providing nucleic acids extracted from a sample; and contacting the sample with a plurality of complexes comprising (i) any one of the collection of gNAs described herein and (ii) nucleic acid-guided nuclease (e.g., CRISPR/Cas) system proteins.

In some embodiments, the gNAs are useful for method of depletion and partitioning of targeted sequences in a sample comprising: providing nucleic acids extracted from a sample, wherein the extracted nucleic acids comprise sequences of interest and targeted sequences for one of depletion and partitioning; contacting the sample with a plurality of complexes comprising (i) a collection of gNAs provided herein; and (ii) nucleic acid-guided nuclease (e.g., CRISPR/Cas) system proteins, under conditions in which the nucleic acid-guided nuclease system proteins cleave the nucleic acids in the sample.

In some embodiments, the gNAs are useful for enriching a sample for non-host nucleic acids comprising: providing a sample comprising host nucleic acids and non-host nucleic acids; contacting the sample with a plurality of complexes comprising (i) a collection of gNAs provided herein comprising targeting sequences directed at the host nucleic acids; and (ii) nucleic acid-guided nuclease (e.g., CRISPR/Cas) system proteins, under conditions in which the nucleic acid-guided nuclease system proteins cleave the host nucleic acids in the sample, thereby depleting the sample of host nucleic acids, and allowing for the enrichment of non-host nucleic acids.

In some embodiments, the gNAs are useful for one method for serially depleting targeted nucleic acids in a sample comprising: providing a biological sample from a host comprising host nucleic acids and non-host nucleic acids, wherein the non-host nucleic acids comprise nucleic acids from at least one known non-host organism and nucleic acids from an unknown non-host organism; providing a plurality of complexes comprising (i) a collection of gNAs provided herein, directed at the host nucleic acids; and (ii) nucleic acid-guided nuclease (e.g., CRISPR/Cas) system proteins; mixing the nucleic acids from the biological sample with the gNA-nucleic acid-guided nuclease system protein complexes (e.g., gRNA-CRISPR/Cas system protein complexes) configured to hybridize to targeted sequences in the host nucleic acids, wherein at least a portion of the complexes hybridizes to the targeted sequences in the host nucleic acids, and wherein at least a portion of the host nucleic acids are cleaved; mixing the remaining nucleic acids from the biological sample with the gNA-nucleic acid-guided nuclease system protein complexes configured to hybridize to targeted sequences in the at least one known non-host nucleic acids, wherein at least a portion of the complexes hybridizes to the targeted sequences in the at least one non-host nucleic acids, and wherein at least a portion of the non-host nucleic acids are cleaved; and isolating the remaining nucleic acids from the unknown non-host organism and preparing for further analysis.

In some embodiments, the gNAs generated herein are used to perform genome-wide or targeted functional screens in a population of cells. In such an embodiment, libraries of in vitro-transcribed gNAs (e.g., gRNAs) or vectors encoding the gNAs can be introduced into a population of cells via transfection or other laboratory techniques known in the art, along with a nucleic acid-guided nuclease (e.g., CRISPR/Cas) system protein, in a way that gNA-directed nucleic acid-guided nuclease system protein editing can be achieved to sequences across the entire genome or to a specific region of the genome. In one embodiment, the nucleic acid-guided nuclease system protein can be introduced as a DNA. In one embodiment, the nucleic acid-guided nuclease system protein can be introduced as mRNA. In one embodiment, the nucleic acid-guided nuclease system protein can be introduced as protein. In one exemplary embodiment, the nucleic acid-guided nuclease system protein is Cas9.

In some embodiments, the gNAs generated herein are used for the selective capture and/or enrichment of nucleic acid sequences of interest. For example, in some embodiments, the gNAs generated herein are used for capturing target nucleic acid sequences comprising: providing a sample comprising a plurality of nucleic acids; and contacting the sample with a plurality of complexes comprising (i) a collection of gNAs provided herein; and (ii) nucleic acid-guided nuclease (e.g., CRISPR/Cas) system proteins. Once the sequences of interest are captured, they can be further ligated to create, for example, a sequencing library.

In some embodiments, the gNAs generated herein are used for introducing labeled nucleotides at targeted sites of interest comprising: (a) providing a sample comprising a plurality of nucleic acid fragments; (b) contacting the sample with a plurality of complexes comprising (i) a collection of gNAs provided herein; and (ii) nucleic acid-guided nuclease (e.g., CRISPR/Cas) system protein-nickases (e.g. Cas9-nickases), wherein the gNAs are complementary to targeted sites of interest in the nucleic acid fragments, thereby generating a plurality of nicked nucleic acid fragments at the targeted sites of interest; and (c) contacting the plurality of nicked nucleic acid fragments with an enzyme capable of initiating nucleic acid synthesis at a nicked site, and labeled nucleotides, thereby generating a plurality of nucleic acid fragments comprising labeled nucleotides in the targeted sites of interest.

In some embodiments, the gNAs generated herein are used for capturing target nucleic acid sequences of interest comprising: (a) providing a sample comprising a plurality of adapter-ligated nucleic acids, wherein the nucleic acids are ligated to a first adapter at one end and are ligated to a second adapter at the other end; and (b) contacting the sample with a collection of gNAs which comprise a plurality of dead nucleic acid-guided nuclease-gNA complexes (e.g., dCas9-gRNA complexes), wherein the dead nucleic acid-guided nuclease (e.g., dCas9) is fused to a transposase, wherein the gNAs are complementary to targeted sites of interest contained in a subset of the nucleic acids, and wherein the dead nucleic acid-guided nuclease-gNA transposase complexes (e.g., dCas9-gRNA transposase complexes) are loaded with a plurality of third adapters, to generate a plurality of nucleic acids fragments comprising either a first or second adapter at one end and a third adapter at the other end. In one embodiment the method further comprises amplifying the product of step (b) using first or second adapter and third adapter-specific PCR.

In some embodiments, the gNAs generated herein are used to perform genome-wide or targeted activation or repression in a population of cells. In such an embodiment, libraries of in vitro-transcribed gNAs (e.g., gRNAs) or vectors encoding the gNAs can be introduced into a population of cells via transfection or other laboratory techniques known in the art, along with a catalytically dead nucleic acid-guided nuclease (e.g., CRISPR/Cas) system protein fused to an activator or repressor domain (catalytically dead nucleic acid-guided nuclease system protein-fusion protein), in a way that gNA-directed catalytically dead nucleic acid-guided nuclease system protein-mediated activation or repression can be achieved at sequences across the entire genome or to a specific region of the genome. In one embodiment, the catalytically dead nucleic acid-guided nuclease system protein-fusion protein can be introduced as DNA. In one embodiment, the catalytically dead nucleic acid-guided nuclease system protein-fusion protein can be introduced as mRNA. In one embodiment, the catalytically dead nucleic acid-guided nuclease system protein-fusion protein can be introduced as protein. In some embodiments, the collection of gNAs or nucleic acids encoding for gNAs exhibit specificity for more than one nucleic acid-guided nuclease system protein. In one exemplary embodiment, the catalytically dead nucleic acid-guided nuclease system protein is dCas9.

In some embodiments, the collection comprises gRNAs or nucleic acids encoding for gRNAs with specificity for Cas9 and one or more CRISPR/Cas system proteins selected from selected from the group consisting of Cpf1, Cas3, Cas8a-c, Cas10, Cse1, Csy1, Csn2, Cas4, Csm2, and Cm5. In some embodiments, the collection comprises gRNAs or nucleic acids encoding for gRNAs with specificity for various catalytically dead CRISPR/Cas system proteins fused to different fluorophores, for example for use in the labeling and/or visualization of different genomes or portions of genomes, for use in the labeling and/or visualization of different chromosomal regions, or for use in the labeling and/or visualization of the integration of viral genes/genomes into a genome.

In some embodiments, the collection of gNAs (or nucleic acids encoding for gNAs) have specificity for different nucleic acid-guided nuclease (e.g., CRISPR/Cas) system proteins, and target different sequences of interest, for example from different species. For example, a first subset of gNAs from a collection of gNAs (or transcribed from a population of nucleic acids encoding such gNAs) targeting a genome from a first species can be first mixed with a first nucleic acid-guided nuclease system protein member (or an engineered version); and a second subset of gNAs from a collection of gNAs (or transcribed from a population of nucleic acids encoding such gNAs) targeting a genome from a second species can be mixed with a second different nucleic acid-guided nuclease system protein member (or an engineered version). In one embodiment, the nucleic acid-guided nuclease system proteins can be a catalytically dead version (for example dCas9) fused with different fluorophores, so that different targeted sequence of interest, e.g. different species genome, or different chromosomes of one species, can be labeled by different fluorescent labels. For example, different chromosomal regions can be labeled by different gRNA-targeted dCas9-fluorophores, for visualization of genetic translocations. For example, different viral genomes can be labeled by different gRNA-targeted dCas9-fluorophores, for visualization of integration of different viral genomes into the host genome. In another embodiment, the nucleic acid-guided nuclease system protein can be dCas9 fused with either activation or repression domain, so that different targeted sequence of interest, e.g. different chromosomes of a genome, can be differentially regulated. In another embodiment, the nucleic acid-guided nuclease system protein can be dCas9 fused different protein domain which can be recognized by different antibodies, so that different targeted sequence of interest, e.g. different DNA sequences within a sample mixture, can be differentially isolated.

Exemplary Compositions of the Invention

In one embodiment, provided herein is a composition comprising a nucleic acid fragment, a nickase nucleic acid-guided nuclease-gNA complex, and labeled nucleotides. In one exemplary embodiment, provided herein is a composition comprising a nucleic acid fragment, a nickase Cas9-gRNA complex, and labeled nucleotides. In such embodiments, the nucleic acid may comprise DNA. The nucleotides can be labeled, for example with biotin. The nucleotides can be part of an antibody-conjugate pair.

In one embodiment, provided herein is a composition comprising a nucleic acid fragment and a catalytically dead nucleic acid-guided nuclease-gNA complex, wherein the catalytically dead nucleic acid-guided nuclease is fused to a transposase. In one exemplary embodiment, provided herein is a composition comprising a DNA fragment and a dCas9-gRNA complex, wherein the dCas9 is fused to a transposase.

In one embodiment, provided herein is a composition comprising a nucleic acid fragment comprising methylated nucleotides, a nickase nucleic acid-guided nuclease-gNA complex, and unmethylated nucleotides. In an exemplary embodiment, provided herein is a composition comprising a DNA fragment comprising methylated nucleotides, a nickase Cas9-gRNA complex, and unmethylated nucleotides.

In one embodiment, provided herein is a gDNA complexed with a nucleic acid-guided-DNA endonuclease. In an exemplary embodiment, the nucleic acid-guided-DNA endonuclease is NgAgo.

In one embodiment, provided herein is a gDNA complexed with a nucleic acid-guided-RNA endonuclease.

In one embodiment, provided herein is a gRNA complexed with a nucleic acid-guided-DNA endonuclease.

In one embodiment, provided herein is a gRNA complexed with a nucleic acid-guided-RNA endonuclease. In one embodiment, the nucleic acid-guided-RNA endonuclease comprises C2c2.

Kits and Articles of Manufacture

The present application provides kits comprising any one or more of the compositions described herein, not limited to adapters, gNAs (e.g., gRNAs), gNA collections (e.g., gRNA collections), nucleic acid molecules encoding the gNA collections, and the like.

In one exemplary embodiment, the kit comprises a collection of DNA molecules capable of transcribing into a library of gRNAs wherein the gRNAs are targeted to human genomic or other sources of DNA sequences.

In one embodiment, the kit comprises a collection of gNAs wherein the gNAs are targeted to human genomic or other sources of DNA sequences.

In some embodiments, provided herein are kits comprising any of the collection of nucleic acids encoding gNAs, as described herein. In some embodiments, provided herein are kits comprising any of the collection of gNAs, as described herein.

The present application also provides all essential reagents and instructions for carrying out the methods of making the gNAs and the collection of nucleic acids encoding gNAs, as described herein. In some embodiments, provided herein are kits that comprise all essential reagents and instructions for carrying out the methods of making individual gNAs and collections of gNAs as described herein.

Also provided herein is computer software monitoring the information before and after contacting a sample with a gNA collection produced herein. In one exemplary embodiment, the software can compute and report the abundance of non-target sequence in the sample before and after providing gNA collection to ensure no off-target targeting occurs, and wherein the software can check the efficacy of targeted-depletion/encrichment/capture/partitioning/labeling/regulation/editing by comparing the abundance of the target sequence before and after providing gNA collection to the sample.

The following examples are included for illustrative purposes and are not intend to limit the scope of the invention.

EXAMPLES

Example 1: Construction of a gRNA Library from a T7 Promoter Human DNA Library

T7 Promoter Library Construction

Human genomic DNA (400 ng) was fragmented using an S2 Covaris sonicator (Covaris) for 8 cycles, to yield fragments of 200-300 bp in length. Fragmented DNA was repaired using the NEBNext End Repair Module (NEB) and incubated at 25° C. for 30 min, then heat inactivated at 75° C. for 20 min. To make T7 promoter adapters, oligos T7-1 (5'GCCTCGAGC*T*A*ATACGACTCACTATAGAG3', * denotes a phosphorothioate backbone linkage)(SEQ ID NO: 4397) and T7-2 (sequence 5'Phos-CTCTATAGTGAGTCG-TATTA3') (SEQ ID NO: 4398) were admixed at 15 µM, heated to 98° C. for 3 min then cooled slowly (0.1° C./min) to 30° C. T7 promoter blunt adapters (15 pmol total) were then added to the blunt-ended human genomic DNA fragments, and incubated with Blunt/TA Ligase Master Mix (NEB) at 25° C. for 30 min ((2) in FIG. 1). Ligations were amplified with 2 µM oligo T7-1, using Hi-Fidelity 2× Master Mix (NEB) for 10 cycles of PCR (98° C. for 20 s, 63° C. for 20 s, 72° C. for 35 s). Amplification was verified by running a small aliquot on agarose gel electrophoresis. PCR amplified products were recovered using 0.6× AxyPrep beads (Axygen) according to the manufacturer's instructions, and resuspended in 15 µL of 10 mM Tris-HCl pH 8.

Digestion of DNA

PCR amplified T7 promoter DNA (2 µg total per digestion) was digested with 0.1 µL of Nt.CviPII (NEB) in 10 µL of NEB buffer 2 (50 mM NaCl, 10 mM Tris-HCl pH 7.9, 10 mM MgCl$_2$, 100 µg/mL BSA) for 10 min at 37° C. ((3) in FIG. 1), then heat inactivated at 75° C. for 20 min. An additional 10 µL of NEB buffer 2 with 1 µL of T7 Endonuclease I (NEB) was added to the reaction, and incubated at 37° C. for 20 min ((4) in FIG. 1). Enzymatic digestion of DNA was verified by agarose gel electrophoresis. Digested DNA was recovered by adding 0.6× AxyPrep beads (Axygen), according to the manufacturer's instructions, and resuspended in 15 µL of 10 mM Tris-HCl pH 8.

Ligation of Adapters and Removal of HGG

DNA was then blunted using T4 DNA Polymerase (NEB) for 20 min at 25° C., followed by heat inactivation at 75° C. for 20 min ((5) in FIG. 1).

To make MlyI adapters, oligos MlyI-1 (sequence 5'>3', 5'Phos-GGGACTCGGATCCCTATAGTGATA-CAAAGACGATGACGACAAGCG) (SEQ ID NO: 4399) and MlyI-2 (sequence 5'>3', TCACTATAGGGATC-CGAGTCCC) (SEQ ID NO: 4400) were admixed at 15 µM, heated to 98° C. for 3 min then cooled slowly (0.1° C./min) to 30° C. MlyI adapters (15 pmol total) were then added to T4 DNA Polymerase-blunted DNA, and incubated with Blunt/TA Ligase Master Mix (NEB) at 25° C. for 30 min ((6) in FIG. 1). Ligations were heat inactivated at 75° C. for 20 min, then digested with MlyI and XhoI (NEB) for 1 hr at 37° C., so that HGG motifs are eliminated ((7) in FIG. 1). Digests were then cleaned using 0.8× AxyPrep beads (Axygen), and DNA was resuspended in 10 µL of 10 mM Tris-Cl pH 8.

To make StlgR adapters, oligos stlgR (sequence 5'>3', 5'Phos-GTTTTAGAGCTAGAAATAGCAAGT-TAAAATAAGGCTAGTCCGTTATCAACTT-GAAAAAGTGGCACCG AGTCGGTGCTTTTTTTG-GATCCGATGC) (SEQ ID NO: 4401) and stlgRev (sequence 5'>3', GGATCCAAAAAAAGCACCGACTCG-GTGCCACTTTTTCAAGTTGATAACGGACTAGCCTT-ATTTTAAC TTGCTATTTCTAGCTCTAAAAC) (SEQ ID NO: 4402) were admixed at 15 µM, heated to 98° C. for 3 min then cooled slowly (0.1° C./min) to 60° C. StlgR adapters (5 pmol total) were added to HGG-removed DNA fragments, and incubated with Blunt/TA Ligase Master Mix (NEB) at 25° C. for 30 min ((8) in FIG. 1). Ligations were then incubated with Hi-Fidelity 2× Master Mix (NEB), using 2 µM of both oligos T7-1 and gRU (sequence 5'>3', AAAAAAAGCACCGACTCGGTG) (SEQ ID NO: 4403), and amplified using 20 cycles of PCR (98° C. for 20 s, 60° C. for 20 s, 72° C. for 35 s). Amplification was verified by running a small aliquot on agarose gel electrophoresis. PCR amplified products were recovered using 0.6× AxyPrep beads (Axygen) according to the manufacturer's instructions, and resuspended in 15 µL of 10 mM Tris-HCl pH 8.

In Vitro Transcription

The T7/gRU amplified library of PCR products was then used as template for in vitro transcription, using the HiScribe T7 In Vitro Transcription Kit (NEB). 500-1000 ng of template was incubated overnight at 37° C. according to the manufacturer's instructions. To transcribe the guide libraries into gRNAs, the following in vitro transcription reaction mixture was assembled: 10 µL of purified library (~500 ng), 6.5 µL of H$_2$O, 2.25 µL of ATP, 2.25 µL of CTP, 2.25 µL of GTP, 2.25 µL of UTP, 2.25 µL of 10× reaction buffer (NEB) and 2.25 µL of T7 RNA Polymerase mix. The reaction was incubated at 37° C. for 24 hr, then purified using the RNA cleanup kit (Life Technologies), eluted with 100 µL of RNase-free water, quantified and stored at −20° C. until use.

Example 2: Construction of gRNA Library from Intact Human Genomic DNA

Digestion of DNA

Human genomic DNA ((1) in FIG. 2; 20 µg total per digestion) was digested with 0.1 µL of Nt.CviPII (NEB) in 40 µL of NEB buffer 2 (50 mM NaCl, 10 mM Tris-HCl pH 7.9, 10 mM MgCl$_2$, 100 µg/mL BSA) for 10 min at 37° C., then heat inactivated at 75° C. for 20 min. An additional 40 µL of NEB buffer 2 and 1 µL of T7 Endonuclease I (NEB) was added to the reaction, with 20 min incubation at 37° C. (e.g., (2) in FIG. 2). Fragmentation of genomic DNA was verified with a small aliquot by agarose gel electrophoresis. DNA fragments between 200 and 600 bp were recovered by adding 0.3× AxyPrep beads (Axygen), incubating at 25° C. for 5 min, capturing beads on a magnetic stand and transferring the supernatant to a new tube. DNA fragments below 600 bp do not bind to beads at this bead/DNA ratio and remain in the supernatant. 0.7× AxyPrep beads (Axygen) were then added to the supernatant (this will bind all DNA molecules longer than 200 bp), allowed to bind for 5 min. Beads were captured on a magnetic stand and washed twice with 80% ethanol, air dried. DNA was then resuspended in 15 µL of 10 mM Tris-HCl pH 8. DNA concentration was determined using a Qbit assay (Life Technologies).

Ligation of Adapters

To make T7/MlyI adapters, oligos MlyI-1 (sequence 5'>3', 5'Phos-GGGGGACTCGGATCCCTATAGTGATA-CAAAGACGATGACGACAAGCG) (SEQ ID NO: 4404) and T7-7 (sequence 5'>3', GCCTCGAGC*T*A*ATACGACTCACTATAGGGATCCAAGTCCC, * denotes a phosphorothioate backbone linkage) (SEQ ID NO: 4405) were admixed at 15 µM, heated to 98° C. for 3 min then cooled slowly (0.1° C./min) to 30° C. The purified, Nt.CviPII/T7 Endonuclease I digested DNA (100 ng) was then ligated to 15 pmol of T7/MlyI adapters using Blunt/TA Ligase Master Mix (NEB) at 25° C. for 30 min ((3) in FIG. 2). Ligations were then amplified by 10 cycles of PCR (98° C. for 20 s, 60° C. for 20 s, 72° C. for 35 s) using Hi-Fidelity 2× Master Mix (NEB), and 2 µM of both oligos T7-17 (GCCTCGAGC*T*A*ATACGACTCACTATAGGG * denotes a phosphorothioate backbone linkage) (SEQ ID NO: 4406) and Flag (sequence 5'>3', CGCTTGTCGTCATCGTCTTTGTA) (SEQ ID NO: 4407). PCR amplification increases the yield of DNA and, given the nature of the Y-shaped adapters we used, always resulted in T7 promoter being added distal to the HGG site and MlyI site being added next to the HGG motif ((4) in FIG. 2).

PCR products were then digested with MlyI and XhoI (NEB) for 1 hr at 37° C., and heat inactivated at 75° C. for 20 min ((5) in FIG. 2). Following that, 5 pmol of adapter StlgR (in Example 1) was ligated using Blunt/TA Ligase Master Mix (NEB) at 25° C. for 30 min ((6) in FIG. 2). Ligations were then amplified by PCR using Hi-Fidelity 2× Master Mix (NEB), 2 µM of both oligos T7-7 and gRU (in Example 1) and 20 cycles of PCR (98° C. for 20 s, 60° C. for 20 s, 72° C. for 35 s). Amplification was verified by running a small aliquot on agarose gel electrophoresis. PCR amplified products were recovered using 0.6× AxyPrep beads (Axygen) according to the manufacturer's instructions, and resuspended in 15 µL of 10 mM Tris-HCl pH 8.

Samples were then used as templates for in vitro transcription reaction as described in Example 1.

Example 3: Direct Cutting with CviPII

30 µg of human genomic DNA was digested with 2 units of NtCviPII (New England Biolabs) for 1 hour at 37° C., followed by heat inactivation at 75° C. for 20 minutes. The size of the fragments was verified to be 200-1,000 base pairs using a fragment analyzer instrument (Advanced Analytical). The 5' or 3' protruding ends (as shown, for example, in FIG. 3) were converted to blunt ends by adding 100 units of T4 DNA polymerase (New England Biolabs), 100 µM dNTPs and incubating at 12° C. for 30 minutes. DNA was then recovered using a PCR cleanup kit (Zymo) and eluted in 20 µL elution buffer. The DNA was then ligated to MlyI adapter (see, for example, Example 4) or BaeI/EcoP15I adapters (see, for example, Example 4) or BaeI/EcoP15I adapters (see, for example, Example 5)

Example 4: Use of MlyI Adapter

Adapter MlyI was made by combining 2 µmoles of MlyI Ad1 and MlyAd2 in 40 µL water. Adapter BsaXI/MmeI was made by combining 2 moles oligo BsMm-Ad1 and 2 moles oligo BsMm-Ad2 in 40 µL water. T7 adapter was made by combining 1.5 µmoles of T7-Ad1 and T7-Ad2 oligos in 100 µL water. Stem-loop adapter was made by combining 1.5 µmoles of gR-top and gR-bot oligos in 100 µL water. In all cases, after mixing adapters were heated to 98° C. for 3 min then cooled to room temperature at a cooling rate of 1° C./min in a thermal cycler.

TABLE 5

Oligonucleotides used with MlyI Adapter.

| SEQ ID NO | Oligo name | Sequence (5' > 3') | Modification |
|---|---|---|---|
| 4408 | MlyI-Ad1 | gagatcagcttctgcattgatgccagcagcccgagtcag | none |
| 4409 | MlyI-Ad2 | ctgactcgggctgctgtacaaagacgatgacgacaagcgtta | 5'phosphate |
| 4410 | BsMm-Ad1 | gagatcagcttctgcattgatgcGGAGCCGCAGTACACTATCCAAC | none |
| 4411 | BsMm-Ad2 | GTTGGATAGTGTACTGCGGCTCCtacaaagacgatgacgacaagcg | 5'phosphate |
| 4412 | T7-Ad1 | gcctcgagctaatacgactcactatagagNN | none |

TABLE 5-continued

Oligonucleotides used with MlyI Adapter.

| SEQ ID NO | Oligo name | Sequence (5' > 3') | Modification |
|---|---|---|---|
| 4398 | T7-Ad2 | Ctctatagtgagtcgtatta | 5'phosphate |
| 4413 | gR-top | ttagagctagaaatagcaagttaaaataaggctagtccgttatcaa cttgaaaaagtggcaccgatcggtgcttttt | 5'phosphate |
| 4414 | gR-bot | aaaaaagcaccgactcggtgccactttttcaagttgataacggact agccttattttaacttgctatttctagctctaaaac | none |

The DNA containing the CCD blunt ends (from earlier section) was then ligated to 50 pmoles of adapter MlyI, using the blunt/TA ligation master mix (New England Biolabs) at room temperature for 30 minutes. The DNA was then recovered by incubating with 0.6× Kapa SPRI beads (Kapa Biosystems) for 5 minutes, capturing the beads with a magnetic rack, washing twice with 80% ethanol, air drying the beads for 5 minutes and finally resuspending the DNA in 50 µL buffer 4 (50 mM potassium acetate, 20 mM Tris-acetate, 10 mM magnesium acetate, 100 µg/mL BSA, pH 7.9). These steps eliminate small (<100 nucleotides) DNA and MlyI adapter dimers.

Purified DNA was then digested by adding 20 units of MlyI (New England Biolabs) and incubating at 37° C. for 1 hour to eliminate both the adapter derived sequences and the CCD (and complementary HGG) motifs. DNA was recovered from the digest by incubating with 0.6× Kapa SPRI beads (Kapa Biosystems) for 5 minutes, capturing the beads with a magnetic rack, washing twice with 80% ethanol, air drying the beads for 5 minutes and finally resuspending the DNA in 30 µL buffer 4.

The purified DNA was then ligated to 50 pmoles of adapter BsaXI/MmeI, using the blunt/TA ligation master mix (New England Biolabs) at room temperature for 30 minutes. The DNA was then recovered by incubating with 0.6× Kapa SPRI beads (Kapa Biosystems) for 5 minutes, capturing the beads with a magnetic rack, washing twice with 80% ethanol, air drying the beads for 5 minutes and finally resuspending the DNA in 50 µL buffer 4 (50 mM potassium acetate, 20 mM Tris-acetate, 10 mM magnesium acetate, 100 µg/mL BSA, pH 7.9). DNA was then digested by addition of 20 units MmeI (New England Biolabs) and 40 pmol/µL SAM (S-adenosyl methionine) at 37° C. for 1 hour, followed by heat inactivation at 75° C. for 20 minutes. DNA was then ligated to 30 pmoles T7 adapter using the blunt/TA ligation master mix (New England Biolabs) at room temperature for 30 minutes. DNA was then recovered using a PCR cleanup kit (Zymo) and eluted in 20 µL buffer 4, then digested with 20 units of BsaXI for 1 hour at 37° C. The guide RNA stem-loop sequences were added by adding 15 pmoles stem-loop adapter and using the blunt/TA ligation master mix (New England Biolabs) at room temperature for 30 min. DNA was then recovered using a PCR cleanup kit (Zymo), eluted in 20 µL elution buffer and PCR amplified using HiFidelity 2× master mix (New England Biolabs). Primers T7-Ad1 and gRU (sequence 5'>3' AAAAAAGCACCGACTCGGTG) (SEQ ID NO: 4419) were used to amplify with the following settings (98° C. 3 min; 98° C. for 20 sec, 60° C. for 30 secs, 72° C. for 20 sec, 30 cycles). The PCR amplicon was cleaned up using the PCR cleanup kit and verified by DNA sequencing, then used as template for an in vitro transcription reaction to generate guide RNAs.

Example 5: Use of BaeI/EcoP15I Adapter

Adapter BaeI/EcoP15I was made by combining 2 moles of BE Ad1 and BE Ad2 in 40 µL water. T7-E adapter was made by combining 1.5 µmoles of T7-Ad3 and T7-Ad4 oligos in 100 µL water. In all cases, after mixing adapters were heated to 98° C. for 3 min then cooled to room temperature at a cooling rate of 1° C./min in a thermal cycler.

TABLE 6

Oligonucleotides used with BaeI/EcoP15I Adapter.

| SEQ ID NO: | Oligo name | Sequence (5 > 3) | Modification |
|---|---|---|---|
| 4416 | BE Ad1 | ActgctgacACAAgtatcTTTTTTTTTTgtttaaacTTTTTTTTTT gatacACAAgtcagcagA | 5'phosphate |
| 4416 | Be Ad2 | TctgctgacTTGTgtatcAAAAAAAAAAgtttaaacAAAAAAAAAA gatacTTGTgtcagcagT | 5'phosphate |
| 12 | T7-Ade | gcctcgagctaatacgactcactatagag | none |
| 4417 | T7-Ad4 | NNctctatagtgagtcgtatta | 5'phosphate |
| 4418 | stIgR | ttagagctagaaatagcaagttaaaataaggctagtccgttatcaa cttgaaaaagtggcaccgagtcggtgcttttt | 5'adenylation |

The DNA containing the CCD blunt ends (from earlier section) was then ligated to 50 pmoles of adapter BaeI/EcoP15I, using the blunt/TA ligation master mix (New England Biolabs) at room temperature for 30 minutes. The DNA was then recovered by incubating with 0.6× Kapa SPRI beads (Kapa Biosystems) for 5 minutes, capturing the beads with a magnetic rack, washing twice with 80% ethanol, air drying the beads for 5 minutes and finally resuspending the DNA in 50 µL buffer 4 (50 mM potassium acetate 20 mM Tris-acetate, 10 mM magnesium acetate, 100 µg/mL BSA, pH 7.9). Recovered DNA was then digested with 20 units PmeI for 30 min at 37° C.; DNA was then recovered by incubating with 1.2× Kapa SPRI beads (Kapa Biosystems) for 5 minutes, capturing the beads with a magnetic rack, washing twice with 80% ethanol, air drying the beads for 5 minutes and finally resuspending the DNA in 50 µL buffer 4. These steps eliminate small (<100 nucleotides) DNA and BaeI/EcoP15I adapter multimers.

DNA was then digested by addition of 20 units EcoP15I (New England Biolabs) and 1 mM ATP at 37° C. for 1 hour, followed by heat inactivation at 75° C. for 20 minutes. DNA was then ligated to 30 pmoles T7-E adapter using the blunt/TA ligation master mix (New England Biolabs) at room temperature for 30 minutes. DNA was then recovered using a PCR cleanup kit (Zymo) and eluted in 20 µL buffer 4.

Purified DNA was then digested by adding 20 units of BaeI (New England Biolabs), 40 pmol/µL SAM (S-adenosyl methionine) and incubating at 37° C. for 1 hour to eliminate both the adapter derived sequences and the CCD (and complementary HGG) motifs. DNA was then recovered using a PCR cleanup kit (Zymo) and eluted in 20 µL elution buffer.

Recovered DNA was then ligated to the stlgR oligo using Thermostable 5' AppDNA/RNA Ligase (New England Biolabs) by adding 20 units ligase, 20 pmol stlgR oligo, in 20 µL ss ligation buffer (10 mM Bis-Tris-Propane-HCl, 10 mM MgCl$_2$, 1 mM DTT, 2.5 mM MnCl$_2$, pH 7 @ 25° C.) and incubating at 65° C. for 1 hour followed by heat inactivation at 90° C. for 5 min. DNA product was then PCR amplified using HiFidelity 2× master mix (New England Biolabs). Primers T7-Ad3 and gRU (sequence 5'>3' AAAAAAGCACCGACTCGGTG) (SEQ ID NO: 4419) were used to amplify with the following settings (98° C. 3 min; 98° C. for 20 sec, 60° C. for 30 secs, 72° C. for 20 sec, 30 cycles). The PCR amplicon was cleaned up using the PCR cleanup kit and verified by DNA sequencing, then used as template for an in vitro transcription reaction to generate the guide RNAs.

Example 6: NEMDA Method

NEMDA (Nicking Endonuclease Mediated DNA Amplification) was performed using 50 ng of human genomic DNA. The DNA was incubated in 100 µL thermo polymerase buffer (20 mM Tris-HCl, 10 mM (NH$_4$)$_2$SO$_4$, 10 mM KCl, 6 mM MgSO$_4$, 0.1% Triton® X-100, pH 8.8) supplemented with 0.3 mM dNTPs, 40 units of Bst large fragment DNA polymerase, and 0.1 units of NtCviPII (New England Biolabs) at 55° C. for 45 min, followed by 65° C. for 30 min and finally 80° C. for 20 min in a thermal cycler.

The DNA was then diluted with 300 µL of buffer 4 supplemented with 200 pmoles of T7-RND8 oligo (sequence 5'>3' gcctcgagctaatacgactcactatagagnnnnnnnn) (SEQ ID NO: 4420) and boiled at 98° C. for 10 min followed by rapid cooling to 10° C. for 5 min. The reaction was then supplemented with 40 units of *E. coli* DNA polymerase I and 0.1 mM dNTPs (New England Biolabs) and incubated at room temperature for 20 min followed by heat inactivation at 75° C. for 20 min. DNA was then recovered using a PCR cleanup kit (Zymo) and eluted in 30 µL elution buffer.

DNA was then ligated to 50 pmoles of adapter BaeI/EcoP15I, using the blunt/TA ligation master mix (New England Biolabs) at room temperature for 30 minutes. The DNA was then recovered by incubating with 0.6× Kapa SPRI beads (Kapa Biosystems) for 5 minutes, capturing the beads with a magnetic rack, washing twice with 80% ethanol, air drying the beads for 5 minutes and finally resuspending the DNA in 50 µL buffer 4 (50 mM potassium acetate, 20 mM Tris-acetate, 10 mM magnesium acetate, 100 µg/mL BSA, pH 7.9). Recovered DNA was then digested with 20 units PmeI for 30 min at 37° C.; DNA was then recovered by incubating with 1.2× Kapa SPRI beads (Kapa Biosystems) for 5 minutes, capturing the beads with a magnetic rack, washing twice with 80% ethanol, air drying the beads for 5 minutes and finally resuspending the DNA in 50 µL buffer 4. These steps eliminate small (<100 nucleotides) DNA and BaeI/EcoP15I adapter multimers.

Purified DNA was then digested by adding 20 units of BaeI (New England Biolabs), 40 pmol/µL SAM (S-adenosyl methionine) and incubating at 37° C. for 1 hour to eliminate both the adapter derived sequences and the CCD (and complementary HGG) motifs. DNA was then recovered using a PCR cleanup kit (Zymo) and eluted in 20 µL elution buffer.

Recovered DNA was then ligated to the stlgR oligo using Thermostable 5' AppDNA/RNA Ligase (New England Biolabs) by adding 20 units ligase, 20 pmol stlgR oligo, in 20 µL ss ligation buffer (10 mM Bis-Tris-Propane-HCl, 10 mM MgCl$_2$, 1 mM DTT, 2.5 mM MnCl$_2$, pH 7 @ 25° C.) and incubating at 65° C. for 1 hour followed by heat inactivation at 90° C. for 5 min. DNA product was then PCR amplified using HiFidelity 2× master mix (New England Biolabs). Primers T7-Ad3 (sequence 5'>3' gcctcgagctaatacgactcactatagag) (SEQ ID NO: 12) and gRU (sequence 5'>3' AAAAAAGCACCGACTCGGTG) (SEQ ID NO: 4419) were used to amplify with the following settings (98° C. for 3 min; 98° C. for 20 sec, 60° C. for 30 secs, 72° C. for 20 sec, 30 cycles). The PCR amplicon was cleaned up using the PCR cleanup kit and verified by DNA sequencing, then used as template for an in vitro transcription reaction to generate the guide RNAs.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10787662B2). An electronic copy of the "Sequence Listing" will also be available from the USPTO upon request and payment of the fee set forth in 37 CFR 1.19(b)(3).

The invention claimed is:

1. A method of making a collection of nucleic acids for a nucleic acid-guided nuclease system protein comprising at least $10^5$ unique guide nucleic acids (gNAs), each comprising a DNA comprising a targeting sequence ligated to a DNA comprising a nucleic acid-guided nuclease system protein-binding sequence, comprising:
   a. providing a plurality of double-stranded DNA molecules comprising at least $10^5$ unique sequences of interest, each comprising a sequence of interest 5' to a PAM sequence, and its reverse complementary sequence on the opposite strand, wherein the sequence of interest or its reverse complementary sequence corresponds to a targeting sequence;
   b. performing an enzymatic digestion reaction on the plurality of double stranded DNA molecules, wherein cleavages are generated at the PAM sequence and/or its reverse complementary sequence on the opposite strand, but without completely removing the PAM sequence and/or its reverse complementary sequence on the opposite strand from the double stranded DNA;
   c. ligating adapters comprising a recognition sequence to a plurality of the resulting DNA molecules of step (b);
   d. contacting the DNA molecules of step (c) with a restriction enzyme that recognizes the recognition sequence of step (c), whereby generating DNA fragments comprising blunt-ended double strand breaks immediately 5' to the PAM sequence, whereby removing the PAM sequence and the adapter containing the enzyme recognition site; and
   e. ligating the resulting double stranded DNA fragments of step (d) with a DNA comprising a nucleic acid-guided nuclease system protein-binding sequence, whereby generating a plurality of DNA fragments, each comprising a DNA comprising a targeting sequence ligated to a DNA comprising a nucleic acid-guided nuclease system protein-binding sequence, wherein the plurality of DNA fragments comprises at least $10^5$ unique targeting sequences.

2. The method of claim 1, wherein the nucleic acid-guided nuclease system protein is a CRISPR/Cas system protein.

3. The method of claim 1, wherein the double stranded DNA molecules further comprise a regulatory sequence upstream of the sequence of interest 5' to the PAM sequence.

4. The method of claim 3, wherein the regulatory sequence comprises a promoter.

5. The method of claim 4, wherein the promoter comprises a T7, Sp6, or T3 sequence.

6. The method of claim 1, wherein the double stranded DNA molecules are genomic DNA, intact DNA, or sheared DNA.

7. The method of claim 6, wherein the genomic DNA is human, mouse, avian, fish, plant, insect, bacterial, or viral.

8. The method of claim 1, wherein the DNA segments comprising a targeting sequence are at least 22 bp.

9. The method of claim 1, wherein the DNA segments comprising a targeting sequence are 15-250 bp in size range.

10. The method of claim 1, wherein the PAM sequence is AGG, CGG, or TGG.

11. The method of claim 1, wherein the PAM sequence is specific for a CRISPR/Cas system protein selected from the group consisting of Cas9, Cpf1, Cas3, Cas8a-c, Cas10, Cse1, Csy1, Csn2, Cas4, Csm2, and Cm5.

12. The method of claim 1, wherein step (b) further comprises (1) contacting the double stranded DNA molecules with an enzyme capable of creating a nick in a single strand at a CCD site, whereby generating a plurality of nicked double stranded DNA molecules, each comprising a sequence of interest followed by an HGG sequence, wherein the double stranded DNA molecules are nicked at the CCD sites; and (2) contacting the nicked double stranded DNA molecules with an endonuclease, whereby generating a plurality of double stranded DNA fragments, each comprising a sequence of interest followed by an HGG sequence wherein residual nucleotides from HGG and/or CCD sequences is (are) left behind.

13. The method of claim 1, wherein step (d) further comprises PCR amplification of the adaptor-ligated DNA fragments from step (c) before cutting with the restriction enzyme recognizing the recognition sequence of step (c), wherein after PCR, the recognition sequence is positioned 3' of the PAM sequence, and a regulatory sequence is positioned at the 5' distal end of the PAM sequence.

14. The method of claim 1, wherein the enzymatic digestion reaction comprises a first and a second nicking enzyme.

15. The method of claim 1, wherein step (c) further comprises a blunt-end reaction with a T4 DNA Polymerase, if the adapter to be ligated does not comprise an overhang.

16. The method of claim 1, wherein the adapter of step (c) is either (1) double stranded, comprising a restriction enzyme recognition sequence in one strand, and a regulatory sequence in the other strand, if the adapter is Y-shaped and comprises an overhang; or (2) has a palindromic enzyme recognition sequence in both strands, if the adapter is not Y-shaped.

17. The method of claim 1, wherein the restriction enzyme of step (d) is MlyI.

18. The method of claim 1, wherein step (d) further comprises contacting the DNA molecules with an XhoI enzyme.

19. The method of claim 1, wherein in step (e) the DNA comprising a nucleic acid-guided nuclease system protein-binding sequence encodes for a RNA comprising the sequence (SEQ ID NO: 1)
GUUUUAGAGCUAGAAAUAGCAAGUUAAAAUAAGGCUAGUCCGUUAUCAA

CUUGAAAAAGUGGCACCGAGUCGGUGCUUUUUUU or encodes for a RNA comprising the sequence (SEQ ID NO: 2)
GUUUUAGAGCUAUGCUGGAAACAGCAUAGCAAGUUAAAAUAAGGCUAGU

CCGUUAUCAACUUGAAAAAGUGGCACCGAGUCGGUGCUUUUUUUC.

20. The method of claim 1, wherein the sequences of interest are from an organism, and wherein the sequences of interest are spaced every 10,000 bp or less across the genome of the organism.

21. The method of claim 14, wherein the first nicking enzyme is a Nt.CviPII enzyme, and the second nicking enzyme is a T7 Endonuclease I enzyme.

* * * * *